US 11,492,352 B2

(12) United States Patent
Ishii et al.

(10) Patent No.: US 11,492,352 B2
(45) Date of Patent: Nov. 8, 2022

(54) ARENAVIRUS GROWTH INHIBITOR COMPRISING POLYCYCLIC CARBAMOYLPYRIDONE DERIVATIVE

(71) Applicants: NATIONAL UNIVERSITY CORPORATION HOKKAIDO UNIVERSITY, Hokkaido (JP); Shionogi & Co., Ltd., Osaka (JP)

(72) Inventors: Akihiro Ishii, Hokkaido (JP); Akihiko Sato, Hokkaido (JP); Makoto Kawai, Osaka (JP); Yoshiyuki Taoda, Osaka (JP)

(73) Assignees: NATIONAL UNIVERSITY CORPORATION HOKKAIDO UNIVERSITY, Hokkaido (JP); SHIONOGI & CO., LTD., Osaka (JP)

( * ) Notice: Subject to any disclaimer, the term of this patent is extended or adjusted under 35 U.S.C. 154(b) by 0 days.

(21) Appl. No.: 17/255,566

(22) PCT Filed: Jun. 29, 2019

(86) PCT No.: PCT/JP2019/025312
§ 371 (c)(1),
(2) Date: Dec. 23, 2020

(87) PCT Pub. No.: WO2020/004443
PCT Pub. Date: Jan. 2, 2020

(65) Prior Publication Data
US 2021/0292321 A1 Sep. 23, 2021

(30) Foreign Application Priority Data

Jun. 27, 2018 (JP) .............................. JP2018-122467

(51) Int. Cl.
*A61K 31/53* (2006.01)
*A61K 31/498* (2006.01)
(Continued)

(52) U.S. Cl.
CPC ............ *C07D 471/04* (2013.01); *A61P 31/14* (2018.01); *C07D 471/14* (2013.01); *C07D 498/14* (2013.01)

(58) Field of Classification Search
CPC .. A61K 31/53; A61K 31/498; A61K 31/5025; A61P 31/14
(Continued)

(56) References Cited

U.S. PATENT DOCUMENTS 8,927,710 B2 * 1/2015 Akiyama ................ A61P 31/16
544/111
2006/0052361 A1 3/2006 Miyazaki et al.
(Continued)

FOREIGN PATENT DOCUMENTS

EP   1 544 199   6/2005
EP   1 950 212   7/2008
(Continued)

OTHER PUBLICATIONS

International Search Report dated Sep. 3, 2019 in International (PCT) Application No. PCT/JP2019/025312 with English-language translation.
International Preliminary Report on Patentability and Written Opinion of The International Searching Authority dated Jan. 7, 2021 in International (PCT) Application No. PCT/JP2019/025312.
Charrel et al., "Zoonotic aspects of arenavirus infections", Veterinary Microbiology, 2010, vol. 140, pp. 213-220.
Capul et al., "Conserved Residues in Lassa Fever Virus Z Protein Modulate Viral Infectivity at the Level of the Ribonucleoprotein", Journal of Virology, 2011, vol. 85, No. 7, pp. 3172-3178.
(Continued)

*Primary Examiner* — Charanjit Aulakh
(74) *Attorney, Agent, or Firm* — Wenderoth, Lind & Ponack, L.L.P.

(57) ABSTRACT

The present invention provides a compound having antiviral activity, especially having arenavirus proliferation inhibitory activity, and/or a medicament comprising the compound. More preferably, the present invention provides a compound having proliferation inhibitory activity on the Old World arenaviruses such as Luna virus, Lassa virus, and lymphocytic choriomeningitis virus and/or the New World arenaviruses such as Junin virus, and/or a medicament comprising the compound.

An arenavirus proliferation inhibitor comprising a compound represented by Formula (I) or a prodrug thereof or a pharmaceutically acceptable salt thereof:

(I)

(wherein $R^1$ is carboxy, or the like; $A^3$ is $CR^2$ or N; $R^2$ is a hydrogen atom, halogen, hydroxy, or the like; $R^3$ is a hydrogen atom, hydroxy, carboxy, cyano, formyl, alkyl optionally substituted with Substituent group F, or the like; either $A^1$ or $A^2$ is $CR^6R^6$, and the other is $NR^7$, or $A^1$ is $CR^8R^9$, and $A^2$ is $CR^{10}R^{11}$; and $R^5$, $R^6$, $R^7$, $R^8$, $R^9$, $R^{10}$, and $R^{11}$ are each independently a hydrogen atom, carboxy, cyano, alkyl optionally substituted with Substituent group F, or the like).

24 Claims, 1 Drawing Sheet

(51) Int. Cl.
  *C07D 471/04*    (2006.01)
  *A61P 31/14*     (2006.01)
  *C07D 471/14*    (2006.01)
  *C07D 498/14*    (2006.01)

(58) Field of Classification Search
  USPC .............................. 514/243, 248, 249, 250
  See application file for complete search history.

(56) References Cited

U.S. PATENT DOCUMENTS

| | | |
|---|---|---|
| 2012/0184734 A1 | 7/2012 | Akiyama et al. |
| 2013/0197219 A1 | 8/2013 | Takahashi et al. |
| 2016/0002227 A1 | 1/2016 | Schulz-Gasch et al. |
| 2016/0213647 A1 | 7/2016 | Schlesinger et al. |

FOREIGN PATENT DOCUMENTS

| | | |
|---|---|---|
| EP | 3 290 424 | 3/2018 |
| JP | 2017-137291 | 8/2017 |
| JP | 2017-521424 | 8/2017 |
| JP | 2019-59697 | 4/2019 |
| WO | 2005/016927 | 2/2005 |
| WO | 2007/049675 | 5/2007 |
| WO | 2010/147068 | 12/2010 |
| WO | 2012/039414 | 3/2012 |
| WO | 2016/005330 | 1/2016 |
| WO | 2016/123259 | 8/2016 |
| WO | 2016/123541 | 8/2016 |
| WO | 2016/160677 | 10/2016 |
| WO | 2016/175224 | 11/2016 |
| WO | 2017/023694 | 2/2017 |
| WO | 2017/141104 | 8/2017 |

OTHER PUBLICATIONS

Zapata et al., "Lymphocytic choriomeningitis vims (LCMV) infection of macaques: A model for Lassa fever", Antiviral Research, 2011, vol. 92, pp. 125-138.

Djavani et al., "Early Blood Profiles of Virus Infection in a Monkey Model for Lassa Fever", Journal of Virology, 2007, vol. 81, No. 15, pp. 7960-7973.

Tomassini et al. "Inhibition of Cap ($m^7$GpppXm)-Dependent Endonuclease of Influenza Virus by 4-Substituted 2,4-Dioxobutanoic Acid Compounds", Antimicrobial Agents and Chemotherapy, 1994, vol. 38, No. 12, pp. 2827-2837.

Hensens et al., "Isolation and Structure of Flutimide, a Novel Endonuclease Inhibitor of Influenza Virus", Tetrahedron Letters, 1995, vol. 36, No. 12, pp. 2005-2008.

Cianci et al., "Identification of N-hydroxamic acid and N-hydroxyimide compounds that inhibit the influenza virus polymerase", Antiviral Chemishy and Chemotherapy, 1996, vol. 7, No. 6, pp. 353-360.

Bauman et al., "Crystallographic Fragment Screening and Structure-Based Optimization Yields a New Class of Influenza Endonuclease Inhibitors", ACS Chem. Biol., 2013, vol. 8, pp. 2501-2508.

Miyagawa et al., "Discovery of novel 5-hydroxy-4-pyridone-3-carboxy acids as potent inhibitors of influenza Cap-dependent endonuclease", Bioorganic & Medicinal Chemistry Letters, 2016, vol. 26, pp. 4739-4742.

Miyagawa et al., "Synthesis and SAR Study of Carbamoyl Pyridone Bicycle Derivatives as Potent Inhibitors of Influenza Cap-dependent Endonuclease", J. Med. Chem., 2019, vol. 62, pp. 8101-8114.

Omoto et al., "Characterization of influenza virus variants induced by treatment with endonuclease inhibitor baloxavir marboxil", Scientific Reports, 2018, 8:9633, 15 pages.

Noshi et al., "In vitro characterization of baloxavir acid, a first-in-class cap-dependent endonuclease inhibitor of the influenza virus polymerase PA subunit", Antiviral Research, 2018, vol. 160, pp. 109-117.

Saez-Ayala et al., "Crystal suuctures of *Lymphocytic choriomeningitis* virus endonuclease domain complexed with diketoacid ligands", IUCrJ, 2018, vol. 5, pp. 223-235.

Saez-Ayala et al., "Metal chelators for the inhibition of the lymphocytic choriomeningitis virus endonuclease domain", Antiviral Research, 2019, vol. 162, pp. 79-89.

Extended European Search Report dated Mar. 17, 2022 in corresponding European patent Application No. 19826492.1.

Jonas Demeulemeester et al., "LEDGINs, non-catalytic site inhibitors of HIV-1 integrase: a patent review (2006- 2014)", Expert Opinion On Therapeutic Patents, 2014, vol. 24, No. 6, pp. 609-632.

\* cited by examiner

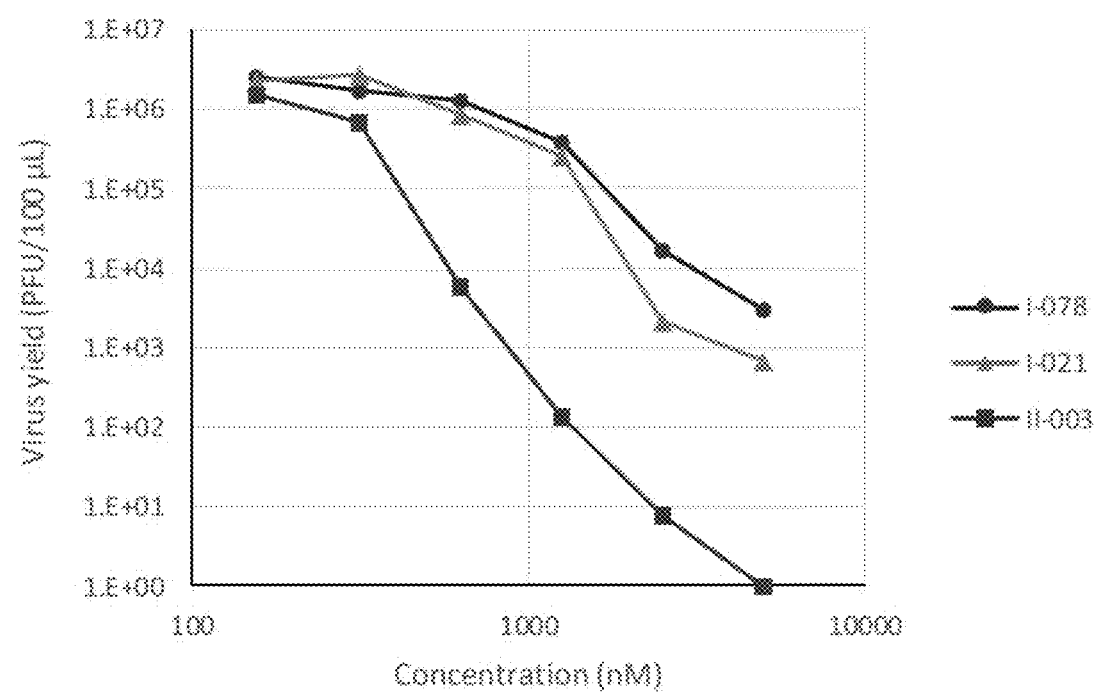

ARENAVIRUS GROWTH INHIBITOR COMPRISING POLYCYCLIC CARBAMOYLPYRIDONE DERIVATIVE

TECHNICAL FIELD

The present invention relates to a polycyclic carbamoylpyridone derivative that exhibits arenavirus proliferation inhibitory activity and/or a pharmaceutical composition containing a polycyclic carbamoylpyridone derivative that exhibits arenavirus proliferation inhibitory activity.

BACKGROUND ART

Viral hemorrhagic fever, which have mainly occurred in Africa and South America continents, includes filovirus infections including ebola virus infection, bunya virus infections including Crimean Congo hemorrhagic fever, and arenavirus infections including Lassa fever and South American hemorrhagic fever. These pathogens are zoonotic viruses which are possessed by bats, rodents, mites, and the like. Since rodents live in overlapping areas with human living areas and possess a variety of pathogens, they are natural hosts of zoonotic infections that pose threats to humans. Viral hemorrhagic fever is an infection that arises from infection with a virus by contacting with a natural host of the virus, such as rodents, or by being bitten by a virus-vector insect, then leads to platelet decrease due to inflammatory reactions associated with viral proliferation in the body, and bleeding from tissues throughout the body, or death due to multiple organ failure. The fatality varies depending on each virus, but the disease has a high fatality of 10 to 70% when it becomes severe.

Viruses in Arenaviridae family have been molecular genetically classified and are roughly divided into the Old World arenaviruses, which have been reported in the Old World such as the African continent, and the New World arenaviruses which have been pathogens of South American hemorrhagic fever in the South American continent (Non-patent Document 1). The Old World arenaviruses include: Lassa virus, which is the cause of Lassa fever; Lujo Virus; Luna Virus; and lymphocytic choriomeningitis virus (LCMV) (Non-patent Documents 2 to 4). The New World arenaviruses include Junin Virus, which is the cause of Argentine hemorrhagic fever; Machupo virus, which is the cause of Bolivia hemorrhagic fever; Sabia virus, which is the cause of Brazil hemorrhagic fever; and Guanarito virus, which is the cause of Venezuela hemorrhagic fever.

The primary route of infection of the arenaviruses is contacts with excreta, saliva or blood of virus carrier rodents. The incubation period is one to two weeks. After three to four days of initial symptoms like a cold, the body is debilitated, and in severe cases, high fever and bleeding (hematemesis, blood in stool) occur. The fatality is more than 30%. In epidemic areas of Lassa virus, hundreds of thousands of people are infected with Lassa virus every year, leading to many patients. Lassa fever patients outside the epidemic areas have also been reported, and many of them have occurred in Europe. Lassa fever patients have also been confirmed in the United States and Japan as imported infection cases. No vaccine against Lassa virus has been developed. Junin virus, the cause of Argentine hemorrhagic fever, caused thousands of infected people annually in mainly agricultural workers. Nowadays, infected people tend to decrease due to routine vaccination of attenuated vaccines and improved agricultural work.

For these infections, Ribavirin, a nucleic acid analog that acts broadly on viruses, is only used as an antiviral drug. It has been reported that a large amount of intravenous administration of Ribavirin in the early stage after onset of Lassa fever improves the mortality. However, no therapeutic agents have been developed for many other viruses, and there are still no clear conclusions about the efficacy of Ribavirin. Furthermore, intravenous administration of Ribavirin has not been approved in Japan. The antiviral drug that has a wide range of effects on these viruses would be useful not only for the treatment of infected people but also for the prevention of global pandemics, thus the development of a therapeutic agent against these viruses is desired.

Documents such as Patent Documents 1 to 4 report polycyclic carbamoylpyridone derivatives, but have no descriptions about the arenavirus proliferation inhibitory activity.

PRIOR ART REFERENCES

Patent Document

[Patent Document 1] WO2010/147068
[Patent Document 2] WO2012/039414
[Patent Document 3] WO2016/005330
[Patent Document 4] JP2019-59697

Non-Patent Document

[Non-patent Document 1] Veterinary Microbiology. 2010, 140 (3-4): 213-220.
[Non-patent Document 2] Journal of Virology. 2011, 85 (7), 3172-3178.
[Non-patent Document 3] Antiviral Research, 2011, 92 (2), 125-138.
[Non-patent Document 4] Journal of Virology. 2007, 81 (15), 7960-7973.

SUMMARY OF THE INVENTION

Problems to be Solved by the Invention

An object of the present invention is to provide a compound having an antiviral activity, in particular an arenavirus proliferation inhibitory activity, and/or a medicament containing the compound. The present invention preferably provides a compound having proliferation inhibitory activity on the Old World arenaviruses (e.g., Lassa Virus, Lujo Virus, Luna Virus, and lymphocytic choriomeningitis virus) and/or the New World arenaviruses (e.g., Junin Virus), and/or a medicament containing the compound. More preferably, the present invention provides a compound having proliferation inhibitory activity on Lassa virus, lymphocytic choriomeningitis virus and/or Junin virus, and/or a medicament containing the compound.

Means for Solving the Problem (Item 1)

An arenavirus proliferation inhibitor comprising a compound represented by Formula (I) or a prodrug thereof or a pharmaceutically acceptable salt thereof:

[Chemical Formula 1]

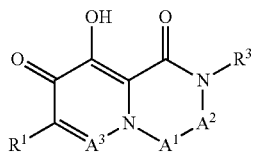

(wherein
R$^1$ is —Z$^X$—C(=O)—O—R$^{X15}$,
—Z$^X$—C(=O)—N(R$^{X9}$)(R$^{X10}$), or
—Z$^X$—N(R$^{X14}$)—C(=O)—O—R$^{X15}$
(wherein, R$^{X9}$, R$^{X14}$, and R$^{X15}$ are each independently a hydrogen atom, alkyl optionally substituted with Substituent group E, alkenyl optionally substituted with Substituent group E, or alkynyl optionally substituted with Substituent group E; R$^{X10}$ is a hydrogen atom, alkyl optionally substituted with Substituent group E, alkenyl optionally substituted with Substituent group E, alkynyl optionally substituted with Substituent group E, or alkyloxy optionally substituted with Substituent group E; Z$^X$ is a single bond or a linear or branched alkylene; and
R$^{X9}$ and R$^{X10}$ may be taken together with an adjacent atom to form a heterocycle);
A$^3$ is CR$^2$ or N;
R$^2$ is a hydrogen atom, halogen, hydroxy, carboxy, cyano, formyl, alkyl optionally substituted with Substituent group F, alkenyl optionally substituted with Substituent group F, alkynyl optionally substituted with Substituent group F, or alkyloxy optionally substituted with Substituent group F;
R$^9$ is a hydrogen atom, hydroxy, carboxy, cyano, formyl, alkyl optionally substituted with Substituent group F, alkenyl optionally substituted with Substituent group F, alkynyl optionally substituted with Substituent group F, alkyloxy optionally substituted with Substituent group F, alkenyloxy optionally substituted with Substituent group F, alkylcarbonyl optionally substituted with Substituent group F, alkyloxycarbonyl optionally substituted with Substituent group F, a carbocyclic group optionally substituted with Substituent group A, carbocyclealkyl optionally substituted with Substituent group A, carbocycleoxyalkyl optionally substituted with Substituent group A, carbocyclecarbonyl optionally substituted with Substituent group A, carbocycleoxy optionally substituted with Substituent group A, carbocycleoxycarbonyl optionally substituted with Substituent group A, a heterocyclic group optionally substituted with Substituent group A, heterocyclealkyl optionally substituted with Substituent group A, heterocycleoxyalkyl optionally substituted with Substituent group A, heterocyclecarbonyl optionally substituted with Substituent group A, heterocycleoxy optionally substituted with Substituent group A, or heterocycleoxycarbonyl optionally substituted with Substituent group A,
—Z$^Z$—N(R$^{Z1}$)—SO$_2$—R$^{Z2}$,
—Z$^Z$—N(R$^{Z3}$)—C(=O)—R$^{Z4}$,
—Z$^Z$—N(R$^{Z5}$)—C(=O)—O—R$^{Z6}$,
—Z$^Z$—C(=O)—N(Z$^{Z7}$)(R$^{Z8}$),
—Z$^Z$—N(R$^{Z9}$)(R$^{Z10}$),
—Z$^Z$—SO$_2$—R$^{Z11}$, or
—Z$^Z$—N(R$^{Z12}$)—O—C(=O)—R$^{Z13}$
(wherein R$^{Z1}$, R$^{Z2}$, R$^{Z4}$, R$^{Z5}$, R$^{Z6}$, R$^{Z7}$, R$^{Z8}$, R$^{Z9}$, R$^{Z10}$, R$^{Z12}$, and R$^{Z13}$ are each independently selected from a substituent group consisting of a hydrogen atom, alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;
R$^{Z2}$ and R$^{Z11}$ are each independently selected from a substituent group consisting of alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;
R$^{Z7}$ and R$^{Z8}$ may be taken together with an adjacent atom to form a heterocycle; and
Z$^{Z2}$ is a single bond or a linear or branched alkylene);
a) either A$^1$ or A$^2$ is CR$^5$R$^6$, and the other is NR$^7$, or
b) A$^1$ is CR$^8$R$^9$, and A$^2$ is CR$^{10}$R$^{11}$,
R$^5$, R$^6$, R$^7$, R$^8$, R$^9$, R$^{10}$, and R$^{11}$ are each independently a hydrogen atom, carboxy, cyano, alkyl optionally substituted with Substituent group F, alkenyl optionally substituted with Substituent group F, alkynyl optionally substituted with Substituent group F, alkylcarbonyl optionally substituted with Substituent group F, alkyloxycarbonyl optionally substituted with Substituent group F, a carbocyclic group optionally substituted with Substituent group B, carbocyclealkyl optionally substituted with Substituent group B, carbocycleoxyalkyl optionally substituted with Substituent group B, carbocyclecarbonyl optionally substituted with Substituent group B, carbocycleoxycarbonyl optionally substituted with Substituent group B, a heterocyclic group optionally substituted with B, heterocyclealkyl optionally substituted with Substituent group B, heterocycleoxyalkyl optionally substituted with Substituent group B, heterocyclecarbonyl optionally substituted with Substituent group B, or heterocycleoxycarbonyl optionally substituted with Substituent group B,
—Z$^V$—S—R$^{V1}$,
—Z$^V$—S(=O)—R$^{V2}$,
—Z$^V$—SO$_2$—R$^{V3}$,
—C(=O)—C(=O)—R$^{V4}$,
—C(=O)—N(R$^{V5}$)(R$^{V6}$),
—Z$^V$—N(R$^{V7}$)—C(=O)—O—R$^{V8}$, or
—Z$^V$—N(R$^{V9}$)—C(=O)—R$^{V10}$
(wherein R$^{V1}$, R$^{V4}$, R$^{V5}$, R$^{V6}$, R$^{V7}$, R$^{V8}$, R$^{V9}$, and R$^{V10}$ are each independently selected from a substituent group consisting of a hydrogen atom, alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;
R$^{V2}$ and R$^{V3}$ are each independently selected from a substituent group consisting of alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;

$R^{V5}$ and $R^{V6}$ may be taken together with an adjacent atom to form a heterocycle, and
$Z^V$ is a single bond or a linear or branched alkylene);
$R^5$ and $R^6$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure;
$R^8$ and $R^9$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure;
$R^{10}$ and $R^{11}$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure;
1) when $A^1$ is $CR^5R^8$ and $A^2$ is $NR^7$,
then $R^5$ and $R^7$ may be taken together to form a bond, or $R^5$ and $R^7$ may be taken together with an adjacent atom to form a heterocycle optionally substituted with Substituent group B, wherein the heterocycle may form a condensed ring and/or a spiro ring and/or a bridged structure, or
$R^3$ and $R^7$ may be taken together with an adjacent atom to form a heterocycle optionally substituted with Substituent group B, wherein the heterocycle may form a condensed ring and/or a spiro ring and/or a bridged structure,
2) when $A^1$ is $NR^7$ and $A^2$ is $CR^5R^6$,
then $R^7$ and $R^5$ may be taken together to form a bond, or $R^7$ and $R^5$ may be taken together with an adjacent atom to form a heterocycle optionally substituted with Substituent group B, wherein the heterocycle may form a condensed ring and/or a spiro ring and/or a bridged structure, or
$R^3$ and $R^6$ may be taken together with an adjacent atom to form a heterocycle optionally substituted with Substituent group B, wherein the heterocycle may form a condensed ring and/or a spiro ring and/or a bridged structure,
3) when $A^1$ is $CR^8R^9$, and $A^2$ is $CR^{10}R^{11}$,
then $R^3$ and $R^{10}$ may be taken together to form a bond, or $R^8$ and $R^{10}$ may be taken together with an adjacent atom to form a carbocycle optionally substituted with Substituent group B or a heterocycle optionally substituted with Substituent group B, wherein the carbocycle or the heterocycle may form a condensed ring and/or a spiro ring and/or a bridged structure, or
$R^3$ and $R^{11}$ may be taken together with an adjacent atom to form a heterocycle optionally substituted with Substituent group B, wherein the heterocycle may form a condensed ring and/or a spiro ring and/or a bridged structure,
with a proviso that the following cases of c) and d) are excluded;
c) $R^5$, $R^6$, and $R^7$ are all a hydrogen atom,
d) $R^8$, $R^9$, $R^{10}$, and $R^{11}$ are all a hydrogen atom,
Substituent group A: halogen, cyano, hydroxy, carboxy, formyl, amino, oxo, nitro, alkyl, halogenoalkyl, alkyloxy, alkylthio, alkylamino, hydroxyalkyl, carboxyalkyl, aminoalkyl, a carbocyclic group, a heterocyclic group, an oxo-substituted heterocyclic group, carbocyclealkyloxy, carbocycleoxyalkyl, carbocyclealkyloxyalkyl, carbocyclealkylthio, heterocyclealkyloxy, heterocycleoxyalkyl, heterocyclealkyloxyalkyl, halogenoalkyloxy, alkyloxyalkyl, alkyloxyalkyloxy, alkylcarbonyl, alkylcarbonyloxy, alkyloxycarbonyl, alkyloxycarbonyloxy, alkylamino, alkylcarbonylamino, halogenoalkylcarbonylamino, alkylaminocarbonyl, alkylsulfonyl, alkylsulfinyl, and alkylsulfonylamino;

Substituent group B: halogen, cyano, hydroxy, carboxy, formyl, amino, oxo, nitro, alkyl, halogenoalkyl, alkyloxy, alkylthio, alkylamino, hydroxyalkyl, carboxyalkyl, alkylamino, carbocyclealkyloxy, heterocyclealkyloxy, halogenoalkyloxy, alkyloxyalkyl, alkyloxyalkyloxy, alkylcarbonyl, alkyloxycarbonyl, alkyloxycarbonyloxy, alkylamino, alkylcarbonylamino, alkylaminocarbonyl, alkylsulfonyl, alkylsulfonylamino, a carbocyclic group optionally substituted with Substituent group A, a heterocyclic group optionally substituted with Substituent group A, carbocyclealkyl optionally substituted with Substituent group A, heterocyclealkyl optionally substituted with Substituent group A, carbocyclealkyloxy optionally substituted with Substituent group A, heterocyclealkyloxy optionally substituted with Substituent group A, carbocyclealkylthio optionally substituted with Substituent group A, heterocyclealkylthio optionally substituted with Substituent group A, carbocycleoxyalkyl optionally substituted with Substituent group A, heterocycleoxyalkyl optionally substituted with Substituent group A, carbocyclealkyloxyalkyl optionally substituted with Substituent group A, and heterocyclealkyloxyalkyl optionally substituted with Substituent group A;
Substituent group E: halogen, hydroxy, carboxy, alkyloxy, alkylcarbonyl, alkyloxycarbonyl, alkylcarbonyloxy, alkylaminocarbonyl, and alkylsulfonyl;
Substituent group F: halogen, cyano, hydroxy, carboxy, formyl, amino, oxo, nitro, alkyloxy, alkylthio, a carbocyclic group, a heterocyclic group, an oxo-substituted heterocyclic group, carbocyclealkyloxy, carbocyclealkylthio, heterocyclealkyloxy, halogenoalkyloxy, alkyloxyalkyloxy, alkylcarbonyl, alkylcarbonyloxy, alkyloxycarbonyl, alkyloxycarbonyloxy, alkylamino, alkylcarbonylamino, halogenoalkylcarbonylamino, alkylaminocarbonyl, alkylsulfonyl, alkylsulfinyl, and alkylsulfonylamino).
(Item 1') An arenavirus proliferation inhibitor comprising a compound represented by Formula (I″) or a prodrug thereof or a pharmaceutically acceptable salt thereof

[Chemical Formula 2]

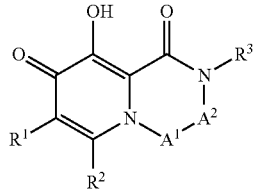

(I″)

(wherein
$R^1$ is carboxy,
—$Z^X$—C(=O)—N($R^{X9}$)($R^{X10}$), or
—$Z^X$—N($R^{X14}$)—C(=O)—O—$R^{X15}$
(wherein, $R^{X9}$, $R^{X10}$, $R^{X14}$, and $R^{X15}$ are each independently selected from a substituent group consisting of a hydrogen atom, alkyl optionally substituted with Substituent group E, alkenyl optionally substituted with Substituent group E, and alkynyl optionally substituted with Substituent group E; $Z^X$ is a single bond or a linear or branched alkylene; and $R^{X9}$ and $R^{X10}$ may be taken together with an adjacent atom to form a heterocycle);
$R^2$ is a hydrogen atom, halogen, hydroxy, carboxy, cyano, formyl, alkyl optionally substituted with Substituent group F, alkenyl optionally substituted with Substituent group F, alkynyl optionally substituted with Substituent group F, or alkyloxy optionally substituted with Substituent group F;

R³ is a hydrogen atom, hydroxy, carboxy, cyano, formyl, alkyl optionally substituted with Substituent group F, alkenyl optionally substituted with Substituent group F, alkynyl optionally substituted with Substituent group F, alkyloxy optionally substituted with Substituent group F, alkenyloxy optionally substituted with Substituent group F, alkylcarbonyl optionally substituted with Substituent group F, alkyloxycarbonyl optionally substituted with Substituent group F, a carbocyclic group optionally substituted with Substituent group A, carbocyclealkyl optionally substituted with Substituent group A, carbocycleoxyalkyl optionally substituted with Substituent group A, carbocyclecarbonyl optionally substituted with Substituent group A, carbocycleoxy optionally substituted with Substituent group A, carbocycleoxyalkyl optionally substituted with Substituent group A, carbocycleoxycarbonyl optionally substituted with Substituent group A, a heterocyclic group optionally substituted with Substituent group A, heterocyclealkyl optionally substituted with Substituent group A, heterocycleoxyalkyl optionally substituted with Substituent group A, heterocyclecarbonyl optionally substituted with Substituent group A, heterocycleoxy optionally substituted with Substituent group A, or heterocycleoxycarbonyl optionally substituted with Substituent group A,
—$Z^Z$—N($R^{Z1}$)—$SO_2$—$R^{Z2}$,
—$Z^Z$—N($R^{Z3}$)—C(=O)—$R^{Z4}$,
—$Z^Z$—N($R^{Z3}$)—C(=O)—O—$R^{Z6}$,
—$Z^Z$—C(=O)—N($R^{Z7}$)($R^{Z8}$),
—$Z^Z$—N($R^{Z9}$)($R^{Z10}$),
—$Z^Z$—$SO_2$—$R^{Z11}$, or
—$Z^Z$—N($R^{Z12}$)—O—C(=O)—$R^{Z13}$
(wherein $R^{Z1}$, $R^{Z3}$, $R^{Z4}$, $R^{Z5}$, $R^{Z6}$, $R^{Z7}$, $R^{Z8}$, $R^{Z9}$, $R^{Z10}$, $R^{Z12}$, and $R^{Z13}$ are each independently selected from a substituent group consisting of a hydrogen atom, alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;
$R^{Z2}$ and $R^{Z11}$ are each independently selected from a substituent group consisting of alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;
$R^{Z7}$ and $R^{Z8}$, and $R^{Z9}$ and $R^{Z10}$ each may be taken together with an adjacent atom to form a heterocycle, and
$Z^Z$ is a single bond or a linear or branched alkylene);
Substituent groups A, B, E, and F are the same as defined in Item 1;
a) either $A^1$ or $A^2$ is $CR^5R^6$, and the other is $NR^7$, or
b) $A^1$ is $CR^8R^9$, and $A^2$ is $CR^{10}R^{11}$,
$R^5$, $R^6$, $R^7$, $R^8$, $R^9$, $R^{10}$, and $R^{11}$ are each independently a hydrogen atom, carboxy, cyano, alkyl optionally substituted with Substituent group F, alkenyl optionally substituted with Substituent group F, alkynyl optionally substituted with Substituent group F, alkylcarbonyl optionally substituted with Substituent group F, alkyloxycarbonyl optionally substituted with Substituent group F, a carbocyclic group optionally substituted with Substituent group B, carbocyclealkyl optionally substituted with Substituent group B, carbocycleoxyalkyl optionally substituted with Substituent group B, carbocyclecarbonyl optionally substituted with Substituent group B, carbocycleoxycarbonyl optionally substituted with Substituent group B, a heterocyclic group optionally substituted with B, heterocyclealkyl optionally substituted with Substituent group B, heterocycleoxyalkyl optionally substituted with Substituent group B, heterocyclecarbonyl optionally substituted with Substituent group B, or heterocycleoxycarbonyl optionally substituted with Substituent group B,
—$Z^V$—S—$R^{V1}$,
—$Z^V$—S(=O)—$R^{V2}$,
—$Z^V$—$SO_2$—$R^{V3}$,
—C(=O)—C(=O)—$R^{V4}$,
—C(=O)—N($R^{V5}$)($R^{V6}$),
—$Z^V$—N($R^{V7}$)—C(=O)—O—$R^{V8}$, or
—$Z^V$—N($R^{V9}$)—C(=O)—$R^{V10}$
(wherein $R^{V1}$, $R^{V4}$, $R^{V5}$, $R^{V6}$, $R^{V7}$, $R^{V8}$, $R^{V9}$, and $R^{V10}$ are each independently selected from a substituent group consisting of a hydrogen atom, alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;
$R^{V2}$ and $R^{V3}$ are each independently selected from a substituent group consisting of alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;
$R^{V5}$ and $R^{V6}$ may be taken together with an adjacent atom to form a heterocycle, and $Z^V$ is a single bond or a linear or branched alkylene);
$R^5$ and $R^6$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure;
$R^8$ and $R^9$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure;
$R^{10}$ and $R^{11}$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure;
1) when $A^1$ is $CR^5R^6$ and $A^2$ is $NR^7$,
then $R^5$ and $R^7$ may be taken together to form a bond, or $R^5$ and $R^7$ may be taken together with an adjacent atom to form a heterocycle optionally substituted with Substituent group B, wherein the heterocycle may form a condensed ring and/or a spiro ring and/or a bridged structure, or
$R^3$ and $R^7$ may be taken together with an adjacent atom to form a heterocycle optionally substituted with Substituent group B, wherein the heterocycle may form a condensed ring and/or a spiro ring and/or a bridged structure,
2) when $A^1$ is $NR^7$ and $A^2$ is $CR^5R^6$,
then $R^7$ and $R^5$ may be taken together to form a bond, or $R^7$ and $R^5$ may be taken together with an adjacent atom to form a heterocycle optionally substituted with Substituent group B, wherein the heterocycle may form a condensed ring and/or a spiro ring and/or a bridged structure, or $R^3$ and $R^6$ may be taken together with an adjacent atom to form a heterocycle optionally substituted with Substituent group B, wherein the heterocycle may form a condensed ring and/or a spiro ring and/or a bridged structure, 3) when $A^1$ is $CR^8R^9$, and $A^2$ is $CR^{10}R^{11}$, then $R^3$ and $R^{10}$ may be taken together to form a bond, or $R^8$ and $R^{10}$ may be taken together with an adjacent atom to form a carbocycle optionally substituted with Substituent group B or a heterocycle optionally substituted with Substituent group B, wherein the carbocycle or the heterocycle may form a condensed ring and/or a spiro ring and/or a bridged structure, or $R^3$ and $R^{11}$ may be taken together with an adjacent atom to form a heterocycle optionally substituted with Substituent group B, wherein the heterocycle may form a condensed ring and/or a spiro ring and/or a bridged structure, with a proviso that the following cases of c) and d) are excluded;

c) $R^5$, $R^6$, and $R^7$ are all a hydrogen atom, d) $R^6$, $R^9$, $R^{10}$, and $R^{11}$ are all a hydrogen atom).

(Item 2) The arenavirus proliferation inhibitor comprising the compound or a prodrug thereof or a pharmaceutically acceptable salt thereof according to Item 1 or 1', wherein a) either $A^1$ or $A^2$ is $CR^5R^6$, and the other is $NR^7$, or b) $A^1$ is $CR^8R^9$, and $A^2$ is $CR^{10}R^{11}$, $R^3$, $R^4$, $R^7$, $R^8$, $R^9$, $R^{10}$, and $R^{11}$ are each independently a hydrogen atom, carboxy, cyano, alkyl optionally substituted with Substituent group F, alkenyl optionally substituted with Substituent group F, alkynyl optionally substituted with Substituent group F, alkylcarbonyl optionally substituted with Substituent group F, alkyloxycarbonyl optionally substituted with Substituent group F, a carbocyclic group optionally substituted with Substituent group B, carbocyclealkyl optionally substituted with Substituent group B, carbocycleoxyalkyl optionally substituted with Substituent group B, carbocyclecarbonyl optionally substituted with Substituent group B, carbocycleoxycarbonyl optionally substituted with Substituent group B, a heterocyclic group optionally substituted with Substituent group B, heterocyclealkyl optionally substituted with Substituent group B, heterocycleoxyalkyl optionally substituted with Substituent group B, heterocyclecarbonyl optionally substituted with Substituent group B, or heterocycleoxycarbonyl optionally substituted with Substituent group B, —$Z^V$—S—$R^{V1}$,
—$Z^V$—S(=O)—$R^{V2}$,
—$Z^V$—$SO_2$—$R^{V3}$,
—C(=O)—C(=O)—$R^{V4}$,
—C(=O)—N($R^{V6}$)($R^{V1}$),
—$Z^V$—N($R^{V7}$)—C(=O)—O—$R^{V8}$, or
—$Z^V$—N($R^{V9}$)—C(=O)—$R^{V10}$ (wherein $R^{V1}$, $R^{V4}$, $R^{V5}$, $R^{V6}$, $R^{V7}$, $R^{V8}$, $R^{V9}$, and $R^{V10}$ are each independently selected from a substituent group consisting of a hydrogen atom, alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A; $R^{V2}$ and $R^{V3}$ are each independently selected from a substituent group consisting of alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A; $R^{V5}$ and $R^{V6}$ may be taken together with an adjacent atom to form a heterocycle, and $Z^V$ is a single bond or a linear or branched alkylene);

$R^3$ and $R^6$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure;

$R^8$ and $R^9$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure:

$R^{10}$ and $R^{11}$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure;

with a proviso that when $A^1$ is $CR^5R^6$ and $A^2$ is $NR^7$, then the 1) defined in Item 1 is not applied: when $A^1$ is $NR^7$ and $A^2$ is $CR^6R^6$, then the 2) defined in Item 1 is not applied; and when $A^1$ is $CR^8R^9$ and $A^2$ is $CR^{10}R^{11}$, then the 3) defined in Item 1 is not applied.

(Item 3) The arenavirus proliferation inhibitor comprising the compound or the prodrug thereof or the pharmaceutically acceptable salt thereof according to Item 1, 2, or 1', wherein $A^1$ is $CR^8R^9$, and $A^2$ is $CR^{10}R^{11}$.

(Item 4) The arenavirus proliferation inhibitor comprising the compound or the prodrug thereof or the pharmaceutically acceptable salt thereof according to Item 1, 2, or 1', wherein $A^1$ is $NR^7$, and $A^2$ is $CR^5R^6$.

(Item 5) The arenavirus proliferation inhibitor comprising the compound or the prodrug thereof or the pharmaceutically acceptable salt thereof according to Item 1, 2, or 1', wherein $A^1$ is $CR^5R^6$, and $A^2$ is $NR^7$.

(Item 6) The arenavirus proliferation inhibitor comprising the compound or the prodrug thereof or the pharmaceutically acceptable salt thereof according to any one of Items 1 to 3 and 1', wherein $R^9$ and $R^{10}$ are each independently a hydrogen atom or alkyl optionally substituted with Substituent group F; and either $R^9$ or $R^{10}$ is a carbocyclic group optionally substituted with Substituent group B, carbocyclealkyl optionally substituted with Substituent group B, a heterocyclic group optionally substituted with Substituent group B, or heterocyclealkyl optionally substituted with Substituent group B, and the other is a hydrogen atom or alkyl optionally substituted with Substituent group F.

(Item 7) The arenavirus proliferation inhibitor comprising the compound or the prodrug thereof or the pharmaceutically acceptable salt thereof according to any one of Items 1, 2, 4, 5 and 1', wherein either $R^6$ or $R^7$ is a carbocyclic group optionally substituted with Substituent group B, carbocyclealkyl optionally substituted with Substituent group B, a heterocyclic group optionally substituted with Substituent group B, or heterocyclealkyl optionally substituted with Substituent group B, and the other is a hydrogen atom; and $R^6$ is a hydrogen atom or alkyl optionally substituted with Substituent group F.

(Item 8) The arenavirus proliferation inhibitor comprising the compound or the prodrug thereof or the pharmaceutically acceptable salt thereof according to Item 4, wherein $R^7$ is a carbocyclic group optionally substituted with Substituent group B, carbocyclealkyl optionally substituted with Substituent group B, a heterocyclic group optionally substituted with Substituent group B, or heterocyclealkyl optionally substituted with Substituent group B;
$R^3$ is a hydrogen atom; and
$R^6$ is a hydrogen atom or alkyl optionally substituted with Substituent group F.

(Item 9) The arenavirus proliferation inhibitor comprising the compound or the prodrug thereof or the pharmaceutically acceptable salt thereof according to any one of Items 1 to 8 and 1', wherein $R^1$ is carboxy.

(Item 10) The arenavirus proliferation inhibitor comprising the compound or the prodrug thereof or the pharmaceutically acceptable salt thereof according to any one of Items 1 to 9 and 1', wherein $R^2$ is a hydrogen atom or alkyl.

(Item 11) The arenavirus proliferation inhibitor comprising the compound or the prodrug thereof or the pharmaceutically acceptable salt thereof according to any one of Items 1 to 10 and 1', wherein
$R^3$ is alkyl optionally substituted with Substituent group F, alkenyl optionally substituted with Substituent group F, alkynyl optionally substituted with Substituent group F, carbocyclealkyl optionally substituted with Substituent group A, a carbocyclic group optionally substituted with Substituent group A, heterocyclealkyl optionally substituted with Substituent group A, or carbocycleoxyalkyl optionally substituted with Substituent group A.

(Item 12) The arenavirus proliferation inhibitor comprising the compound or the prodrug thereof or the pharmaceutically acceptable salt thereof according to any one of Items 1 to 11, wherein $A^3$ is $CR^2$.

(Item 13) The arenavirus proliferation inhibitor comprising the compound or the prodrug thereof or the pharmaceutically acceptable salt thereof according to any one of Items 1 to 12 and 1', wherein
when either $A^1$ or $A^2$ is $CR^5R^6$ and the other is $NR^7$, then either $R^5$ or $R^7$ is a group shown below; and
when $A^1$ is $CR^8R^8$ and $A^2$ is $CR^{10}R^{11}$, then either $R^8$ or $R^{10}$ is a group shown below:

[Chemical Formula 3]

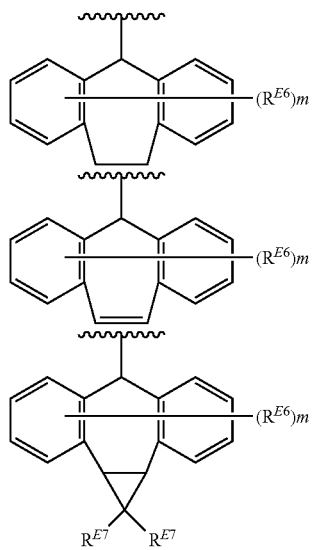

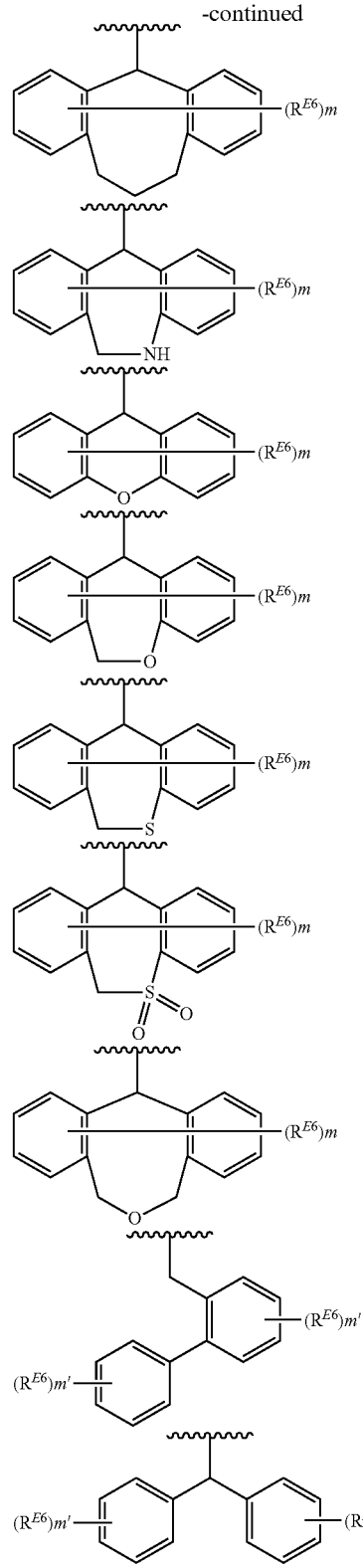

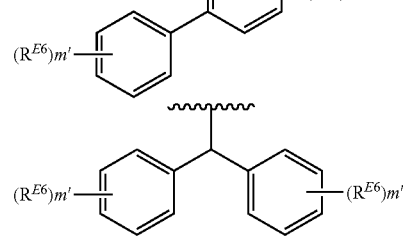

(wherein $R^{E6}$ are each independently a group selected from Substituent group A, and $R^{E7}$ are each independently a hydrogen atom, halogen, or alkyl;
m are each independently an integer of 0 to 7, m' are each independently an integer of 0 to 4, and Substituent group A is the same as defined in Item 1).

(Item 13') The arenavirus proliferation inhibitor comprising the compound or the prodrug thereof or the pharmaceutically acceptable salt thereof according to any one of Items 1 to 12 and 1', wherein
when either $A^1$ or $A^2$ is $CR^5R^6$ and the other is $NR^7$, then either $R^5$ or $R^7$ is a group shown below; and
when $A^1$ is $CR^8R^9$ and $A^2$ is $CR^{10}R^{11}$, then either $R^8$ or $R^{10}$ is a group shown below:

[Chemical Formula 4]

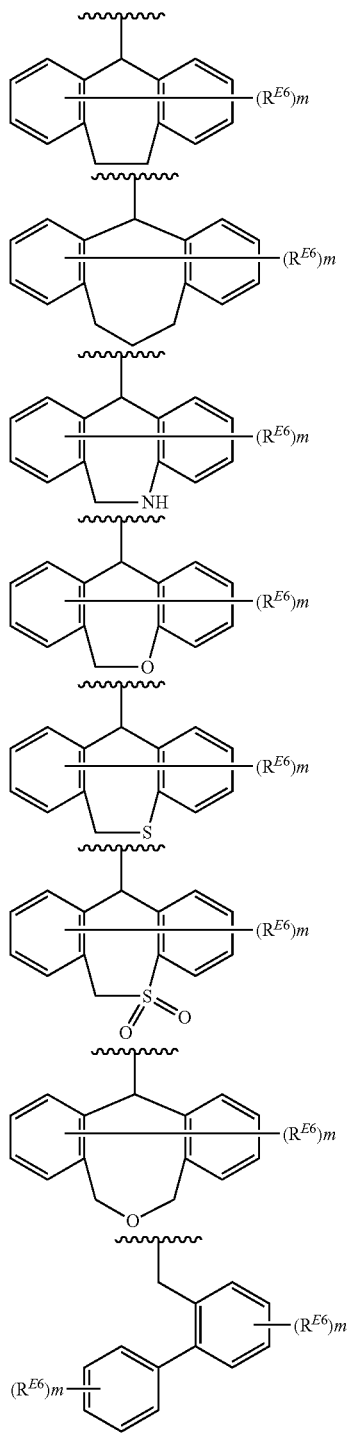

(wherein $R^{E6}$ are each independently a group selected from Substituent group A, and m is an integer of 0 to 7, and Substituent group A is the same as defined in Item 1).

(Item 14) The arenavirus proliferation inhibitor comprising the compound or the prodrug thereof or the pharmaceutically acceptable salt thereof according to Item 1 or V, wherein
$A^3$ is $CR^2$; $R^1$ is carboxy; $R^3$ is a hydrogen atom; $R^3$ is alkyl optionally substituted with Substituent group F, alkenyl optionally substituted with Substituent group F, a carbocycle optionally substituted with Substituent group A, carbocyclealkyl optionally substituted with Substituent group A, or heterocyclealkyl optionally substituted with Substituent group A;
a) $A^1$ is $NR^7$, $A^2$ is $CR^5R^6$, or
b) $A^1$ is $CR^9R^9$, $A^2$ is $CR^{10}R^{11}$;
$R^5$ and $R^6$ are each independently a hydrogen atom or alkyl optionally substituted with alkyloxy or alkylthio;
$R^9$, $R^{10}$, and $R^{11}$ are each a hydrogen atom; and
$R^7$ or $R^8$ is a group shown below:

[Chemical Formula 5]

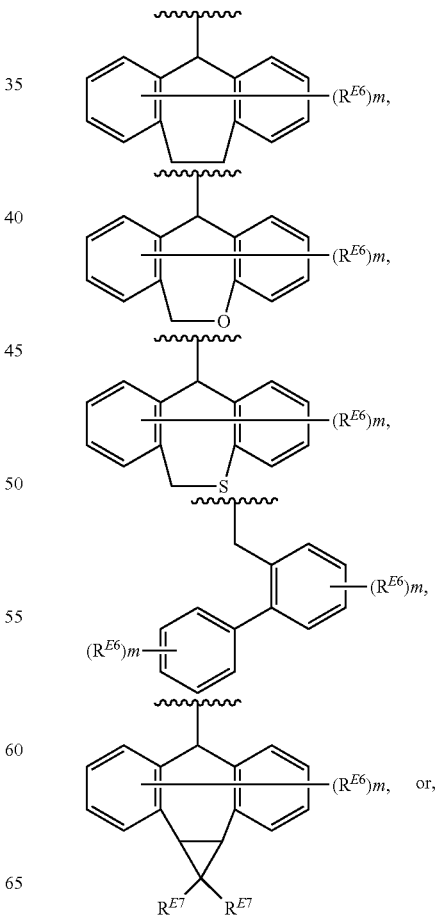

-continued

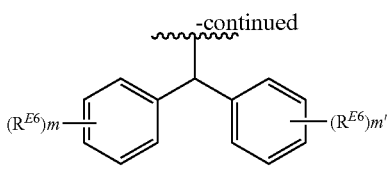

(wherein $R^{E6}$ are each independently a group selected from Substituent group A; and $R^{E7}$ are each independently a hydrogen atom, halogen, or alkyl;
m are each independently an integer of 0 to 7, m' are each independently an integer of 0 to 4, and Substituent group A is the same as defined in Item 1).
(Item 14') The arenavirus proliferation inhibitor comprising the compound or the prodrug thereof or the pharmaceutically acceptable salt thereof according to Item 1 or 1', wherein
$A^2$ is $CR^3$; $R^1$ is carboxy; $R^2$ is a hydrogen atom: $R^3$ is alkyl optionally substituted with Substituent group F, alkenyl optionally substituted with Substituent group F, carbocyclealkyl optionally substituted with Substituent group A, or heterocyclealkyl optionally substituted with Substituent group A;
a) $A^3$ is $NR^7$, $A^2$ is $CR^5R^6$, or
b) $A^1$ is $CR^8R^9$, $A^2$ is $CR^{10}R^{11}$;
$R^5$ and $R^6$ are each independently a hydrogen atom or alkyl optionally substituted with alkyloxy or alkylthio;
$R^9$, $R^{10}$, and $R^{11}$ are each a hydrogen atom; and
$R^7$ or $R^8$ is a group shown below:

[Chemical Formula 6]

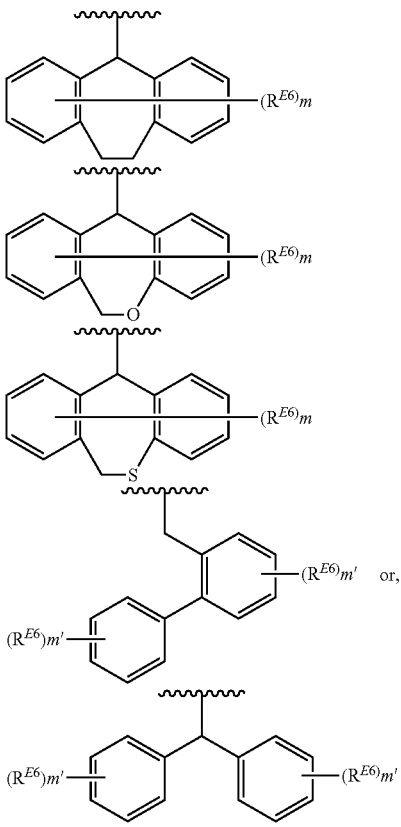

(wherein $R^{E6}$ are each independently a group selected from Substituent group A, and m is an integer of 0 to 7, m' are each independently an integer of 0 to 4, and Substituent group A is the same as defined in Item 1).
(Item 15) A compound represented by Formula (II) or a prodrug thereof or a pharmaceutically acceptable salt thereof:

[Chemical Formula 7]

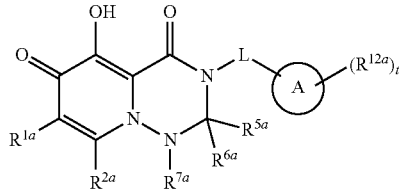

(wherein
$R^{1a}$ is $-Z^X-C(=O)-O-R^{X15}$,
$-Z^X-C(=O)-N(R^9)(R^{X10})$, or
$-Z^X-N(R^{X14})-C(=O)-O-R^{X15}$
(wherein, $R^{X9}$, $R^{X14}$, and $R^{X15}$ are each independently a hydrogen atom, alkyl optionally substituted with Substituent group E, alkenyl optionally substituted with Substituent group E, or alkynyl optionally substituted with Substituent group E; $R^{X10}$ is a hydrogen atom, alkyl optionally substituted with Substituent group E, alkenyl optionally substituted with Substituent group E, alkynyl optionally substituted with Substituent group E, or alkyloxy optionally substituted with Substituent group E; $Z^X$ is a single bond or a linear or branched alkylene; and
$R^{X9}$ and $R^{X10}$ may be taken together with an adjacent atom to form a heterocycle);
$R^{2a}$ is a hydrogen atom, halogen, hydroxy, carboxy, cyano, alkyl optionally substituted with Substituent group F, alkenyl optionally substituted with Substituent group F, alkynyl optionally substituted with Substituent group F, or alkyloxy optionally substituted with Substituent group F;
-L- is $-(CR^{3a}R^{3b})n-$ or a single bond;
$R^{3a}$ and $R^{3b}$ are each independently a hydrogen atom, halogen, carboxy, cyano, alkyl optionally substituted with Substituent group F, alkenyl optionally substituted with Substituent group F, alkynyl optionally substituted with Substituent group F, a carbocyclic group optionally substituted with Substituent group A, carbocyclealkyl optionally substituted with Substituent group A, a heterocyclic group optionally substituted with Substituent group A, heterocyclealkyl optionally substituted with Substituent group A, or alkyloxy optionally substituted with Substituent group F;
n is an integer of 1 to 4;
Ring A is a non-aromatic carbocycle, an aromatic carbocycle, a non-aromatic heterocycle, or an aromatic heterocycle;
$R^{12a}$ are each independently halogen, cyano, hydroxy, carboxy, amino, oxo, alkyl, halogenoalkyl, alkyloxy, alkylthio, alkylamino, hydroxyalkyl, carboxyalkyl, aminoalkyl, a carbocyclic group, a heterocyclic group, an oxo-substituted heterocyclic group, carbocyclealkyloxy, carbocycleoxyalkyl, carbocyclealkyloxyalkyl, carbocyclealkylthio, heterocyclealkyloxy, heterocycleoxyalkyl, heterocyclealkyloxyalkyl, halogenoalkyloxy, alkyloxyalkyl, alkyloxyalkyloxy, alkylcarbonyl, alkylcarbonyloxy, alkyloxycarbonyl, alkyloxycarbonyloxy, alkylamino, alkylcarbonylamino, halogenoalkylcarbonylamino, alkylaminocarbonyl, alkylsulfonyl, alkylsulfinyl, or alkylsulfonylamino;

t is an integer of 0 to 4;

$R^{5a}$ and $R^{6a}$ are each independently a hydrogen atom, alkyl optionally substituted with Substituent group F, alkenyl optionally substituted with Substituent group F, or alkynyl optionally substituted with Substituent group F;

$R^{5a}$ and $R^{6a}$ may be taken together with the carbon atom to which they are attached to form a carbocycle optionally substituted with Substituent group B or a heterocycle optionally substituted with Substituent group B, wherein the carbocycle or the heterocycle may form a condensed ring and/or a bridged structure;

$R^{7a}$ is a carbocyclic group optionally substituted with Substituent group B, carbocyclealkyl optionally substituted with Substituent group B, a heterocyclic group optionally substituted with Substituent group B, heterocyclealkyl optionally substituted with Substituent group B, alkyl optionally substituted with Substituent group F, alkenyl optionally substituted with Substituent group F, or alkynyl optionally substituted with Substituent group F;

Substituent groups A, B, E, and F are the same as defined in Item 1; with a proviso that (i) when

[Chemical Formula 8]

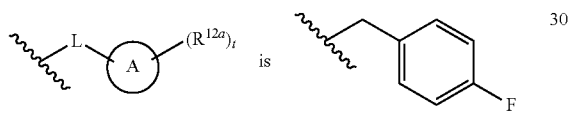

is then $R^{7a}$ is a carbocyclic group optionally substituted with Substituent group B or a heterocyclic group optionally substituted with Substituent group B; and (ii) a compound shown below is excluded:

[Chemical Formula 9]

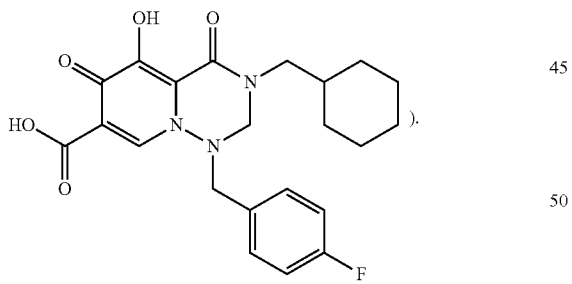

(Item 16) The compound or the prodrug thereof or the pharmaceutically acceptable salt thereof according to Item 15, wherein Ring A is a 3- to 5-membered non-aromatic carbocycle.

(Item 17) The compound or the prodrug thereof or the pharmaceutically acceptable salt thereof according to Item 15 or 16, wherein $R^{7a}$ is a carbocyclic group optionally substituted with Substituent group B, or a heterocyclic group optionally substituted with Substituent group B.

(Item 18) The compound or the prodrug thereof or the pharmaceutically acceptable salt thereof according to any one of Items 15 to 17, wherein $R^{7a}$ is a group shown

[Chemical Formula 10]

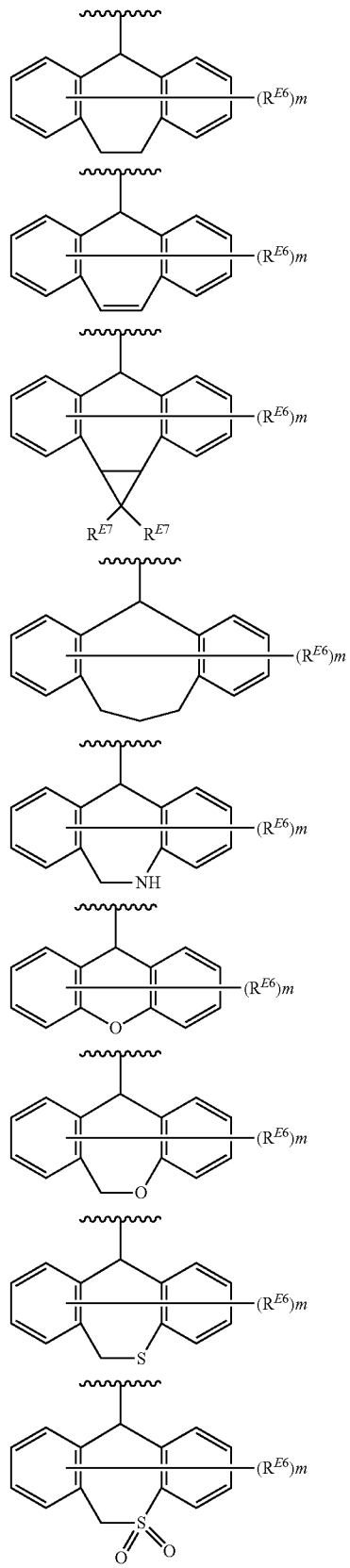

-continued

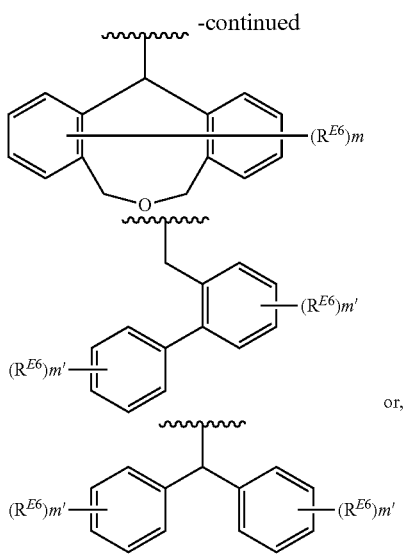

(wherein $R^{E6}$ are each independently a group selected from Substituent group A; and
$R^{E7}$ are each independently a hydrogen atom, halogen, or alkyl; m are each independently an integer of 0 to 7, m' are each independently an integer of 0 to 4, and Substituent group A is the same as defined in Item 1).

(Item 19) The compound or the prodrug thereof or the pharmaceutically acceptable salt thereof according to any one of Items 15 to 18, wherein $R^{1a}$ is carboxy.

(Item 20) A compound selected from Compounds II-001, 11-002, II-003, III-010, III-013, III-016, III-017, III-021, III-028, III-029, III-031, III-032, III-033, III-034, III-035 and III-036, a prodrug thereof, or a pharmaceutically acceptable salt thereof.

(Item 21) A pharmaceutical composition comprising the compound or the prodrug thereof or the pharmaceutically acceptable salt thereof according to any one of Items 15 to 20.

(Item 21') The compound or the pharmaceutically acceptable salt thereof according to any one of Items 15 to 20.

(Item 22) An arenavirus proliferation inhibitor comprising the compound or the prodrug thereof or the pharmaceutically acceptable salt thereof according to any one of Items 15 to 20.

(Item 23) The arenavirus proliferation inhibitor according to Item 1, comprising a compound selected from Compounds I-004, I-005, I-006, I-019, I-020, I-021, I-022, I-023, I-024, I-025, I-026, I-027, I-028, I-074, I-077, I-078, I-081, II-003, III-013, III-016, III-017, III-021, III-028, III-029, III-031, III-032, III-034, and III-036, or a prodrug thereof, or a pharmaceutically acceptable salt thereof.

(Item 23') The arenavirus proliferation inhibitor according to Item 1, comprising a compound selected from Compounds 1-004, I-005, I-006, I-019, I-020, I-021, I-022, I-023, I-024, I-025, I-026, I-027, I-028, and I-081, or a prodrug thereof, or a pharmaceutically acceptable salt thereof.

(Item 23") An arenavirus proliferation inhibitor comprising the compound or the pharmaceutically acceptable salt thereof according to any one of Items 1 to 20, 22, 23, 1', 13', 14', 21' and 23', (Item 24) The Lassa virus proliferation inhibitor according to any one of Items 1 to 14, 22, 23, 1', 13', 14', 23' and 23".

(Item 25) A pharmaceutical composition comprising the compound or the prodrug thereof or the pharmaceutically acceptable salt thereof according to any one of Items 1 to 23, 1', 13', 14', 21', 23', and 23", for preventing and/or treating Lassa fever, Argentine hemorrhagic fever, Bolivia hemorrhagic fever, Brazil hemorrhagic fever, and/or Venezuela hemorrhagic fever.

(Item 26) A pharmaceutical composition comprising the compound or the prodrug thereof or the pharmaceutically acceptable salt thereof according to any one of Items 1 to 23, 1', 13', 14', 21', 23', and 23", for preventing and/or treating an arenavirus infection.

(Item 27) A pharmaceutical composition comprising the compound or the prodrug thereof or the pharmaceutically acceptable salt thereof according to any one of Items 1 to 23, 1', 13', 14', 21', 23', and 23", for preventing and/or treating Lassa fever.

(Item 28) A method for treating and/or preventing an arenavirus infection, comprising administering the compound or the prodrug thereof or the pharmaceutically acceptable salt thereof according to any one of Items 1 to 23, 1', 13', 14', 21', 23', and 23".

(Item 29) A method for inhibiting arenavirus proliferation, comprising administering the compound or the prodrug thereof or the pharmaceutically acceptable salt thereof according to any one of Items 1 to 23, 1', 13', 14', 21', 23', and 23".

(Item 30) A method for inhibiting Lassa virus proliferation, comprising administering the compound or the prodrug thereof or the pharmaceutically acceptable salt thereof according to any one of Items 1 to 23, 1', 13', 14', 21', 23', and 23".

(Item 31) A method for preventing and/or treating Lassa fever, Argentine hemorrhagic fever, Bolivia hemorrhagic fever, Brazil hemorrhagic fever, or Venezuela hemorrhagic fever, comprising administering the compound or the prodrug thereof or the pharmaceutically acceptable salt thereof according to any one of Items 1 to 23, 1', 13', 14', 21', 23', and 23".

(Item 32) A method for preventing and/or treating Lassa fever, comprising administering the compound or the prodrug thereof or the pharmaceutically acceptable salt thereof according to any one of Items 1 to 23, 1', 13', 14', 21', 23', and 23".

(Item 33) A use of the compound or the prodrug thereof or the pharmaceutically acceptable salt thereof according to any one of Items 1 to 23, 1', 13', 14', 21', 23', and 23", for manufacturing an agent for treating and/or preventing an arenavirus infection.

(Item 34) A use of the compound or the prodrug thereof or the pharmaceutically acceptable salt thereof according to any one of Items 1 to 23, 1', 13', 14', 21', 23', and 23", for manufacturing an arenavirus proliferation inhibitor.

(Item 35) A use of the compound or the prodrug thereof or the pharmaceutically acceptable salt thereof according to any one of Items 1 to 23, 1', 13', 14', 21', 23', and 23", for manufacturing a Lassa virus proliferation inhibitor.

(Item 36) A use of the compound or the prodrug thereof or the pharmaceutically acceptable salt thereof according to any one of Items 1 to 23, 1', 13', 14', 21', 23', and 23", for manufacturing an agent for treating and/or preventing Lassa fever, Argentine hemorrhagic fever, Bolivia hemorrhagic fever, Brazil hemorrhagic fever, and/or Venezuela hemorrhagic fever.

(Item 37) A use of the compound or the prodrug thereof or the pharmaceutically acceptable salt thereof according to any one of Items 1 to 23, 1', 13', 14', 21', 23', and 23", for manufacturing an agent for treating and/or preventing Lassa fever.

(Item 38) The compound or the prodrug thereof or the pharmaceutically acceptable salt thereof according to any one of Items 1 to 23, 1', 13', 14', 21', 23', and 23", for use in treating and/or preventing an arenavirus infection.

(Item 39) The compound or the prodrug thereof or the pharmaceutically acceptable salt thereof according to any one of Items 1 to 23, 1', 13', 14', 21', 23', and 23", for use in inhibiting arenavirus proliferation.

(Item 40) The compound or the prodrug thereof or the pharmaceutically acceptable salt thereof according to any one of Items 1 to 23, 1', 13', 14', 21', 23', and 23", for use in inhibiting Lassa virus proliferation.

(Item 41) The compound or the prodrug thereof or the pharmaceutically acceptable salt thereof according to any one of Items 1 to 23, 1', 13', 14', 21', 23', and 23", for use in treating and/or preventing Lassa fever, Argentine hemorrhagic fever, Bolivia hemorrhagic fever, Brazil hemorrhagic fever, and/or Venezuela hemorrhagic fever.

(Item 42) The compound or the prodrug thereof or the pharmaceutically acceptable salt thereof according to any one of Items 1 to 23, 1', 13', 14', 21', 23', and 23", for use in treating and/or preventing Lassa fever.

(Item 1A) An arenavirus proliferation inhibitor comprising a compound represented by Formula (I") or a pharmaceutically acceptable salt thereof:

[Chemical Formula 11]

$$\text{(I'')}$$

(wherein
$R^1$ is halogen, hydroxy, carboxy, cyano, formyl, alkyl optionally substituted with Substituent group F, alkenyl optionally substituted with Substituent group F, alkynyl optionally substituted with Substituent group F, alkyloxy optionally substituted with Substituent group F, alkenyloxy optionally substituted with Substituent group F, alkylcarbonyl optionally substituted with Substituent group F, alkyloxycarbonyl optionally substituted with Substituent group F, a carbocyclic group optionally substituted with Substituent group A, carbocyclealkyl optionally substituted with Substituent group A, carbocyclecarbonyl optionally substituted with Substituent group A, carbocycleoxy optionally substituted with Substituent group A, carbocycleoxycarbonyl optionally substituted with Substituent group A, a heterocyclic group optionally substituted with Substituent group A, heterocyclealkyl optionally substituted with Substituent group A, heterocyclecarbonyl optionally substituted with Substituent group A, heterocycleoxy optionally substituted with Substituent group A, heterocycleoxycarbonyl optionally substituted with Substituent group A, —$Z^X$—N($R^{X1}$)($R^{X2}$),
—$Z^X$—N($R^{X3}$)—$SO_2$—($R^{X4}$),
—$Z^X$—C(=O)—N($R^{X5}$)—$SO_2$($R^{X6}$),
—$Z^X$—N($R^{X7}$)—C(=O)—$R^{X8}$,
—$Z^X$—C(=O)—N($R^{X9}$)($R^{X10}$),
—$Z^X$—S—$R^{X11}$,
—$Z^X$—$SO_2$—$R^{X12}$,
—$Z^X$—S(=O)—$R^{X13}$,
—$Z^X$—N($R^{X14}$)—C(=O)—O—$R^{X15}$,
—$Z^X$—N($R^{X16}$)—C(=O)—N($R^{X17}$)($R^{X18}$),
—$Z^X$—C(=O)—N($R^{X19}$)—C(=O)—N($R^{X20}$)($R^{X21}$),
—$Z^X$—N($R^{X22}$)—C(=O)—C(=O)—$R^{X23}$,
—$Z^X$—$SO_2$—N($R^{X24}$)($R^{X26}$),
—$Z^X$—C(=O)—N($R^{X26}$)—O—$R^{X27}$,
—$Z^X$—N($R^{X28}$)—C(=O)—N($R^{X29}$)—C(=O)—$R^{X30}$,
—$Z^X$—O—N($R^{X31}$)—C(=O)—$R^{X32}$,
—$Z^X$—C(=O)—N($R^{X33}$)—$SO_2$—N($R^{34}$)—$R^{X35}$, or
—$Z^X$—N($R^{X36}$)—C(=O)—N($R^{X37}$)—$SO_2$—$R^{X38}$,
(wherein $R^{X1}$, $R^{X2}$, $R^{X3}$, $R^{X5}$, $R^{X7}$, $R^{X8}$, $R^{X9}$, $R^{X10}$, $R^{X11}$, $R^{X14}$, $R^{X15}$, $R^{X16}$, $R^{X17}$, $R^{X18}$, $R^{X19}$, $R^{X20}$, $R^{X21}$, $R^{X22}$, $R^{X23}$, $R^{X24}$, $R^{X25}$, $R^{X26}$, $R^{X27}$, $R^{Z28}$, $R^{X29}$, $R^{Z30}$, $R^{X31}$, $R^{X32}$, $R^{X33}$, $R^{X34}$, $R^{X35}$, $R^{X36}$, and $R^{X37}$ are each independently selected from a substituent group consisting of a hydrogen atom, alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A, $R^{X4}$, $R^{X6}$, $R^{X12}$, $R^{X13}$, and $R^{X36}$ are each independently selected from a substituent group consisting of hydroxy, alkyl optionally substituted with Substituent group F, alkenyl optionally substituted with Substituent group F, alkynyl optionally substituted with Substituent group F, alkyloxy optionally substituted with Substituent group F, alkenyloxy optionally substituted with Substituent group F, an alkynyloxy optionally substituted with Substituent group F, a carbocyclic group optionally substituted with Substituent group A, a heterocyclic group optionally substituted with A, carbocycleoxy optionally substituted with Substituent group A, heterocycleoxy optionally substituted with Substituent group A, carbocyclealkyl optionally substituted with Substituent group A, heterocyclealkyl optionally substituted with Substituent group A, carbocyclealkyloxy optionally substituted with Substituent group A, and heterocyclealkyloxy optionally substituted with Substituent group A, $R^{X1}$ and $R^{X2}$, $R^{X8}$ and $R^{X10}$, $R^{X17}$ and $R^{X18}$, $R^{X20}$ and $R^{X21}$, and $R^{X24}$ and $R^{X25}$ each may be taken together with an adjacent atom to form a heterocycle, and $Z^X$ is a single bond or a linear or branched alkylene);
$R^2$ is a hydrogen atom, halogen, hydroxy, carboxy, cyano, formyl, alkyl optionally substituted with Substituent group F, alkenyl optionally substituted with Substituent group F, alkynyl optionally substituted with Substituent group F, alkyloxy optionally substituted with Substituent group F, alkenyloxy optionally substituted with Substituent group F, alkylcarbonyl optionally substituted with Substituent group F, alkyloxycarbonyl optionally substituted with Substituent group F, a carbocyclic group optionally substituted with Substituent group A, carbocyclealkyl optionally substituted with Substituent group A, carbocyclecarbonyl optionally substituted with Substituent group A, carbocycleoxy optionally substituted with Substituent group A, carbocycleoxycarbonyl optionally substituted with Substituent group A, a heterocyclic group optionally substituted with Substituent group A, heterocyclealkyl optionally substituted with Substituent group A, heterocyclecarbonyl optionally substituted with Substituent group A, heterocycleoxy optionally substituted with Substituent group A, heterocycleoxycarbonyl optionally substituted with Substituent group A, —$Z^Y$—N($R^{Y1}$)—$SO_2$—$R^{Y2}$,
—$Z^Y$—N($R^{Y3}$)—C(=O)—$R^{Y4}$,
$Z^Y$—N($R^{Y5}$)—C(=O)—O—$R^{Y6}$, —$Z^Y$—C(=O)—N($R^{Y7}$)($R^{Y8}$),
—$Z^Y$—N($R^{Y9}$)($R^{Y10}$), or
—$Z^Y$—$SO_2$—$R^{Y11}$
(wherein $R^{Y1}$, $R^{Y3}$, $R^{Y4}$, $R^{Y5}$, $R^{Y6}$, $R^{Y7}$, $R^{Y8}$, $R^{Y9}$, and $R^{Y10}$ are each independently selected from a substituent group consisting of a hydrogen atom, alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A; $R^{Y2}$ and $R^{Y11}$ are each independently selected from a substituent group consisting of alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A; $R^{Y7}$ and $R^{Y8}$, and $R^{Y9}$ and $R^{Y10}$ may be taken together with an adjacent atom to form a heterocycle, and $Z^Y$ is a single bond or a linear or branched alkylene);
$R^3$ is a hydrogen atom, hydroxy, carboxy, cyano, formyl, alkyl optionally substituted with Substituent group F, alkenyl optionally substituted with Substituent group F, alkynyl optionally substituted with Substituent group F, alkyloxy optionally substituted with Substituent group F, alkenyloxy optionally substituted with Substituent group F, alkylcarbonyl optionally substituted with Substituent group F, alkyloxycarbonyl optionally substituted with Substituent group F, a carbocyclic group optionally substituted with Substituent group A, carbocyclealkyl optionally substituted with Substituent group A, carbocycleoxyalkyl optionally substituted with Substituent group A, carbocyclecarbonyl optionally substituted with Substituent group A, carbocycleoxy optionally substituted with Substituent group A, carbocycleoxycarbonyl optionally substituted with Substituent group A, a heterocyclic group optionally substituted with Substituent group A, heterocyclealkyl optionally substituted with Substituent group A, heterocycleoxyalkyl optionally substituted with Substituent group A, heterocyclecarbonyl optionally substituted with Substituent group A, heterocycleoxy optionally substituted with Substituent group A, or heterocycleoxycarbonyl optionally substituted with Substituent group A,
—$Z^Z$—N($R^{Z1}$)—$SO_2$—$R^{Z2}$,
—$Z^Z$—N($R^{Z3}$)—C(=O)—$R^{Z4}$,
—$Z^Z$—N($R^{Z6}$)—C(=O)—O—$R^{Z6}$,
—$Z^Z$—C(=O)—N($R^{Z7}$)($R^{Z8}$),
—$Z^Z$—N($R^{Z9}$)($R^{Z10}$),
—$Z^Z$—$SO_2$—$R^{Z11}$, or
—$Z^Z$—N($R^{Z1}$)—O—C(=O)—$R^{Z13}$
(wherein $R^{Z1}$, $R^{Z3}$, $R^{Z4}$, $R^{Z5}$, $R^{Z6}$, $R^{Z7}$, $R^{Z8}$, $R^{Z9}$, $R^{Z10}$, $R^{Z12}$, and $R^{Z13}$ are each independently selected from a substituent group consisting of a hydrogen atom, alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;
$R^{Z2}$ and $R^{Z11}$ are each independently selected from a substituent group consisting of alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;
$R^{Z7}$ and $R^{Z8}$, and $R^{Z9}$ and $R^{Z10}$ each may be taken together with an adjacent atom to form a heterocycle, and
$Z^Z$ is a single bond or a linear or branched alkylene);
Substituent groups A, B, and F are the same as defined in Item 1;
a) either $A^1$ or $A^2$ is $CR^5R^6$, and the other is $NR^7$, or
b) $A^1$ is $CR^8R^9$, and $A^2$ is $CR^{10}R^{11}$,
$R^3$, $R^6$, $R^7$, $R^8$, $R^9$, $R^{10}$, and $R^{11}$ are each independently a hydrogen atom, carboxy, cyano, alkyl optionally substituted with Substituent group F, alkenyl optionally substituted with Substituent group F, alkynyl optionally substituted with Substituent group F, alkylcarbonyl optionally substituted with Substituent group F, alkyloxycarbonyl optionally substituted with Substituent group F, a carbocyclic group optionally substituted with Substituent group A, carbocyclealkyl optionally substituted with Substituent group A, carbocycleoxyalkyl optionally substituted with Substituent group A, carbocyclecarbonyl optionally substituted with Substituent group A, carbocycleoxycarbonyl optionally substituted with Substituent group A, a heterocyclic group optionally substituted with A, heterocyclealkyl optionally substituted with Substituent group A, heterocycleoxyalkyl optionally substituted with Substituent group A, heterocyclecarbonyl optionally substituted with Substituent group A, or heterocycleoxycarbonyl optionally substituted with Substituent group A,
—$Z^V$—S—$R^{V1}$,
—$Z^V$—S(=O)—$R^{V2}$,
—$Z^V$—$SO_2$—$R^{V3}$,
—C(=O)—C(=O)—$R^{V4}$,
—C(=O)—N($R^{V5}$)($R^{V6}$),
—$Z^V$—N($R^{V7}$)—C(=O)—O—$R^{V8}$, or
—$Z^V$—N($R^{V9}$)—C(=O)—$R^{V10}$
(wherein $R^{V1}$, $R^{V4}$, $R^{V5}$, $R^{V6}$, $R^{V7}$, $R^{V8}$, $R^{V9}$, and $R^{V10}$ are each independently selected from a substituent group consisting of a hydrogen atom, alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;
$R^{V2}$ and $R^{V3}$ are each independently selected from a substituent group consisting of alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;
$R^{V5}$ and $R^{V6}$ may be taken together with an adjacent atom to form a heterocycle, and $Z^V$ is a single bond or a linear or branched alkylene);
$R^5$ and $R^6$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure;

$R^8$ and $R^9$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure;

$R^{10}$ and $R^{11}$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure;

1) when $A^1$ is $CR^5R^6$ and $A^2$ is $NR^7$, then $R^5$ and $R^7$ may be taken together to form a bond, or $R^5$ and $R^7$ may be taken together with an adjacent atom to form a heterocycle optionally substituted with Substituent group B, wherein the heterocycle may form a condensed ring and/or a spiro ring and/or a bridged structure, or $R^3$ and $R^7$ may be taken together with an adjacent atom to form a heterocycle optionally substituted with Substituent group B, wherein the heterocycle may form a condensed ring and/or a spiro ring and/or a bridged structure, 2) when $A^1$ is $NR^7$ and $A^2$ is $CR^5R^6$, then $R^7$ and $R^5$ may be taken together to form a bond, or $R^7$ and $R^5$ may be taken together with an adjacent atom to form a heterocycle optionally substituted with Substituent group B, wherein the heterocycle may form a condensed ring and/or a spiro ring and/or a bridged structure, or $R^3$ and $R^6$ may be taken together with an adjacent atom to form a heterocycle optionally substituted with Substituent group B, wherein the heterocycle may form a condensed ring and/or a spiro ring and/or a bridged structure, 3) when $A^1$ is $CR^8R^9$, and $A^2$ is $CR^{10}R^{11}$, then $R^8$ and $R^{10}$ may be taken together to form a bond, or $R^8$ and $R^{10}$ may be taken together with an adjacent atom to form a carbocycle optionally substituted with Substituent group B or a heterocycle optionally substituted with Substituent group B, wherein the carbocycle or the heterocycle may form a condensed ring and/or a spiro ring and/or a bridged structure, or $R^3$ and $R^{11}$ may be taken together with an adjacent atom to form a heterocycle optionally substituted with Substituent group B, wherein the heterocycle may form a condensed ring and/or a spiro ring and/or a bridged structure, with a proviso that the following cases of c) and d) are excluded;

c) $R^5$, $R^6$, and $R^7$ are all a hydrogen atom, d) $R^8$, $R^9$, $R^{10}$, and $R^{11}$ are all a hydrogen atom).

(Item 2A) An arenavirus proliferation inhibitor according to Item 1A, wherein Formula (I) is represented by Formula (I'):

[Chemical Formula 12]

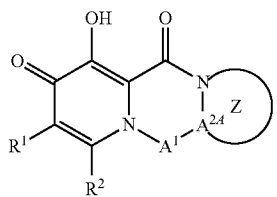

(I')

(wherein, $A^1$ is $CR^5R^6$ and $A^{2A}$ is N, $A^1$ is $NR^7$ and $A^{2A}$ is $CR^5$, or $A^1$ is $CR^8R^9$ and $A^{2A}$ is $CR^{11}$; and Ring Z is a 5 to 8-membered heterocycle optionally substituted with Substituent group B; and other symbols are the same as defined in Item 1A).

(Item 3A) An arenavirus proliferation inhibitor according to Item 1A, wherein $A^1$ is $CR^8R^9$ and $A^2$ is $CR^{10}R^{11}$.

(Item 4A) An arenavirus proliferation inhibitor according to Item 1A, wherein $A^1$ is $NR^7$ and $A^2$ is $CR^5R^6$.

(Item 5A) An arenavirus proliferation inhibitor according to Item 1A, wherein $A^1$ is $CR^5R^6$ and $A^2$ is $NR^7$.

(Item 6A) The arenavirus proliferation inhibitor according to Item 1A or 3A, wherein $R^9$ and $R^{11}$ are each independently a hydrogen atom or alkyl optionally substituted with Substituent group F; and either $R^8$ or $R^{10}$ is a carbocyclic group optionally substituted with Substituent group A, carbocyclealkyl optionally substituted with Substituent group A, a heterocyclic group optionally substituted with Substituent group A, or heterocyclealkyl optionally substituted with Substituent group F, and the other is a hydrogen atom or alkyl optionally substituted with Substituent group F.

(Item 7A) The arenavirus proliferation inhibitor according to Item 1A or 3A, wherein $R^9$ and $R^{10}$ are each independently a hydrogen atom or alkyl optionally substituted with Substituent group F; $R^3$ and $R^{11}$ are taken together with an adjacent atom to form a heterocycle optionally substituted with Substituent group B; and $R^8$ is a carbocyclic group optionally substituted with Substituent group A, carbocyclealkyl optionally substituted with Substituent group A, a heterocyclic group optionally substituted with Substituent group A, or heterocyclealkyl optionally substituted with Substituent group A.

(Item 8A) The arenavirus proliferation inhibitor according to any one of Items 1A, 4A or 5A, wherein either $R^3$ or $R^7$ is a carbocyclic group optionally substituted with Substituent group A, carbocyclealkyl optionally substituted with Substituent group A, a heterocyclic group optionally substituted with Substituent group A, or heterocyclealkyl optionally substituted with Substituent group A, and the other is a hydrogen atom; and $R^6$ is a hydrogen atom or alkyl optionally substituted with Substituent group F.

(Item 9A) The arenavirus proliferation inhibitor according to any one of Items 1A, 4A or 5A, wherein $R^3$ and $R^6$, or $R^3$ and $R^7$ are taken together with an adjacent atom to form a heterocycle optionally substituted with Substituent group B.

(Item 10A) The arenavirus proliferation inhibitor according to any one of Items 1A to 9A, wherein $R^1$ is carboxy.

(Item 11A) The arenavirus proliferation inhibitor according to any one of Items 1A to 10A, wherein $R^3$ is alkyl optionally substituted with Substituent group F, alkenyl optionally substituted with Substituent group F, carbocyclealkyl optionally substituted with Substituent group A, heterocyclealkyl optionally substituted with Substituent group A, or carbocycleoxyalkyl optionally substituted with Substituent group A.

(Item 12A) The arenavirus proliferation inhibitor according to any one of Items 1A to 11A, wherein when either $A^1$ or $A^2$ is $CR^5R^6$ and the other is $NR^7$, then either $R^5$ or $R^7$ is a group shown below; and when $A^1$ is $CR^8R^9$ and $A^2$ is $CR^{10}R^{11}$, then either $R^9$ or $R^{10}$ is a group shown below:

[Chemical Formula 13]

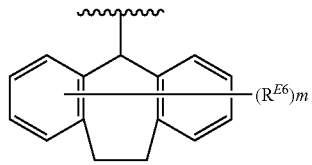

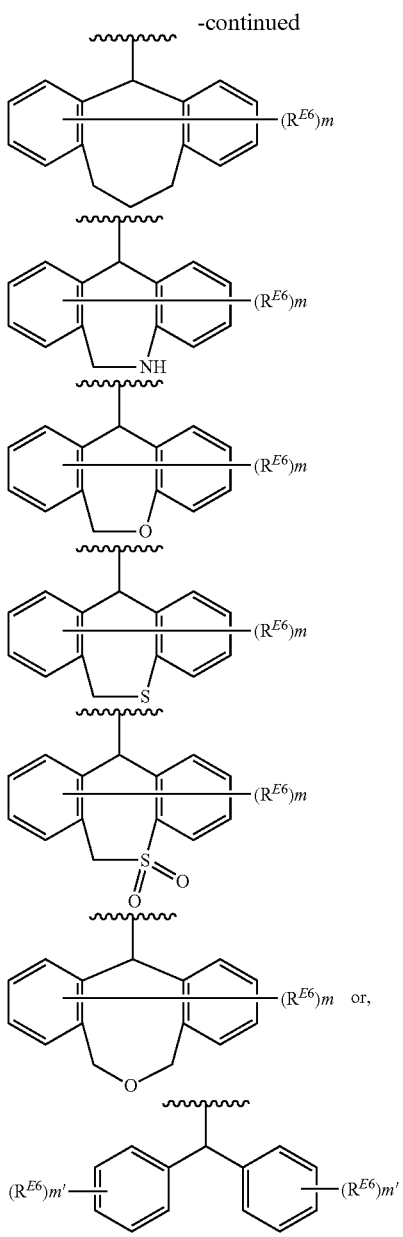

(wherein $R^E$ are each independently a group selected from Substituent group A, and m is an integer of 0 to 7, m' are each independently an integer of 0 to 4, and Substituent group A is the same as defined in Item 1A), (Item 13A) The virus proliferation inhibitor according to any one of Items 1 to 14, 22, 23, 1', 13', 14', 21', 23', 23", and 1A to 12A, wherein the arenavirus is an Old arenavirus.

(Item 14A) The virus proliferation inhibitor according to any one of Items 1 to 14, 22, 23, 1', 13', 14', 21', 23', 23", and 1A to 13A, wherein the arenavirus is LCMV.

(Item 15A) The virus proliferation inhibitor according to any one of Items 1 to 14, 22, 23, 1', 13', 14', 21', 23', 23", and 1A to 13A, wherein the arenavirus is Lassa virus.

(Item 16A) The virus proliferation inhibitor according to any one of Items 1 to 14, 22, 23, 1', 13', 14', 21', 23', 23", and 1A to 12A, wherein the arenavirus is a New arenavirus.

(Item 17A) The virus proliferation inhibitor according to any one of Items 1 to 14, 22, 23, 1', 13', 14', 21', 23', 23", 1A to 12A, and 16A, wherein the arenavirus is Junin virus.

(Item 101) A pharmaceutical composition comprising the compound or the prodrug thereof or the pharmaceutically acceptable salt thereof according to any one of Items 1 to 23, 1', 13', 14', 21', 23', 23", and 1A to 12A, for oral administration.

(Item 102) The pharmaceutical composition according to Item 101, which is a tablet, a powder, a granule, a capsule, a pill, a film, a suspension, an emulsion, an elixir, a syrup, a lemonade, a spirit, an aromatic water, an extract, a decoction or a tincture.

(Item 103) The pharmaceutical composition according to Item 102, which is a sugar-coated tablet, a film-coated tablet, an enteric-coated tablet, a sustained-release tablet, a troche tablet, a sublingual tablet, a buccal tablet, a chewable tablet, an orally disintegrated tablet, a dry syrup, a soft capsule, a microcapsule or a sustained-release capsule.

(Item 104) A pharmaceutical composition comprising the compound or the prodrug thereof or the pharmaceutically acceptable salt thereof according to any one of Items 1 to 23, 1', 13', 14', 21', 23', 23", and 1A to 12A, for parenteral administration.

(Item 105) The pharmaceutical composition according to Item 104, for dermal, subcutaneous, intravenous, intraarterial, intramuscular, intraperitoneal, transmucosal, inhalation, transnasal, ophthalmic, inner ear or vaginal administration.

(Item 106) The pharmaceutical composition according to Item 104 or 105, which is an injection, an infusion, an eye drop, a nose drop, an ear drop, an aerosol, an inhalation, a lotion, an impregnation, a liniment, a mouthwash, an enema, an ointment, a plaster, a jelly, a cream, a patch, a cataplasm, an external powder or a suppository.

(Item 107) A pharmaceutical composition comprising the compound or the prodrug thereof or the pharmaceutically acceptable salt thereof according to any one of Items 1 to 23, 1', 13', 14', 21', 23', and 23", for children or elderly.

(Item 108) A pharmaceutical composition comprising the compound or the prodrug thereof or the pharmaceutically acceptable salt thereof according to any one of Items 1 to 23, 1', 13', 14', 21', 23', and 23" in combination with an RNA polymerase inhibitor and/or an Entry inhibitor.

(Item 108') A method for treating and/or preventing an arenavirus infection, comprising administering a combination of the compound or the prodrug thereof or the pharmaceutically acceptable salt thereof according to any one of Items 1 to 23, 1', 13', 14', 21', 23', and 23" in combination with an RNA polymerase inhibitor and/or an Entry inhibitor.

(Item 108") The compound or the prodrug thereof or the pharmaceutically acceptable salt thereof according to any one of Items 1 to 23, 1', 13', 14', 21', 23', and 23", which is used in combination with an RNA polymerase inhibitor and/or an Entry inhibitor, for treating and/or preventing an arenavirus infection.

Examples of the RNA polymerase inhibitor include Ribavirin (RBV) and Favipiravir (T-705).

Examples of the Entry inhibitor include LHF-535.

(Item 109) A pharmaceutical composition comprising the compound or the prodrug thereof or the pharmaceutically acceptable salt thereof according to any one of Items 1 to 23, 1', 13', 14', 21', 23', 23" and 1A to 12A, for a combination therapy with an RNA polymerase inhibitor and/or an Entry inhibitor.

(Item 109") An RNA polymerase inhibitor and/or an Entry inhibitor being used in combination with the compound or the prodrug thereof or the pharmaceutically acceptable salt thereof according to any one of Items 1 to 23, 1', 13', 14', 21', 23', and 23".

(Item 110) The pharmaceutical composition according to any one of Items 101 to 109, for treating and/or preventing an arenavirus infection.

Effect of the Invention

The compounds of the present invention have an arenavirus proliferation inhibitory activity, and are useful as an agent for treating and/or preventing an arenavirus infection.

BRIEF DESCRIPTION OF DRAWING

FIG. 1 shows the test results of a Lassa virus proliferation inhibitory effect confirmation test of Compounds I-021, I-078, and II-003 (Test Example 3-2). The vertical axis indicates the virus yield (plaque-forming unit per 100 μL of sample) and the horizontal axis indicates the concentration (nM) of the compound.

MODE FOR CARRYING OUT THE INVENTION

The meaning of each term used in the present description is explained below. Each term is used in a unified sense, and is used in the same sense when used alone, or when used in combination of other term.

The term "consist of" means having only components.

The term "comprise" means not restricting with components and not excluding undescribed factors.

"Optionally substituted with Substituent group A" means that not being substituted or being substituted at any position with one or two or more, same or different substituents selected from Substituent group A.

"Optionally substituted with Substituent group B", "optionally substituted with Substituent group C", "optionally substituted with Substituent group D", "optionally substituted with Substituent group E", "optionally substituted with Substituent group F", and "optionally substituted with Substituent group G" are also as described above.

The term "halogen" includes a fluorine atom, a chlorine atom, a bromine atom and an iodine atom. Preferably, halogen is a fluorine atom, a chlorine atom, or a bromine atom. More preferably, halogen is a fluorine atom or a chlorine atom.

"Alkyl" includes a straight or branched alkyl of a carbon number of 1 to 15, preferably a carbon number of 1 to 10, more preferably a carbon number of 1 to 6, further preferably a carbon number of 1 to 4, and examples thereof include methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl and n-decyl. Examples of a preferred embodiment of "alkyl" include methyl, ethyl, n-propyl, isopropyl, n-butyl, isobutyl, sec-butyl, tert-butyl and n-pentyl. Examples of a more preferred embodiment include methyl, ethyl, n-propyl, isopropyl and tert-butyl.

"Alkenyl" includes a straight or branched alkenyl of a carbon number of 2 to 15, preferably a carbon number of 2 to 10, more preferably a carbon number of 2 to 6, further preferably a carbon number of 2 to 4, having one or more double bonds at any position. Specific examples include vinyl, allyl, propenyl, isopropenyl, butenyl, isobutenyl, prenyl, butadienyl, pentenyl, isopentenyl, pentadienyl, hexenyl, isohexenyl, dodecenyl, tridecenyl, tetradecenyl, and pentadecenyl. Examples of a preferred embodiment of "alkenyl" include vinyl, allyl, propenyl, isopropenyl and butenyl.

"Alkynyl" includes a straight or branched alkynyl of a carbon number of 2 to 10, preferably a carbon number of 2 to 8, further preferably a carbon number of 3 to 6, having one or more triple bonds at any position. Specific examples include ethynyl, propynyl, butynyl, pentynyl, hexynyl, heptynyl, octynyl, nonynyl, and decynyl. These may further have a double bond at any position. Examples of a preferred embodiment of "alkynyl" include ethynyl, propynyl, butynyl or pentynyl.

An alkyl part of "alkyloxy", "alkylcarbonyl", "alkyloxycarbonyl", "carbocyclealkyl", "heterocyclealkyl", "carbocycleoxyalkyl", "heterocycleoxyalkyl", "halogenoalkyl", "alkylthio", "hydroxyalkyl", "carbocyclealkyloxy", "carbocyclealkyloxyalkyl", "heterocyclealkyloxy", "heterocyclealkyloxyalkyl", "halogenoalkyloxy", "alkyloxyalkyl", "alkyloxyalkyloxy", "alkylcarbonyl", "alkylcarbonyloxy", "alkyloxycarbonyl", "alkyloxycarbonyloxy", "alkylamino", "alkylcarbonylamino", "halogenoalkylcarbonylamino", "alkylaminocarbonyl", "alkylsulfonyl", "alkylsulfinyl" or "alkylsulfonylamino" is as described for "alkyl" above.

An "alkenyl" part of "alkenyloxy" is as described for "alkenyl" above.

A halogen part of "halogenoalkyl", "halogenoalkyloxy", or "halogenoalkylcarbonylamino" is as described for "halogen" above. Herein, any position on alkyl group of "alkyl", "alkyloxy", or "alkylcarbonylamino" may be substituted with the same or different, one or plural halogen atoms.

The "carbocyclic group" means a carbocyclic group of a carbon number of 3 to 20, preferably a carbon number of 3 to 16, further preferably a carbon number of 4 to 12, and includes "aromatic carbocyclic group" and "non-aromatic carbocyclic group".

"Aromatic carbocyclic group" means a monocyclic or bicyclic or higher polycyclic aromatic hydrocarbon group. Examples thereof include phenyl, naphthyl, anthryl, and phenanthryl. Examples of a preferred embodiment of "aromatic carbocyclic group" include phenyl.

"Non-aromatic carbocyclic group" means a monocyclic or bicyclic or higher polycyclic saturated hydrocarbon group or a monocyclic or bicyclic or higher polycyclic non-aromatic unsaturated hydrocarbon group. Examples thereof include cycloalkyl and cycloalkenyl. The bicyclic or higher polycyclic "non-aromatic carbocyclic group" includes a group in which a monocyclic or bicyclic or higher polycyclic non-aromatic carbocyclic group is condensed with a ring in the "aromatic carbocyclic group" described above.

In addition, the "non-aromatic carbocyclic group" also includes a group having a bridge or a group forming a spiro ring as shown below.

[Chemical Formula 14]

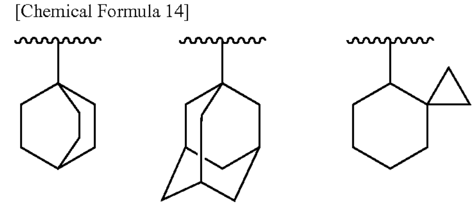

The monocyclic non-aromatic carbocyclic group has preferably a carbon number of 3 to 16, more preferably a carbon number of 3 to 12, further preferably a carbon number of 4 to 8. Examples include cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptenyl, and cyclohexadienyl.

The bicyclic or higher polycyclic non-aromatic carbocyclic group has preferably a carbon number of 8 to 20, more preferably a carbon number of 8 to 16. Examples include indanyl, indenyl, acenaphthyl, tetrahydronaphthyl, and fluorenyl.

"Cycloalkyl" is a carbocyclic group of a carbon number of 3 to 16, preferably a carbon number of 3 to 12, more preferably a carbon number of 4 to 8, and examples include cyclopropyl, cyclobutyl, cyclopentyl, cyclohexyl, cycloheptyl, cyclooctyl, cyclononyl and cyclodecyl.

"Cycloalkenyl" includes cycloalkenyl having one or more double bonds at any position in the ring of the "cycloalkyl" described above, and examples include cyclopropenyl, cyclobutenyl, cyclopentenyl, cyclohexenyl, cycloheptynyl, cyclooctynyl and cyclohexadienyl.

"Carbocycle" means a ring derived from the "carbocyclic group" described above.

"Aromatic carbocycle" means a ring derived from the "aromatic carbocyclic group" described above.

"Non-aromatic carbocycle" means a ring derived from the "non-aromatic carbocyclic group" described above.

A carbocycle part of "carbocyclealkyl", "carbocyclecarbonyl", "carbocycleoxy", "carbocycleoxycarbonyl", "carbocycleoxyalkyl", "carbocyclealkyloxyalkyl", or "carbocyclealkyloxy" is as described for "carbocyclic group" above.

"Heterocyclic group" means a cyclic group of 3 to 20 members, preferably 3 to 15 members, further preferably 5 to 15 members, comprising one or more, same or different heteroatoms independently selected from O, S and N, and includes "aromatic heterocyclic group" and "non-aromatic heterocyclic group".

"Aromatic heterocyclic group" means a monocyclic or bicyclic or higher polycyclic aromatic cyclic group, comprising one or more, same or different heteroatoms independently selected from O, S and N. The bicyclic or higher polycyclic aromatic heterocyclic group also includes a group in which a monocyclic or bicyclic or higher polycyclic aromatic heterocyclic group is condensed with a ring in the "aromatic carbocyclic group" described above, and the bond may be present on any of the rings.

The monocyclic aromatic heterocyclic group preferably has 5 to 8 members, more preferably 5 or 6 members. Examples include pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl, and thiadiazolyl.

The bicyclic aromatic heterocyclic group preferably has 8 to 10 members, more preferably 9 or 10 members. Examples include indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl, thiazolopyridyl, thienopyridine, thienopyrrolyl, thienopyrazolyl, thienopyrazinyl, furopyrrolyl, and thienothienyl.

Examples of the tricyclic or higher polycyclic aromatic heterocyclic group include carbazolyl, acridinyl, xanthenyl, phenothiazinyl, phenoxathiinyl, phenoxazinyl, and dibenzofuryl.

"Non-aromatic heterocyclic group" means a monocyclic or bicyclic or higher polycyclic non-aromatic cyclic group comprising one or more, same or different heteroatoms independently selected from O, S and N in the ring. The bicyclic or higher polycyclic non-aromatic heterocyclic group also includes a monocyclic or bicyclic or higher polycyclic non-aromatic heterocyclic group condensed with the ring in the "aromatic carbocyclic group", the "non-aromatic carbocyclic group" and/or the "aromatic heterocyclic group" described above, and a monocyclic or bicyclic or higher polycyclic non-aromatic carbocyclic group condensed with the ring in the "aromatic heterocyclic group" described above. The bond may be present on any of the rings.

In addition, the "non-aromatic heterocyclic group" also includes a group having a bridge or a group forming a spiro ring as shown below.

[Chemical Formula 15]

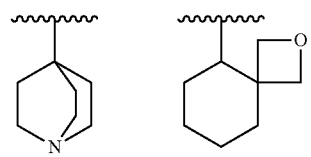

The monocyclic non-aromatic heterocyclic group preferably has 3 to 8 members, more preferably 5 or 6 members. Examples include dioxanyl, thiiranyl, oxiranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridinyl, tetrahydropyridinyl, tetrahydrofuryl, tetrahydropyranyl, dihydrothiazolyl, tetrahydroisothiazolyl, dihydrooxazinyl, hexahydroazepinyl, tetrahydrodiazepinyl, tetrahydropyridazinyl, hexahydropyrimidinyl, dioxolanyl, dioxazinyl, aziridinyl, dioxolyl, oxepanyl, thiolanyl, thiinyl, and thiazinyl.

The bicyclic non-aromatic heterocyclic group preferably has 8 to 12 members, more preferably 9 to 12 members. Examples include indolinyl, isoindolinyl, chromanyl, isochromanyl, benzopyranyl, dihydrothiazolopyrimidinyl, tetrahydroquinolyl, tetrahydroisoquinolyl, dihydrobenzofuryl, dihydrobenzoxazinyl, dihydrobenzimidazolyl, tetrahydrobenzothienyl, tetrahydrobenzofuryl, benzodioxolyl, benzodioxonyl, chromenyl, octahydrochromenyl, dihydrobenzodioxinyl, dihydrobenzooxedinyl, dihydrobenzodioxepinyl, and dihydrothienodioxinyl.

The tricyclic non-aromatic heterocyclic group preferably has 11 to 20 members, more preferably 13 to 16 members. Examples thereof include tetrahydrocarbazolyl and groups shown below:

[Chemical Formula 16]

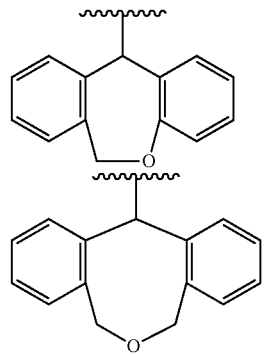

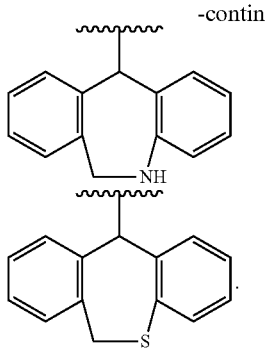

Examples of a preferred embodiment of "heterocyclic group" include a 5- to 6-membered monocyclic aromatic heterocyclic group, a 5- to 7-membered monocyclic non-aromatic heterocyclic group, a 9- to 10-membered bicyclic aromatic heterocyclic group, a 9- to 10-membered bicyclic non-aromatic heterocyclic group, a 13- to 14-membered tricyclic aromatic heterocyclic group, and a 13- to 16-membered tricyclic non-aromatic heterocyclic group.

"Heterocycle" means a ring derived from the "heterocyclic group" described above.

"Aromatic heterocycle" means a ring derived from the "aromatic heterocyclic group" described above.

"Non-aromatic heterocycle" means a ring derived from the "non-aromatic heterocyclic group" described above.

A heterocycle part of "heterocyclealkyl", "heterocyclecarbonyl", "heterocycleoxy", "heterocycleoxycarbonyl", "heterocycleoxyalkyl", "heterocyclealkyloxyalkyl", and "heterocyclealkyloxy" is the same as the "heterocyclic group" described above.

The "oxo-substituted heterocyclic group" means those in which the "heterocyclic group" described above is substituted with oxo. Examples thereof include groups shown below:

[Chemical Formula 17]

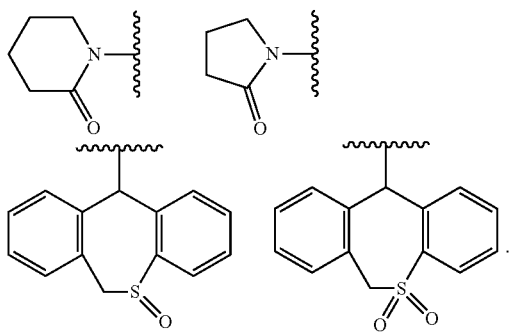

"Linear or branched alkylene" is a divalent of the "alkyl" described above, and examples thereof include methylene, ethylene, propylene, butylene, isobutylene, pentylene, heptylene, dimethylmethylene, ethylmethylmethylene, and 1,2-dimethylethylene.

Examples of "alkyloxy" include methoxy, ethoxy, propyloxy, isopropyloxy, tert-butyloxy, isobutyloxy, sec-butyloxy, pentyloxy, isopentyloxy, and hexyloxy. Examples of a preferred embodiment include methoxy, ethoxy, propyloxy, isopropyloxy, and tert-butyloxy.

Examples of "alkylcarbonyl" include methylcarbonyl, ethylcarbonyl, propylcarbonyl, isopropylcarbonyl, tert-butylcarbonyl, isobutylcarbonyl, sec-butylcarbonyl, pentylcarbonyl, isopentylcarbonyl, and hexylcarbonyl. Examples of a preferred embodiment include methylcarbonyl, ethylcarbonyl, and propylcarbonyl.

Examples of "alkyloxycarbonyl" include methyloxycarbonyl, ethyloxycarbonyl, propyloxycarbonyl, isopropyloxycarbonyl, tert-butyloxycarbonyl, isobutyloxycarbonyl, sec-butyloxycarbonyl, pentyloxycarbonyl, isopentyloxycarbonyl, and hexyloxycarbonyl. Examples of a preferred embodiment include methyloxycarbonyl, ethyloxycarbonyl, and propyloxycarbonyl.

"Carbocyclealkyl" means alkyl substituted with one or two or more carbocyclic groups. Examples of "carbocyclealkyl" include benzyl, phenethyl, phenylpropynyl, benzhydryl, trityl, cyclopropylmethyl, cyclobutylmethyl, cyclopentylmethyl, cyclohexylmethyl, naphthylmethyl, and a group shown below:

[Chemical Formula 18]

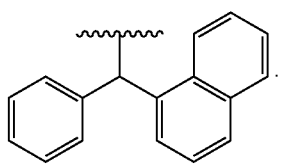

Examples of a preferred embodiment include benzyl, phenethyl, and benzhydryl.

"Heterocyclealkyl" means alkyl substituted with one or two or more heterocyclic groups, and includes those in which the alkyl part is substituted with a carbocyclic group. Examples of "heterocyclealkyl" include pyridylmethyl, tetrahydropyranylmethyl, furanylmethyl, morpholinylethyl, imidazolylmethyl, indolylmethyl, benzothiophenylmethyl, oxazolylmethyl, isooxazolylmethyl, thiazolylmethyl, isothiazolylmethyl, pyrazolylmethyl, isopyrazolylmethyl, pyrrolidinylmethyl, benzoxazolylmethyl, piperidinylmethyl, piperazinylmethyl, and groups shown below

[Chemical Formula 19]

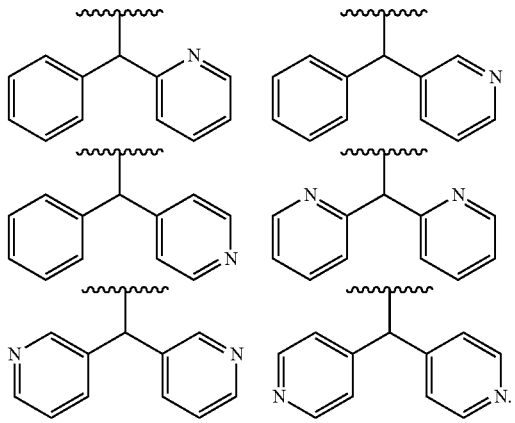

Examples of a preferred embodiment include pyridylmethyl, tetrahydropyranylmethyl, furanylmethyl, and morpholinylethyl.

Examples of "carbocycleoxyalkyl" include phenyloxymethyl, phenyloxyethyl, cyclopropyloxymethyl, cyclopropyloxyethyl, cyclobutyloxymethyl, cyclobutyloxyethyl, cyclohexyloxymethyl, and cyclohexyloxyethyl. Examples of a preferred embodiment include phenyloxymethyl and phenyloxyethyl.

Examples of "heterocycleoxyalkyl" include pyridyloxymethyl, pyridyloxyethyl, morpholinyloxymethyl, morpholinyloxyethyl, and benzoxazolyloxymethyl. Examples of a preferred embodiment include pyridyloxymethyl and morpholinyloxymethyl.

"Carbocyclealkyloxy" represents alkyloxy in which the alkyl part is substituted with one or two or more carbocyclic groups, and examples of "carbocyclealkyloxy" include phenylmethyloxy, phenylethyloxy, cyclopropylmethyloxy, cyclobutylmethyloxy, cyclopentylmethyloxy, and cyclohexylmethyloxy. Examples of a preferred embodiment include phenylmethyloxy and cyclopropylmethyloxy.

"Heterocyclealkyloxy" represents alkyloxy in which the alkyl part is substituted with one or two or more heterocyclic groups, and also includes those in which the alkyl part is substituted with a carbocyclic group. Examples of "heterocyclealkyloxy" include pyridylmethyloxy, pyridylethyloxy, imidazolylmethyloxy, imidazolylethyloxy, benzoxazolylmethyloxy, and benzoxazolylethyloxy.

Examples of "alkyloxyalkyl" include methoxymethyl, methoxyethyl, ethoxymethyl, ethoxyethyl, methoxypropyl, methoxybutyl, ethoxypropyl, ethoxybutyl, isopropyloxymethyl, and tert-butyloxymethyl. Examples of a preferred embodiment include methoxymethyl, methoxyethyl, ethoxymethyl, and ethoxyethyl.

Examples of "alkyloxyalkyloxy" include methoxymethoxy, methoxyethoxy, ethoxymethoxy, ethoxyethoxy, methoxypropyloxy, methoxybutyloxy, ethoxypropyloxy, ethoxybutyloxy, isopropyloxymethyloxy, and tert-butyloxymethyloxy. Examples of a preferred embodiment include methoxymethoxy, methoxyethoxy, ethoxymethoxy, and ethoxyethoxy.

Examples of "alkyloxycarbonyloxy" include methyloxycarbonyloxy, ethyloxycarbonyloxy, propyloxycarbonyloxy, isopropyloxycarbonyloxy, tert-butyloxycarbonyloxy, isobutyloxycarbonyloxy, sec-butyloxycarbonyloxy, pentyloxycarbonyloxy, isopentyloxycarbonyloxy, and hexyloxycarbonyloxy. Examples of a preferred embodiment include methyloxycarbonyloxy, ethyloxycarbonyloxy, and propyloxycarbonyloxy.

Examples of "alkylcarbonyloxy" include methylcarbonyloxy, ethylcarbonyloxy, propylcarbonyloxy, isopropylcarbonyloxy, tert-butylcarbonyloxy, isobutylcarbonyloxy, and sec-butylcarbonyloxy. Examples of a preferred embodiment include methylcarbonyloxy and ethylcarbonyloxy.

Examples of "alkylamino" include methylamino, dimethylamino, ethylamino, diethylamino, isopropylamino, N,N-diisopropylamino. N-methyl-N-ethylamino, and N-isopropyl-N-ethylamino. Examples of a preferred embodiment include methylamino, dimethylamino, ethylamino, and diethylamino.

Examples of "alkylcarbonylamino" include methylcarbonylamino, ethylcarbonylamino, propylcarbonylamino, isopropylcarbonylamino, tert-butylcarbonylamino, isobutylcarbonylamino, and sec-butylcarbonylamino. Examples of a preferred embodiment include methylcarbonylamino and ethylcarbonylamino.

Examples of "alkylaminocarbonyl" include methylaminocarbonyl, dimethylaminocarbonyl, ethylaminocarbonyl, diethylaminocarbonyl, isopropylaminocarbonyl, N,N-diisopropylaminocarbonyl, N-methyl-N-ethylaminocarbonyl, and N-isopropyl-N-ethylaminocarbonyl. Examples of a preferred embodiment include methylaminocarbonyl, dimethylaminocarbonyl, ethylaminocarbonyl, and diethylaminocarbonyl.

Examples of "alkylsulfonyl" include methylsulfonyl, ethylsulfonyl, propylsulfonyl, isopropylsulfonyl, tert-butylsulfonyl, isobutylsulfonyl, and sec-butylsulfonyl. Examples of a preferred embodiment include methylsulfonyl and ethylsulfonyl.

Examples of "alkylsulfinyl" include methylsulfinyl, ethylsulfinyl, propylsulfinyl, isopropylsulfinyl, tert-butylsulfinyl, isobutylsulfinyl, and see-butylsulfinyl. Examples of a preferred embodiment include methylsulfinyl and ethylsulfinyl.

Examples of "alkylsulfonylamino" include methylsulfonylamino, ethylsulfonylamino, propylsulfonylamino, isopropylsulfonylamino, tert-butylsulfonylamino, isobutylsulfonylamino, and sec-butylsulfonylamino. Examples of a preferred embodiment include methylsulfonylamino and ethylsulfonylamino.

Examples of "alkenyloxy" include ethylenyloxy, 1-propylenyloxy, 2-propylenyloxy, 1-butylenyloxy, 2-butylenyloxy, and 3-butylenyloxy.

Examples of "halogenoalkyl" include monofluoromethyl, monofluoroethyl, monofluoropropyl, 2,2,3,3,3-pentafluoropropyl, monochloromethyl, trifluoromethyl, trichloromethyl, 2,2,2-trifluoroethyl, 2,2,2-trichloroethyl, 1,2-dibromoethyl, and 1,1,1-trifluoropropan-2-yl. Examples of a preferred embodiment include trifluoromethyl, trichloromethyl, and 1,1,1-trifluoropropan-2-yl.

Examples of "halogenoalkyloxy" include monofluoromethoxy, monofluoroethoxy, trifluoromethoxy, trichloromethoxy, trifluoroethoxy, and trichloroethoxy. Examples of a preferred embodiment include trifluoromethoxy and trichloromethoxy.

Examples of "alkylthio" include methylthio, ethylthio, and propylthio.

Examples of "hydroxyalkyl" include hydroxymethyl, hydroxyethyl, and hydroxypropyl.

Examples of "carbocyclealkyloxyalkyl" include benzyloxymethyl, benzyloxyethyl, and benzhydryloxymethyl.

Examples of "heterocyclealkyloxyalkyl" include pyridylmethyloxymethyl and pyridylmethyloxyethyl.

Examples of "halogenoalkylcarbonylamino" include trifluoromethylcarbonylamino and 2,2,3,3,3-pentafluoropropylcarbonylamino.

Examples of "carbocyclecarbonyl" include phenylcarbonyl, naphthylearbonyl, cyclopropylcarbonyl, cyclobutylcarbonyl, cyclopentylcarbonyl, and cyclohexylcarbonyl.

Examples of "carbocycleoxy" include phenyloxy, naphthyloxy, cyclopropyloxy, cyclobutyloxy, cyclopentyloxy, and cyclohexyloxy.

Examples of "carbocycleoxycarbonyl" include phenyloxycarbonyl, naphthyloxycarbonyl, cyclopropyloxycarbonyl, cyclobutyloxycarbonyl, cyclopentyloxycarbonyl, and cyclohexyloxycarbonyl.

Examples of "heterocyclecarbonyl" include pyridylcarbonyl, benzoxazolylcarbonyl, morpholinylcarbonyl, and tetrahydropyranylcarbonyl.

Examples of "heterocycleoxy" include pyridyloxy, benzoxazolyloxy, morpholinyloxy, and tetrahydropyranyloxy.

Examples of "heterocycleoxycarbonyl" include pyridyloxycarbonyl, benzoxazolyloxycarbonyl, morpholinyloxycarbonyl, and tetrahydropyranyloxycarbonyl.

Substituent group A is a group shown below:
halogen, cyano, hydroxy, carboxy, formyl, amino, oxo, nitro, alkyl, halogenoalkyl, alkyloxy, alkylthio, hydroxyalkyl, carboxyalkyl, a carbocyclic group, a heterocyclic group, an oxo-substituted heterocyclic group, carbocyclealkyloxy, carbocycleoxyalkyl, carbocyclealkyloxyalkyl, carbocyclealkylthio, heterocyclealkyloxy, heterocycleoxyalkyl, heterocyclealkyloxyalkyl, halogenoalkyloxy, heterocyclyloxyalkyl, alkyloxyalkyloxy, alkylcarbonyl, alkylcarbonyloxy, alkyloxycarbonyl, alkyloxycarbonyloxy, alkylamino, alkylcarbonylamino, halogenoalkylcarbonylamino, alkylaminocarbonyl, alkylsulfonyl, alkylsulfinyl, and alkylsulfonylamino. Examples of a preferred embodiment in Substituent group A include halogen, carboxy, alkyl, alkyloxy, a carbocyclic group, a heterocyclic group, and carbocyclealkylthio.

Substituent group B is a group shown below:
halogen, cyano, hydroxy, carboxy, formyl, amino, oxo, nitro, alkyl, halogenoalkyl, alkyloxy, alkylthio, hydroxyalkyl, carboxyalkyl, carbocyclealkyloxy, heterocyclealkyloxy, halogenoalkyloxy, alkyloxyalkyloxy, alkyloxyalkyloxy, alkylcarbonyl, alkyloxycarbonyl, alkyloxycarbonyloxy, alkylamino, alkylcarbonylamino, alkylaminocarbonyl, alkylsulfonyl, alkylsulfonylamino, a carbocyclic group optionally substituted with Substituent group A, a heterocyclic group optionally substituted with Substituent group A, carbocyclealkyl optionally substituted with Substituent group A, heterocyclealkyl optionally substituted with Substituent group A, carbocyclealkyloxy optionally substituted with Substituent group A, heterocyclealkyloxy optionally substituted with Substituent group A, carbocyclealkylthio optionally substituted with Substituent group A, heterocyclealkylthio optionally substituted with Substituent group A, carbocycleoxyalkyl optionally substituted with Substituent group A, heterocycleoxyalkyl optionally substituted with Substituent group A, carbocyclealkyloxyalkyl optionally substituted with Substituent group A, and heterocyclealkyloxyalkyl optionally substituted with Substituent group A.

Examples of a preferred embodiment in Substituent group B include halogen, alkyl, a carbocyclic group optionally substituted with Substituent group A, carbocyclealkyl optionally substituted with Substituent group A, and carbocyclealkylthio optionally substituted with Substituent group A. Examples of a preferred embodiment of Substituent group A in Substituent group B include halogen, alkyl, alkyloxy, halogenoalkyl, and alkylthio.

Substituent group E is a group shown below:
alkyl, halogenoalkyl, hydroxyalkyl, carboxyalkyl, alkyloxyalkyl, alkylcarbonyl, alkyloxycarbonyl, alkylaminocarbonyl, and alkylsulfonyl.

Examples of a preferred embodiment of Substituent group E include alkyl.

Substituent group F is a group shown below:
halogen, cyano, hydroxy, carboxy, formyl, amino, oxo, nitro, alkyloxy, alkylthio, a carbocyclic group, a heterocyclic group, an oxo-substituted heterocyclic group, carbocyclealkyloxy, carbocyclealkylthio, heterocyclealkyloxy, halogenoalkyloxy, alkyloxyalkyloxy, alkylcarbonyl, alkylcarbonyloxy, alkyloxycarbonyl, alkyloxycarbonyloxy, alkylamino, alkylcarbonylamino, halogenoalkylcarbonylamino, alkylaminocarbonyl, alkylsulfonyl, alkylsulfinyl, and alkylsulfonylamino.

Examples of a preferred embodiment of Substituent group F include halogen, carboxy, alkyloxy, a carbocyclic group, a heterocyclic group, and carbocyclealkylthio.

"$R^{X1}$ and $R^{X2}$, $R^{X9}$ and $R^{X10}$, $R^{X17}$ and $R^{X18}$, $R^{X20}$ and $R^{X21}$, and $R^{X24}$ and $R^{X25}$ may be taken together with an adjacent atom to form a heterocycle", "$R^{Y7}$ and $R^{Y8}$, and $R^{Y9}$ and $R^{Y10}$ may be taken together with an adjacent atom to form a heterocycle", "$R^{Z7}$ and $R^{Z8}$, and $R^{Z9}$ and $R^{Z10}$ may be taken together with an adjacent atom to form a heterocycle" and "$R^{V5}$ and $R^{V9}$ may be taken together with an adjacent atom to form a heterocycle" means a heterocycle comprising an N atom, and examples include groups shown below:

[Chemical Formula 20]

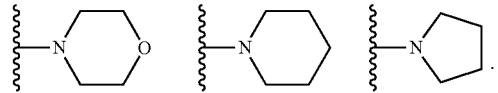

In the present description, $R^{E6}$ in the formula shown below:

[Chemical Formula 21]

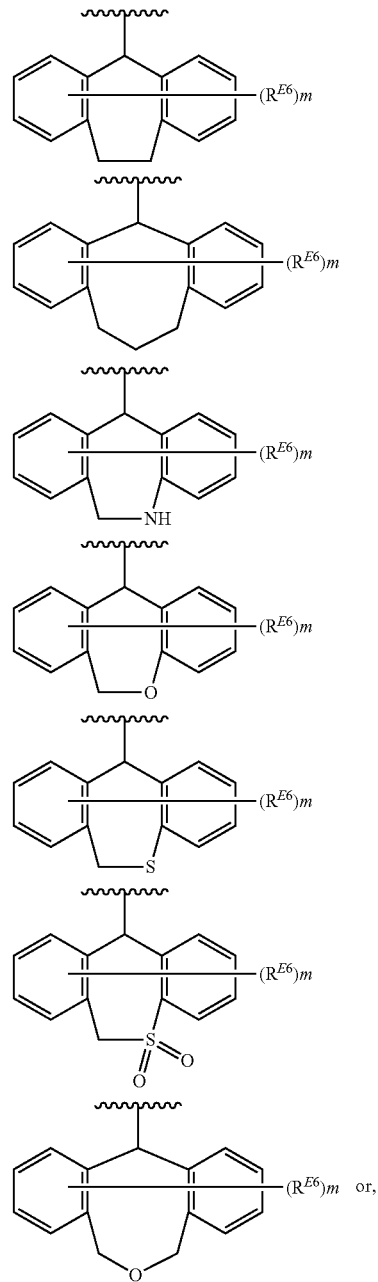

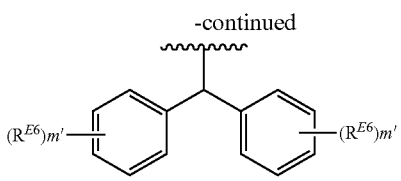

are each independently a group selected from Substituent group A, and Substituent group A is the same as defined above, in is an integer of 0 to 7, preferably an integer of 0 to 6, more preferably an integer of 0 to 4, particularly preferably an integer of 0 to 2, m' are each independently an integer of 0 to 4, preferably an integer of 0 to 2. For example, in the formula below:

[Chemical Formula 22]

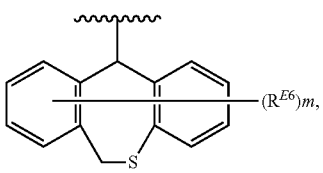

as shown in the substituents shown below:

[Chemical Formula 23]

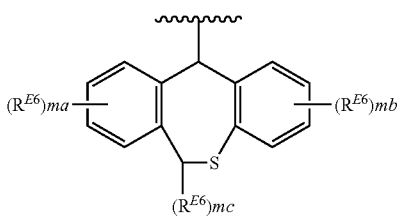

(wherein ma+t mb+me=m, and $R^{E6}$ is the same as defined in Item 11), the substituents $R^{E6}$ may be present on two benzene rings and any hydrogen atom on the 7 membered ring comprising a sulfur atom may be substituted with $R^{E6}$, and respective $R^{E6}$ may be the same or different.

ma is preferably an integer of 0 to 3, mb is preferably an integer of 0 to 3, and mc is preferably an integer of 0 or 1, ma is more preferably an integer of 0 or 2, mb is more preferably an integer of 0 or 1, and me is more preferably 0.

For example, in the formula below:

[Chemical Formula 24]

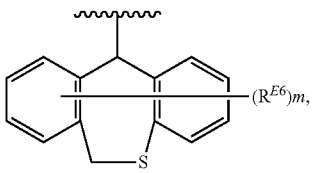

substituents shown below:

[Chemical Formula 25]

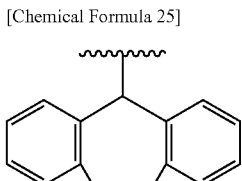

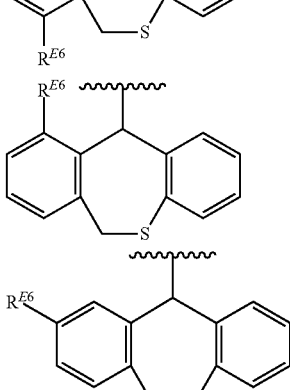

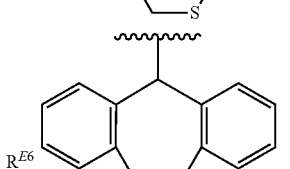

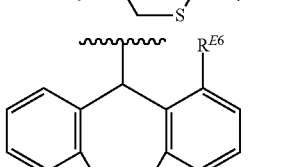

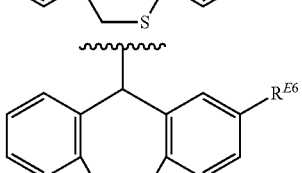

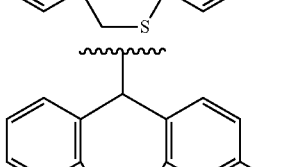

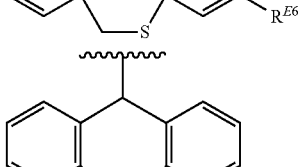

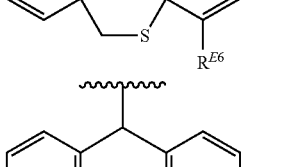

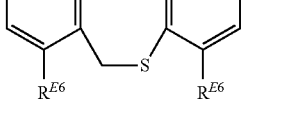

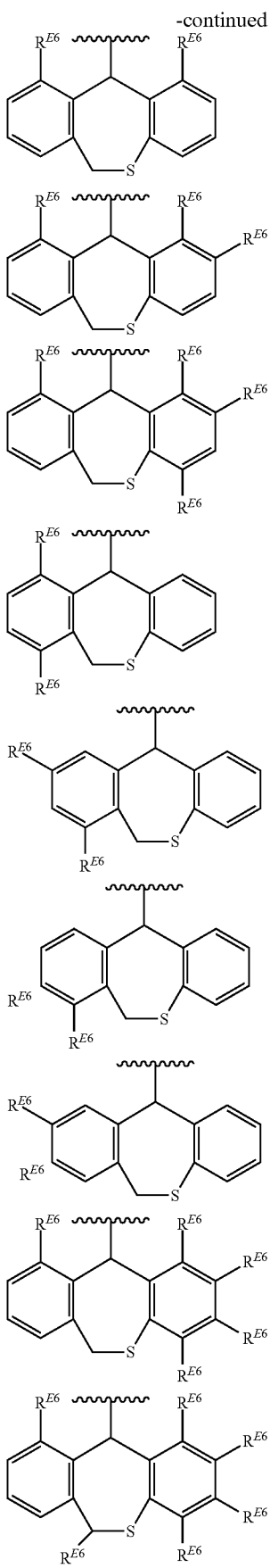

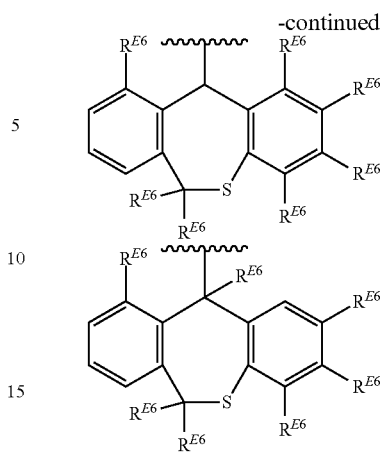

(wherein $R^{E6}$ is the same as defined in Item 11) and the like are included.

"$R^5$ and $R^6$ may be taken together with an, adjacent atom to form a carbocycle optionally substituted with Substituent group B or a heterocycle optionally substituted with Substituent group B, wherein the carbocycle or the heterocycle may form a condensed ring and/or a bridged structure" means Formula (I-1') or (I-21 shown below:

[Chemical Formula 26]

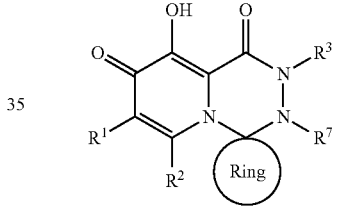
(I-1')

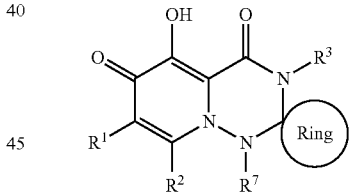
(I-2')

(wherein $R^1$, $R^2$, $R^3$, and $R^7$ are the same as defined in Item 1); and the ring is a carbocycle optionally substituted at any position with an identical or different substituent selected from Substituent group B or a heterocycle optionally substituted at any position with one or two or more identical or different substituents selected from Substituent group B. The carbocycle or the heterocycle is preferably a 5- to 12-membered ring. "The carbocycle or the heterocycle may form a condensed ring and/or a bridged structure" includes, for example, when the ring in Formula (I-11 or (I-2') is further condensed, when the ring has a bridged structure, and when the ring has a bridged structure in the condensed ring part. It indicates that Substituent group B may also be attached to any of a ring in Formula (I-1') or (I-2') described above, a ring condensed to the ring, or a bridged structure part of the ring. The bridged structure is preferably alkylene which may contain one or more heteroatoms selected from O, N, and S at any position, or an alkenylene which may contain one or more heteroatoms selected from O, N, and S at any position.

Examples of Formula (I-1') or (I-2') include compounds represented by formulae shown below:

[Chemical Formula 27]

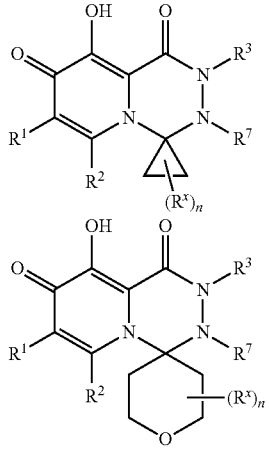
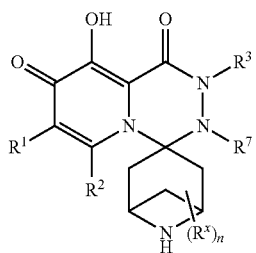
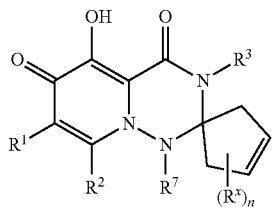
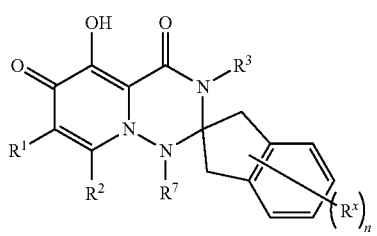

(wherein $R^x$ is a substituent selected from Substituent group B; n is an integer of 0 to 4 and $R^1$, $R^2$, $R^3$, and $R^7$ are the same as defined in Item 1).

"$R^8$ and $R^9$ may be taken together with an adjacent atom to form a carbocycle optionally substituted with Substituent group B or a heterocycle optionally substituted with Substituent group B" means Formula (I-3) shown below:

[Chemical Formula 28]

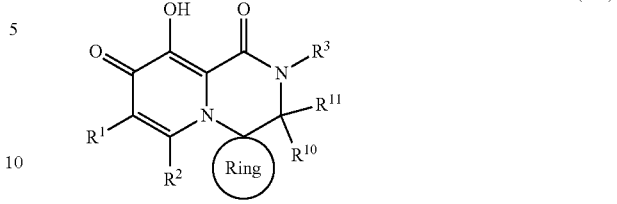

(I-3')

(wherein $R^1$, $R^2$, $R^3$, $R^{10}$ and $R^{11}$ are the same as defined in Item 1); and the ring is a carbocycle optionally substituted at any position with an identical or different substituent selected from Substituent group B or a heterocycle optionally substituted at any position with one or two or more identical or different substituents selected from Substituent group B. The carbocycle or the heterocycle is preferably a 5- to 12-membered ring. "The carbocycle or the heterocycle may form a condensed ring and/or a bridged structure" includes the cases, for example, when the ring in Formula (I-3') is further condensed, when the ring has a bridged structure, and when the ring has a bridged structure in the condensed ring part. It indicates that Substituent group B may also be attached to any of a ring in Formula (I-3) described above, a ring condensed to the ring, or a bridged structure part of the ring. The bridged structure is preferably alkylene which may contain one or more heteroatoms selected from O, N, and S at any position, or an alkenylene which may contain one or more heteroatoms selected from O, N, and S at any position.

Examples of Formula (I-3') include compounds represented b formulae shown below:

[Chemical Formula 29]

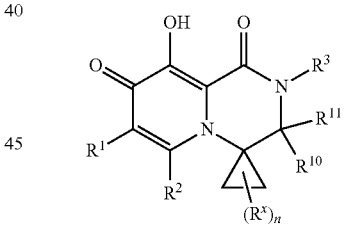
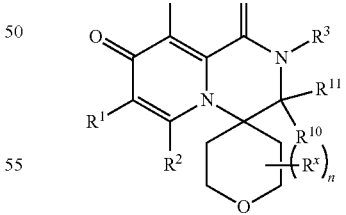
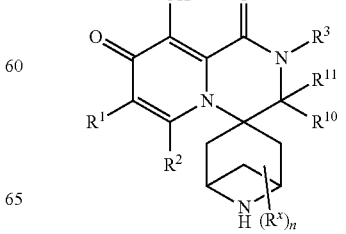

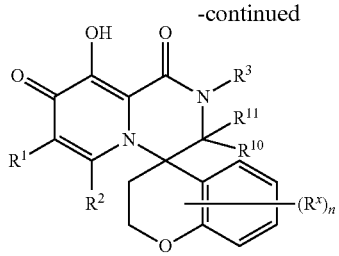

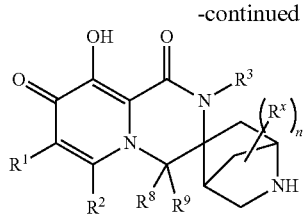

(wherein $R^X$ is a substituent selected from Substituent group B; n is an integer of 0 to 4; and $R^1$, $R^2$, $R^3$, $R^{10}$ and $R^{11}$ are the same as defined in Item 1).

"$R^{10}$ and $R^{11}$ may be taken together with an adjacent atom to form a carbocycle optionally substituted with Substituent group B or a heterocycle optionally substituted with Substituent group B" means a formula shown below:

[Chemical Formula 30]

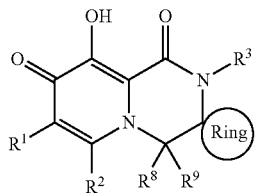

(I-4')

(wherein $R^1$, $R^2$, $R^3$, $R^8$ and $R^9$ are the same as defined in Item 1); and the ring is a carbocycle optionally substituted at any position with an identical or different substituent selected from Substituent group B or a heterocycle optionally substituted at any position with one or two or more identical or different substituents selected from Substituent group B. The carbocycle or the heterocycle is preferably a 5- to 12-membered ring. "The carbocycle or the heterocycle may form a condensed ring and/or a bridged structure" includes the cases, for example, when the ring in Formula (I-4') is further condensed, when the ring has a bridged structure, and when the ring has a bridged structure in the condensed ring part. It indicates that Substituent group B may also be attached to any of a ring in Formula (I-4') described above, a ring condensed to the ring, or a bridged structure part of the ring. The bridged structure is preferably alkylene which may contain one or more heteroatoms selected from O, N, and S at any position, or an alkenylene which may contain one or more heteroatoms selected from O, N, and S at any position.

Examples of Formula (I-4') include compounds represented by formulae shown below:

[Chemical Formula 31]

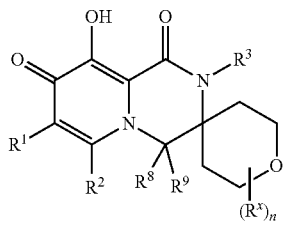

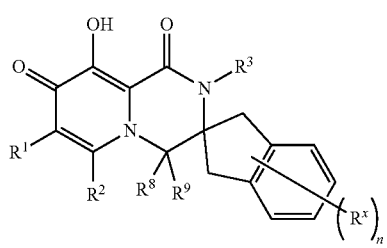

(wherein $R^X$ is a substituent selected from Substituent group B; n is an integer of 0 to 4; and $R^1$, $R^2$, $R^3$, $R^8$ and $R^9$ are the same as defined in Item 1).

"1) When $A^1$ is $CR^5R^6$, and $A^2$ is $NR^7$, then $R^3$ and $R^7$ may be taken together with an adjacent atom to form a heterocycle optionally substituted with Substituent group B" means Formula (I-5') shown below:

[Chemical Formula 32]

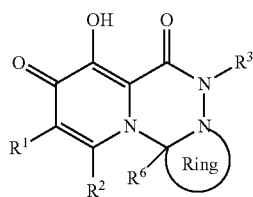

(I-5')

(wherein $R^1$, $R^2$, $R^3$, and $R^6$ are the same as defined in Item 1) and the ring is a heterocycle optionally substituted at any position with one or two or more identical or different substituents selected from Substituent group B. The heterocycle is preferably a 5- to 12-membered ring. "The heterocycle may form a condensed ring and/or a spiro ring and/or a bridged structure" includes the cases, for example, when the ring in Formula (I-5') is further condensed, when the ring forms a spiro ring, and when the ring, the condensed ring and/or the spiro ring has a bridged structure. It indicates that Substituent group B may also be attached to any of a ring in Formula (I-5') described above, a ring condensed to the ring, a ring forming a spiro ring, or a bridged structure part of the ring. The bridged structure is preferably alkylene which may contain one or more heteroatoms selected from O, N, and S at any position, or an alkenylene which may contain one or more heteroatoms selected from O, N, and S at any position.

Examples of Formula (I-5') include compounds represented by formulae shown below:

[Chemical Formula 33]

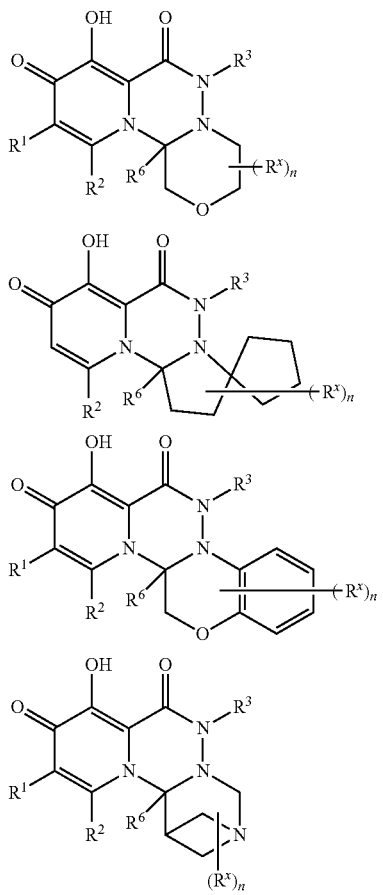

(wherein $R^X$ is a substituent selected from Substituent group B; n is an integer of 0 to 4; and $R^1$, $R^2$, $R^3$ and $R^6$ are the same as defined in Item 1).

"When $A^1$ is $CR^5R^5$, and $A^2$ is $NR^7$, then $R^5$ and $R^7$ may be taken together with an adjacent atom to form a bond" means Formula (I-6') shown below:

[Chemical Formula 34]

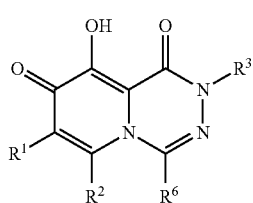

(I-6')

(wherein $R^1$, $R^2$, $R^3$, and $R^6$ are the same as defined in Item 1).

"When $A^1$ is $CR^5R^6$, and $A^2$ is $NR^7$, then $R^3$ and $R^7$ may be taken together with an adjacent atom to form a heterocycle optionally substituted with Substituent group B, wherein the heterocycle may form a condensed ring and/or a spiro ring and/or a bridged structure" means Formula (I-7') shown below:

[Chemical Formula 35]

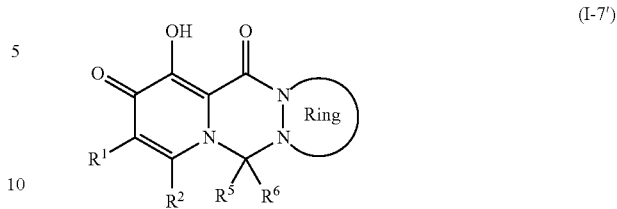

(I-7')

(wherein $R^1$, $R_2$, $R^5$, and $R^6$ are the same as defined in Item 1); and the ring is a heterocycle optionally substituted at any position with one or two or more identical or different substituents selected from Substituent group B. The heterocycle is preferably a 5- to 12-membered ring. "The heterocycle may form a condensed ring and/or a spiro ring and/or a bridged structure" includes the cases, for example, when the ring in Formula (I-7') is further condensed, when the ring forms a spiro ring, and when the ring, the condensed ring and/or the spiro ring has a bridged structure. It indicates that Substituent group B may also be attached to any of a ring in Formula (I-7') described above, a ring condensed to the ring, a ring forming a spiro ring, or a bridged structure part of the ring. The bridged structure is preferably alkylene which may contain one or more heteroatoms selected from O, N, and S at any position, or an alkenylene which may contain one or more heteroatoms selected from O, N, and S at any position. Examples of Formula (I-7') include compounds represented by formulae shown below:

[Chemical Formula 36]

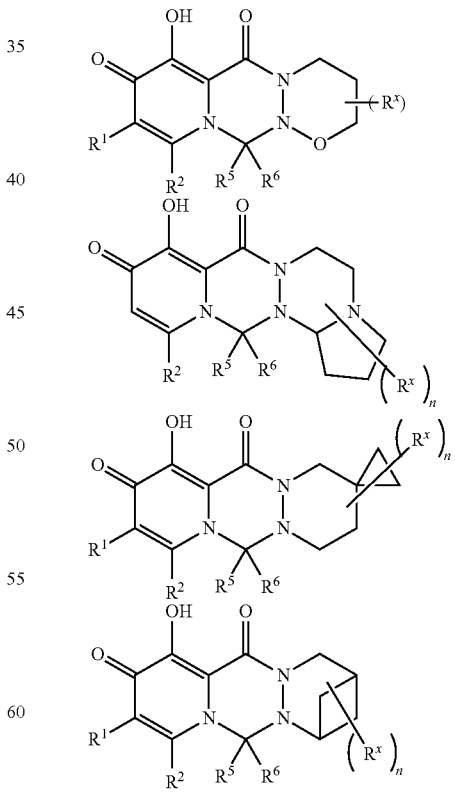

(wherein $R^X$ is a substituent selected from Substituent group B; n is an integer of 0 to 4; and $R^1$, $R^2$, $R^5$, and $R^6$ are the same as defined in Item 1).

"When $A^1$ is $NR^7$, and $A^2$ is $CR^5R^6$, then $R^7$ and $R^6$ may be taken together with an adjacent atom to form a heterocycle optionally substituted with Substituent group B" means Formula (I-8') shown below:

[Chemical Formula 37]

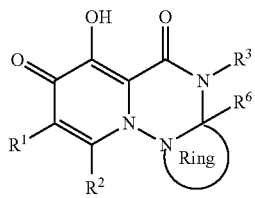

(I-8')

(wherein $R^1$, $R^2$, $R^3$, and $R^6$ are the same as defined in Item 1); and the ring is a heterocycle optionally substituted at any position with one or two or more identical or different substituents selected from Substituent group B. The heterocycle is preferably a 5- to 12-membered ring. "The heterocycle may form a condensed ring and/or a spiro ring and/or a bridged structure" includes the cases, for example, when the ring in Formula (I-8') is further condensed, when the ring forms a spiro ring, and when the ring, the condensed ring and/or the spiro ring has a bridged structure. It indicates that Substituent group B may also be attached to any of a ring in Formula (I-8') described above, a ring condensed to the ring, a ring forming a spiro ring, or a bridged structure part of the ring. The bridged structure is preferably alkylene which may contain one or more heteroatoms selected from O, N, and S at any position, or an alkenylene which may contain one or more heteroatoms selected from O, N, and S at any position.

Examples of Formula (I-8') include compounds represented by formulae shown below:

[Chemical Formula 38]

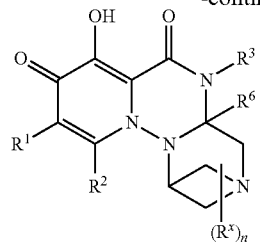

-continued

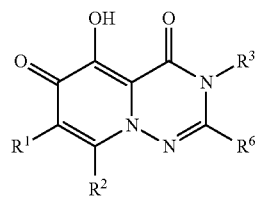

(wherein $R^1$ is a substituent selected from Substituent group B; n is an integer of 0 to 4; and $R^1$, $R^2$, $R^3$, and $R^6$ are the same as defined in Item 1).

"When $A^1$ is $NR^7$, and $A^2$ is $CR^5R^6$, then $R^7$ and $R^5$ may be taken together with an adjacent atom to form a bond" means Formula (I-9') shown below:

[Chemical Formula 39]

(I-9')

(wherein $R^1$, $R^2$, $R^3$, and $R^6$ are the same as defined in Item 1).

"When $A^1$ is $NR^7$, and $A^2$ is $CR^5R^6$, then $R^3$ and $R^6$ may be taken together with an adjacent atom to form a heterocycle optionally substituted with Substituent group B" means Formula (I-10') shown below:

[Chemical Formula 40]

(I-10')

(wherein $R^1$, $R^2$, $R^5$, and $R^7$ are the same as defined in Item 1); and the ring is a heterocycle optionally substituted at any position with one or two or more identical or different substituents selected from Substituent group B. The heterocycle is preferably a 5- to 12-membered ring. "The heterocycle may form a condensed ring and/or a spiro ring and/or a bridged structure" includes the cases, for example, when the ring in Formula (I-10') is further condensed, when the ring forms a spiro ring, and when the ring, the condensed ring and/or the spiro ring has a bridged structure. It indicates that Substituent group B may also be attached to any of a ring in Formula (I-10') described above, a ring condensed to the ring, a ring forming a spiro ring, or a bridged structure part of the ring. The bridged structure is preferably alkylene which may contain one or more heteroatoms selected from O, N, and 8 at any position, or an alkenylene which may contain one or more heteroatoms selected from O, N, and S at any position.

Examples of Formula (I-10') include compounds represented by formulae shown below:

[Chemical Formula 41]

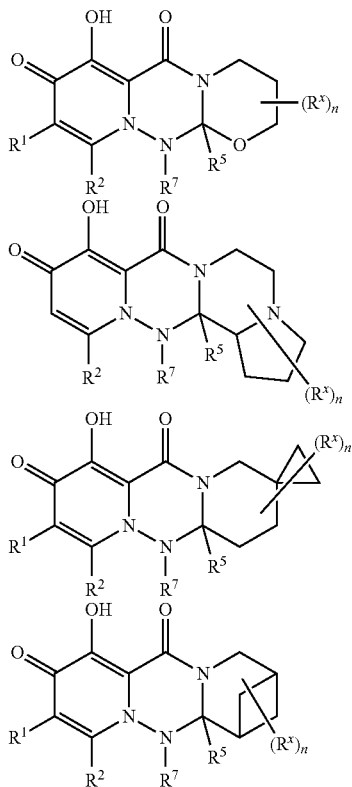

(wherein $R^X$ is a substituent selected from Substituent group B; n is an integer of 0 to 4; and $R^1$, $R^2$, $R^5$, and $R^7$ are the same as defined in Item 1).

"When $A^1$ is $CR^8R^9$, and $A^2$ is $CR^{10}R^{11}$, then $R^8$ and $R^{10}$ may be taken together with an adjacent atom to form a carbocycle optionally substituted with Substituent group B or a heterocycle optionally substituted with Substituent group B" means Formula (I-11) shown below:

[Chemical Formula 42]

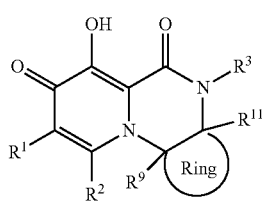
(I-11')

(wherein $R^1$, $R^2$, $R^3$, $R^9$ and $R^{11}$ are the same as defined in Item 1); and the ring is a heterocycle optionally substituted at any position with one or two or more identical or different substituents selected from Substituent group B. The heterocycle is preferably a 5- to 12-membered ring. "The heterocycle may form a condensed ring and/or a spiro ring and/or a bridged structure" includes the cases, for example, when the ring in Formula (I-11') is further condensed, when the ring forms a spiro ring, and when the ring, the condensed ring and/or the spiro ring has a bridged structure. It indicates that Substituent group B may also be attached to any of a ring in Formula (I-11) described above, a ring condensed to the ring, a ring forming a spiro ring, or a bridged structure part of the ring. The bridged structure is preferably alkylene which may contain one or more heteroatoms selected from O, N, and S at any position, or an alkenylene which may contain one or more heteroatoms selected from O, N, and S at any position.

Examples of Formula (I-11') include compounds represented by formulae shown below:

[Chemical Formula 43]

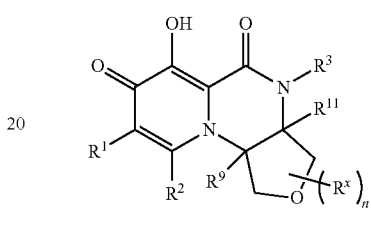

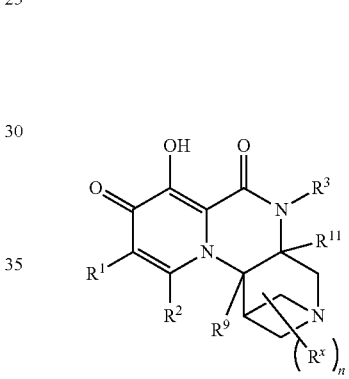

(wherein $R^X$ is a substituent selected from Substituent group B; n is an integer of 0 to 4; and $R^1$, $R^2$, $R^3$, $R^9$ and $R^{11}$ are the same as defined in Item 1).

"When $A^1$ is $CR^8R^9$, and $A^2$ is $CR^{10}R^{11}$, then $R^8$ and $R^{10}$ may be taken together with an adjacent atom to form a bond" means Formula (I-12') shown below:

[Chemical Formula 44]

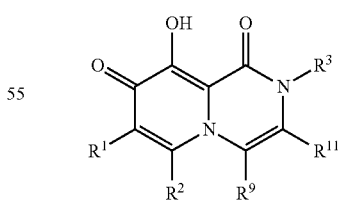
(I-12')

(wherein $R^1$, $R^2$, $R^3$, $R^9$, and $R^{11}$ are the same as defined in Item 1).

"When $A^1$ is $CR^8R^9$, and $A^2$ is $CR^{10}R^{11}$, then $R^8$ and $R^{11}$ may be taken together with an adjacent atom to form a heterocycle optionally substituted with Substituent group B" means Formula (I-13') shown below:

[Chemical Formula 45]

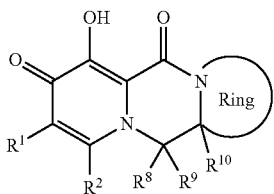

(I-13')

(wherein $R^1$, $R^2$, $R^8$, $R^9$, and $R^{11}$ are the same as defined in Item 1); and the ring is a heterocycle optionally substituted at any position with one or two or more identical or different substituents selected from Substituent group B. The heterocycle is preferably a 5- to 12-membered ring. "The heterocycle may form a condensed ring and/or a spiro ring and/or a bridged structure" includes the cases, for example, when the ring in Formula (I-13') is further condensed, when the ring forms a spiro ring, and when the ring, the condensed ring and/or the spiro ring has a bridged structure. It indicates that Substituent group B may also be attached to any of a ring in Formula (I-13') described above, a ring condensed to the ring, a ring forming a Spiro ring, or a bridged structure part of the ring. The bridged structure is preferably alkylene which may contain one or more heteroatoms selected from O, N, and S at any position, or an alkenylene which may contain one or more heteroatoms selected from O, N, and S at any position.

Examples of Formula (I-13') include compounds shown below:

[Chemical Formula 46]

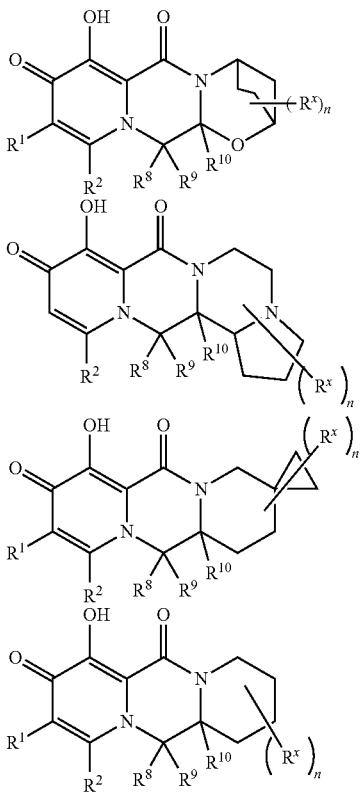

(wherein $R^x$ is a substituent selected from Substituent group B; n is an integer of 0 to 4; and $R^1$, $R^2$, $R^8$, $R^9$ and $R^{10}$ are the same as defined in Item 1).

Preferred embodiments of a substituent in the "carbocycle optionally substituted with Substituent group B", the "heterocycle optionally substituted with Substituent group B", or the "ring" in Formulae (I-1') to (I-5'), (I-7) (I-8'), (I-10'), (I-11'), and (I-13') are unsubstituted, halogen, cyano, hydroxy, carboxy, oxo, alkyl, halogenoalkyl, alkyloxy, carbocyclealkyloxy, heterocyclealkyloxy, halogenoalkyloxy, alkyloxyalkyl, alkyloxyalkyloxy, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A. More preferred embodiments are unsubstituted, halogen, carboxy, alkyl, halogenoalkyl, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A. Still more preferred embodiments are unsubstituted, halogen, alkyl, halogenoalkyl, a carbocyclic group optionally substituted with Substituent group C, a heterocyclic group optionally substituted with Substituent group C, carbocyclealkyl optionally substituted with Substituent group C, and heterocyclealkyl optionally substituted with Substituent group C.

Herein, Substituent group C is a group consisting of halogen, oxo, alkyl, halogenoalkyl, alkyloxy, halogenoalkyloxy, a carbocyclic group, a heterocyclic group, an oxo-substituted heterocyclic group, carbocyclealkyl, heterocyclealkyl, carbocyclealkyloxy, and heterocyclealkyloxy.

$R^x$ is a substituent selected from a hydrogen atom or a Substituent group B. Preferred $R^x$ is a hydrogen atom, halogen, cyano, hydroxy, carboxy, oxo, alkyl, halogenoalkyl, alkyloxy, carbocyclealkyloxy, heterocyclealkyloxy, halogenoalkyloxy, alkyloxyalkyl, alkyloxyalkyloxy, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A. More preferred $R^x$ is a hydrogen atom, halogen, carboxy, alkyl, halogenoalkyl, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A. Still more preferred Rx is a hydrogen atom, halogen, alkyl, halogenoalkyl, a carbocyclic group optionally substituted with Substituent group C, a heterocyclic group optionally substituted with Substituent group C, carbocyclealkyl optionally substituted with Substituent group C, and heterocyclealkyl optionally substituted with Substituent group C.

n is an integer of 0 to 4, preferably an integer of 0 to 2.

Examples of "alkyl optionally substituted with Substituent group F" and "alkyl optionally substituted with Substituent group D" include methyl, ethyl, propyl, isopropyl, butyl, tert-butyl, sec-butyl, pentan-2-yl, hydroxymethyl, hydroxyethyl, carboxymethyl, carboxyethyl, carboxypropyl, ethoxycarbonylpropyl, cyanomethyl, cyanoethyl, fluoromethyl, fluoroethyl, fluoropropyl, difluoromethyl, trifluoromethyl, chloromethyl, dichloromethyl, trichloromethyl, ethyloxycarbonylethyl, methoxymethyl, dimethoxymethyl, methoxyethyl, methoxypropyl, ethoxyethyl, 1-methyl-1-methoxymethyl, propyloxymethyl, aminopropyl, dimethyl-aminomethyl, aminomethyl, aminoethyl, dimethylaminoethyl, diethylaminomethyl, diethylaminoethyl, dimethylaminopropyl, cyclopropylmethyloxyethyl, methylsulfonylaminomethyl, methylaminocarbonylethyl, 1,1,1-trifluoropropan-2-yl, 1,1-difluoroethyl, 1,1,1-trifluoroethyl, 1,1,1-trifluoropropyl, trifluoromethyloxyethyl, trifluoromethylcarbonylaminomethyl, methylsulfonylethyl, methylcarbonyloxyethyl, and groups shown below:

[Chemical Formula 47]

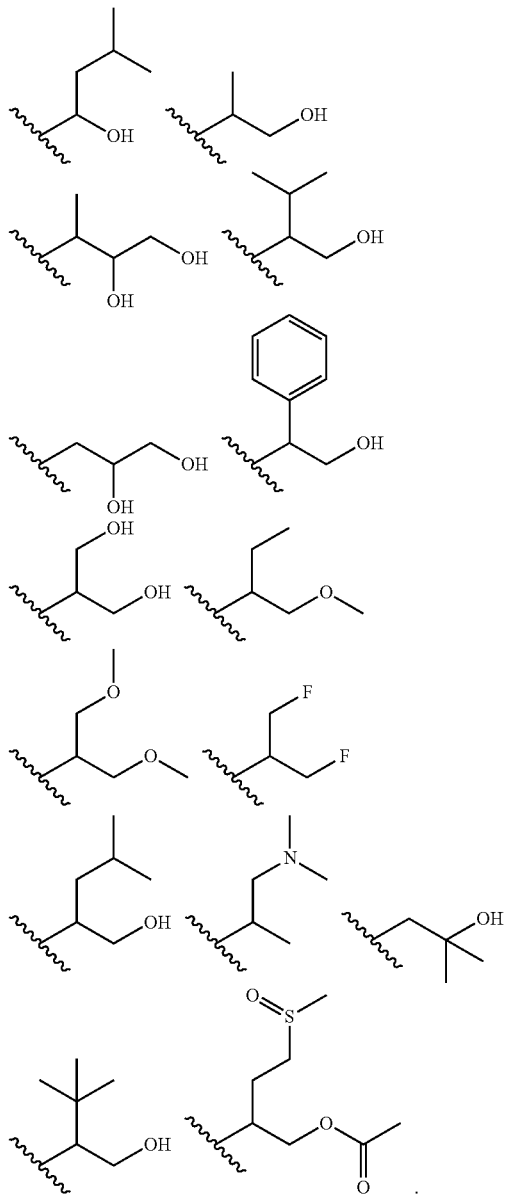

Examples of "alkenyl optionally substituted with Substituent group F" and "alkenyl optionally substituted with Substituent group C" include ethylenyl, 3-methylbuten-2-yl, carboxyethylenyl, hydroxyethylenyl, difluoroethylenyl, and 1-propen-2-yl.

Examples of "alkynyl optionally substituted with Substituent group F" and "alkynyl optionally substituted with Substituent group C" include 1-propynyl, 1-butynyl, 3,3,3-trifluoromethylpropynyl, and 3-hydroxy-propynyl.

Examples of "alkyloxy optionally substituted with Substituent group F" include methyloxy, ethyloxy, trifluoromethyloxy, trichloromethyloxy, hydroxymethyloxy, hydroxyethyloxy, carboxymethyloxy, and carboxyethyloxy.

Examples of "alkenyloxy optionally substituted with Substituent group F" include 3-fluoro-1-propenyloxy, ethylenyl, carboxyethylenyl, hydroxyethylenyloxy, and difluoroethylenyloxy.

Examples of "alkylcarbonyl optionally substituted with Substituent group F" include methylcarbonyl, ethylcarbonyl, propylcarbonyl, isopropylcarbonyl, hydroxymethylcarbonyl, hydroxyethylcarbonyl, trifluoromethylcarbonyl, 2,2,2-trifluoromethylcarbonyl, and carboxymethylcarbonyl.

Examples of "alkyloxycarbonyl optionally substituted with Substituent group F" include methyloxycarbonyl, ethyloxycarbonyl, trifluoromethyl oxycarbonyl, trichloromethyloxycarbonyl, hydroxymethyloxycarbonyl, hydroxyethyloxycarbonyl, and carboxymethyloxycarbonyl.

Examples of "carbocyclic group optionally substituted with Substituent group A" and "carbocyclic group optionally substituted with Substituent group B" include phenyl, naphthyl, anthracenyl, phenanthracenyl, adamantyl, 1-hydroxyadamantyl, 2 hydroxyadamantyl, 3-methylphenyl, 4-methylphenyl, 3-methoxyphenyl, 4-methoxyphenyl, 3-hydroxyphenyl, 4-hydroxyphenyl, 4-chlorophenyl, 4-fluorophenyl, 2-cyanophenyl, 3-cyanophenyl, 4-cyanophenyl, fluorocyclopropyl, difluorocyclobutanyl, difluorocyclohexyl, and groups shown below:

[Chemical Formula 48]

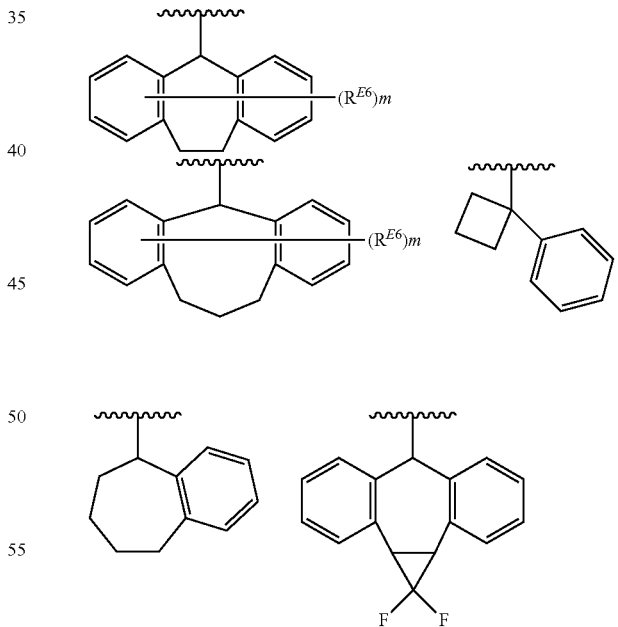

(wherein $R^{E6}$ each independently represents a substituent group selected from Substituent group A, m is an integer of 0 to 7, and when there are a plurality of $R^{E6}$, the R may be the same or different).

Preferred examples of the "carbocyclic group optionally substituted with Substituent group B" in $R^5$, $R^6$, $R^7$, $R^8$, $R^9$, $R^{10}$, $R^{11}$, and $R^{7a}$ include groups shown below:

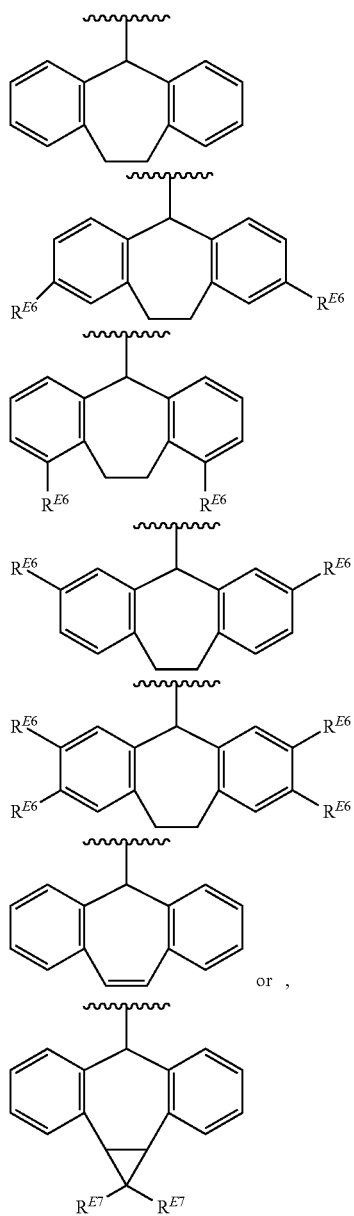

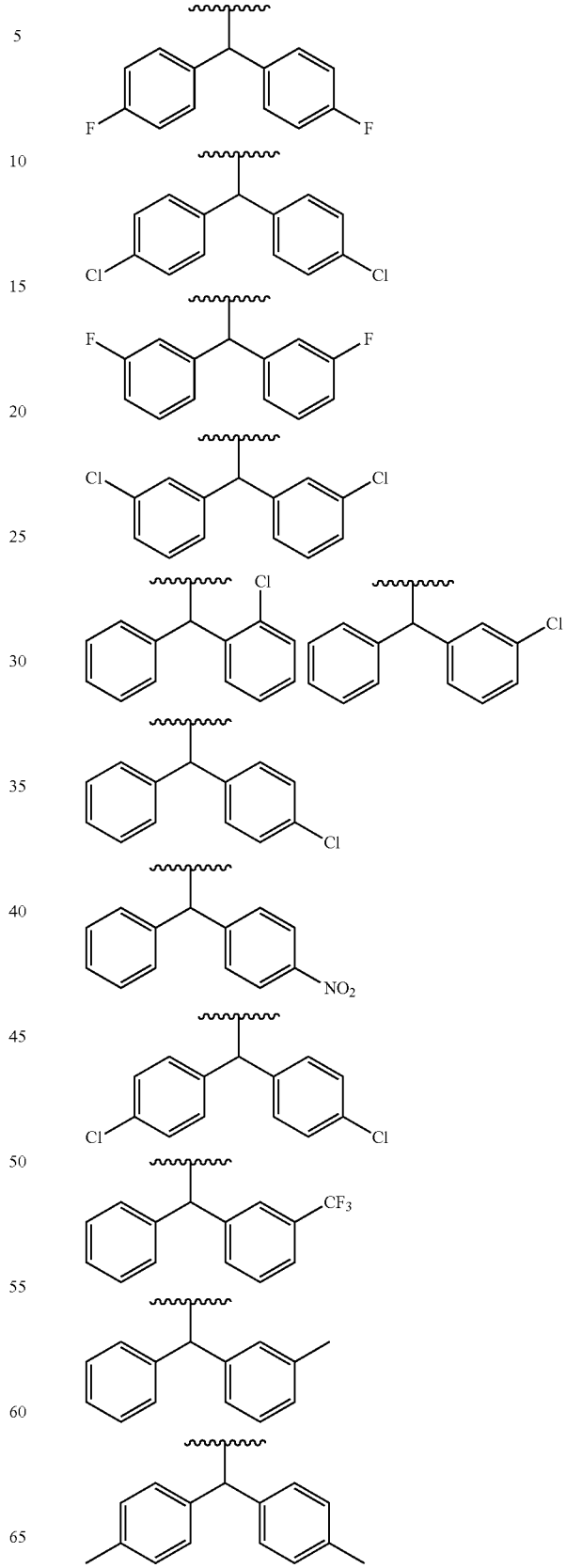

(wherein $R^{E6}$ are each independently a group selected from Substituent group A, preferably halogen or alkyl; and $R^{E7}$ are each independently a hydrogen atom, halogen or alkyl, preferably halogen).

Examples of "carbocyclealkyl optionally substituted with Substituent group A" and "carbocyclealkyl optionally substituted with Substituent group B" include cyclopropylmethyl, 4-hydroxybenzyl, cyclopentylmethyl, cyclohexylmethyl, benzyl, 2-aminobenzyl, 2-cyanobenzyl, 2-fluorobenzyl, 4-fluorobenzyl, 2-trifluoromethylbenzyl, 1,3,5-trifluorobenzyl, 3,4,5-trifluorobenzyl, 4-methoxybenzyl, 2,4-difluorobenzyl, 2-fluoro-3-chlorobenzyl, benzhydryl, 4-phenylbenzyl, phenethyl, phenylpropyl, 4-methylcarbonylaminobenzyl, 3,4-dichlorobenzyl, 4-chloro-2-fluorobenzyl, 3,5-dihydroxybenzyl, and groups shown below:

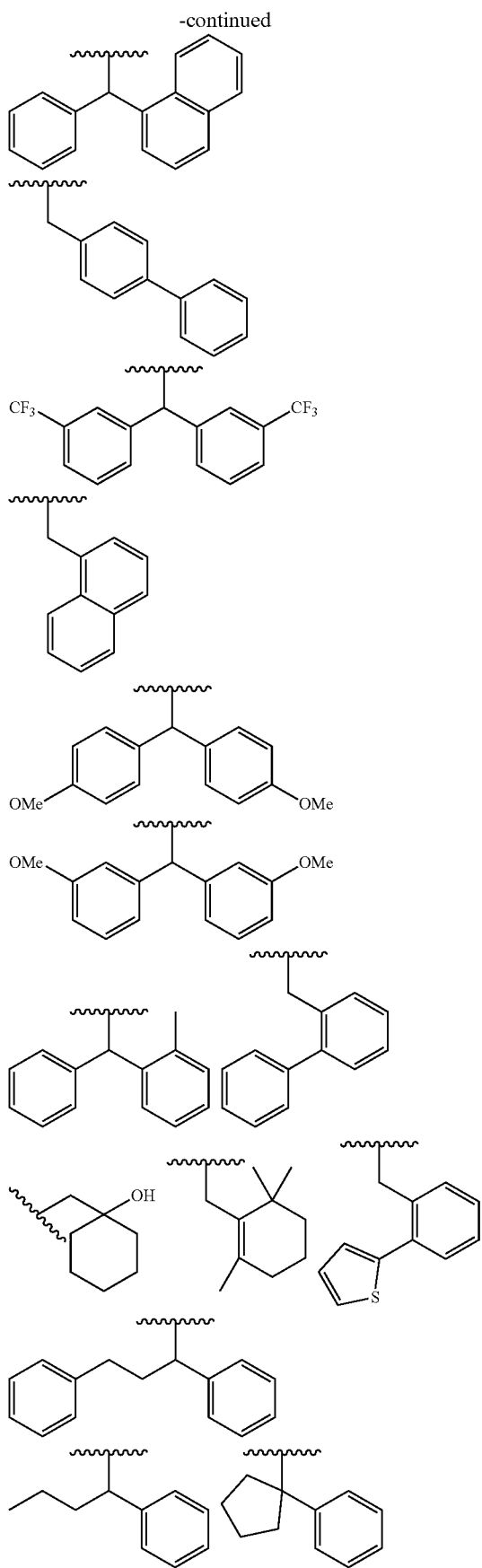
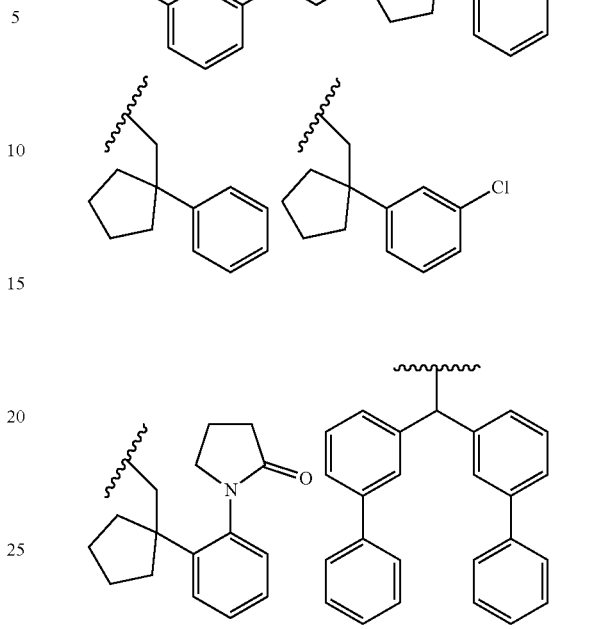

Examples of "carbocycleoxyalkyl optionally substituted with Substituent group A" and "carbocycleoxyalkyl optionally substituted with Substituent group B" include 4-hydroxyphenyloxymethyl, 4-hydroxyphenyloxyethyl, cyclopropyloxymethyl, cyclopentyloxymethyl, 4-fluorophenyloxymethyl, 4-fluorophenyloxyethyl, 4-trifluoromethylphenyloxymethyl, 4-trifluoromethylphenyloxyethyl, 4-methoxyphenyloxymethyl, and 4-methoxyphenyloxyethyl.

Examples of "carbocyclecarbonyl optionally substituted with Substituent group A" and "carbocyclecarbonyl optionally substituted with Substituent group B" include phenylcarbonyl, 4-fluorophenylcarbonyl, 4-trifluoromethylphenylcarbonyl, 4-methoxyphenylcarbonyl, and cyclopropylcarbonyl.

Examples of "carbocycleoxy optionally substituted with Substituent group A" and "carbocycleoxy optionally substituted with Substituent group B" include phenyloxy, cyclopropyloxy, cyclopentyloxy, 4-fluorophenyloxy, 4-trifluoromethylphenyloxy, and 4-methoxyphenyloxy.

Examples of "carbocycleoxycarbonyl optionally substituted with Substituent group A" and "carbocycleoxycarbonyl optionally substituted with Substituent group B" include phenyloxycarbonyl, cyclopropyloxycarbonyl, cyclopentyloxycarbonyl, 4-fluorophenyloxycarbonyl, 4-trifluoromethylphenyloxycarbonyl, and 4-methoxyphenyloxycarbonyl.

Examples of "heterocyclic group optionally substituted with Substituent group A" and "heterocyclic group optionally substituted with Substituent group B" include pyrimidinyl, pyridyl, benzoxazolyl, morpholinyl, tetrahydropyranyl, furyl, thiophenyl, oxazolyl, thiazolyl, pyrazolyl, methylpyrrolidinyl, isopropylpyrrolidinyl, methylsulfonylpyrrolidinyl, hydroxyethylpyrrolidinyl, methylpiperidinyl, methylpiperazinyl, tetrahydrofuryl, and groups shown below:

[Chemical Formula 51]

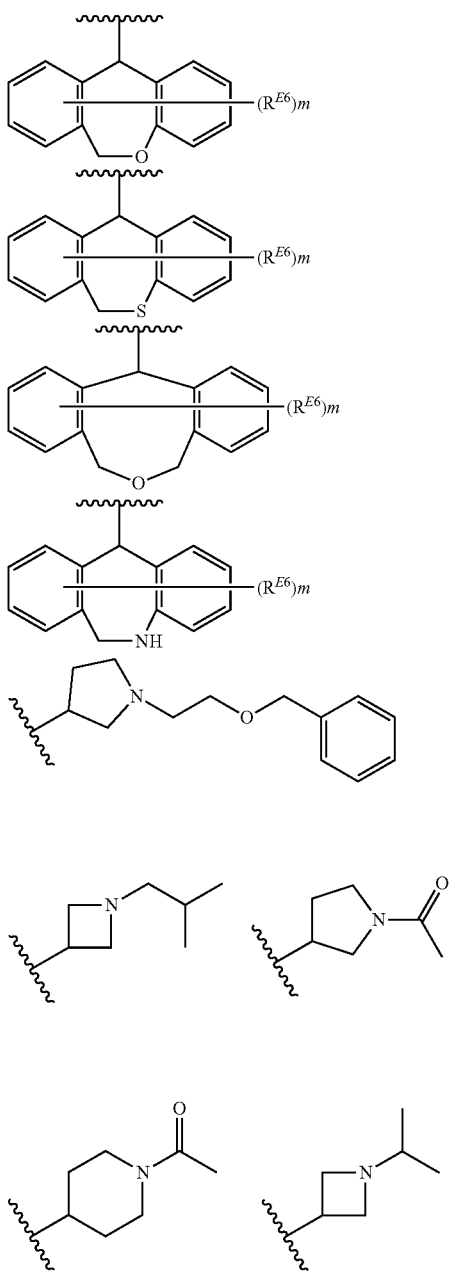

(wherein R^{E6} each independently represents a substituent group selected from Substituent group A, m is an integer of 0 to 7, and when there are a plurality of R^{E6}, the R^{E6} may be the same or different).

Examples of the "heterocyclealkyl optionally substituted with Substituent group A" and "heterocyclealkyl optionally substituted with Substituent group B" include tetrahydropyranyLnethyl, pyridylmethyl, isoxazolylmethyl, 5-methyl-isoxazolylmethyl, 3-methyl-oxadiazolylmethyl, indolylmethyl, benzothiophenylmethyl, 5-chlorobenzothiophenylmethyl, thiazolylmethyl, 2-methyl-thiazolylmethyl, pyrazolylmethyl, 2-methylpyrazolylmethyl, dithiophenylmethyl, tetrazolylinethyl, quinazolylmethyl, and groups shown below:

[Chemical Formula 52]

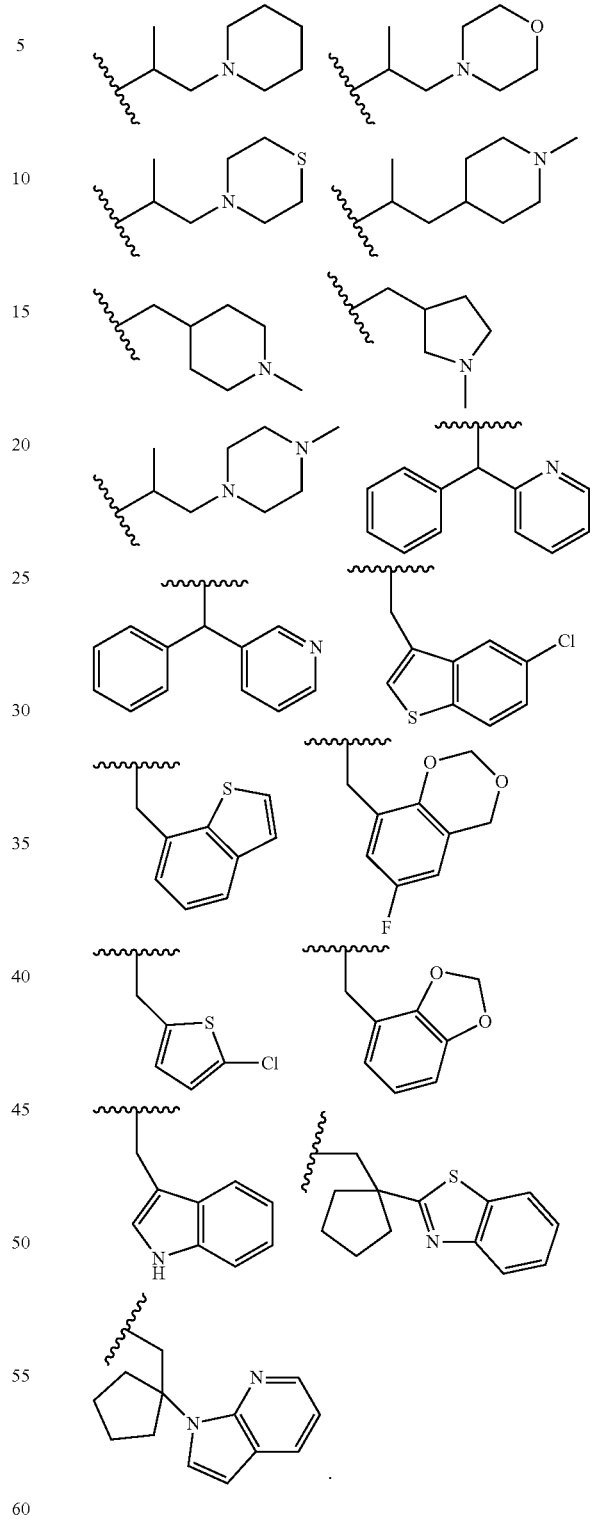

Examples of "heterocycleoxyalkyl optionally substituted with Substituent group A" and "heterocycleoxyalkyl optionally substituted with Substituent group B" include tetrahydropyranyloxymethyl, pyridyloxymethyl, isoxazolyloxymethyl, 5-methyl-isoxazolyloxymethyl, indolyloxymethyl, benzothiophenyloxymethyl, 5-chlorobenzothiophenyloxymethyl, thiazolyloxymethyl, 2-methylthiazolyloxymethyl, pyrazolyloxymethyl, and 2-methylpyrazolyloxymethyl, Examples of "heterocyclecarbonyl optionally substituted with Substituent group A" and "heterocyclecarbonyl optionally substituted with Substituent group B" include tetrahydropyranylcarbonyl, pyridylcarbonyl, isoxazolylearbonyl, 5-methyl-isoxazolylcarbonyl, indolylcarbonyl, benzothiophenylcarbonyl, 5-chlorobenzothiophenylcarbonyl, thiazolylcarbonyl, 2-methylthiazolylcarbonyl, pyrazolylcarbonyl, and 2-methylpyrazolylearbonyl.

Examples of "heterocycleoxy optionally substituted with Substituent group A", and "heterocycleoxy optionally substituted with Substituent group B" include tetrahydropyranyloxy, pyridyloxy, isoxazolyloxy, 5-methyl-isoxazolyloxy, indolyloxy, benzothiophenyloxy, 5-chlorobenzothiophenyloxy, thiazolyloxy, 2-methylthiazolyloxy, pyrazolyloxy, and 2-methylpyrazolyloxy.

Examples of "heterocycleoxycarbonyl optionally substituted with Substituent group A", and "heterocycleoxycarbonyl optionally substituted with Substituent group B" include tetrahydropyranyloxycarbonyl, pyridyloxycarbonyl, isoxazolyloxycarbonyl, 5-methyl-isoxazolyloxycarbonyl, indolyloxycarbonyl, benzothiophenyloxycarbonyl, 5-chlorobenzothiophenyloxycarbonyl, thiazolyloxycarbonyl, 2-methylthiazolyloxycarbonyl, pyrazolyloxycarbonyl, and 2-methylpyrazolyloxycarbonyl.

Examples of "carbocycle optionally substituted with Substituent group B" include cyclopropane, cyclobutane, cyclopentane, cyclohexane, monofluorocyclopropane, difluorocyclopropane, hydroxycyclohexane, cyclopentanone, benzene, 4-chlorobenzene, 2-methylbenzene, naphthalene, fluorene, and suberane.

Examples of "heterocycle optionally substituted with Substituent group B" include azetidine, furan, thiophene, oxazole, aminooxazole, thiazole, morpholine, fluoromorpholine, quinuclidine, pyrrolidine, methylpiperidine, methylpiperazine, tetrahydrofuran, pyridine, hydroxypyridine, pyrimidine, fluoropyrimidine, coumarin, hydroxycoumarin, quinoline, fluoroquinoline, and dihydrodibenzothiepine.

Preferred embodiments of each substituent of Formulae (I), (I'), (I"), and (IA) are shown below: Examples of the compound represented by Formula (I), (I'), (I"), or (IA) or a prodrug thereof or a pharmaceutically acceptable salt thereof, preferably the compound represented by Formula (I), (I"), or (IA) or a pharmaceutically acceptable salt thereof, include all possible combinations of embodiments of each substituent.

$R^1$ is —$Z^X$—C(=O)—O—$R^{X15}$,
—$Z^X$—C(=O)—N($R^{X9}$)($R^{X10}$), or
—$Z^X$—N($R^{X14}$)—C(=O)—O—$R^{X15}$
(wherein, $R^{X9}$, $R^{X14}$, and $R^{X15}$ are each independently a hydrogen atom, alkyl optionally substituted with Substituent group E, alkenyl optionally substituted with Substituent group E, or alkynyl optionally substituted with Substituent group E; $R^{X10}$ is a hydrogen atom, alkyl optionally substituted with Substituent group E, alkenyl optionally substituted with Substituent group E, alkynyl optionally substituted with Substituent group E, or alkyloxy optionally substituted with Substituent group E; $Z^X$ is a single bond or a linear or branched alkylene; and
$R^{X9}$ and $R^{X10}$ may be taken together with an adjacent atom to form a heterocycle).

In another embodiment, $R^1$ is carboxy,
—$Z^X$—C(=O)—N($R^{X9}$)($R^{X0}$), or
—$Z^X$—N($R^{X14}$)—C(=O)—O—$R^{X15}$
(wherein, $R^{X9}$, $R^{X10}$, $R^{X14}$, and $R^{X15}$ are each independently selected from a substituent group consisting of a hydrogen atom, alkyl optionally substituted with Substituent group E, alkenyl optionally substituted with Substituent group E, and alkynyl optionally substituted with Substituent group E; $Z^X$ is a single bond or a linear or branched alkylene; and
$R^{X9}$ and $R^{X10}$ may be taken together with an adjacent atom to form a heterocycle). $R^1$ is preferably carboxy, —C(=O)—N($R^{X9}$)($R^{X10}$), or —N($R^{X14}$)—C(=O)—O—$R^{X15}$. More preferably, $R^1$ is carboxy.

$R^{X9}$, $R^{X10}$, $R^{X14}$, and $R^{X15}$ are preferably, each independently, a hydrogen atom, or alkyl optionally substituted with Substituent group E. More preferably, $R^9$, $R^{X10}$, $R^{X14}$, and $R^{X15}$ are each independently a hydrogen atom or alkyl.

$Z^X$ is preferably a single bond.

Examples of a preferred embodiment of a substituent in "alkyl optionally substituted with Substituent group E", "alkenyl optionally substituted with Substituent group E", and "alkynyl optionally substituted with Substituent group E" include unsubstituted and halogen. More preferably, the substituent is unsubstituted.

Examples of another embodiment of $R^1$ and $R^{1a}$ include carboxy or a bioisostere of carboxy. The "bioisostere" in the present description means a group having chemical and physical similarities resulting in similar biological properties. Thus, the "bioisostere of carboxy" means any group having biological properties similar to the biological properties given by a carboxyl group. Specifically, it means a group that has a relatively similar chemical structure to a carboxyl group and is expected to have substantially equivalent tendencies to a carboxyl group in terms of physical properties such as acidity, water solubility, and/or in vivo kinetics, and has an acidic proton. The acid proton part may form a salt (e.g., an alkali metal salt (e.g., a Na salt)). They are described, for example, in J. Med. Chem. 1992, 35, 1176-1183, J. Med. Chem. 1993, 36, 2485-2493, J. Med. Chem. 1992, 35, 3691-3698, J. Med. Chem. 1995, 38, 617-628, Med. Res. Rev. 1983, 3, 91-118, J. Med. Chem. 2001, 44, 1560-1563, Bioorganic & Medicinal Chemistry Letters, Vol. 4. No. 1, 41-44, 1994, and J. Med. Chem. 2006, 59, 3183-3203. Preferably, it is selected from the group consisting of —$SO_3^-$, —$SO_2N^-$—$R^{13}$, —$PO^-$—($OR^{13}$), —$PO_2^-$—($OR^{13}$), —$N^-$—CO—$R^{13}$, —CO—$N^-$—$OR^{13}$, —CO—NH—$N^-$—$SO_2$—$R^{13}$, —CO—$N^-$—$SO_2$—$R^{13}$, —CO—CH=C(=O)—$R^{13}$, —$N^-$—$SO_2$—$R^{13}$, —CO—$N^-$—$SO_2$—$R^{13}$, —$N^-$—$SO_2$—$R^{13}$, —CO—$N^-$—CO—$R^{13}$, —CO—N—$SO_2$—$R^{13}$, —$N^-$—CO—$R^{15}$ and groups shown below:

[Chemical Formula 53]

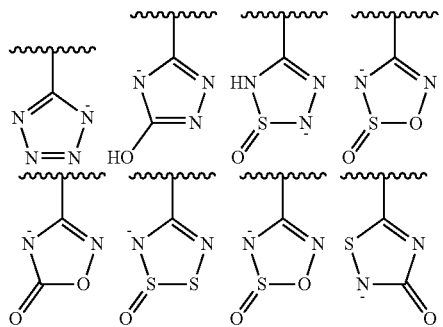

-continued

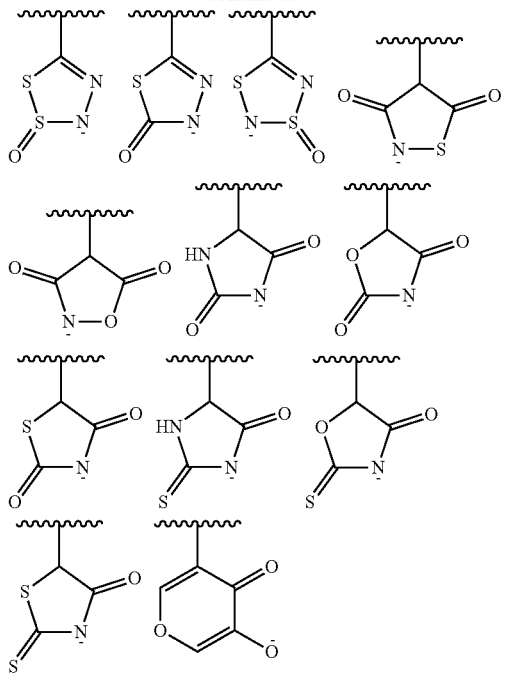

[Chemical Formula 54]

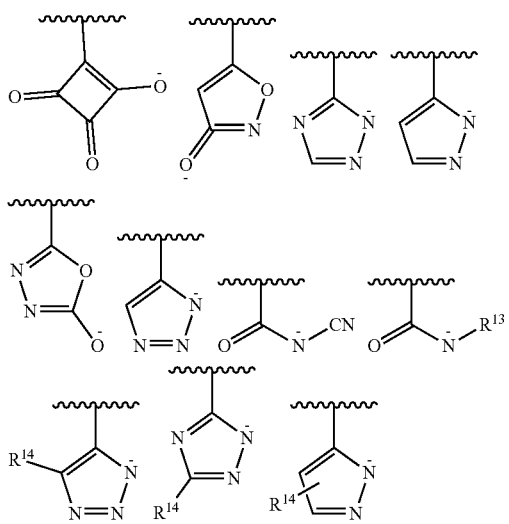

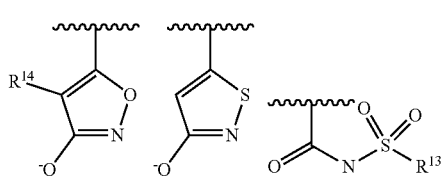

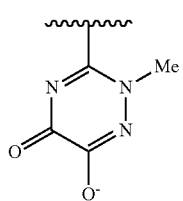

-continued

[Chemical Formula 55]

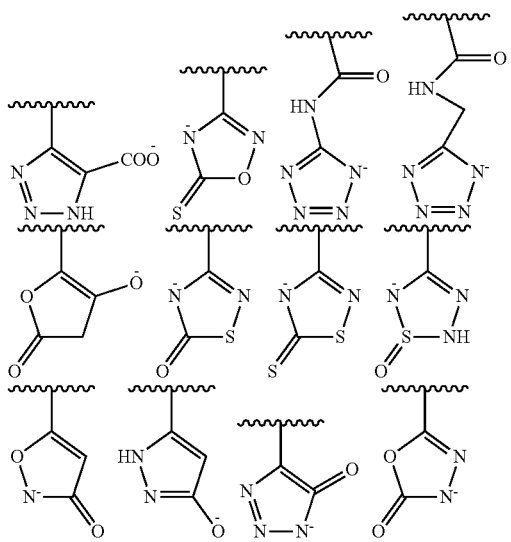

(wherein $R^{13}$ is selected from the group consisting of a hydrogen atom, hydroxy, halogen, alkyl optionally substituted with Substituent group F, alkenyl optionally substituted with Substituent group F, alkynyl optionally substituted with Substituent group F, alkyloxy optionally substituted with Substituent group F, amino optionally substituted with Substituent group A, alkenyloxy, carbocycleoxy optionally substituted with Substituent group A, heterocycleoxy optionally substituted with Substituent group A, cyano, nitro, imino, mercapto, alkylthio, alkylsulfonyl, carbocycleoxy carbocyclic group optionally substituted with Substituent group A, carbocycleoxy heterocyclic group optionally substituted with Substituent group A, and —$CO_2R^{17}$, wherein $R^{17}$ is a hydrogen atom, alkyl or an alkenyl, and $R^{14}$ is an electron withdrawing group). More preferably, it is

[Chemical Formula 56]

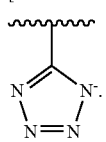

$R^{14}$ is not particularly limited as long as it is an electron-withdrawing group, and preferred examples include fluorine, —$CHF_2$, —$CF_2$, —$CONH_2$, —CN, —C=N—OH, —$SO_2CH_3$, or —$SO_2NH_2$.

$R^2$ is a hydrogen atom, halogen, hydroxy, carboxy, cyano, formyl, alkyl optionally substituted with Substituent group F, alkenyl optionally substituted with Substituent group F, alkynyl optionally substituted with Substituent group F, or alkyloxy optionally substituted with Substituent group F, $R^2$ is preferably a hydrogen atom or alkyl optionally substituted with Substituent group F, more preferably a hydrogen atom or alkyl. More preferably, $R^2$ is a hydrogen atom. Examples of a preferred embodiment of a substituent of "optionally substituted with Substituent group F" in $R^2$ include unsubstituted and halogen. More preferably, the substituent is unsubstituted.

$R^3$ is a hydrogen atom, hydroxy, carboxy, cyano, formyl, alkyl optionally substituted with Substituent group F, alkenyl optionally substituted with Substituent group F, alkynyl optionally substituted with Substituent group F, alkyloxy optionally substituted with Substituent group F, alkenyloxy optionally substituted with Substituent group F, alkylcarbonyl optionally substituted with Substituent group F, alkyloxycarbonyl optionally substituted with Substituent group F, a carbocyclic group optionally substituted with Substituent group A, carbocyclealkyl optionally substituted with Substituent group A, carbocycleoxyalkyl optionally substituted with Substituent group A, carbocyclecarbonyl optionally substituted with Substituent group A, carbocycleoxy optionally substituted with Substituent group A, carbocycleoxyalkyl optionally substituted with Substituent group A, carbocycleoxycarbonyl optionally substituted with Substituent group A, a heterocyclic group optionally substituted with Substituent group A, heterocyclealkyl optionally substituted with Substituent group A, heterocycleoxyalkyl optionally substituted with Substituent group A, heterocyclecarbonyl optionally substituted with Substituent group A, heterocycleoxy optionally substituted with Substituent group A, or heterocycleoxycarbonyl optionally substituted with Substituent group A, —$Z^Z$—N($R^{Z1}$)—$SO_2$—$R^{Z2}$,
—$Z^Z$—N($R^{Z3}$)—C(=O)—$R^{Z4}$,
—$Z^Z$—N($R^{Z3}$)—C(=O)—O—$R^{Z6}$,
—$Z^Z$—C(=O)—N($R^{Z7}$)($R^{Z8}$),
—$Z^Z$—N($R^{Z9}$)($R^{Z10}$),
—$Z^Z$—$SO_2$—$R^{Z1}$, or
—$Z^Z$—N($R^{Z12}$)—O—C(=O)—$R^{13}$ (wherein $R^{Z1}$, $R^{Z3}$, $R^{Z4}$, $R^{Z5}$, $R^{Z6}$, $R^{Z7}$, $R^{Z8}$, $R^{Z9}$, $R^{Z10}$, $R^{Z12}$, and $R^{Z13}$ are each independently selected from a substituent group consisting of a hydrogen atom, alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;

$R^{Z2}$ and $R^{Z11}$ are each independently selected from a substituent group consisting of alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;

$R^{Z7}$ and $R^{Z8}$, and $R^{Z9}$ and $R^{Z10}$ each may be taken together with an adjacent atom to form a heterocycle, and $Z^Z$ is a single bond or a linear or branched alkylene).

$R^3$ is preferably a hydrogen atom, alkyl optionally substituted with Substituent group F, alkenyl optionally substituted with Substituent group F, alkynyl optionally substituted with Substituent group F, a carbocyclic group optionally substituted with Substituent group A, carbocyclealkyl optionally substituted with Substituent group A, carbocycleoxyalkyl optionally substituted with Substituent group A, or heterocyclealkyl optionally substituted with Substituent group A. More preferably, $R^3$ is a hydrogen atom, alkyl, a substituted alkyl (substituent: halogen, carboxy, alkyloxy), an alkenyl, an alkynyl, a carbocyclic group, a substituted carbocyclic group (substituent: halogen), carbocyclealkyl, a substituted carbocyclealkyl (substituent: halogen), carbocycleoxyalkyl, a substituted carbocycleoxyalkyl (substituent: halogen), heterocyclealkyl, or a substituted heterocyclealkyl (substituent: alkyl).

$R^3$ is particularly preferably C1-C6 alkyl, substituted C1-C6 alkyl (substituent: halogen, carboxy, alkyloxy), a 3- to 6-membered carbocyclic group, a substituted 3- to 6-membered carbocyclic group (substituent: halogen, alkyloxy), a 3- to 6-membered carbocyclealkyl, a 3- to 6-membered substituted carbocyclealkyl (substituent on the carbocycle: halogen, alkyloxy), a 3- to 6-membered heterocyclealkyl, or a substituted 3- to 6-membered heterocyclealkyl (substituent on the heterocycle: alkyl).

$R^3$ is particularly preferably a group shown below:

[Chemical Formula 57]

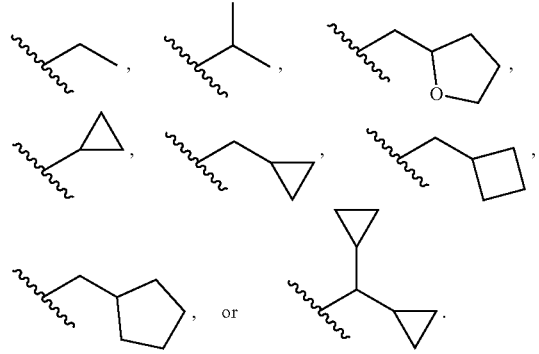

Examples of a preferred substituent of "optionally substituted with Substituent group A" in $R^3$ include unsubstituted, halogen, carboxy, alkyl, and alkyloxy.

Examples of a preferred embodiment of a substituent of "optionally substituted with Substituent group F" in $R^3$ include unsubstituted, halogen, carboxy, and alkyloxy.

In another preferred embodiment, $R^3$ is taken together with an adjacent nitrogen atom of $A^2$ and $R^3$ in Formula (I) to form a heterocycle optionally substituted with Substituent group B. The heterocycle may form a condensed ring and/or a spiro ring and/or a bridged structure. "Taken together with an adjacent nitrogen atom of $A^2$ and $R^3$ in Formula (I) to form a heterocycle optionally substituted with Substituent group B" means Formula (I') shown below:

[Chemical Formula 58]

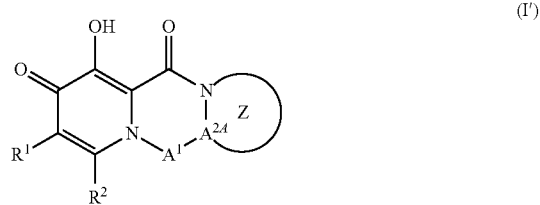

(I')

(wherein $A^{2A}$ is N, $CR^6$, or $CR^{11}$; Ring Z is a heterocycle optionally substituted with Substituent group B; and $R^1$, $R^2$, and $A^1$ are the same as defined in Item 1), and the "heterocycle optionally substituted with Substituent group B" is a heterocycle optionally substituted at any position with one or two or more identical or different substituents selected from Substituent group B. The heterocycle is preferably a 5- to 12-membered ring. More preferably, the heterocycle is a 5- to 8-membered ring. The heterocycle may form a condensed ring and/or a spiro ring and/or a bridged structure. In other words, the heterocycle includes the cases when the ring in Formula (I') is further condensed, when the ring forms a spiro ring, and when the ring, the condensed ring and/or the spiro ring has a bridged structure. It indicates that Substituent group B may also be attached to any of a ring in Formula (I) described above, a ring condensed to the ring, a ring forming a spiro ring, or a bridged structure part of the ring. The bridged structure is preferably alkylene which may contain one or more heteroatoms selected from O, N, and S at any position, or an alkenylene which may contain one or more heteroatoms selected from O, N, and 8 at any position. A preferred embodiment of Ring Z is a 5- to 8-membered non-aromatic heterocyclic group optionally substituted with Substituent group B. A more preferred embodiment of Ring Z is a 5- to 8-membered non-aromatic heterocycle comprising one nitrogen atom and one oxygen atom optionally substituted with Substituent group B or a 5- to 8-membered non-aromatic heterocycle comprising two nitrogen atoms optionally substituted with Substituent group B. Examples of a still more preferred embodiment include morpholine, 1,3-oxazinane, hexahydropyridazine, imidazolidine, 1,3-diazepan, hexahydropyrimidine, and hexahydropyrazine.

Examples of another preferred embodiment of $R^3$ include the cases when $A^1$ is $CR^5R^6$ and $A^2$ is $NR^7$, $R^3$ and $R^7$ are taken together with an adjacent atom to form a heterocycle optionally substituted with Substituent group B;

when $A^1$ is $NR^7$ and $A^2$ is $CR^5R^6$, then $R^3$ and $R^6$ are taken together with an adjacent atom to form a heterocycle optionally substituted with Substituent group B; and when $A^1$ is $CR^8R^9$ and $A^2$ is $CR^{10}R^{11}$, then $R^3$ and $R^{11}$ are taken together with an adjacent atom to form a heterocycle optionally substituted with Substituent group B. Specifically, examples thereof include the formula shown below:

[Chemical Formula 59]

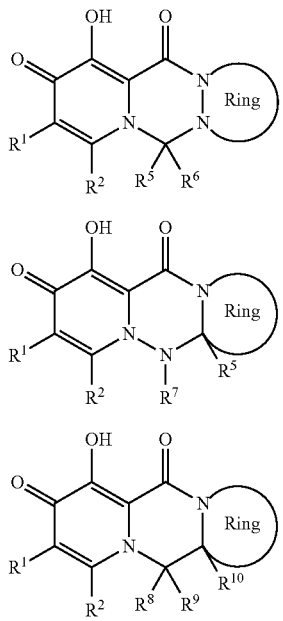

(I-7')

(I-10')

(I-13')

(wherein the ring is a heterocycle optionally substituted with Substituent group B, the heterocycle may form a condensed ring and/or a spiro ring and/or a bridged structure, and $R^1$, $R^2$, $R^5$, $R^6$, $R^7$, $R^8$, $R^9$, and $R^{10}$ are the same as defined in Item 1). A preferred embodiment of the ring in Formula (I-7') is a 5- to 8-membered non-aromatic heterocycle comprising two nitrogen atoms optionally substituted with Substituent group B. More preferred examples include pyrazolidine, hexahydropyridazine, and 1,2-diazepane. A preferred embodiment of the rings in formulae (I-10') and (I-13') is a 5- to 8-membered non-aromatic heterocycle comprising one nitrogen atom and one oxygen atom optionally substituted with Substituent group B or a 5- to 8-membered non-aromatic heterocycle comprising two nitrogen atoms optionally substituted with Substituent group B. More preferred examples include 1,3-oxazinane, morpholine, imidazolidine, 1,3-diazepane, hexahydropyrimidine, and hexahydropyrazine.

$R^5$, $R^6$, $R^7$, $R^8$, $R^9$, $R^{10}$, and $R^{11}$ are each independently a hydrogen atom, carboxy, cyano, alkyl optionally substituted with Substituent group F, alkenyl optionally substituted with Substituent group F, alkynyl optionally substituted with Substituent group F, alkylcarbonyl optionally substituted with Substituent group F, alkyloxycarbonyl optionally substituted with Substituent group F, a carbocyclic group optionally substituted with Substituent group B, carbocyclealkyl optionally substituted with Substituent group B, carbocycleoxyalkyl optionally substituted with Substituent group B, carbocyclecarbonyl optionally substituted with Substituent group B, carbocycleoxycarbonyl optionally substituted with Substituent group B, a heterocyclic group optionally substituted with Substituent group B, heterocyclealkyl optionally substituted with Substituent group B, heterocycleoxyalkyl optionally substituted with Substituent group B, heterocyclecarbonyl optionally substituted with Substituent group B, or heterocycleoxycarbonyl optionally substituted with Substituent group B, —$Z^V$—S—$R^{V1}$,
—$Z^V$—S(=O)—$R^{V1}$,
—$Z^V$—SO$_2$$R^{V3}$,
—C(=O)—C(=O)—$R^{V4}$,
—C(=O)—N($R^{V5}$)($R^{V6}$),
—$Z^V$—N($R^{V7}$)—C(=O)—O—$R^{V8}$, or
—$Z^V$—N($R^{V9}$)—C(=O)—$R^{V10}$ (wherein $R^{V1}$, $R^{V4}$, $R^{V5}$, $R^{V6}$, $R^{V7}$, $R^{V8}$, $R^{V9}$, and $R_{V10}$ are each independently selected from a substituent group consisting of a hydrogen atom, alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;

$R^{V2}$ and $R^{V3}$ are each independently selected from a substituent group consisting of alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;

$R^{V5}$ and $R^{V6}$ may be taken together with an adjacent atom to form a heterocycle, and $Z^V$ is a single bond or a linear or branched alkylene);

$R^5$ and $R^6$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure;

$R^8$ and $R^9$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure:

$R^{10}$ and $R^{11}$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure.

$R^5$, $R^6$, $R^7$, $R^8$, $R^9$, $R^{10}$, and $R^{11}$ are preferably, each independently, each independently, a hydrogen atom, alkyl optionally substituted with Substituent group F, a carbocyclic group optionally substituted with Substituent group B, carbocyclealkyl optionally substituted with Substituent group B, a heterocyclic group optionally substituted with Substituent group B, or heterocyclealkyl optionally substituted with Substituent group B. More preferably, $R^5$, $R^6$, $R^7$, $R^8$, $R^9$, $R^{10}$, and $R^{11}$ are, each independently, a hydrogen atom, alkyl, a substituted alkyl (substituent alkylthio, a carbocyclic group, a heterocyclic group, carbocyclealkylthio), a carbocyclic group, a substituted carbocyclic group (substituent: halogen, alkyl), carbocyclealkyl, a substituted carbocyclealkyl (substituent halogen, alkylthio, a carbocyclic group, carbocyclealkylthio), a heterocyclic group, a substituted heterocyclic group (substituent halogen), heterocyclealkyl, or a substituted heterocyclealkyl (substituent: a carbocyclic group substituted with alkyloxy).

Preferred embodiments of a substituent in "optionally substituted with Substituent group F" in $R^5$, $R^6$, $R^7$, $R^8$, $R^9$, $R^{10}$, and $R^{11}$ include unsubstituted, halogen, alkylthio, alkyloxy, a carbocyclic group, a heterocyclic group, and carbocyclealkylthio. Preferred embodiments of a substituent in the "optionally substituted with Substituent group B" in $R^5$, $R^6$, $R^7$, $R^8$, $R^9$, $R^{10}$, and $R^{11}$ include unsubstituted, halogen, alkyl, alkylthio, a carbocyclic group, carbocyclealkylthio, and a carbocyclic group optionally substituted with alkyloxy.

Preferred embodiments of a substituent in $R^1$ include unsubstituted, halogen, cyano, hydroxy, carboxy, oxo, alkyl, halogenoalkyl, hydroxyalkyl, a carbocyclic group, a heterocyclic group, an oxo-substituted heterocyclic group, carbocycleoxyalkyl, heterocycleoxyalkyl, heterocyclealkyloxyalkyl, alkyloxyalkyl, alkylcarbonyl, alkyloxycarbonyl, alkylaminocarbonyl, alkylsulfonyl, and the like. More preferred embodiments of the substituent include unsubstituted, a hydrogen atom, halogeno, alkyl, and halogenoalkyl. A still more preferred embodiment of the substituent is unsubstituted or alkyl.

Preferred embodiments of a substituent in $R^2$ are unsubstituted, halogen, cyano, alkyl, halogenoalkyl, alkyloxy, alkylthio, carbocyclealkyloxy, carbocycleoxyalkyl, heterocyclealkyloxy, heterocycleoxyalkyl, halogenoalkyloxy, and alkyloxyalkyl. Examples of more preferred embodiments of the substituent include unsubstituted, and halogen. A still more preferred embodiment of the substituent is unsubstituted.

Preferred embodiments of a substituent in $R^3$ are unsubstituted, halogen, hydroxy, carboxy, oxo, alkyl, halogenoalkyl, alkyloxy, alkylthio, hydroxyalkyl, a carbocyclic group, a heterocyclic group, an oxo-substituted heterocyclic group, carbocyclealkyloxy, carbocyclealkylthio, heterocyclealkyloxy, halogenoalkyloxy, alkyloxyalkyloxy, alkylcarbonyl, alkylcarbonyloxy, alkyloxycarbonyl, alkyloxycarbonyloxy, alkylamino, alkylcarbonylamino, halogenoalkylcarbonylamino, alkylaminocarbonyl, alkylsulfonyl, alkylsulfinyl, and alkylsulfonylamino. More preferred embodiments of the substituent are unsubstituted, halogen, carboxy, alkyl, halogenoalkyl, and alkyloxy.

Examples of a preferred embodiment of a substituent in $R^5$, $R^6$, $R^7$, $R^8$, $R^9$, $R^{10}$, and $R^{11}$ include unsubstituted, halogen, oxo, alkyl, halogenoalkyl, alkyloxy, alkylthio, hydroxyalkyl, a carbocyclic group, a heterocyclic group, an oxo-substituted heterocyclic group, carbocyclealkyloxy, carbocyclealkylthio, heterocyclealkyloxy, halogenoalkyloxy, alkyloxyalkyloxy, alkylcarbonyl, alkylcarbonyloxy, alkyloxycarbonyl, alkyloxycarbonyloxy, alkylcarbonylamino, halogenoalkylcarbonylamino, alkylaminocarbonyl, alkylsulfonyl, and alkylsulfonylamino. Examples of a more preferred embodiment of a substituent include unsubstituted, halogen, alkyl, halogenoalkyl, alkyloxy, alkylthio, a carbocyclic group, carbocyclealkylthio, and a carbocyclic group optionally substituted with alkyloxy.

Examples of a preferred embodiment of 1) when $A^1$ is $CR^5R^6$ and $A^2$ is $NR^7$ include the case in which $R^5$, $R^6$, and $R^7$ are each independently a hydrogen atom, alkyl optionally substituted with Substituent group F, a carbocyclic group optionally substituted with Substituent group A, or carbocyclealkyl optionally substituted with Substituent group A, or the case in which $R^5$ and $R^6$ are each independently a hydrogen atom, alkyl optionally substituted with Substituent group F, a carbocyclic group optionally substituted with Substituent group A, or carbocyclealkyl optionally substituted with Substituent group A, and $R^3$ and $R^7$ are taken together with an adjacent atom to form a heterocycle optionally substituted with Substituent group B.

Examples of a preferred embodiment of 2) when $A^1$ is $NR^7$ and $A^2$ is $CR^5R^6$ include the case in which $R^5$, $R^6$, and $R^7$ are each independently a hydrogen atom, alkyl optionally substituted with Substituent group F, a carbocyclic group optionally substituted with Substituent group A, carbocyclealkyl optionally substituted with Substituent group A, a heterocyclic group optionally substituted with Substituent group A, or heterocyclealkyl optionally substituted with Substituent group A; or the case in which $R^5$ and $R^7$ are each independently a hydrogen atom, alkyl optionally substituted with Substituent group F, a carbocyclic group optionally substituted with Substituent group A, carbocyclealkyl optionally substituted with Substituent group A, a heterocyclic group optionally substituted with Substituent group A, or heterocyclealkyl optionally substituted with Substituent group A, and $R^3$ and $R^6$ are taken together with an adjacent atom to form a heterocycle optionally substituted with Substituent group B.

Examples of a more preferred embodiment include the case in which $R^6$ is a hydrogen atom, alkyl optionally substituted with Substituent group F, a carbocyclic group optionally substituted with Substituent group A, carbocyclealkyl optionally substituted with Substituent group A, a heterocyclic group optionally substituted with Substituent group A, or heterocyclealkyl optionally substituted with Substituent group A, and $R^6$ and $R^7$ are each independently a hydrogen atom or alkyl optionally substituted with Substituent group F; and the case in which $R^6$ is a hydrogen atom, alkyl optionally substituted with Substituent group F, a carbocyclic group optionally substituted with Substituent group A, carbocyclealkyl optionally substituted with Substituent group A, a heterocyclic group optionally substituted with Substituent group A, or heterocyclealkyl optionally substituted with Substituent group A, $R^7$ is a hydrogen atom, and $R^3$ and $R^6$ are taken together with an adjacent atom to form a heterocycle optionally substituted with Substituent group B.

Examples of a still more preferred embodiment include the case in which $R^5$ is a hydrogen atom, alkyl optionally substituted with Substituent group F, a carbocyclic group optionally substituted with Substituent group A, carbocyclealkyl optionally substituted with Substituent group A, a heterocyclic group optionally substituted with Substituent group A, or heterocyclealkyl optionally substituted with Substituent group A, and $R^6$ and $R^7$ are each independently a hydrogen atom or alkyl optionally substituted with Substituent group F.

Examples of a preferred embodiment of 3) when $A^1$ is $CR^8R^9$ and $A^2$ is $CR^{10}R^{11}$ include
the case in which $R^8$, $R^9$, $R^{10}$ and $R^{11}$ are each independently a hydrogen atom, alkyl optionally substituted with Substituent group F, a carbocyclic group optionally substituted with Substituent group A, carbocyclealkyl optionally substituted with Substituent group A, a heterocyclic group optionally substituted with Substituent group A, or heterocyclealkyl optionally substituted with Substituent group A; or the case in which $R^8$, $R^9$, and $R^{10}$ are each independently a hydrogen atom, alkyl optionally substituted with Substituent group F, a carbocyclic group optionally substituted with Substituent group A, carbocyclealkyl optionally substituted with Substituent group A, a heterocyclic group optionally substituted with Substituent group A, or heterocyclealkyl optionally substituted with Substituent group A, and $R^3$ and $R^{11}$ are taken together with an adjacent atom to form a heterocycle optionally substituted with Substituent group B.

Examples of a more preferred embodiment include the case in which $R^8$, $R^9$, $R^{10}$ and $R^{11}$ are each independently a hydrogen atom, alkyl optionally substituted with Substituent group F, a carbocyclic group optionally substituted with Substituent group A, carbocyclealkyl optionally substituted with Substituent group A, a heterocyclic group optionally substituted with Substituent group A, or heterocyclealkyl optionally substituted with Substituent group A.

Examples of a still more preferred embodiment include the case in which $R^8$ and $R^9$ are each independently a hydrogen atom, alkyl optionally substituted with Substituent group F, carbocyclealkyl optionally substituted with Substituent group A, a heterocyclic group optionally substituted with Substituent group A, or heterocyclealkyl optionally substituted with Substituent group A, and $R^{10}$ and $R^{11}$ are each a hydrogen atom.

It is more preferred when either $A^1$ or $A^2$ is $CR^5R^6$ and the other is $NR^7$, when $A^1$ is $NR^7$ and $A^2$ is $CR^5R^6$.

When either $A^1$ or $A^2$ is $CR^5R^6$, and the other is $NR^7$, it is preferred that at least one of $R^5$ or $R^6$ is hydrogen. In a more preferred embodiment, $R^5$ is a hydrogen atom, and $R^6$ is a hydrogen atom. In this case, $R^7$ is not a hydrogen atom.

Preferred embodiments of $R^7$ are alkyl optionally substituted with Substituent group F, a carbocyclic group optionally substituted with Substituent group A, carbocyclealkyl optionally substituted with Substituent group A, a heterocyclic group optionally substituted with Substituent group A, and heterocyclealkyl optionally substituted with Substituent group A.

More preferred embodiments of $R^7$ are alkyl, substituted alkyl (substituent: a carbocyclic group), a carbocyclic group, a substituted carbocyclic group (substituent: halogen, alkyl), carbocyclealkyl, substituted carbocyclealkyl (substituent: halogen, alkyl, a carbocyclic group), a heterocyclic group, a substituted heterocyclic group (substituent: halogen), heterocyclealkyl, and substituted heterocyclealkyl (substituent: a carbocyclic group optionally substituted with alkyloxy). Still more preferred embodiments are a carbocyclic group, a heterocyclic group, carbocyclealkyl, and substituted carbocyclealkyl (substituent: a carbocyclic group).

Examples of another preferred embodiment of $R^7$ include benzyl, benzhydryl, 2-fluorobenzyl, 4-fluorobenzyl, p-methoxybenzyl, m-phenylbenzyl, p-phenylbenzyl, and groups shown below:

[Chemical Formula 60]

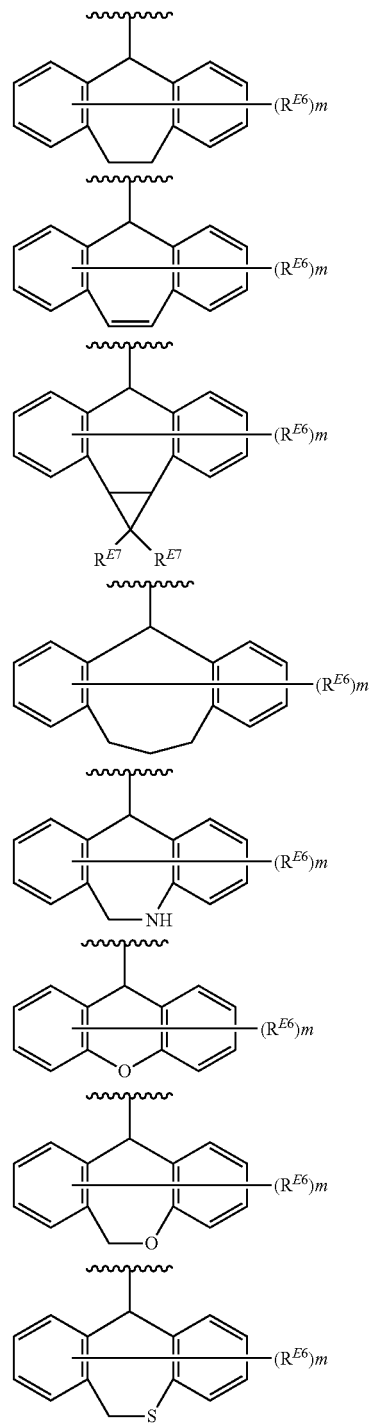

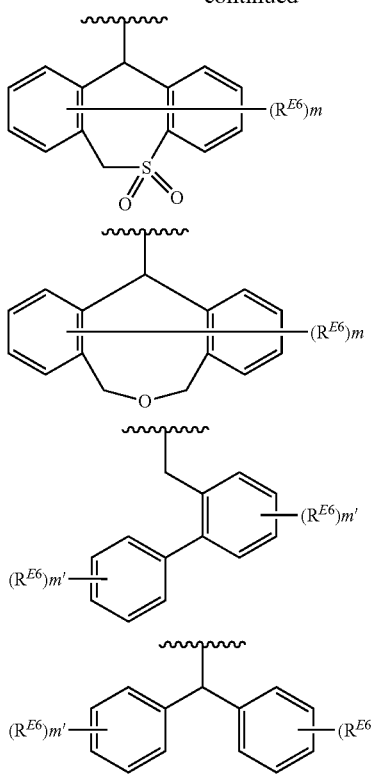

(wherein $R^{E6}$ are each independently a group selected from Substituent group A, and $R^{E7}$ are each independently a hydrogen atom, halogen, or alkyl:

m are each independently an integer of 0 to 7, m' are each independently an integer of 0 to 4, and Substituent group A is the same as defined above).

Examples of another preferred embodiment of $R^7$ include benzyl, benzhydryl, 2-fluorobenzyl, 4-fluorobenzyl, p-methoxybenzyl, m-phenylbenzyl, p-phenylbenzyl, and groups shown below:

[Chemical Formula 61]

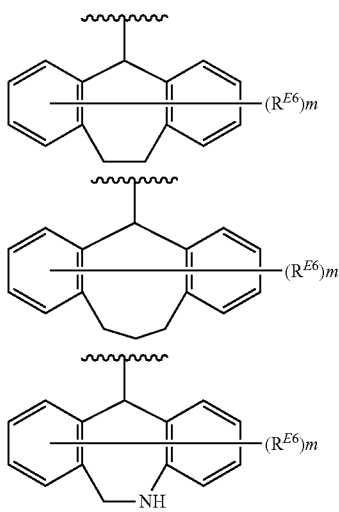

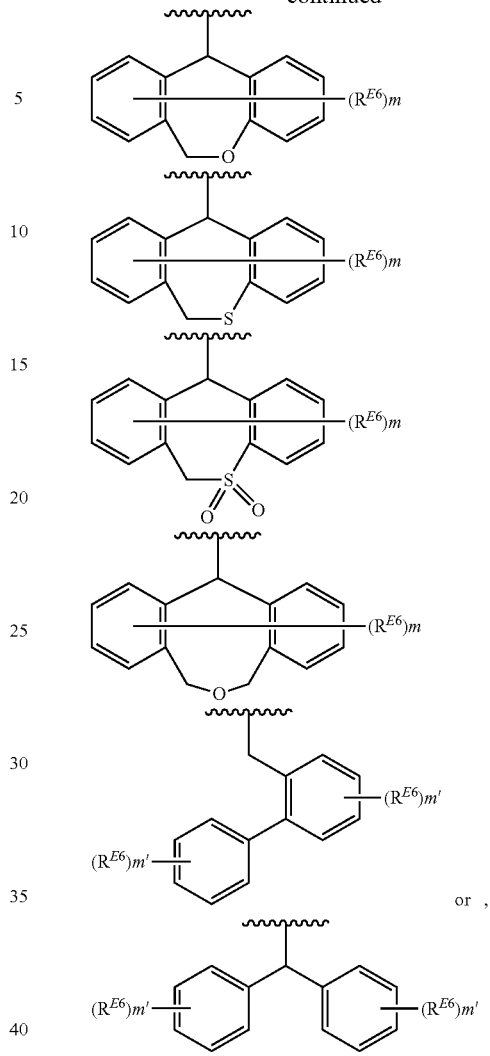

(wherein $R^{E6}$ are each independently a group selected from Substituent group A, and Substituent group A is the same as defined above, m is an integer of 0 to 4, m' are each independently an integer of 0 to 4).

More preferred embodiments of $R^7$ are benzyl, benzhydryl, 2-fluorobenzyl, 4-fluorobenzyl, p-methoxybenzyl, m-phenylbenzyl, p-phenylbenzyl, and groups shown below:

[Chemical Formula 62]

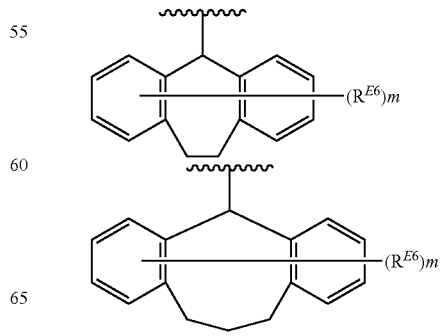

-continued

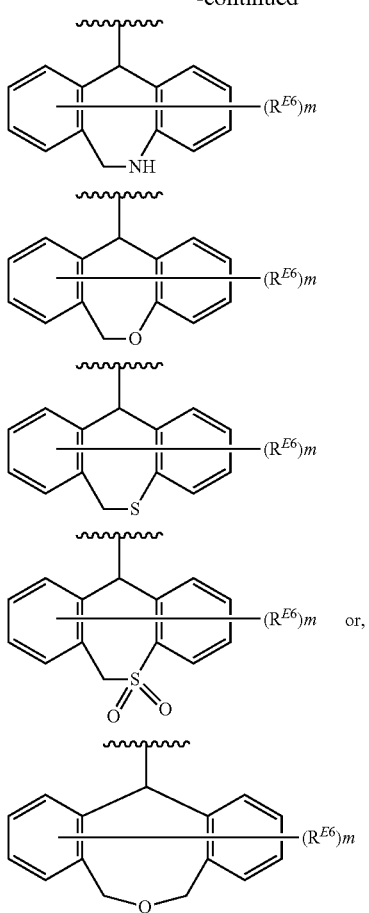

(wherein $R^{E6}$ are each independently a group selected from Substituent group A, and Substituent group A is the same as defined above, m is an integer of: 0 to 4).

Another preferred embodiments of $R^7$ is a group shown below:

[Chemical Formula 63]

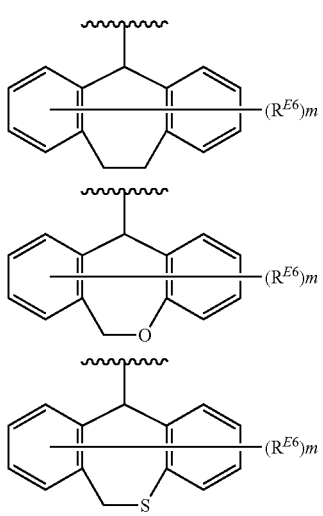

-continued

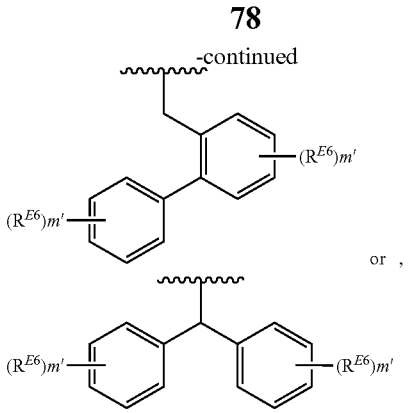

(wherein $R^{E6}$ are each independently a group selected from Substituent group A, and Substituent group A is the same as defined above, m is an integer of 0 to 4, m' are each independently an integer of 0 to 4).

Particularly preferred embodiments of $R^7$ are benzyl, benzhydryl, m-phenylbenzyl, p-phenylbenzyl, and groups shown below:

[Chemical Formula 64]

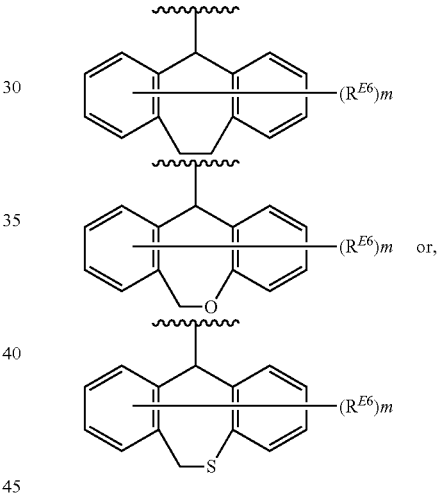

(wherein $R^{E6}$ are each independently a group selected from Substituent group A, and Substituent group A is the same as defined above, m is an integer of 0 to 4).

Another preferred embodiment of $R^7$ is a group shown below:

[Chemical Formula 65]

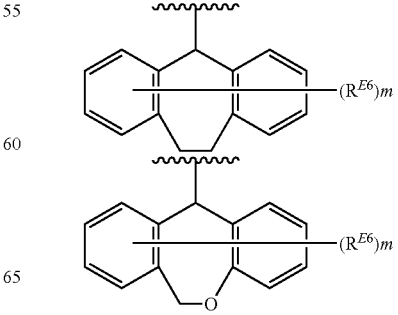

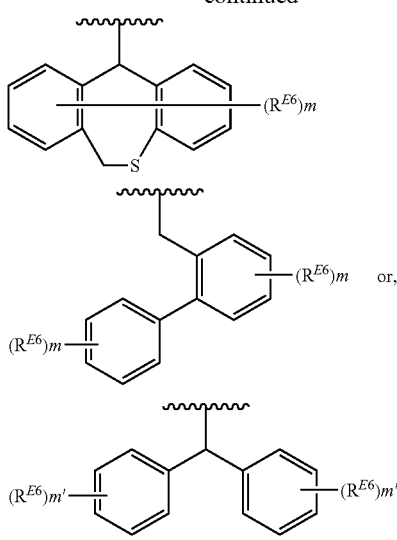

(wherein $R^{E6}$ are each independently a group selected from Substituent group A, and Substituent group A is the same as defined above, m is an integer of 0 to 4, m' are each independently an integer of 0 to 4).

When $A^1$ is $CR^8R^9$, and $A^2$ is $CR^{10}R^{11}$, it is preferable that $R^9$ and $R^{11}$ are hydrogen. In a preferred embodiment of $R^7$ and $R^{10}$, any one of them is hydrogen. When $R^9$ and $R^{11}$ are hydrogen and any one of $R^8$ and $R^{10}$ is hydrogen, a preferred embodiment of the other of $R^8$ and $R^{10}$ is a carbocyclic group optionally substituted with Substituent group A, carbocyclealkyl optionally substituted with Substituent group A, a heterocyclic group optionally substituted with Substituent group A, and heterocyclealkyl optionally substituted with Substituent group A.

A more preferred embodiment is alkyl, cycloalkyl, cycloalkenyl, aryl, a non-aromatic condensed carbocyclic group, heteroaryl, a non-aromatic heterocyclic group, a bicyclic condensed heterocyclic group, a tricyclic condensed heterocyclic group, alkyl substituted with one or two carbocyclic groups, or alkyl substituted with one or two heterocyclic groups.

When any one of $R^8$ and $R^{10}$ is hydrogen, a preferred embodiment of the other of $R^8$ and $R^{10}$ is benzyl, benzhydryl, 2-fluorobenzyl, 4-fluorobenzyl, p-methoxybenzyl, m-phenylbenzyl, p-phenylbenzyl, and groups shown below:

[Chemical Formula 66]

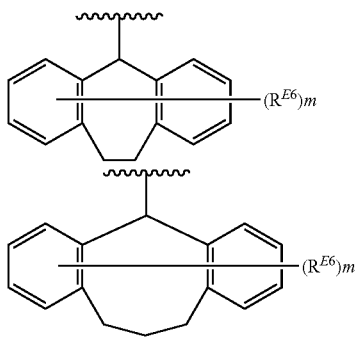

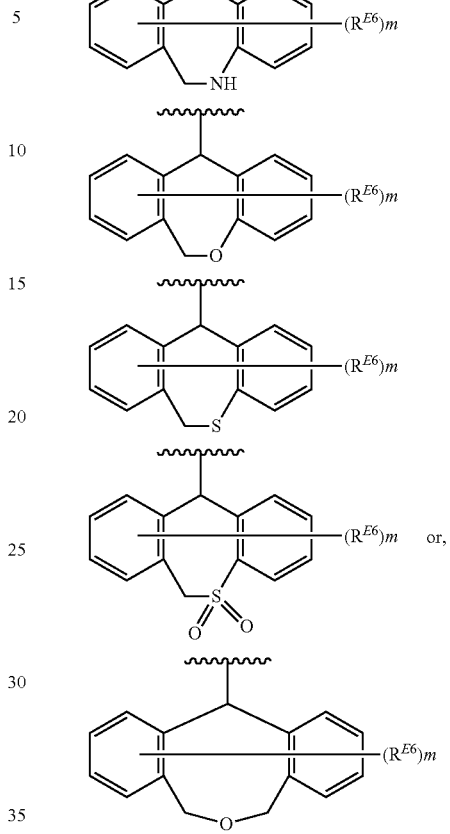

(wherein $R^{E8}$ are each independently a group selected from Substituent group A, and Substituent group A is the same as defined above, m is an integer of 0 to 7).

When any one of $R^8$ and $R^{10}$ is hydrogen, another preferred embodiment of the other of $R^8$ and $R^{10}$ is group shown below:

[Chemical Formula 67]

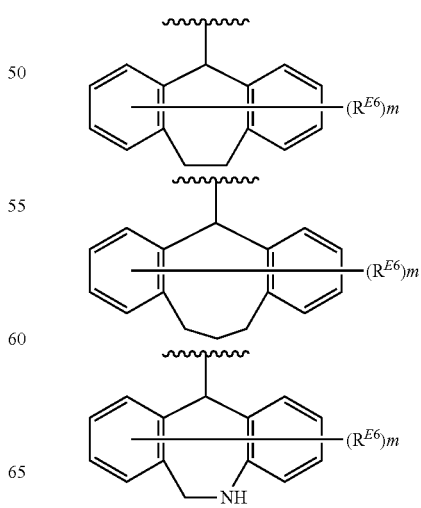

-continued

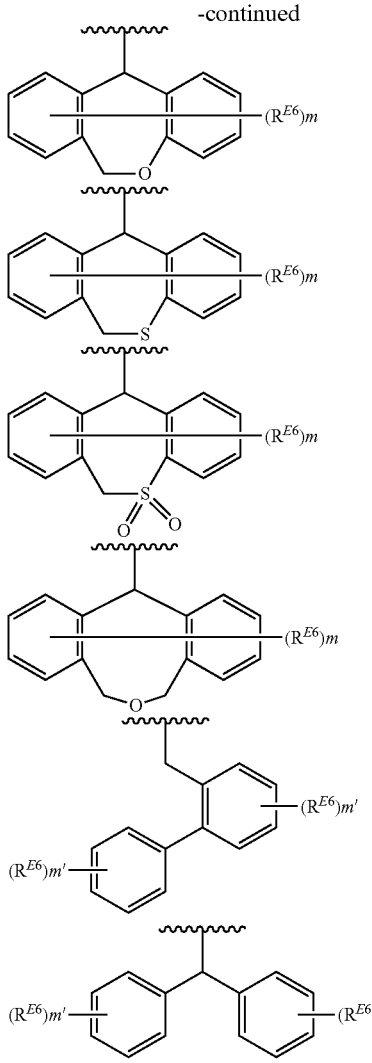

(wherein $R^{E6}$ are each independently a group selected from Substituent group A, and Substituent group A is the same as defined above, m is an integer of 0 to 4, m' are each independently an integer of 0 to 4).

When any one of $R^8$ and $R^{10}$ is hydrogen, a more preferred embodiment of the other of $R^8$ and $R^{10}$ is benzyl, benzhydryl, m-phenylbenzyl, p-phenylbenzyl, and a group shown below:

[Chemical Formula 68]

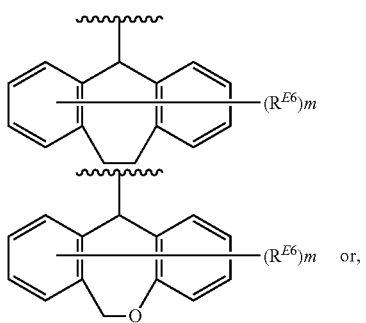 or,

-continued

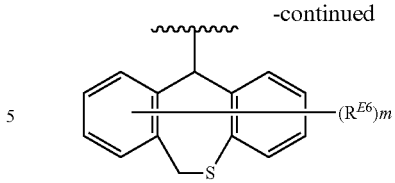

(wherein $R^{11}$ are each independently a group selected from Substituent group A, and Substituent group A is the same as defined above, m is an integer of 0 to 7).

When any one of $R^8$ and $R^{10}$ is hydrogen, another preferred embodiment of the other of $R^8$ and $R^{10}$ is a group shown below:

[Chemical Formula 69]

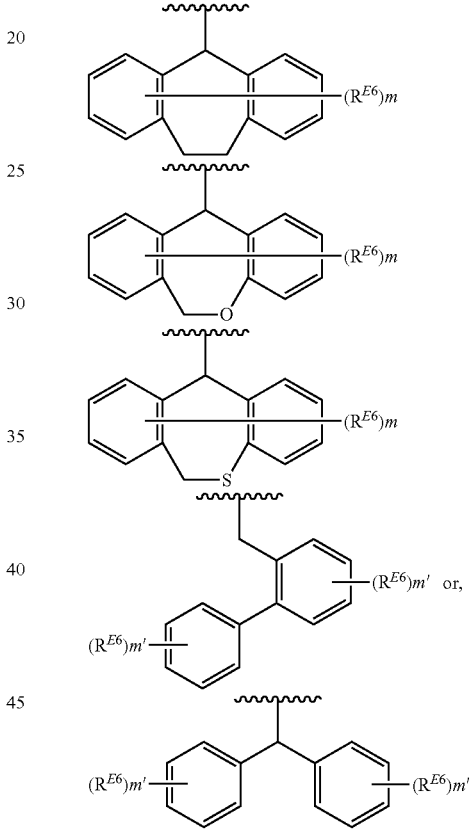

(wherein $R^{E6}$ are each independently a group selected from Substituent group A, and Substituent group A is the same as defined above, m is an integer of 0 to 4, m' are each independently an integer of 0 to 4).

Preferred examples of $R^{E6}$ each independently include halogen, oxo, alkyl, halogenoalkyl, alkyloxy, and halogenoalkyloxy.

More preferred examples of $R^{E6}$ each independently include halogen, alkyl, and alkyloxy.

Still more preferred examples of $R^{E6}$ include a fluorine atom, a chlorine atom, a bromine atom, cyano, methyl, hydroxymethyl, isopropyl, methoxy, trifluoromethyl, oxo, and carboxy.

A preferred embodiment of m is an integer of 0 to 6, more preferably an integer of 0 to 4, still more preferably an integer of 0 to 2.

Examples of another preferred embodiment of the compound represented by Formula (I) or a pharmaceutically acceptable salt thereof are illustrated bellow.

A compound represented by, a compound represented by Formula (IA) or a pharmaceutically acceptable salt thereof:

[Chemical Formula 70]

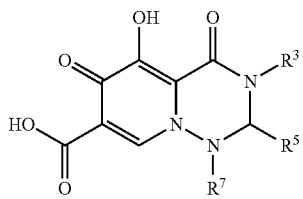
(IA)

(wherein each symbol is the same as defined above).

In a preferred embodiment of Formula (IA), $R^3$ is C1-C6 alkyl, substituted C1-C6 alkyl (substituent: halogen, carboxy, alkyloxy), a 3- to 6-membered carbocyclic group, a substituted 3- to 6-membered carbocyclic group (substituent: halogen, alkyloxy), 3- to 6-membered carbocyclealkyl, 3- to 6-membered substituted carbocyclealkyl (substituent on the carbocycle: halogen, alkyloxy), 3- to 6-membered heterocyclealkyl, or substituted 3- to 6-membered heterocyclealkyl (substituent on the heterocycle: alkyl).

$R^5$ is a hydrogen atom; and $R^7$ is a group shown below:

[Chemical Formula 71]

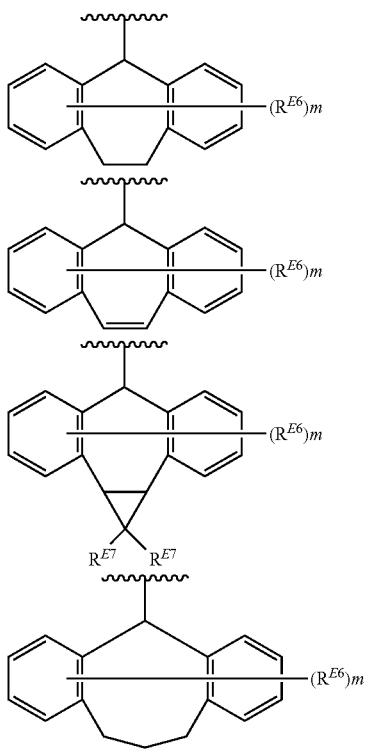

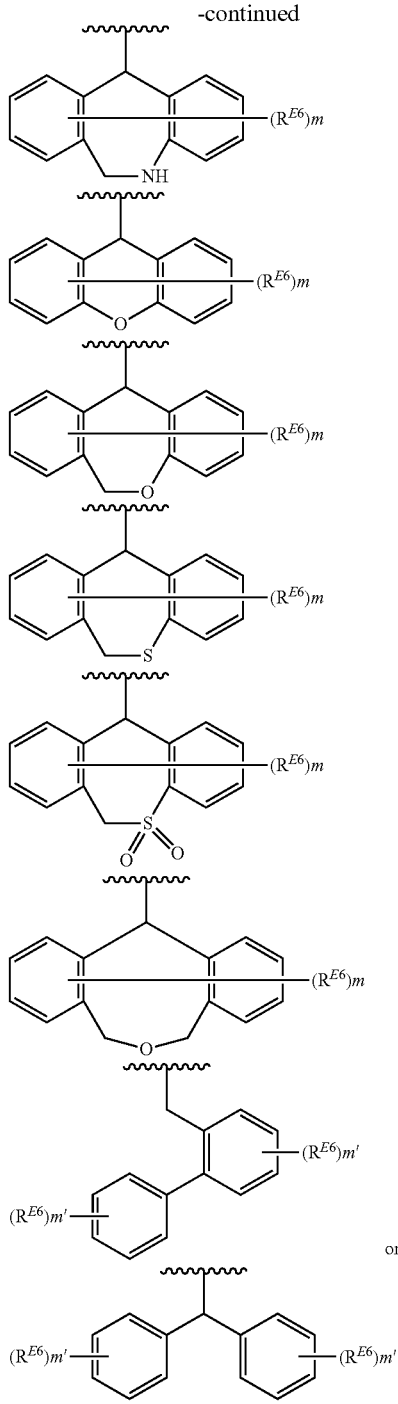

(wherein $R^{E6}$ are each independently a group selected from Substituent group A (preferably, halogen, alkyl, or phenyl); $R^{E7}$ are each independently a hydrogen atom or halogen; m are each independently an integer of 0 to 4; and m' are each independently an integer of 0 to 4).

In another preferred embodiment of Formula (IA), $R^3$ is C1-C6 alkyl, C1-C6 haloalkyl, a 3- to 6-membered carbocyclic group, a substituted 3- to 6-membered carbocyclic group (substituent: halogen, alkyloxy), 3- to 6-membered carbocyclemethyl, substituted 3- to 6-membered carbocyclemethyl (substituent on the carbocycle: halogen, alkyloxy), 3- to 6-membered heterocyclealkyl, or substituted 3- to 6-membered heterocyclemethyl (substituent on the heterocycle: alkyl);

$R^5$ is a hydrogen atom; and $R^7$ is a group shown below:

[Chemical Formula 72]

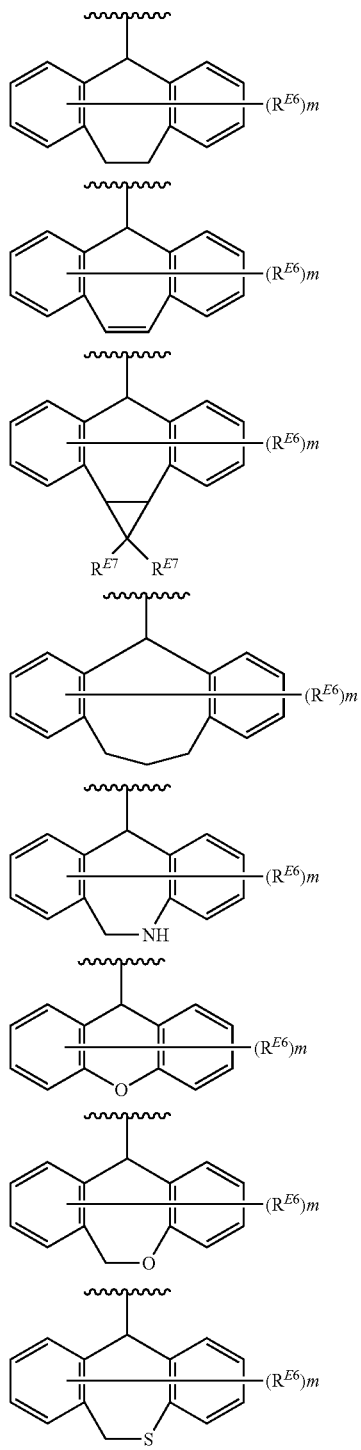

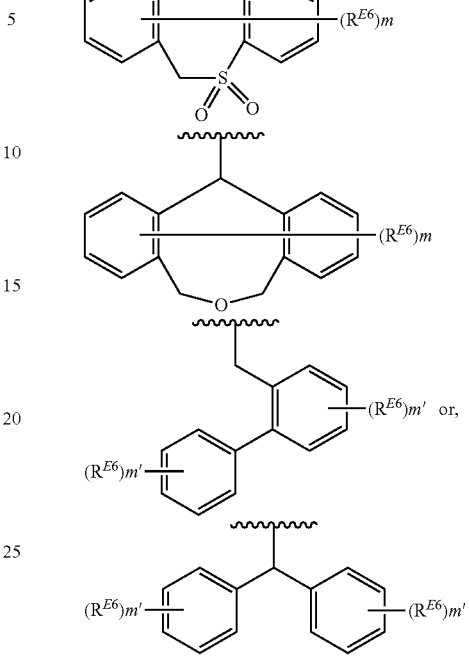

(wherein $R^{E6}$ are each independently a group selected from Substituent group A (preferably, halogen, alkyl, or phenyl); $R^{E7}$ are each independently a hydrogen atom or halogen; m are each independently an integer of 0 to 4; and m' are each independently an integer of 0 to 4).

Preferred embodiments of each substituent of Formula (II) are shown below. Examples of the compound represented by Formula (II) or a prodrug thereof or a pharmaceutically acceptable salt thereof, preferably the compound represented by Formula (II) or a pharmaceutically acceptable salt thereof, include all possible combinations of embodiments of each substituent.

$R^{1a}$ is $-Z^X-C(=O)-O-R^{X15}$,
$-Z^X-C(=O)-N(R^{X9})(R^{X10})$, or
$-Z^X-N(R^{X14})-C(=O)-O-R^{X15}$
(wherein, $R^{X9}$, $R^{X14}$, and $R^{X15}$ are each independently a hydrogen atom, alkyl optionally substituted with Substituent group E, alkenyl optionally substituted with Substituent group E, or alkynyl optionally substituted with Substituent group E; $R^{X10}$ is a hydrogen atom, alkyl optionally substituted with Substituent group E, alkenyl optionally substituted with Substituent group E, alkynyl optionally substituted with Substituent group E, or alkyloxy optionally substituted with Substituent group E; $Z^X$ is a single bond or a linear or branched alkylene; and $R^{X9}$ and $R^{X10}$ may be taken together with an adjacent atom to form a heterocycle).

In another embodiment, $R^{1a}$ is $-Z^X-C(=O)-O-R^{X15}$.

$R^{1a}$ is preferably carboxy, $-C(=O)-N(R^9)(R^{X10})$, or $-N(R^{X14})-C(=O)-O-R^{X15}$.

$R^{1a}$ is more preferably carboxy.

$R^{X9}$, $R^{X10}$, $R^{X14}$, and $R^{X15}$ are preferably, each independently, a hydrogen atom, or alkyl optionally substituted with Substituent group E, $R^{X9}$, $R^{X10}$, $R^{X14}$, and $R^{X15}$ are more preferably, each independently, a hydrogen atom or alkyl.

$Z^X$ is preferably a single bond.

Preferred embodiments of a substituent in "alkyl optionally substituted with Substituent group E", "alkenyl optionally substituted with Substituent group E", and "alkynyl optionally substituted with Substituent group E" include unsubstituted and halogen. More preferably, the substituent is unsubstituted.

$R^{2a}$ is a hydrogen atom, halogen, hydroxy, carboxy, cyano, alkyl optionally substituted with Substituent group F, alkenyl optionally substituted with Substituent group F, alkynyl optionally substituted with Substituent group F. or alkyloxy optionally substituted with Substituent group F.

$R^{2a}$ is preferably a hydrogen atom or alkyl optionally substituted with Substituent group F, more preferably a hydrogen atom or alkyl, still more preferably a hydrogen atom.

Examples of a preferred substituent of "optionally substituted with Substituent group F" in $R^{2a}$ include unsubstituted and halogen. More preferably, the substituent is unsubstituted.

-L- is —$(CR^{3a}R^{3b})$n- or a single bond.

-L- is preferably —$(CR^{3a}R^{3b})$n-.

More preferably, -L- is —$CH_2$— or a single bond.

Particularly preferably, -L- is —$CH_2$—.

$R^{3a}$ and $R^{3b}$ are each independently a hydrogen atom, halogen, carboxy, cyano, alkyl optionally substituted with Substituent group F, alkenyl optionally substituted with Substituent group F, alkynyl optionally substituted with Substituent group F, a carbocyclic group optionally substituted with Substituent group A, carbocyclealkyl optionally substituted with Substituent group A, a heterocyclic group optionally substituted with Substituent group A, heterocyclealkyl optionally substituted with Substituent group A, or alkyloxy optionally substituted with Substituent group F.

$R^{3a}$ and $R^{3b}$ are preferably, each independently, a hydrogen atom, halogen, carboxy, cyano, alkyl optionally substituted with Substituent group F, alkenyl optionally substituted with Substituent group F, alkynyl optionally substituted with Substituent group F, alkyloxy optionally substituted with Substituent group F, a 3- to 6-membered non-aromatic carbocyclic group optionally substituted with Substituent group A, or a 3- to 6-membered non-aromatic heterocyclic group optionally substituted with Substituent group A.

Preferably, $R^{3a}$ and $R^{3b}$ are each independently a hydrogen atom, alkyl, or a 3- to 6-membered non-aromatic carbocyclic group.

More preferably, $R^{3a}$ is a hydrogen atom; $R^{3b}$ is a hydrogen atom, alkyl, or a 3- to 6-membered non-aromatic carbocyclic group;

More preferably, $R^{3a}$ and $R^{3b}$ are each a hydrogen atom;

n is an integer of 1 to 4.

Preferably, n is 1 or 2.

More preferably, n is 1.

Ring A is a non-aromatic carbocycle, an aromatic carbocycle, a non-aromatic heterocycle, or an aromatic heterocycle.

Preferably, Ring A is a 3- to 6-membered non-aromatic carbocycle, a benzene ring, a 3- to 6-membered non-aromatic heterocycle, or a 5- to 6-membered aromatic heterocycle.

More preferably, Ring A is a 3- to 6-membered non-aromatic carbocycle, a benzene ring, or a 5- to 6-membered aromatic heterocycle.

More preferably, Ring A is a 3- to 6-membered non-aromatic carbocycle.

Particularly preferably, Ring A is a 3- to 5-membered non-aromatic carbocycle.

Particularly preferably, Ring A is cyclopropane, cyclobutane, or cycloheptane.

Particularly preferably, Ring A is cyclopropane.

$R^{12a}$ are each independently halogen, cyano, hydroxy, carboxy, amino, oxo, alkyl, halogenoalkyl, alkyloxy, alkylthio, alkylamino, hydroxyalkyl, carboxyalkyl, aminoalkyl, a carbocyclic group, a heterocyclic group, an oxo-substituted heterocyclic group, carbocyclealkyloxy, carbocycleoxyalkyl, carbocyclealkyloxyalkyl, carbocyclealkylthio, heterocyclealkyloxy, heterocycleoxyalkyl, heterocyclealkyloxyalkyl, halogenoalkyloxy, alkyloxyalkyl, alkyloxyalkyloxy, alkylcarbonyl, alkylcarbonyloxy, alkyloxycarbonyl, alkyloxycarbonyloxy, alkylamino, alkylcarbonylamino, halogenoalkylcarbonylamino, alkylaminocarbonyl, alkylsulfonyl, alkylsulfinyl, or alkylsulfonylamino.

Preferably, $R^{12a}$ are each independently halogen, alkyl, halogenoalkyl, alkyloxy, or halogenoalkyloxy.

More preferably, $R^{12a}$ are each independently halogen or alkyloxy.

t is an integer of 0 to 4.

Preferably, t is an integer of 0 to 2.

Particularly preferably, t is 0.

[Chemical Formula 73]

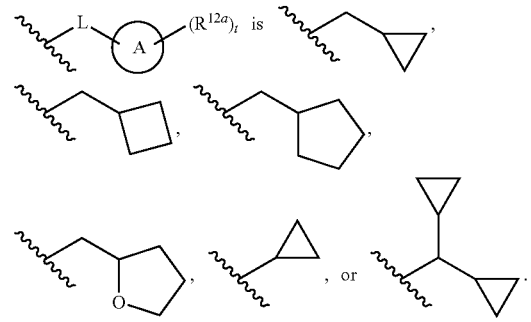

[Chemical Formula 74]

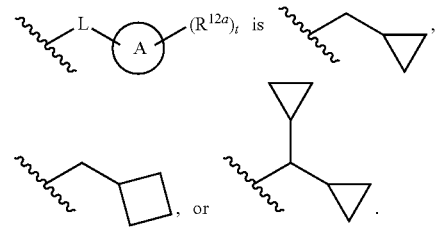

[Chemical Formula 75]

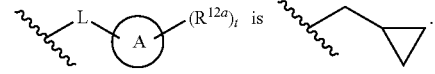

[Chemical Formula 76]

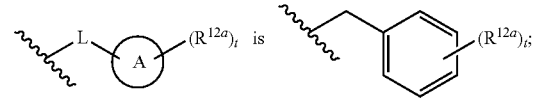

$R^{12a}$ are each independently halogen, and t is 2 to 3.

$R^{5a}$ and $R^{6a}$ are each independently a hydrogen atom, alkyl optionally substituted with Substituent group F, alkenyl optionally substituted with Substituent group F, or alkynyl optionally substituted with Substituent group F; and $R^{5a}$ and $R^{6a}$ may be taken together with the carbon atom to which they are attached to form a carbocycle optionally substituted with Substituent group B or a heterocycle optionally substituted with Substituent group B, wherein the carbocycle or the heterocycle may form a condensed ring and/or a bridged structure.

Preferably, $R^{5a}$ and $R^{6a}$ are each independently a hydrogen atom, or alkyl optionally substituted with Substituent group F.

Particularly preferably, $R^{5a}$ and $R^{6a}$ are each a hydrogen atom.

$R^{7a}$ a is a carbocyclic group optionally substituted with Substituent group B, carbocyclealkyl optionally substituted with Substituent group B, a heterocyclic group optionally substituted with Substituent group B, heterocyclealkyl optionally substituted with Substituent group B, alkyl optionally substituted with Substituent group F, alkenyl optionally substituted with Substituent group F, or alkynyl optionally substituted with Substituent group F.

Preferably, $R^{7a}$ is a carbocyclic group optionally substituted with Substituent group B or a heterocyclic group optionally substituted with Substituent group B.

Preferably, $R^{7a}$ is a group shown below:

[Chemical Formula 77]

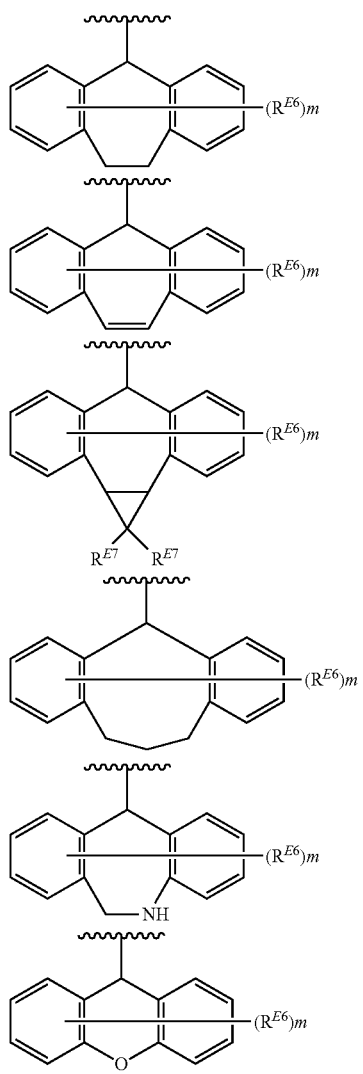

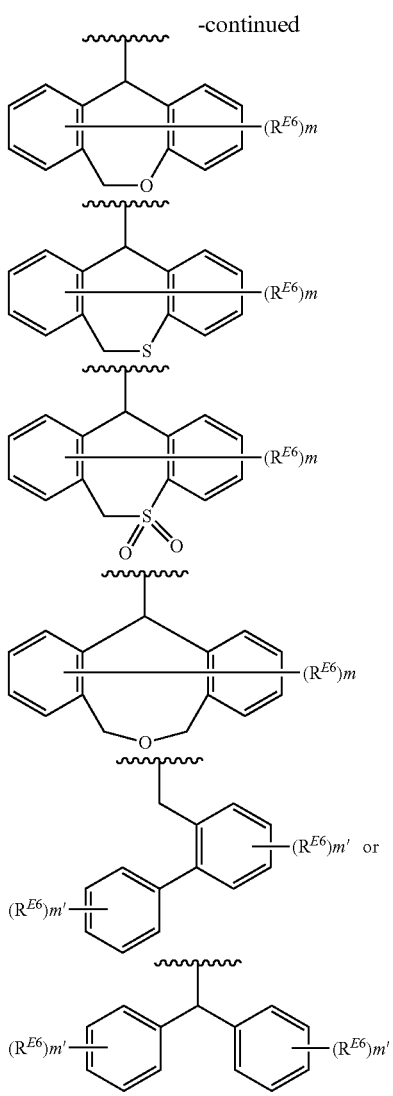

(wherein $R^{E6}$ are each independently a group selected from Substituent group A; and $R^{E7}$ are each independently a hydrogen atom, halogen, or alkyl: m are each independently an integer of 0 to 7; m' are each independently an integer of 0 to 4; and Substituent group A is the same as defined above).

More preferably, $R^{7a}$ is a group shown below:

[Chemical Formula 78]

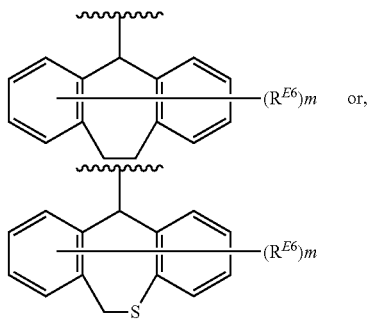

(wherein $R^{E6}$ are each independently a group selected from Substituent group A; m are each independently an integer of 0 to 7; and Substituent group A is the same as defined above). Preferably, m is 0 to 2, more preferably m, is 0.

More preferably, $R^{7a}$ is a group shown below:

[Chemical Formula 79]

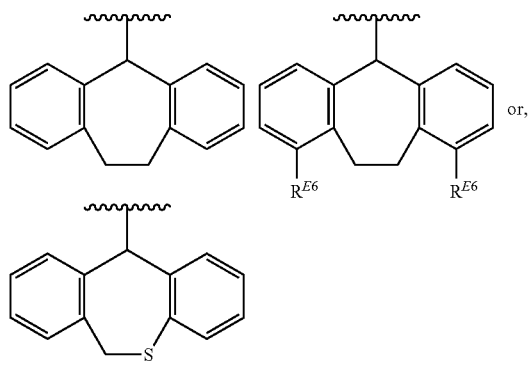

(wherein $R^{E6}$ are each independently a group selected from Substituent group A).

Particularly preferably, $R^{7a}$ is a group shown below:

[Chemical Formula 80]

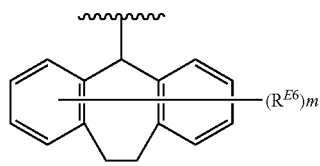

(wherein $R^{E6}$ are each independently a group selected from Substituent group A; m are each independently an integer of 0 to 7; and Substituent group A is the same as defined above).

Preferred examples of $R^{E6}$ each independently include halogen, oxo, alkyl, halogenoalkyl, alkyloxy, and halogenoalkyloxy.

More preferred examples of $R^{E6}$ each independently include halogen, alkyl, and alkyloxy.

Still more preferred examples of $R^{E6}$ include a fluorine atom, a chlorine atom, a bromine atom, cyano, methyl, hydroxymethyl, isopropyl, methoxy, trifluoromethyl, oxo, and carboxy.

In another embodiment, $R^{E6}$ are preferably each independently halogen, alkyl or an aromatic carbocyclic group, particularly preferably halogen or alkyl.

A preferred embodiment of m is an integer of 0 to 6, more preferably an integer of 0 to 4, still more preferably an integer of 0 to 2, particularly preferably 0.

Examples of another preferred embodiment of the compound represented by Formula (II) or a pharmaceutically acceptable salt thereof are illustrated bellow.

$R^{1a}$ is carboxy; $R^{2a}$ is a hydrogen atom:
-L- is —$(CR^{3a}R^{3b})n$- or a single bond; n is 1;
$R^{3a}$ and $R^{3b}$ are each independently a hydrogen atom, alkyl, or a 3- to 6-membered non-aromatic carbocyclic group;

Ring A is cyclopropane, cyclobutane, or cycloheptane; preferably Ring A is cyclopropane;

$R^{12a}$ are each independently halogen, alkyl, halogenoalkyl, alkyloxy, or halogenoalkyloxy;

t is an integer of 0 to 2;

$R^{7a}$ is a group shown below:

[Chemical Formula 81]

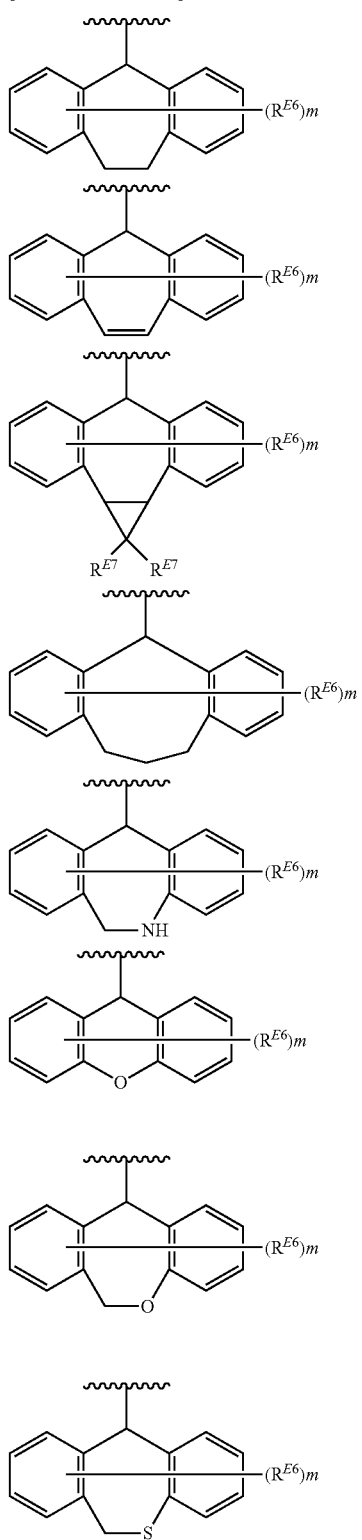

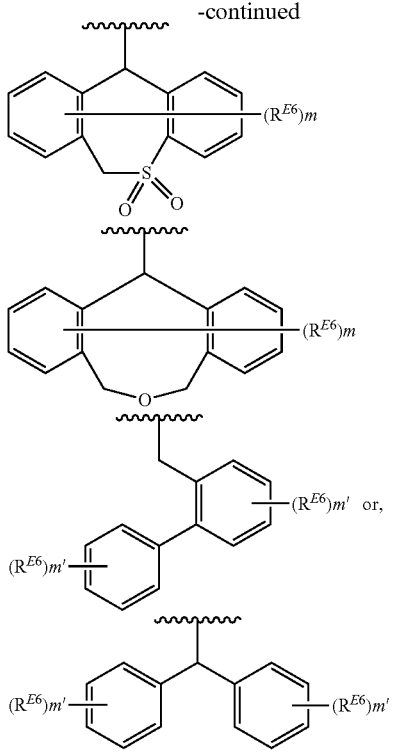

(wherein $R^{E6}$ are each independently a group selected from Substituent group A; and $R^{E7}$ are each independently a hydrogen atom, halogen, or alkyl: m are each independently an integer of 0 to 7, m' are each independently an integer of 0 to 4, and Substituent group A is the same as defined above). Preferably, m is an integer of 0 to 2, more preferably m is 0. $R^{E6}$ is preferably, each independently halogen, alkyl, or an aromatic carbocyclic group, m' is preferably an integer of 0 to 2.

One characteristic of the compound according to the present invention is that a polycyclic carbamoylpyridone derivative in which two or more rings are condensed as shown in Formula (i) in Item 1, and/or a composition comprising the same, have high proliferation inhibitory activity against arenaviruses, more preferably the Old World arenaviruses (e.g., Lassa Virus. Lujo Virus, Luna Virus, and lymphocytic choriomeningitis virus) and the New World arenaviruses (e.g., Junin Virus).

Another characteristic of the compound according to the present invention is that the compound in which a functional group as shown below is further applied to $R^1$ in Formula (I) in the polycyclic carbamoylpyridone derivative in which two or more rings are condensed as shown in Formula (I), have high proliferation inhibitory activity against arenaviruses, more preferably against the Old World arenaviruses (e.g., Lassa Virus, Lujo Virus, Luna Virus, and lymphocytic choriomeningitis virus) and the New World arenaviruses (e.g., Junin Virus).
Functional group: carboxy,
—$Z^X$—C(=O)—N($R^{X9}$)($R^{X10}$), or
—$Z^X$—N($R^{X14}$)—C(=O)—O—$R^{X15}$,
(wherein $R^{X9}$, $R^{X10}$, $R^{X14}$, $R^{X15}$, and $Z^X$ are the same as defined in Item 1).

Another more preferred characteristic of the compound according to the present invention is that the compound in which a functional group as shown below is further applied to $R^1$ in Formula (I) in the polycyclic carbamoylpyridone derivative in which two or more rings are condensed as shown in Formula (I), have high proliferation inhibitory activity against arenaviruses, preferably against the Old World arenaviruses (e.g., Lassa Virus, Lujo Virus, Luna Virus, and lymphocytic choriomeningitis virus) and the New World arenaviruses (e.g., Junin Virus). Functional group: carboxy, —C(=O)—N($R^{X9}$)($R^{X10}$), or
—N($R^{X14}$)—C(=O)—O—$R^{X15}$,
(wherein $R^{X9}$, $R^{X10}$, $R^{X14}$, and $R^{X15}$ are each independently a hydrogen atom, alkyl, or halogenoalkyl).

Another particularly preferred characteristic of the compound according to the present invention is that the compound in which carboxy is further applied to $R^1$ in Formula (I) in the polycyclic carbamoylpyridone derivative in which two or more rings are condensed as shown in Formula (I), have high proliferation inhibitory activity against arenaviruses, preferably against the Old World arenaviruses (e.g., Lassa Virus, Lujo Virus, Luna Virus, and lymphocytic choriomeningitis virus) and the New World arenaviruses (e.g., Junin Virus).

Another preferred characteristic of the compound according to the present invention is that the compound in which a functional group as shown below is further applied to $R^1$ in Formula (I) in the polycyclic carbamoylpyridone derivative in which two or more rings are condensed as shown in Formula (I), have high proliferation inhibitory activity against arenaviruses, preferably against the Old World arenaviruses (e.g., Lassa Virus, Lujo Virus, Luna Virus, and lymphocytic choriomeningitis virus) and the New World arenaviruses (e.g., Junin Virus). Functional group: carboxy or a bioisostere of carboxy.

Still another characteristic of the compound according to the present invention is that the compound in which one or two or more lipophilic functional groups as shown below are introduced to a carbon atom or a nitrogen atom of $A^1$ and/or $A^2$ in Formula (I) in the polycyclic carbamoylpyridone derivative in which two or more rings are condensed as shown in Formula (I), have high proliferation inhibitory activity against arenaviruses, preferably against the Old World arenaviruses (e.g., Lassa Virus, Lujo Virus, Luna Virus, and lymphocytic choriomeningitis virus) and the New World arenaviruses (e.g., Junin Virus).
Lipophilic functional group: a carbocyclic group optionally substituted with Substituent group A, carbocyclealkyl optionally substituted with Substituent group A, carbocycleoxyalkyl optionally substituted with Substituent group A, carbocycleoxycarbonyl optionally substituted with Substituent group A, a heterocyclic group optionally substituted with Substituent group A, heterocyclealkyl optionally substituted with Substituent group A, heterocycleoxyalkyl optionally substituted with Substituent group A, or heterocycleoxycarbonyl optionally substituted with Substituent group A (wherein Substituent group A is the same as defined in Item 1).

A preferred characteristic of the compound according to the present invention is that the compound in which one lipophilic functional group as shown below is introduced to a carbon atom or a nitrogen atom of A1 and/or A2 in Formula (I) in the polycyclic carbamoylpyridone derivative in which two or more rings are condensed as shown in Formula (I), have high proliferation inhibitory activity against arenaviruses, preferably against the Old World arenaviruses (e.g., Lassa Virus, Lujo Virus, Luna Virus, and lymphocytic choriomeningitis virus) and the New World arenaviruses (e.g., Junin Virus).
Lipophilic functional group: alkyl optionally substituted with Substituent group F, a carbocyclic group optionally substituted with Substituent group B, carbocyclealkyl optionally substituted with Substituent group B, a heterocyclic group optionally substituted with Substituent group B, or heterocyclealkyl optionally substituted with Substituent group B (wherein Substituent group A is the same as defined in Item 1).

A more preferred characteristic of the compound according to the present invention is that the compound in which one lipophilic functional group as shown below is introduced to a carbon atom or a nitrogen atom of A1 and/or A2 in Formula (I) in the polycyclic carbamoylpyridone derivative in which two or more rings are condensed as shown in Formula (I), have high proliferation inhibitory activity against arenaviruses, preferably against the Old World arenaviruses (e.g., Lassa Virus. Lujo Virus, Luna Virus, and lymphocytic choriomeningitis virus) and the New World arenaviruses (e.g., Junin Virus).

Lipophilic functional group: alkyl, substituted alkyl (substituent: alkylthio, a carbocyclic group, a heterocyclic group, carbocyclealkylthio), a carbocyclic group, a substituted carbocyclic group (substituent: halogen, alkyl), carbocyclealkyl, substituted carbocyclealkyl (substituent: halogen, alkylthio, a carbocyclic group, carbocyclealkylthio), a heterocyclic group, a substituted heterocyclic group (substituent: halogen), heterocyclealkyl, or substituted heterocyclealkyl (substituent: a carbocyclic group substituted with alkyloxy).

Examples of a pharmaceutically acceptable salt of the compound represented by Formula (I) or Formula (II) include salts of the compound represented by Formula (I) or Formula (II) with alkaline metals (e.g., lithium, sodium, or potassium), alkaline earth metals (e.g., calcium or barium), magnesium, transition metals (e.g., zinc or iron), ammonia, organic bases (e.g., trimethylamine, triethylamine, dicyclohexylamine, ethanolamine, diethanolamine, triethanolamine, meglumine, diethanolamine, ethylenediamine, pyridine, picoline, or quinoline) or amino acids, or salts with inorganic acids (e.g., hydrochloric acid, sulfuric acid, nitric acid, carbonic acid, hydrobromic acid, phosphoric acid, or hydroiodic acid) or organic acids (e.g., formic acid, acetic acid, propionic acid, trifluoroacetic acid, citric acid, lactic acid, tartaric acid, oxalic acid, maleic acid, fumaric acid, succinic acid, mandelic acid, glutaric acid, malic acid, benzoic acid, phthalic acid, ascorbic acid, benzenesulfonic acid, p-toluenesulfonic acid, methanesulfonic acid, ethanesulfonic acid, or trifluoroacetic acid). These salts can be formed by the method which is usually performed.

The compound represented by Formula (I) or Formula (II) of the present invention or a pharmaceutically acceptable salt thereof may form solvates (e.g., hydrates), cocrystals and/or crystal polymorphs. The present invention encompasses those various solvates, cocrystals and crystal polymorphs. "Solvates" may be those wherein any number of solvent molecules (e.g., water molecules) are coordinated with the compound represented by Formula (I) or Formula (II). When the compound represented by Formula (I) or Formula (II) or a pharmaceutically acceptable salt thereof are allowed to stand in the atmosphere, the compound may absorb water, resulting in attachment of adsorbed water or formation of hydrates. Recrystallization of the compound represented by Formula (I) or Formula (II) or a pharmaceutically acceptable salt thereof may produce crystal polymorphs. The "cocrystals" mean that the compound represented by Formula (I) or Formula (II) or a salt and a counter molecule coexist in the same crystal lattice, and may include any number of counter molecules.

The compound represented by Formula (I) or Formula (II) of the present invention or a pharmaceutically acceptable salt thereof may form prodrugs. The present invention also encompasses such various prodrugs. Prodrugs are derivatives of the compounds of the present invention that have chemically or metabolically degradable groups, and compounds that are converted to the pharmaceutically active compounds of the present invention through solvolysis or under physiological conditions in vivo. The prodrugs include, for example, a compound that is converted to the compound represented by Formula (I) or Formula (II) through enzymatic oxidation, reduction, hydrolysis, or the like under physiological conditions in vivo, and a compound that is converted to the compound represented by Formula (I) or Formula (II) through hydrolysis by gastric juice or the like. Methods for selecting and preparing suitable prodrug derivatives are described in, for example, "Design of Prodrugs. Elsevier, Amsterdam, 1985". Prodrugs themselves may have some activity.

Reference can also be made, for example, to the method described in WO2012/039414.

When the compound represented by Formula (I) or Formula (II) or a pharmaceutically acceptable salt thereof has a hydroxyl group, examples of a prodrug include prodrugs such as acyloxy derivatives and sulfonyloxy derivatives produced by reacting the compound having a hydroxyl group with an appropriate acyl halide, an appropriate acid anhydride, an appropriate sulfonyl chloride, an appropriate sulfonyl anhydride and a mixed anhydride, or by reacting using a condensing agent. For example, they include $CH_3COO$—, $C_2H_5COO$—, tert-BuCOO—, $C_{15}H_{31}COO$—, PhCOO—, (m-NaOOCPh)COO—, $NaOOCCH_2CH_2COO$—, $CHSCH(NH_2)COO$—, $CH_2N(CH_3)_2COO$—, $CH_3SO_3$, $CH_3CH_2SO_3$—, $CF_3SO_3$—, $CH_2FSO_3$—, $CFSCH_2SO_3$—, p-$CH_3O$-$PhSO_3$—, $PhSO_3$— and p-$CH_3PhSO_3$.

The compound of Formula (I) or Formula (II) according to the present invention can also form a prodrug, for example, as shown in Formula (I-P) below. Prodrugs are expected to be efficiently absorbed into the body after administration (e.g., oral administration) to the living body and exhibit a high pharmacological effect.

[Chemical Formula 82]

(I-P)

(wherein $P^R$ is a group to form a prodrug, and $R^1$, $R^2$, $R^3$, $A^1$, and $A^2$ are the same as defined in Item 1).

The "group to form a prodrug" in the present description refers to a "$P^R$" group in Formula (I-P) in the following reaction formula:

[Chemical Formula 83]

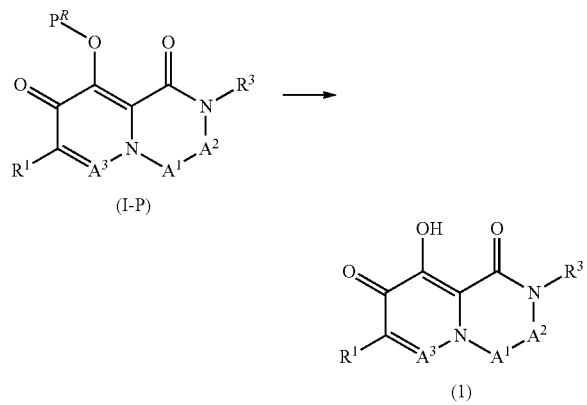

(wherein each symbol is the same as defined above) and the part of —OP$^R$ group is converted into —OH group in Formula (I) by a decomposition reaction caused by drug-metabolizing enzymes, hydrolases, gastric acids, enterobacteria, or the like under physiological conditions in vivo.

The "group to form a prodrug" more preferably means a group that improves bioavailability and/or AUC (area under the blood concentration curve) of the compound represented by Formula (I) by being added to the compound represented by Formula (U.

Examples of the "group to form a prodrug" include the groups described in Prog. Med. 5: 2157-2161 (1985) and Supplied by The British Library—"The world's Knowledge".

The "P$^R$" group in the —OP group of Formula (I-P) may be a group that is converted to an —OH group in vivo, and preferable examples thereof include various substituted carbonyl groups, substituted oxyalkyl groups (e.g., substituted oxymethyl), optionally substituted cyclic group alkyl (e.g., optionally substituted cyclic group methyl), or optionally substituted iminoalkyl (e.g., optionally substituted iminomethyl), and more preferable examples thereof include a group selected from Formulae a) to y) below.

a) —C(=O)—P$^{R0}$,
b) —C(=O)—P$^{R1}$,
c) —C(=O)-L-P$^{R1}$,
d) —C(=O)-L-O—P$^{R1}$,
e) —C(=O)-L-O-L-O—P$^{R1}$,
f) —C(=O)-L-O—C(=O)—P$^{R1}$,
g) —C(=O)—O—P$^{R2}$,
h) —C(=O)—N(P$^{R2}$)$_2$,
i) —C(=O)—O-L-O—P$^{R2}$,
j) —CH$_2$—P$^{R1}$,
k) —CH$_2$—O-L-O—P$^{R3}$,
l) —CH$_2$—O—C(=O)—P$^{R3}$,
m) —CH$_2$O—C(=O)—O—P$^{R3}$,
n) —CH(—CH$_2$)—O—C(=O)—O—P$^{R3}$,
o) —CH$_2$—O—C(=O)—N(—K)—P$^{R3}$,
p) —CH$_2$O—C(=O)—O-L-O—P$^{R3}$,
q) —CH$_2$—O—C(=O)—O-L-N(P$^{R3}$)$_2$,
r) —CH$_2$—O—C(=O)—N(—K)-L-O—P$^{R3}$,
s) —CH$_2$O—C(=O)—N(—K)-L-N(P$^{R3}$)$_2$,
t) —CH$_2$—O—C(=O)—O-L-O-L-O—P$^{R3}$,
u) —CH$_2$—O—C(=O)—O-L-N(—K)—C(=O)—P$^{R3}$,
v) —CH$_2$O—P(=O)(—OH)$_2$,
w) —CH$_2$—O—P(=O)(—OBn)$_2$,
x) —CH$_2$—P$^{R4}$,
y) —C(=N$^+$P$^{R5}$$_2$)(—NP$^{R5}$$_2$)

(wherein L is a straight or branched alkylene;
K is a hydrogen atom, a straight or branched alkylene, or a straight or branched alkenylene.
P$^{R0}$ is alkyl optionally substituted with Substituent group D, or alkenyl optionally substituted with Substituent group D;
P$^{R1}$ is a carbocyclic group optionally substituted with Substituent group D, a heterocyclic group optionally substituted with Substituent group D, alkylamino optionally substituted with Substituent group D, or alkylthio optionally substituted with Substituent group D:
P$^{R2}$ is alkyl optionally substituted with Substituent group D, a carbocyclic group optionally substituted with Substituent group G, or a heterocyclic group optionally substituted with Substituent group G;
P$^{R3}$ is alkyl optionally substituted with Substituent group D, a carbocyclic group optionally substituted with Substituent group G, a heterocyclic group optionally substituted with Substituent group G, alkylamino optionally substituted with Substituent group D, carbocyclealkyl optionally substituted with Substituent group G, heterocyclealkyl optionally substituted with Substituent group G, or alkylsilyl;
P$^{R4}$ is a carbocyclic group optionally substituted with Substituent group G, or a heterocyclic group optionally substituted with Substituent group G; and
P$^{P5}$ is alkyl optionally substituted with Substituent group D.
Substitute group D; oxo, hydroxy, amino, alkylamino, alkylcarbonyl, halogen, hydroxy, carboxy, alkylcarbonylamino, alkylcarbonyloxy, alkyloxycarbonyl, alkyloxy, cyano, and nitro.
Substituent group G; oxo, alkyl, hydroxyalkyl, amino, alkylamino, carbocyclealkyl, alkylcarbonyl, halogen, hydroxy, carboxy, alkylcarbonylamino, alkylcarbonyloxy, alkyloxycarbonyl, alkyloxy, cyano, and nitro.)

As the "group to form a prodrug", the "P$^R$" group in the —OP$^R$ group of Formula (I-P) is preferably a group selected from b), l), m) and n) below.
b) —C(=O)—P$^{R1}$,
L) —CH$_2$—O—C(=O)—P$^{R3}$,
m) —CH$_2$—O—C(=O)—O—P$^{R3}$,
n) —CH(—CH$_3$)—O—C(=O)—O—P$^{R3}$,
(wherein each symbol is the same as defined above.)

"Form a prodrug" in the present description means that, as shown in the following reaction formula:

[Chemical Formula 84]

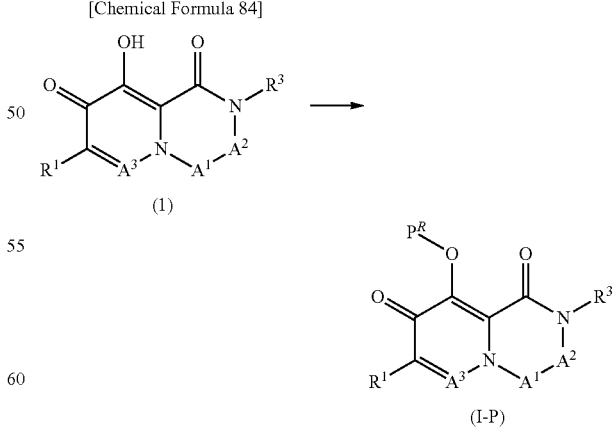

(wherein each symbol is the same as defined above), a hydroxy group in Formula (I) or Formula (II) or a pharmaceutically acceptable salt thereof is converted into a —OP$^R$ group.

Examples of another embodiment of the prodrug of the compound of Formula (I) or Formula (II) according to the present invention include a compound in which, when $R^1$ or $R^{1a}$ is a carboxy group, the hydrogen atom of the carboxy group is substituted with a "group to form a prodrug". Examples of the "group to form a prodrug" include the groups described in Prog. Med. 5: 2157-2161 (1985) and Supplied by The British Library—"The world's Knowledge", and, for example, a substituted or unsubstituted alkyl.

"Parent compound" in the present description means a compound to be a source before synthesizing the "prodrug" and/or a compound released from the "prodrug" by the reaction by kozo, a gastric acid, and the like under physiological conditions in vivo, and, for example, means a compound represented by Formula (I) or a pharmaceutically acceptable salt thereof.

In addition, the compound of the present invention is not limited to a particular isomer, and includes all possible isomers (keto-enol isomers, imine-enamine isomers, diastereoisomers, optical isomers, rotation isomers, and the like) and racemic forms.

Formula (I) or Formula (II) of the present invention is not limited to a particular isomer, and includes all possible isomers and racemic forms. For example, they contain a tautomer and a steric isomer as follows.

[Chemical Formula 85]

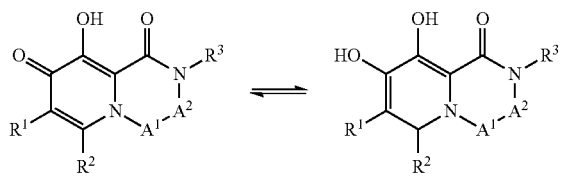

[Chemical Formula 86]

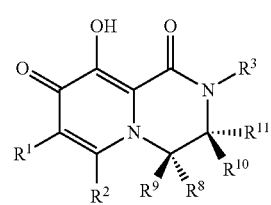
(Ia)-1

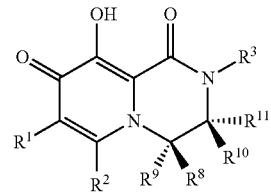
(Ia)-2

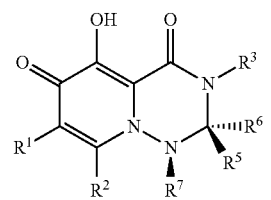
(Ib)-1

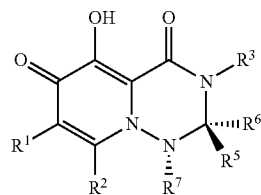
(Ib)-2

Further in Formula (I) or Formula (II) of the present invention, one or more hydrogen atoms, carbon atoms or other atoms can be substituted with an isotope of a hydrogen atom, a carbon atom or other atoms, respectively.

In addition, the compound of Formula (I) or Formula (II) include all radioactive labeled bodies of the compounds of Formula (I) or Formula (II). Such "radioactive labeling", "radioactive labeled form", and the like of the compound of Formula (I) or Formula (I each are included in the present invention, and are useful as a study and/or diagnostic tool in metabolized drug dynamic state studies and binding assays. Examples of an isotope which can be incorporated into the compound of Formula (I) or Formula (I of the present invention include a hydrogen atom, a carbon atom, a nitrogen atom, an oxygen atom, a phosphorus atom, a sulfur atom, a fluorine atom and a chlorine atom, such as $^2H$, $^3H$, $^{13}C$, $^{14}C$, $^{15}N$, $^{19}O$, $^{17}O$, $^{31}P$, $^{32}P$, $^{35}S$, $^{13}F$, and $^9Cl$. A particularly preferred example of an isotope which can be incorporated into the compound of Formula (I) or Formula (II) of the present invention is $^2H$ (i.e. heavy hydrogen atom), and can be adjusted by the method shown in Examples of the present description, or the method well-known in the art. In addition, a heavy hydrogen atom is expressed as "D" in Examples of the present description. The compounds in which a hydrogen atom of Formula (I) or Formula (II) of the present invention has been converted into a heavy hydrogen atom exhibit excellent effects in bioavailability, metabolic stability, drug efficacy, or toxicity as compared to unconverted forms, in some cases, and can be useful as medicaments.

In the general synthesis methods and Examples, the meaning of each abbreviation is as follows.
DMF: N,N-dimethylformamide
DMA: N,N-dimethylacetamide
NMP: N-methylpyrrolidone
DMI: dimethylimidazolidinone
THF: tetrahydrofuran
Ms: methanesulfonyl
Ts: paratoluenesulfonyl
Boc: tert-butoxycarbonyl
DIBALH: diisobutylaluminum hydride
WSC or EDCI: N-ethyl-N'-(3-dimethylaminopropyl)carbodiimide
HOBt: 1-hydroxybenzotriazole
HATU: 0-(7-azabenzotriazol-1-yl)-N,N,N',N'-tetramethyluronium hexafluorophosphate
NBS: N-bromosuccinimide
NCS: N-chlorosuccinimide
TEMPO: 2,2,6,6-tetramethylpiperidine-1-oxyl radical
PDC: pyridinium dichloromate
DEAD: diethyl azodicarboxylate
DIAD: diisopropyl azodicarboxylate
DMAP: 4-dimethylaminopyridine
mCPBA: m-chloroperbenzoic acid
DBU: 1,8-diazabicyclo[5.4.0]-7-undecene DIPEA: diisopropylethylamine
TBAF: tetrabutylammonium fluoride
T3P: propyl phoshonic anhydride
IBX: 2-iodoxybenzoic acid
DMSO: dimethyl sulfoxide
NaHMDS: sodium hexamethyldisilazide
TFA: trifluoroacetic acid
Bn: benzyl The compounds according to the present invention can be synthesized based on the methods described in WO2010/147068, WO2012/039414, WO2014/100323, or JP2019-59697.

(Preparation A)

[Chemical Formula 87]

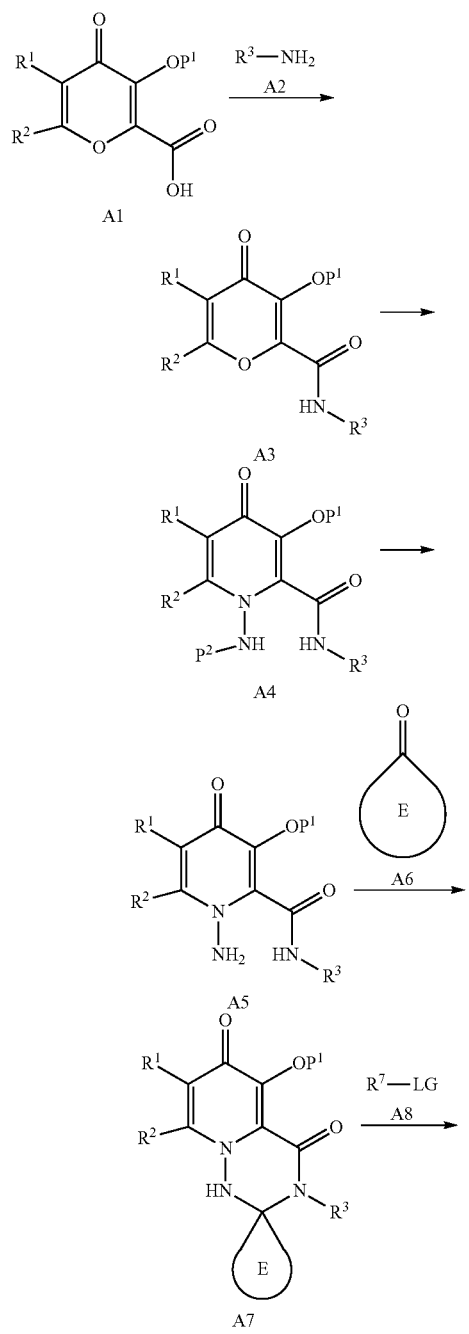

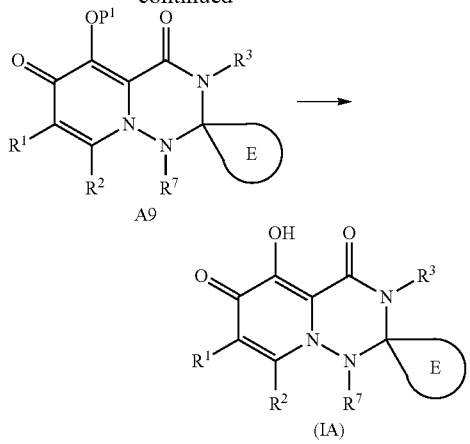

(wherein, Ring E is a carbocycle optionally substituted with Substituent group B or a heterocycle optionally substituted with Substituent group B; and each symbol is the same as defined above).

First Step

Compound A3 can be obtained by adding a condensation agent such as HATU or WSC-HCl to Compound A1 in the presence of a solvent such as DMF, DMA, NMP, or THF or in a mixed solvent thereof, adding amine A2 ($R^{7a}$—$NH_2$) corresponding to an objective substance and, if necessary, tertiary amine such as triethylamine or N-methylmorpholine, and performing a reaction at 10° C. to 60° C., preferably 20° C. to 40° C. for 0.1 hours to 24 hours, preferably 1 hour to 12 hours.

Second Step

Compound A4 can be obtained by adding $P^2$-protected hydrazine and PPTS, acetic acid, and the like to Compound A3 in the presence of a solvent such as DMF, DMA, NMP, THF, or EtOH, or in a mixed solvent thereof, and performing a reaction at 20° C. to 160° C. for 0.1 hours to 24 hours, preferably 1 hour to 12 hours.

Third Step

Compound A5 can be obtained by carrying out a deprotection reaction suitable for the protecting group.

Fourth Step

Compound A7 can be obtained by adding potassium carbonate, sodium carbonate, and Compound A6 to Compound A5 in the presence of a solvent such as DMF, DMA, NMP, or THF, and performing a reaction at 10° C. to 60° C., preferably 20° C. to 40° C. for 0.1 hours to 24 hours, preferably 1 hour to 12 hours.

Fifth Step

Compound A9 can be obtained by adding Compound A8, and a base such as sodium carbonate, potassium carbonate, or cesium carbonate, to Compound A7 in the presence of a solvent such as DMF, DMA, NMP, or THF, or in a mixed solvent thereof, and performing a reaction at 0° C. to 60° C., preferably 10° C. to 40° C. for 0.1 hours to 48 hours, preferably 1 hour to 24 hours.

Alternatively, Compound A9 can be obtained by adding Compound A8, and T3P, methane sulfonic acid or paratoluene sulfonic acid to Compound A7 in the presence of a solvent such as DMF, ethyl acetate, butyl acetate, or 1,4-dioxane or in a mixed solvent thereof, and performing a reaction at 40° C. to 150° C., preferably 60° C. to 120° C. for 0.1 hours to 48 hours, preferably 1 hour to 24 hours. As another method, Compound A9 can be obtained by adding Compound A8 to Compound A7 in an acetic acid solvent, and performing a reaction at 40° C. to 150° C., preferably 60° C. to 120° C. for 0.1 hours to 48 hours, preferably 1 hour to 24 hours.

Sixth Step

Compound (IA) can be obtained by carrying out a deprotecting reaction of a protecting group of the hydroxyl group of Compound A9. The deprotecting reaction of the protecting group of the hydroxyl group of Compound A9 can be carried out by a general method described in Protective Groups in Organic Synthesis, Theodora W Green (John Wiley & Sons) and the like.

Hereinafter, the present invention is described in further detail with reference to Examples and Test Examples of the present invention, but the present invention is not limited by these.

(LC/MS Measurement Conditions)

(1) Column: ACQUITY UPLC(R) BEH C18 (1.7 μm, i.d. 2.1×50 mm) (Waters)

Flow rate: 0.8 mL/min

UV detection wavelength: 254 nm

Mobile phases: [A] is a 0.1% formic acid-containing aqueous solution, and [B] is a 0.1% formic acid-containing acetonitrile solution Gradient: linear gradient of 10% to 100% solvent [B] for 3.5 minutes was performed, and 100% solvent [B] was maintained for 0.5 minutes.

(2) Column: Shim-pack XR-ODS (2.2 μm, i.d.50×3.0 mm) (Shimadzu)

Flow rate: 1.6 mL/min; UV detection wavelength: 254 nm;

Mobile phase: [A]: a 0.1% formic acid-containing aqueous solution, [B]: a 0.1% formic acid-containing acetonitrile solution Gradient: linear gradient of 10% to 100% solvent [B] for 3 minutes was performed, and 100% solvent [B] was maintained for 0.5 minutes.

(3) Column: Gemini-NX (5 μm, i.d. 4.6×50 mm) (Phenomenex) Flow rate: 3 mL/min

UV detection wavelength: 254 nm

Mobile phases: [A] is a 0.1% formic acid-containing aqueous solution, and [B] is a 0.1% formic acid-containing acetonitrile solution Gradient: linear gradient of 5% to 100% solvent [B] for 3.5 minutes was performed, and 100% solvent [B] was maintained for 0.5 minutes.

Example 1

Synthesis of Compound I-001

[Chemical Formula 88]

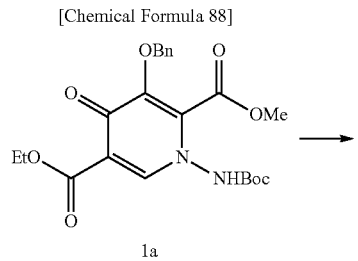

1a

Step 1 Synthesis of Compound 2a

Compound 1a (10.4 g, 23.3 mmol) was dissolved in ethyl acetate (25 ml), and a solution of 4 mol/L hydrochloride in ethyl acetate was added thereto. The mixture was stirred at room temperature for one hour, and then allowed to stand still overnight. The solvent was distilled off under reduced pressure, and then the residue was neutralized by addition of an aqueous sodium hydrogen carbonate solution. The mixture was then extracted with ethyl acetate. The organic layer was washed with a saturated aqueous sodium chloride solution, and then dried over anhydrous magnesium sulfate, and the solvent was distilled off under reduced pressure to give Compound 2a (8.04 g, yield 99%).

$^1$H-NMR (CDCl$_3$) δ: 1.37 (t, J=7.8 Hz, 3H), 3.79 (s, 3H), 4.36 (t, J=7.8 Hz, 2H), 5.20-5.40 (m, 4H), 7.30-7.44 (m, 5H), 8.30 (s, 1H)

Step 2 Synthesis of Compound 3a

Compound 2a (7.2 g, 20.8 mmol) and allyl-3-methoxymorpholine-4-carboxylate (5.02 g, 25.0 mmol) were dissolved in acetonitrile (200 ml), and then cooled to −30 degrees. To this, tin tetrachloride (3.66 ml, 31.2 mmol) was added, and the mixture was stirred. After the mixture was stirred for 4 hours, 3-methoxymorpholine-4-carboxylate (2.09 g, 10.4 mmol) and tin tetrachloride (1.22 ml, 10.4 mmol) were added to the reaction solution, and the mixture was stirred for further 2 hours. Saturated sodium hydrogen carbonate was added to the reaction solution, and the reaction solution was extracted with methylene chloride. The obtained organic layer was washed with a saturated aqueous sodium chloride solution, dried over sodium sulfate, filtered, and the solvent was distilled off under reduced pressure to give a crude product. The obtained residue was dissolved in tetrahydrofuran (250 ml), and morpholine (9.06 ml, 104 mmol) and tetrakistriphenylphosphine palladium (1.20 g, 1.04 mmol) were added thereto, and the mixture was stirred at room temperature for 30 minutes. The reaction solution was diluted with diethyl ether (500 ml), and the produced precipitate was filtered to give Compound 5a (6.2 g, 75%).

$^1$H-NMR (CDCl$_3$) δ: 1.27 (t, J=6.4 Hz, 3H), 2.97-3.05 (m, 2H), 3.10-3.25 (m, 1H), 3.30-3.52 (m, 1H) 3.95-4.30 (m, 5H), 4.80-4.95 (m, 1H) 5.08 (s, 2H), 7.30-7.50 (m, 4H), 7.53-7.65 (m, 2H), 8.16 (s, 1H)

Step 3 Synthesis of Compounds 4a and 5a

Compound 3a (733 mg, 1.84 mmol) and (728 mg, 2.75 mmol) were dissolved in a solution of 50% TSP in ethyl acetate (7.0 mL), and the mixture was stirred under sealed tube conditions at 110° C. for 1.5 hours. A saturated aqueous sodium hydrogen carbonate solution was added thereto. The mixture was extracted with ethyl acetate, and then the organic layer was washed with brine. The organic layer was dried over anhydrous sodium sulfate, the solvent was distilled off under reduced pressure. The obtained residue was purified by silica gel column chromatography (chloroform-ethyl acetate) to give Compounds 4a and 5a (770 mg, yield 65%) as a diastereomeric mixture.

LC/MS (ESI): m/z=646, [M+H]+, RT=2.37 min, LC/MS measurement condition: (1)

LC/MS (ESI): m/z=646, [M+H]+, RT=2.44 min. LC/MS measurement condition: (1)

Step 4 Synthesis of Compound I-001

A mixture (109 mg, 0.169 mmol) of Compounds 4a and 5a was dissolved in tetrahydrofuran (1.0 ml) and water (1.0 ml), and then the mixture was cooled to 0 degrees. To this, 2 mol/L aqueous sodium hydroxide solution (0.084 ml, 0.169 mmol) was added, and the mixture was stirred for 1 hour, then 2 mol/L aqueous sodium hydroxide solution (0.084 ml, 0.169 mmol) was added again, and the mixture was stirred for further 4 hours. A 2 mol/L aqueous hydrochloric acid solution (0.170 ml, 0.340 mmol) was added, and the mixture was extracted with ethyl acetate. The organic layer was washed with a saturated aqueous sodium chloride solution, and then dried over sodium sulfate, filtered, and then the solvent was distilled off under reduced pressure to give a crude product. The residue was dissolved in N,N-dimethylacetamide (1.0 mL), and lithium chloride (36.4 mg, 0.858 mmol) was added thereto, and the mixture was stirred at 100° C. for 5 hours. The resultant was purified by Gemini-NX AXIA Packed (C18 5 μm, i.d.30×100 mm, acetonitrile-water) to give Compound I-001 (27.9 mg, 30.8%).

$^1$H-NMR (CDCl$_3$) δ: 3.00-3.15 (m, 1H), 3.40-3.60 (m, 2H), 3.80-3.90 (m, 1H), 3.95-4.15 (m, 2H), 4.60-4.75 (m, 2H), 5.20-5.30 (m, 2H), 6.55-6.65 (m, 1H), 6.75-6.88 (m, 1H) 7.00-7.20 (m, 4H), 8.09 (s, 1H), 13.8 (brs, 1H) LC/MS (ESI): m/z=528, [M+H]+, RT=2.02 min, LC/MS measurement condition: (1)

Example 2

Synthesis of Compound I-002

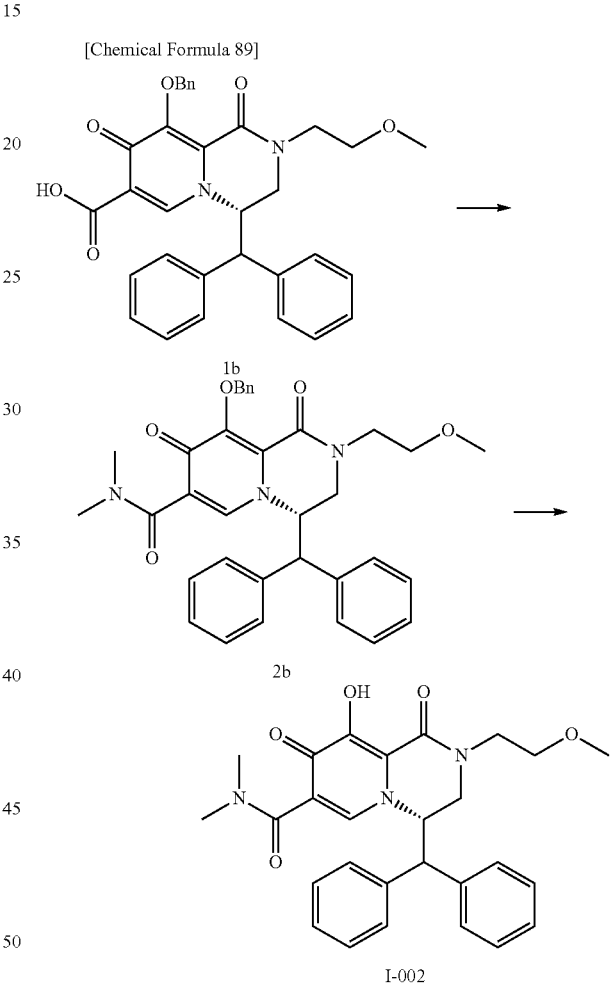

Step 1 Synthesis of Compound 2b

Compound 1b (80 mg, 0.15 mmol) was dissolved in N,N-dimethylformamide (1 ml), and ethyl chloroformate (48 mg, 0.45 mmol) was added thereto at 0° C., and the mixture was stirred for 30 minutes. Dimethylamine hydrochloride (61 mg, 0.74 mmol), triethylamine (45 mg, 0.45 mmol) and N,N-dimethyl-4-aminopyridine (catalytic amount) were added thereto at 0° C., and the mixture was stirred at room temperature for 30 minutes. Water was added to the reaction mixture. The mixture was extracted with ethyl acetate. The organic layer was washed with dilute hydrochloric acid, dried over anhydrous sodium sulfate, and then the solvent was distilled off under reduced pressure to give 90 mg of a crude product of Compound 2b as a colorless gum.

Step 2 Synthesis of Compound I-002

To Compound 2b, trifluoroacetic acid (1 ml) was added, and the mixture was stirred at room temperature for 1 hour. After the reaction solution was concentrated under reduced pressure, a saturated aqueous sodium hydrogen carbonate solution was added thereto, and the mixture was acidified with 2N hydrochloric acid. The mixture was extracted with chloroform, and then the solvent was distilled off under reduced pressure. The obtained crude product was recrystallized from chloroform-diisopropyl ether-diethyl ether to give Compound I-002 (56 mg, 79% yield over 2 steps) as a colorless solid.

$^1$H-NMR (DMSO-D$_6$) δ: 2.41 (s, 3H), 2.79 (s, 3H), 3.14 (s, 3H), 3.32-3.62 (m, 5H), 4.10 (dd, J=3.3, 13.5 Hz, 1H), 4.41 (d, J=11.6 Hz, 1H), 5.48 (d, J=11.4 Hz, 1H), 7.11-7.59 (m, 11H), 12.37 (br s, 1H).

The following compounds were synthesized with commercially available compounds or known compounds according to the synthesis methods described in Examples above, WO20101/47068, WO2012/039414, and JP2019-59697.

Compound I-003

[Chemical Formula 90]

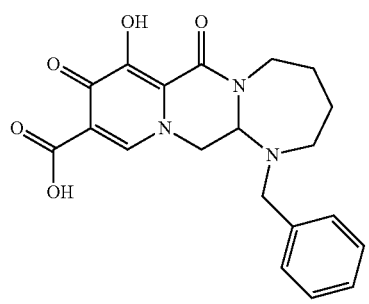

I-003

1H-NMR (DMSO-d6) δ: 1.45-1.86 (4H, m), 2.67-2.87 (2H, m), 3.36-3.42 (9H, m), 3.88 (2H, dd, J=22.72, 14.64 Hz), 4.04-4.14 (1H, m), 4.59 (2H, d, J=5.64 Hz), 5.04 (1H, t, J=5.64 Hz), 7.19-7.34 (5H, m), 8.55 (1H, s).

Compound II-003

[Chemical Formula 91]

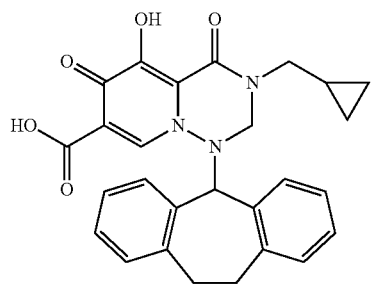

II-003

$^1$H-NMR (DMSO-D$_6$) δ: 14.84 (s, 1H), 12.40 (s, 1H), 7.48 (s, 1H), 7.43-7.35 (m, 3H), 7.27-7.16 (m, 3H), 6.90 (m, 1H), 6.76 (d, J=7.7 Hz, 1H), 5.39 (s, 1H), 5.14 (d, J=13.4 Hz, 1H), 4.29 (d, J=13.4 Hz, 1H), 4.16-4.09 (m, 1H), 3.75-3.64 (m, 2H), 3.03-2.73 (m, 3H), 0.95 (m, 1H), 0.42 (m, 2H), 0.19-0.13 (m, 2H).

Example 3

Synthesis of Compound I-072

[Chemical Formula 92]

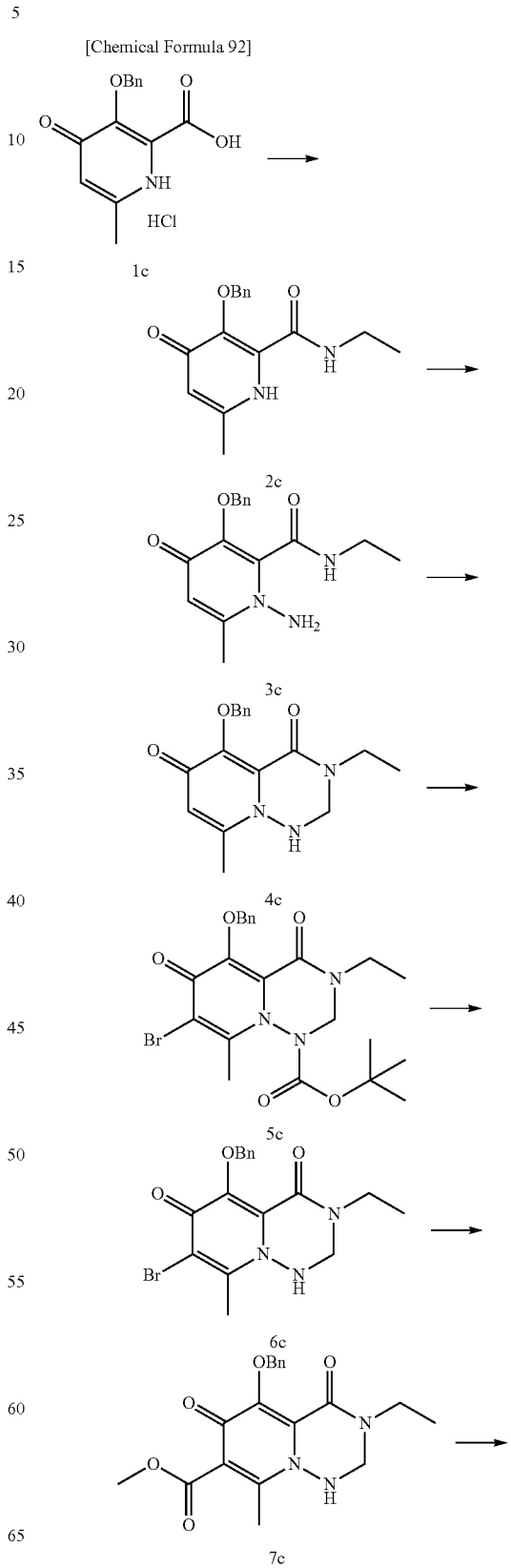

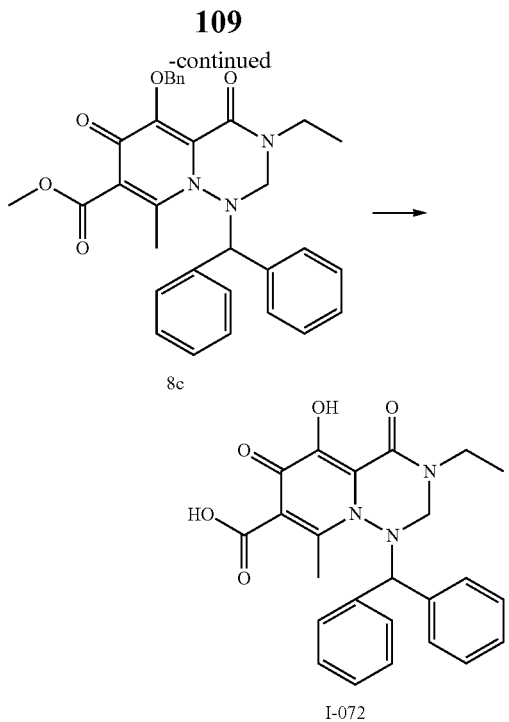

Step 1 Synthesis of Compound 2c

Compound 1c (1 g, 3.38 mmol), ethylamine hydrochloride (331 mg, 4.03 mmol), and HOBt (503 mg, 3.72 mmol) were dissolved in pyridine (10 ml), and WSCD hydrochloride (843 mg, 4.40 mmol) was added thereto, and the mixture was stirred at room temperature for 1 hour, then the solvent was distilled off under reduced pressure. The obtained residue was purified by silica gel column chromatography (chloroform-methanol) to give Compound 2c (536 mg, yield 55%).
LC/MS (ESI): m/z=287, [M+H]+, RT=1.21 min, LC/MS measurement condition: (1)

Step 2 Synthesis of Compound 3c

Compound 2c (529 mg, 1.85 mmol) was dissolved in dimethylformamide (6 ml), and potassium carbonate (1.23 g, 9.23 mmol) was added thereto, and the mixture was stirred at room temperature for 30 minutes. Then, O-(2,4-dinitrophenyl) hydroxyamine (1.10 g, 5.54 mmol) was added thereto, and the mixture was stirred for further 2 hours. Potassium carbonate (638 mg, 4.62 mmol) and O-(2,4-dinitrophenyl) hydroxyamine (552 mg, 2.77 mmol) were added thereto, and the mixture was stirred for 30 minutes, then diluted with chloroform (20 ml), and filtered. The filtrate was concentrated under reduced pressure and the obtained residue was purified by silica gel column chromatography (chloroform-methanol) and amino column chromatography (chloroform-methanol) to give Compound 3c (416 mg, yield 75%). LC/MS (ESI): m/z=302, [M+H]+, RT=1.01 min, LC/MS measurement condition: (1)

Step 3 Synthesis of Compound 4c

Compound 3c (416 mg, 1.38 mmol) was dissolved in dimethylformamide (6 ml), and paraformaldehyde (41.5 mg, 1.38 mmol) and acetic acid (0.34 ml, 5.94 mmol) were added thereto, and the mixture was stirred at 120° C. for 2 hours, then the solvent was distilled off under reduced pressure. The reaction solution was diluted with diethyl ether (5 ml), and then the precipitate produced was collected by filtration to give Compound 4c (415 mg, yield 96%).
LC/MS (ESI): m/z=314, [M+H]+, RT=1.08 min, LC/MS measurement condition: (1)

Step 4 Synthesis of Compound 5c

Compound 4c (270 mg, 0.86 mmol) was dissolved in dichloromethane (5.4 ml), and Boc2O (0.26 ml, 1.12 mmol) and DMAP (5.26 mg, 0.04 mmol) were added thereto, and the mixture was stirred at room temperature for 7 hours, then N-bromosuccinimide (369 mg, 2.07 mmol) was added thereto under ice cooling. The mixture was stirred at room temperature for 16 hours, then N-bromosuccinimide (29.0 mg, 0.16 mmol) was added, and the mixture was stirred at room temperature for further 1.5 hours. The solvent was distilled off under reduced pressure, and the obtained residue was purified by silica gel column chromatography (hexane-ethyl acetate) to give Compound 5c (495 mg, yield 91%).
LC/MS (ESI): m/z=492, [M+H]+, RT=1.99 min, LC/MS measurement condition: (1)

Step 5 Synthesis of Compound 6c

Compound 5c (500 mg, 1.02 mmol) was dissolved in methanol (5 ml), and 2 mol/L aqueous sodium hydroxide solution (0.76 ml, 1.52 mmol) was added thereto, and the mixture was stirred at 40° C. for 1 hour. An aqueous citric acid solution was added thereto, and the mixture was extracted with chloroform-methanol. The organic phase was concentrated to give a crude product 6c (384 mg, yield 96%).

Step 6 Synthesis of Compound 7c

The crude product 6c (100 mg, 0.255 mmol) and tetrakis (triphenylphosphine) palladium (147 mg, 0.127 mmol) were dissolved in dimethyl sulfoxide (3 ml), and N,N-diisopropylethylamine (0.445 ml, 2.55 mmol) and methanol (1.5 ml) were added, and the mixture was degassed. The mixture was stirred under the carbon monoxide atmosphere at 100° C. for 19.5 hours. To the reaction solution, the crude product 6c (1.19 g, 3.02 mmol), tetrakis(triphenylphosphine) palladium (2.62 g, 2.27 mmol), N,N-diisopropylethylamine (5.28 ml, 30.2 mmol), methanol (17.8 ml) and dimethyl sulfoxide (35.6 ml) were added, and the mixture was degassed. The mixture was stirred under the carbon monoxide atmosphere at 100° C. for 20.5 hours, then an aqueous citric acid solution was added, and the mixture was extracted with chloroform-methanol. The organic phase was concentrated and the obtained residue was purified by silica gel column chromatography (chloroform-methanol) to give Compound 7c (614 mg, yield 50%).
LC/MS (ESI): m/z=372.15, [M+H]+, RT=1.35 min, LC/MS measurement condition: (2)

Step 7 Synthesis of Compound 8c

Compound 7c (20.0 mg, 0.054 mmol) was dissolved in dimethylformamide (0.12 ml), and cesium carbonate (70.2 mg, 0.22 mmol) and bromodiphenylmethane (26.6 mg, 0.11 mmol) were added thereto, and the mixture was stirred at room temperature for 18.5 hours. Water was added thereto, and the mixture was extracted with chloroform-methanol, and the organic phase was concentrated. The obtained residue was purified by silica gel column chromatography (chloroform-methanol) to give Compound 8c (18.2 mg, yield 63%).
RT=2.31 min, LC/MS measurement condition: (2)

Step 8 Synthesis of Compound I-072

Compound 8c (18.2 mg, 0.034 mmol) was dissolved in tetrahydrofuran (0.3 ml), and methanol (0.1 ml) and 2 mol/L aqueous sodium hydroxide solution (0.10 ml, 0.20 mmol) were added thereto, and the mixture was stirred at 50° C. for 7 hours. An aqueous citric acid solution was added thereto, and the mixture was extracted with chloroform-methanol. The organic phase was dehydrated, and the mixture was concentrated. The obtained residue and lithium chloride (28.7 mg, 0.68 mmol) were dissolved in dimethylformamide (0.3 ml), and the mixture was stirred at 100° C. for 30 minutes. An aqueous citric acid solution was added thereto, and the mixture was extracted with chloroform-methanol. The organic phase was dehydrated, and the mixture was concentrated. Toluene was added thereto, and the solvent was distilled off under reduced pressure, and then ethyl acetate was added. The precipitated solid was collected by filtration to give Compound I-072 (5.2 mg, yield 35%). LC/MS (ESI): m/z=434.25, [M+H]+, RT=1.91 min, LC/MS measurement condition: (2)

Example 4

Synthesis of Compound I-073

[Chemical Formula 93]

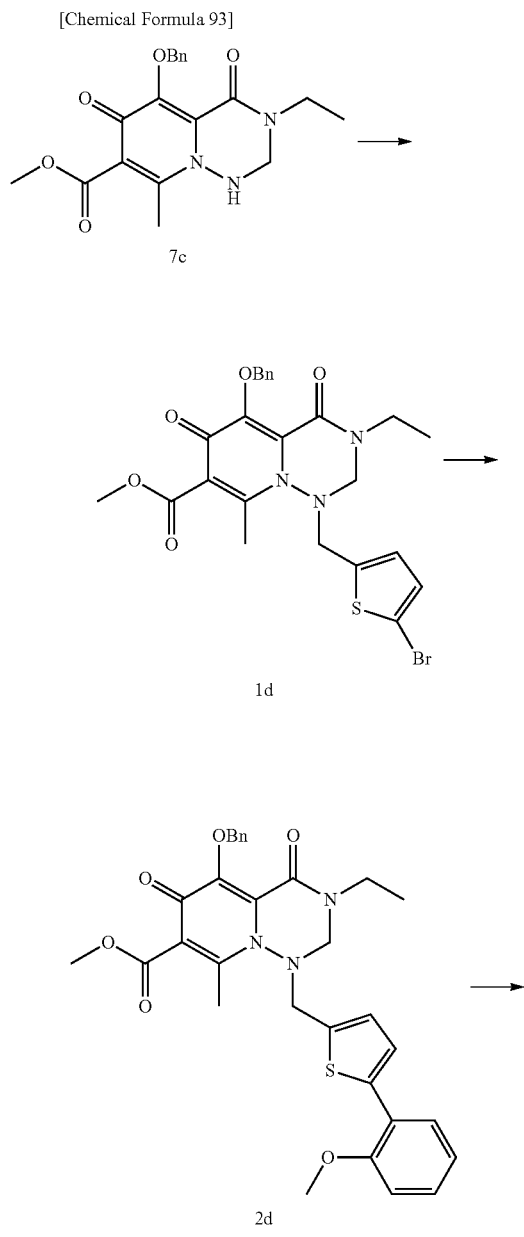

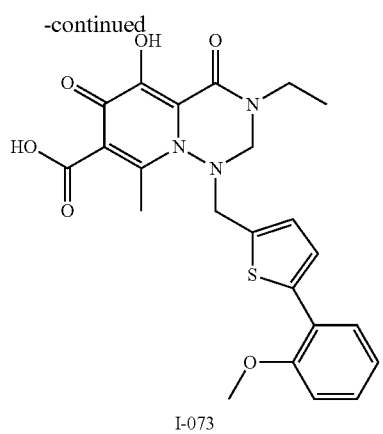

Step 1 Synthesis of Compound 1d

Compound 7c (69.0 mg, 0.186 mmol) was dissolved in dimethyl sulfoxide (0.8 ml), and 2-bromo-5-(bromomethyl)thiophene (95.0 mg, 0.371 mmol) and cesium carbonate (242 mg, 0.742 mmol) were added thereto, and the mixture was stirred at room temperature overnight. The chloroform was added, the mixture was filtered centrifugally, and then the organic phase was concentrated under reduced pressure. The obtained residue was purified by reverse phase chromatography (acetonitrile-water) to give Compound 1d (48.4 mg, yield 48%).
LC/MS (ESI): m/z=546, [M+H]+, RT=2.18 min, LC/MS measurement condition: (2)
Step 2 Synthesis of Compound 2d
Compound 1d (25.0 mg, 0.046 mmol), (2-methoxyphenyl)boronic acid (13.9 mg, 0.092 mmol), [1,1'-bis(diphenylphosphino)ferrocene]palladium(II) dichloride dichloromethane adduct (3.74 mg, 0.05 mmol) were dissolved in tetrahydrofuran (1 ml), and 2 mol/L aqueous sodium carbonate solution (0.114 ml, 0.229 mmol) was added thereto, and the mixture was stirred under sealing tube conditions in a microwave reactor at 120° C. for 30 minutes. An aqueous ammonium chloride solution was added thereto, and the mixture was extracted with chloroform. The organic phase was dehydrated. The solvent was distilled off under reduced pressure, and the obtained residue was purified by silica gel column chromatography (chloroform-methanol) to give Compound 2d (18.9 mg, yield 72%).
Step 3 Synthesis of Compound I-073
Compound 2d (18.9 mg, 0.033 mmol) was dissolved in tetrahydrofuran (0.3 ml), and methanol (0.1 ml) and 2 mol/L aqueous sodium hydroxide solution (0.099 ml, 0.198 mmol) were added thereto, and the mixture was stirred at 50° C. for 4 hours. An aqueous citric acid solution was added thereto, and the mixture was extracted with chloroform-methanol. The organic phase was dehydrated, and the mixture was concentrated. The obtained residue and lithium chloride (27.9 mg, 0.659 mmol) were dissolved in dimethylformamide (0.3 ml), and the mixture was stirred at 100° C. for 1 hour. An aqueous citric acid solution was added thereto, and the mixture was extracted with chloroform-methanol. The organic phase was dehydrated, and the mixture was concentrated. Toluene was added thereto, and the solvent was distilled off under reduced pressure, and then ethyl acetate was added. The precipitated solid was collected by filtration to give Compound I-073 (9.4 mg, yield 61%).
LC/MS (ESI: m/z=470.10, [M+H]+, RT=2.18 min, LC/MS measurement condition: (2)

In the Table, "Comp. No." represents the compound number, "Structure" represents the chemical structure formula, "Ms cond." represents the above LC/MS (liquid chromatography/mass spectrometry) measurement conditions, and "RT (min)" represents the retention time (min).

III-010 is a single optically active substance, but the absolute configuration has not been determined. II-013 and III-014 are each a single optically active substance, and one has R configuration and the other has S configuration.

III-020 and III-021 are each a single optically active substance, and one has R configuration and the other has S configuration.

III-028 and III-029 are each a single optically active substance, and one has R configuration and the other has S configuration.

TABLE 1

| Comp. No. | Structure | Ms cond. | RT(min) | MS | |
|---|---|---|---|---|---|
| I-004 | 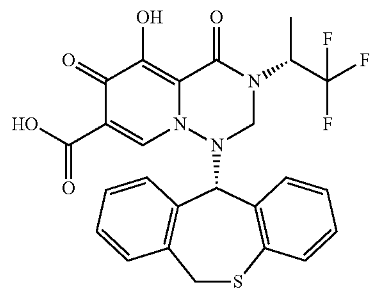 [SMILES: C[C@@H](N1CN([C@H]2c3ccccc3CSc3ccccc32)n2cc(C(=O)O)c(=O)c(O)c2C1=O)C(F)(F)F] | (2) | 2.19 | 532 | [M + H]+ |
| I-005 | 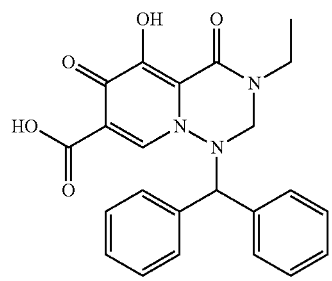 [SMILES: CCN1CN(C(c2ccccc2)c2ccccc2)n2cc(C(=O)O)c(=O)c(O)c2C1=O] | (1) | 1.92 | 420 | [M + H]+ |
| I-006 | 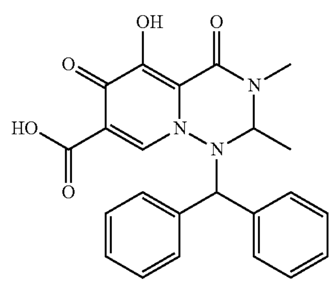 | (1) | 1.88 | 420 | [M + H]+ |
| I-007 | 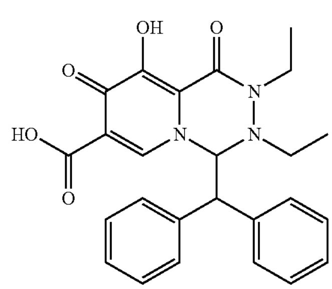 [SMILES: CCN1C(=O)c2c(O)c(=O)c(C(=O)O)cn2C(C(c2ccccc2)c2ccccc2)N1CC] | (1) | 2.14 | 448 | [M + H]+ |

TABLE 1-continued

| Comp. No. | Structure | Ms cond. | RT(min) | MS | |
|---|---|---|---|---|---|
| I-008 | 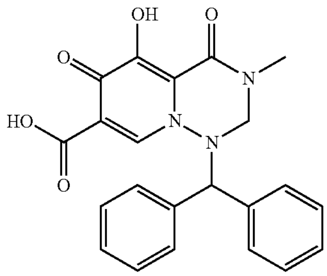 [SMILES: CN1CN(C(c2ccccc2)c2ccccc2)n2cc(C(=O)O)c(=O)c(O)c2C1=O] | (1) | 1.76 | 406 | [M + H]+ |

TABLE 2

| Comp. No. | Structure | Ms cond. | RT(min) | MS | |
|---|---|---|---|---|---|
| I-009 | 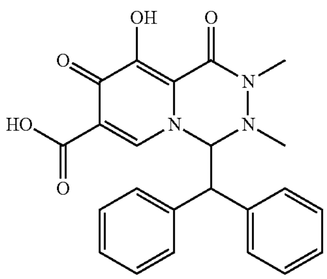 [SMILES: CN1C(=O)c2c(O)c(=O)c(C(=O)O)cn2C(C(c2ccccc2)c2ccccc2)N1C] | (1) | 1.9 | 420 | [M + H]+ |
| I-010 | 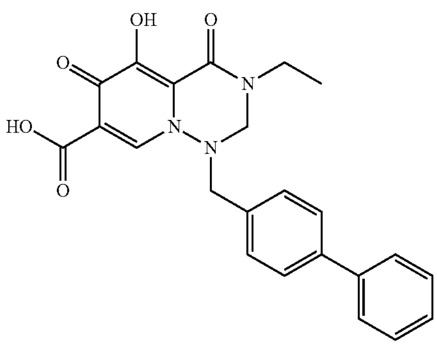 [SMILES: CCN1CN(Cc2ccc(-c3ccccc3)cc2)n2cc(C(=O)O)c(=O)c(O)c2C1=O] | (1) | 2.01 | 420 | [M + H]+ |
| I-011 | 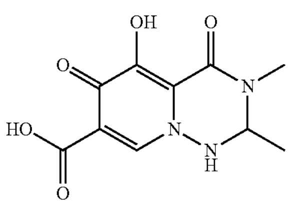 [SMILES: CC1Nn2cc(C(=O)O)c(=O)c(O)c2C(=O)N1C] | (1) | 0.69 | 254 | [M + H]+ |
| I-012 | 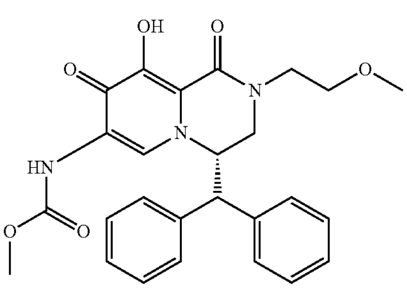 [SMILES: COCCN1C[C@H](C(c2ccccc2)c2ccccc2)n2cc(NC(=O)OC)c(=O)c(O)c2C1=O] | (2) | 1.84 | 478 | [M + H]+ |

TABLE 2-continued

| | | | | |
|---|---|---|---|---|
| I-013 | (structure) | (3) | 2.05 | 432 [M + H]+ |

TABLE 3

| | | | | |
|---|---|---|---|---|
| I-014 | (structure) | (2) | 1.51 | 344 [M + H]+ |
| I-015 | (structure) | (1) | 1.54 | 357 [M + H]+ |
| I-016 | (structure) | (3) | 1.23 | 325 [M + H]+ |
| I-017 | (structure) | (2) | 1.79 | 380 [M + H]+ |
| I-018 | (structure) | (3) | 1.45 | 339 [M + H]+ |

TABLE 4

| Comp. No. | Structure |
|---|---|
| I-019 | (structure) |
| I-020 | (structure) |

TABLE 4-continued

| Comp. No. | Structure |
|---|---|
| I-021 | (structure) |
| I-022 | (structure) |
| I-023 | (structure) |
| I-024 | (structure) |
| I-025 | (structure) |

TABLE 4-continued

| Comp. No. | Structure |
|---|---|
| I-026 | (structure) |

TABLE 5

| I-027 | (structure) |
| I-028 | (structure) |
| I-029 | (structure) |

TABLE 5-continued
I-030 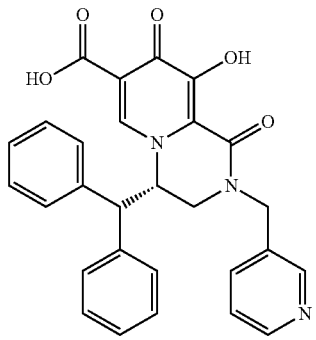 [SMILES: O=C(O)c1cn2c(c(O)c1=O)C(=O)N(Cc1cccnc1)C[C@@H]2C(c1ccccc1)c1ccccc1]
I-031 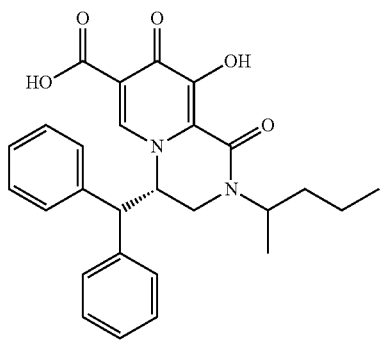 [SMILES: CCCC(C)N1C[C@H](C(c2ccccc2)c2ccccc2)n2cc(C(=O)O)c(=O)c(O)c2C1=O]
I-032 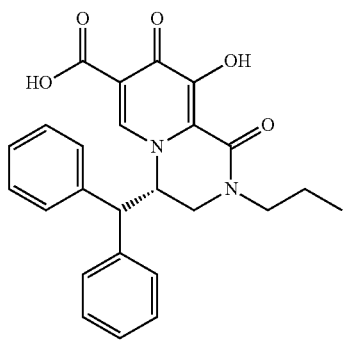 [SMILES: CCCN1C[C@H](C(c2ccccc2)c2ccccc2)n2cc(C(=O)O)c(=O)c(O)c2C1=O]
I-033 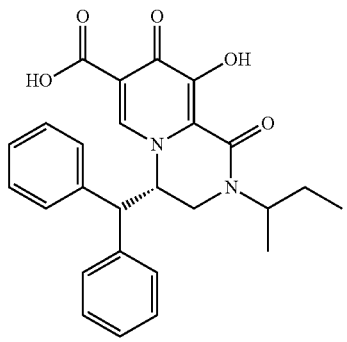 [SMILES: CCC(C)N1C[C@H](C(c2ccccc2)c2ccccc2)n2cc(C(=O)O)c(=O)c(O)c2C1=O]
TABLE 5-continued
I-034 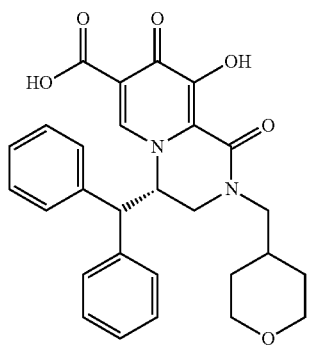 [SMILES: O=C(O)c1cn2c(c(O)c1=O)C(=O)N(CC1CCOCC1)C[C@@H]2C(c1ccccc1)c1ccccc1]
TABLE 6
I-035 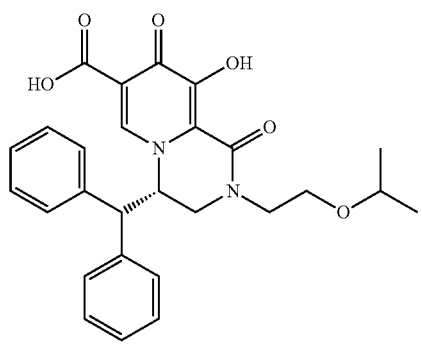 [SMILES: CC(C)OCCN1C[C@H](C(c2ccccc2)c2ccccc2)n2cc(C(=O)O)c(=O)c(O)c2C1=O]
I-036 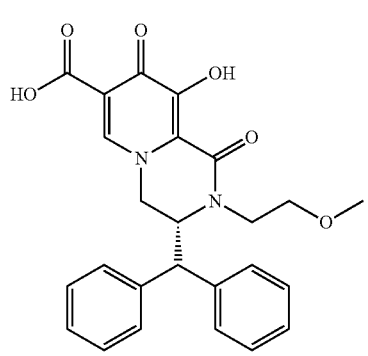 [SMILES: COCCN1C(=O)c2c(O)c(=O)c(C(=O)O)cn2C[C@H]1C(c1ccccc1)c1ccccc1]
I-037 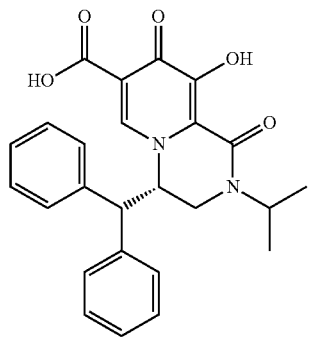 [SMILES: CC(C)N1C[C@H](C(c2ccccc2)c2ccccc2)n2cc(C(=O)O)c(=O)c(O)c2C1=O]

TABLE 6-continued
I-038 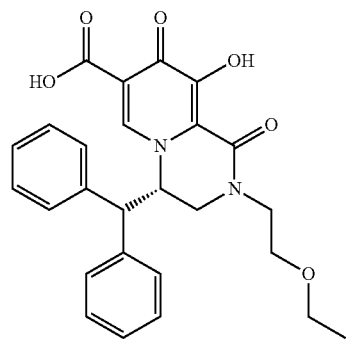
I-039 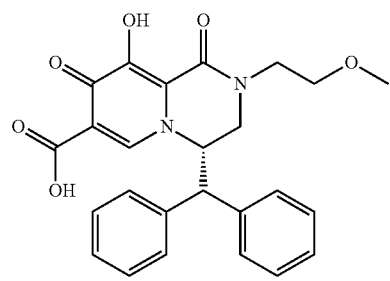 [SMILES: COCCN1C[C@H](C(c2ccccc2)c2ccccc2)n2cc(C(=O)O)c(=O)c(O)c2C1=O]
I-040 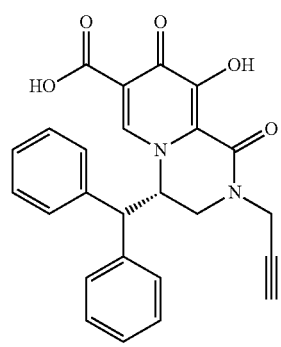 [SMILES: C#CCN1C[C@H](C(c2ccccc2)c2ccccc2)n2cc(C(=O)O)c(=O)c(O)c2C1=O]
I-041 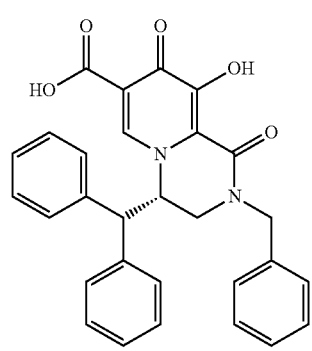 [SMILES: O=C(O)c1cn2c(c(O)c1=O)C(=O)N(Cc1ccccc1)C[C@@H]2C(c1ccccc1)c1ccccc1]
I-042 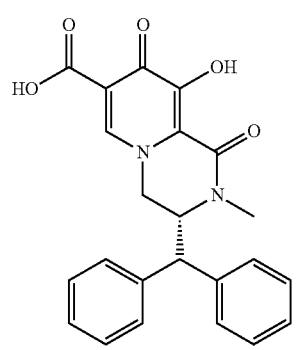 [SMILES: CN1C(=O)c2c(O)c(=O)c(C(=O)O)cn2C[C@H]1C(c1ccccc1)c1ccccc1]
TABLE 6-continued
TABLE 7
I-043 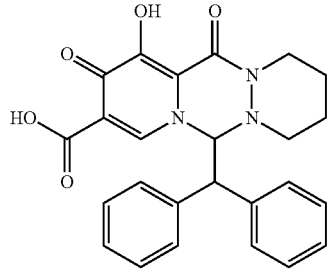 [SMILES: O=C(O)c1cn2c(c(O)c1=O)C(=O)N1CCCCN1C2C(c1ccccc1)c1ccccc1]
I-044 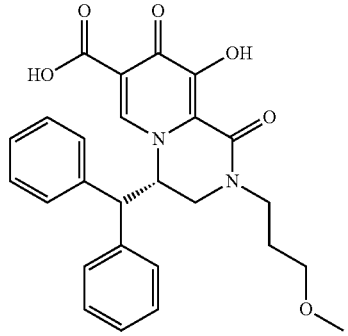
I-045 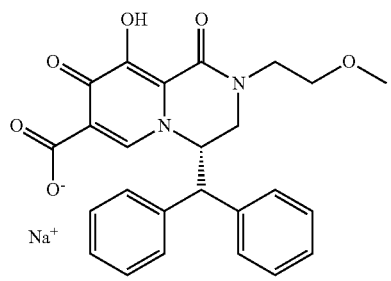 [SMILES: COCCN1C[C@H](C(c2ccccc2)c2ccccc2)n2cc(C(=O)[O-])c(=O)c(O)c2C1=O ; [Na+]]
I-046 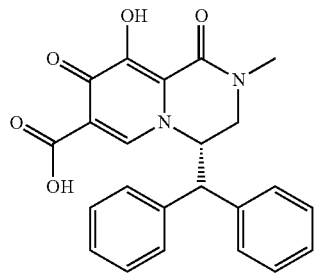 [SMILES: CN1C[C@H](C(c2ccccc2)c2ccccc2)n2cc(C(=O)O)c(=O)c(O)c2C1=O]
I-047 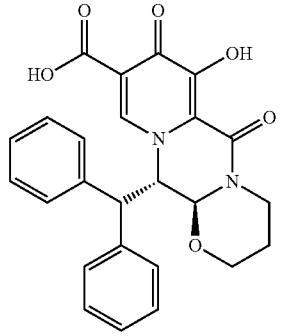 [SMILES: O=C(O)c1cn2c(c(O)c1=O)C(=O)N1CCCO[C@H]1[C@@H]2C(c1ccccc1)c1ccccc1]

TABLE 7-continued
I-048 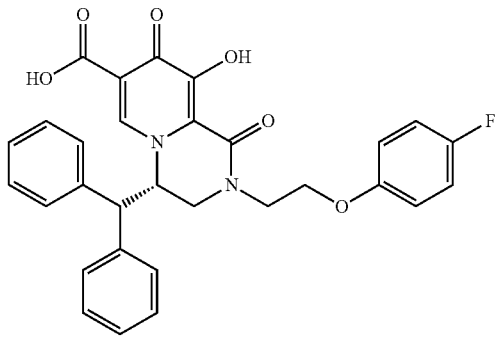 [SMILES: O=C(O)c1cn2c(c(O)c1=O)C(=O)N(CCOc1ccc(F)cc1)C[C@@H]2C(c1ccccc1)c1ccccc1]
I-049 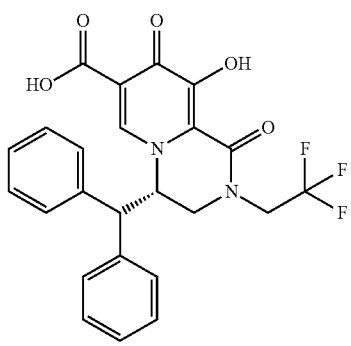 [SMILES: O=C(O)c1cn2c(c(O)c1=O)C(=O)N(CC(F)(F)F)C[C@@H]2C(c1ccccc1)c1ccccc1]
I-050 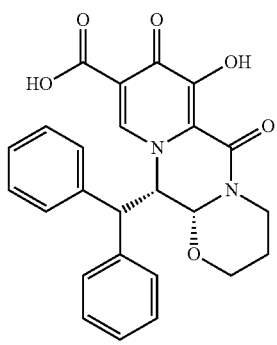 [SMILES: O=C(O)c1cn2c(c(O)c1=O)C(=O)N1CCCO[C@@H]1[C@@H]2C(c1ccccc1)c1ccccc1]
TABLE 8
I-051 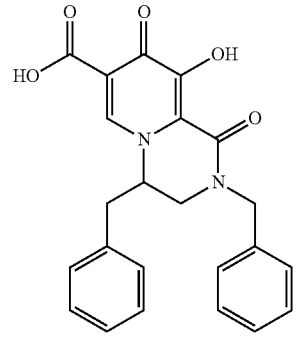 [SMILES: O=C(O)c1cn2c(c(O)c1=O)C(=O)N(Cc1ccccc1)CC2Cc1ccccc1]
TABLE 8-continued
I-052 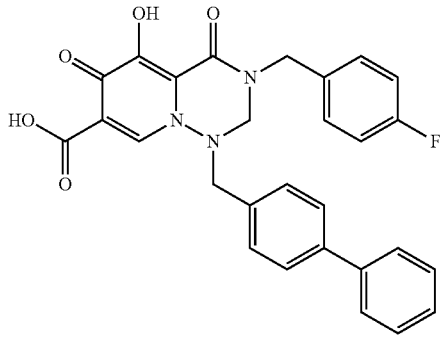 [SMILES: O=C(O)c1cn2c(c(O)c1=O)C(=O)N(Cc1ccc(F)cc1)CN2Cc1ccc(-c2ccccc2)cc1]
I-053 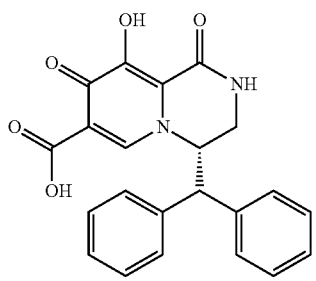 [SMILES: O=C(O)c1cn2c(c(O)c1=O)C(=O)NC[C@@H]2C(c1ccccc1)c1ccccc1]
I-054 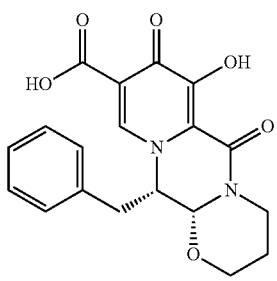 [SMILES: O=C(O)c1cn2c(c(O)c1=O)C(=O)N1CCCO[C@@H]1[C@@H]2Cc1ccccc1]
I-055 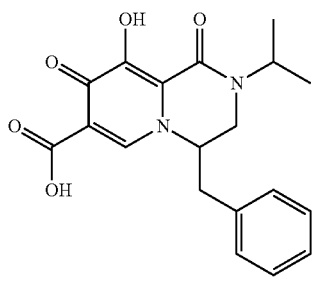 [SMILES: CC(C)N1CC(Cc2ccccc2)n2cc(C(=O)O)c(=O)c(O)c2C1=O]
I-056 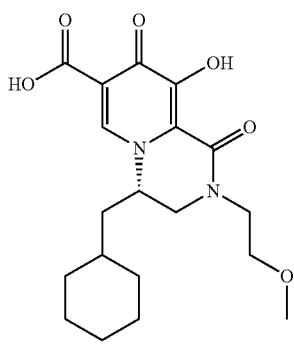

TABLE 8-continued
I-057 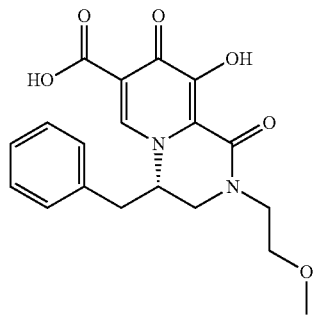 [SMILES: COCCN1C[C@H](Cc2ccccc2)n2cc(C(=O)O)c(=O)c(O)c2C1=O]
I-058 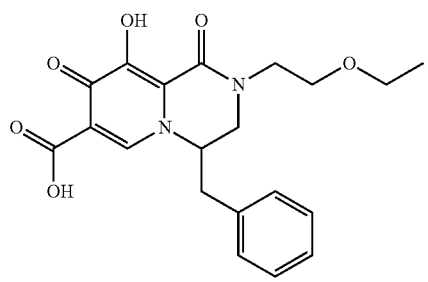 [SMILES: CCOCCN1CC(Cc2ccccc2)n2cc(C(=O)O)c(=O)c(O)c2C1=O]
TABLE 9
I-059 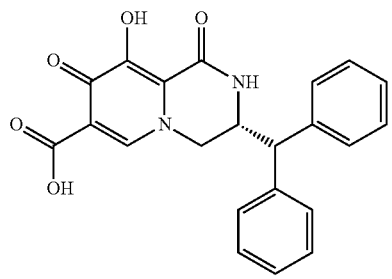 [SMILES: O=C(O)c1cn2c(c(O)c1=O)C(=O)N[C@H](C(c1ccccc1)c1ccccc1)C2]
I-060 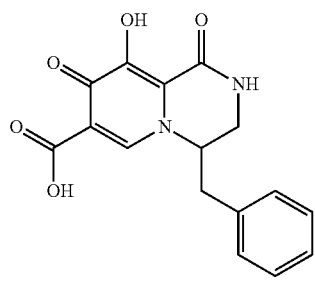 [SMILES: O=C(O)c1cn2c(c(O)c1=O)C(=O)NCC2Cc1ccccc1]
I-061 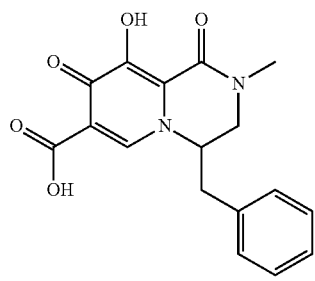 [SMILES: CN1CC(Cc2ccccc2)n2cc(C(=O)O)c(=O)c(O)c2C1=O]
TABLE 9-continued
I-062 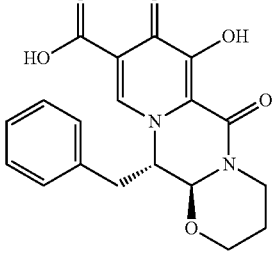
I-063 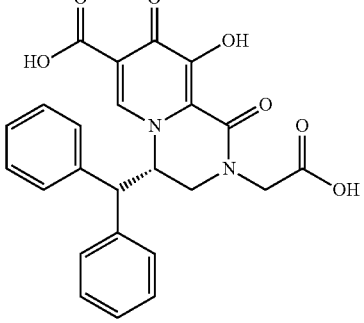
I-064 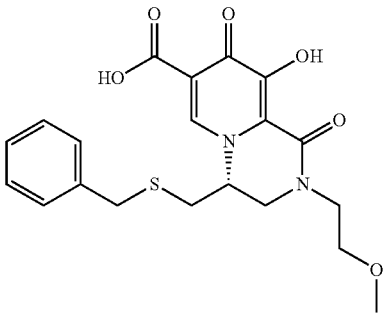 [SMILES: COCCN1C[C@H](CSCc2ccccc2)n2cc(C(=O)O)c(=O)c(O)c2C1=O]
I-065 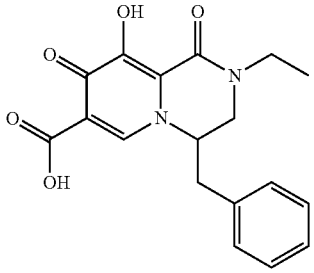 [SMILES: CCN1CC(Cc2ccccc2)n2cc(C(=O)O)c(=O)c(O)c2C1=O]
I-066 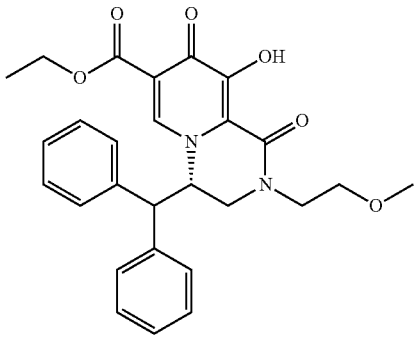 [SMILES: CCOC(=O)c1cn2c(c(O)c1=O)C(=O)N(CCOC)C[C@@H]2C(c1ccccc1)c1ccccc1]

TABLE 10
I-067 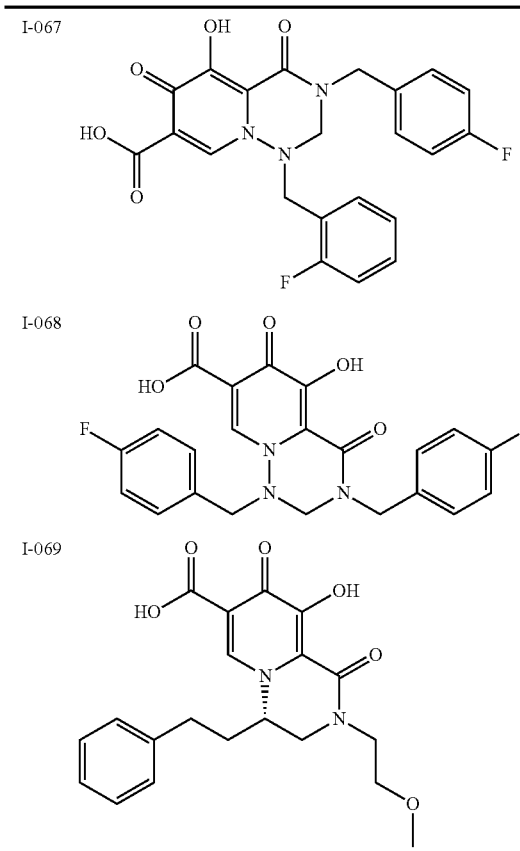
I-068
I-069
TABLE 10-continued
I-070 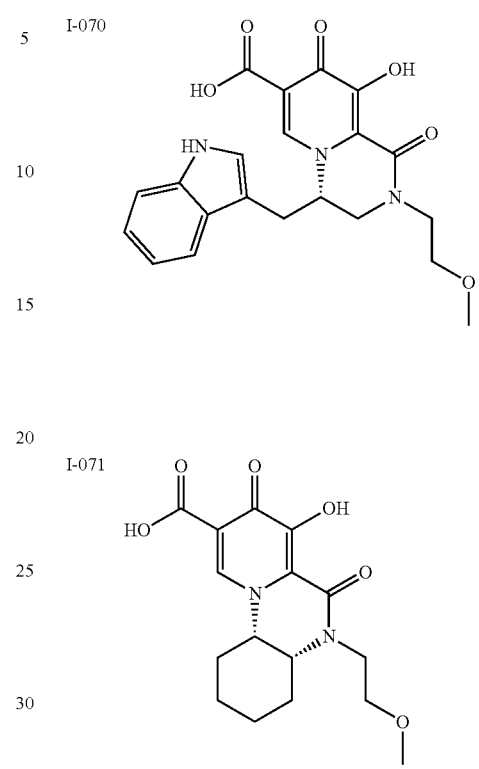
I-071
TABLE 11
| Comp. No. | Structure | Ms cond. | RT(min) | MS |
|---|---|---|---|---|
| I-074 | 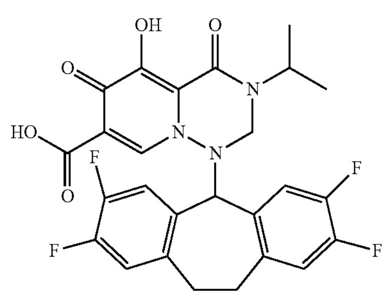 [SMILES: CC(C)N1CN(C2c3cc(F)c(F)cc3CCc3cc(F)c(F)cc32)n2cc(C(=O)O)c(=O)c(O)c2C1=O] | (1) | 2.44 | 532 [M + H]+ |
| I-075 | 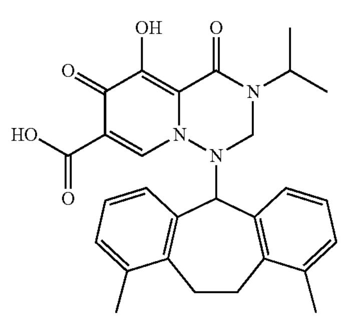 [SMILES: Cc1cccc2c1CCc1c(C)cccc1C2N1CN(C(C)C)C(=O)c2c(O)c(=O)c(C(=O)O)cn21] | (1) | 2.56 | 488 [M + H]+ |

TABLE 11-continued

| Comp. No. | Structure | Ms cond. | RT(min) | MS |
|---|---|---|---|---|
| I-076 | 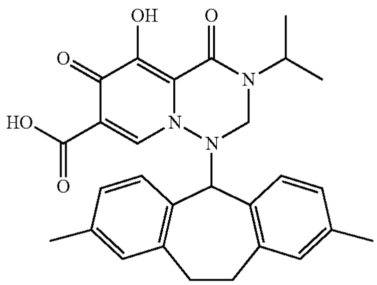 [SMILES: Cc1ccc2c(c1)CCc1cc(C)ccc1C2N1CN(C(C)C)C(=O)c2c(O)c(=O)c(C(=O)O)cn21] | (1) | 2.63 | 488 [M + H]+ |
| I-077 | 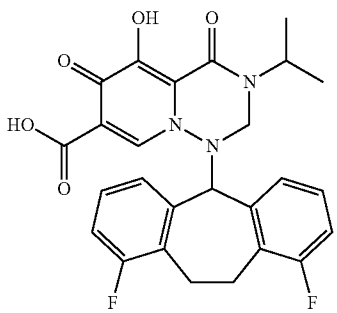 [SMILES: CC(C)N1CN(C2c3cccc(F)c3CCc3c(F)cccc32)n2cc(C(=O)O)c(=O)c(O)c2C1=O] | (1) | 2.4 | 496 [M + H]+ |
| I-078 | 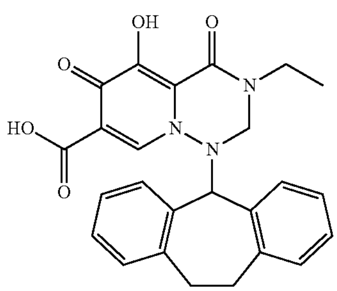 [SMILES: CCN1CN(C2c3ccccc3CCc3ccccc32)n2cc(C(=O)O)c(=O)c(O)c2C1=O] | (1) | 2.22 | 446 [M + H]+ |
| I-079 | 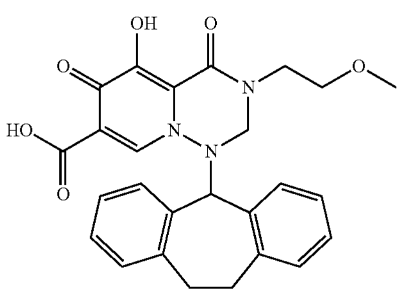 [SMILES: COCCN1CN(C2c3ccccc3CCc3ccccc32)n2cc(C(=O)O)c(=O)c(O)c2C1=O] | (1) | 2.2 | 476 [M + H]+ |

TABLE 12
| I-080 | 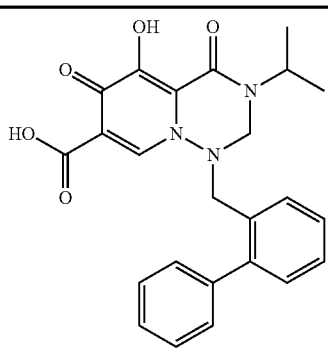 | (1) | 2.15 | 434 | [M + H]+ |
| I-081 | 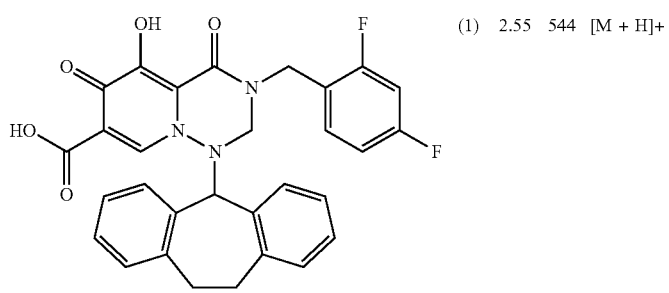 | (1) | 2.55 | 544 | [M + H]+ |
TABLE 13
| II-001 | 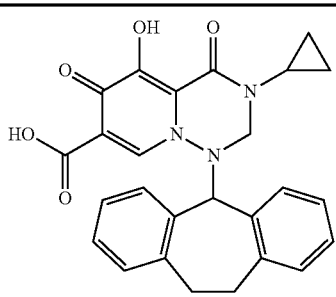 | (1) | 2.201 | 458 | [M + H]+ |
| II-002 | 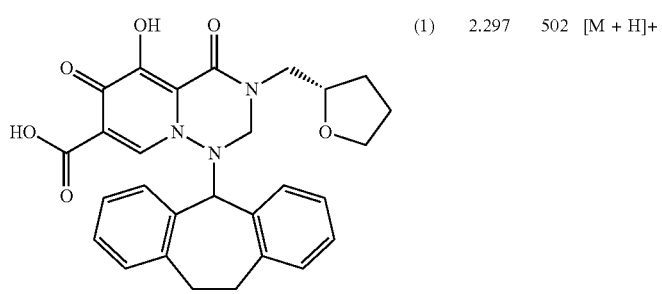 | (1) | 2.297 | 502 | [M + H]+ |
| II-003 | 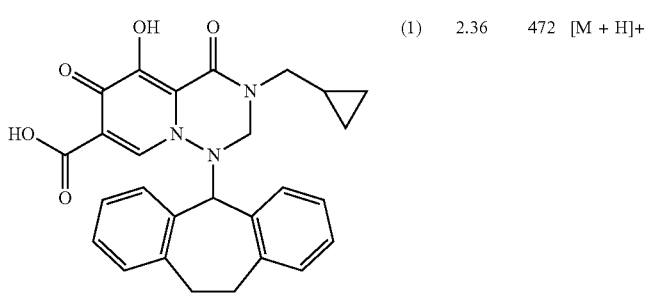 | (1) | 2.36 | 472 | [M + H]+ |

TABLE 13-continued

| II-004 | [structure] | (1) | 2.054 | 432 [M + H]+ |

TABLE 14

| III-001 | [structure] | (1) | 2.19 | 448 [M + H]+ |
| III-002 | [structure] | (1) | 2.27 | 458 [M + H]+ |
| III-003 | [structure] | (1) | 2.03 | 459 [M + H]+ |
| III-004 | [structure] | (1) | 2.05 | 503 [M + H]+ |

TABLE 14-continued
III-005 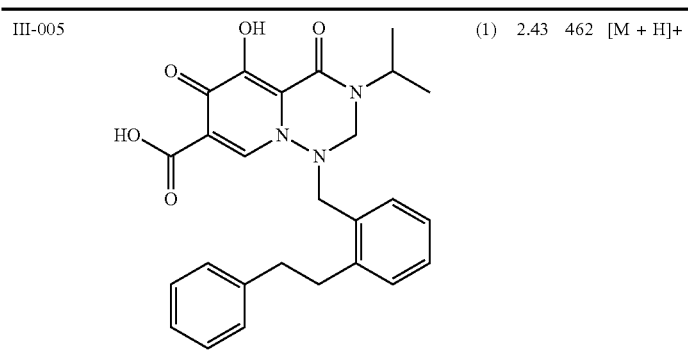 (1) 2.43 462 [M + H]+
TABLE 15
III-006 (1) 2.67 488 [M + H]+
III-007 (1) 2.18 516 [M + H]+
III-008 (1) 2.53 538 [M + H]+
III-009 (1) 2.71 560 [M + H]+
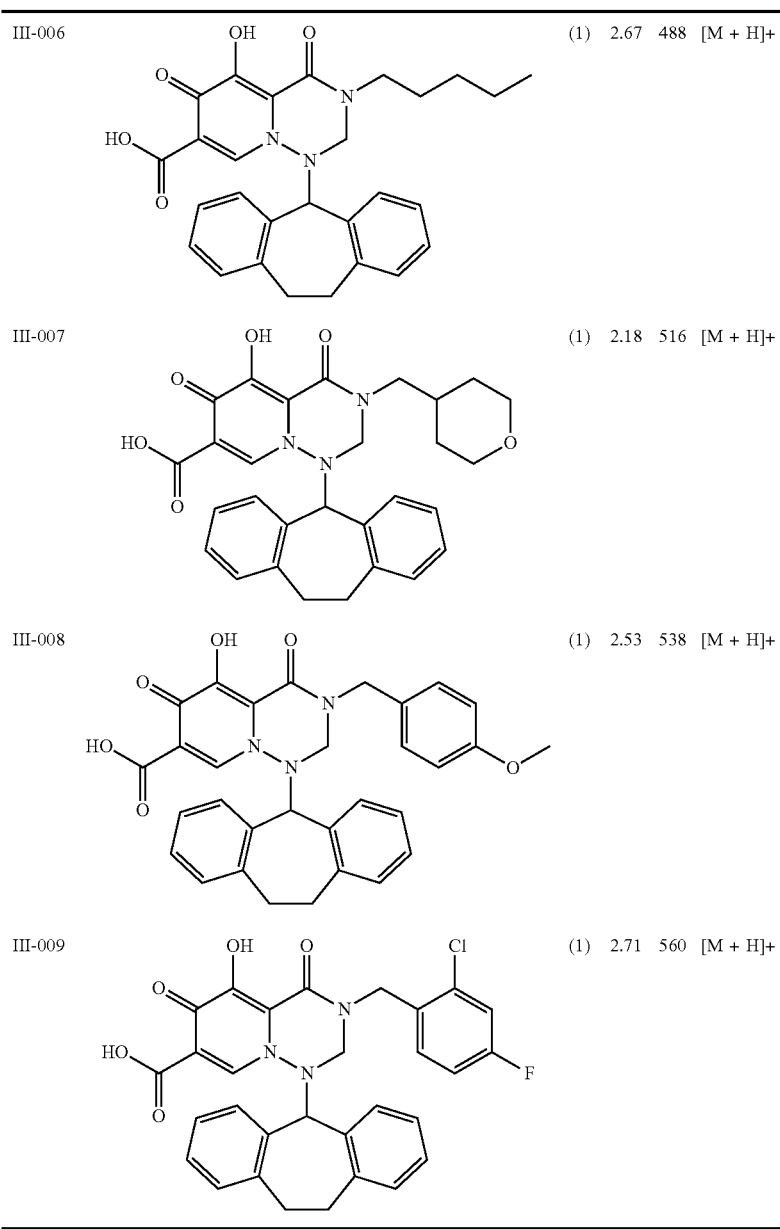

TABLE 16
III-010 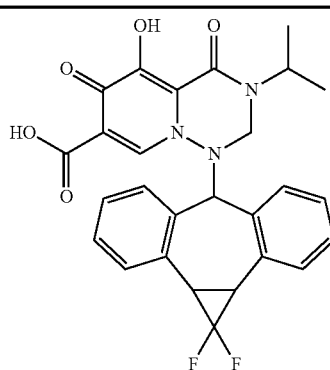 (1) 2.31 508 [M + H]+
III-011 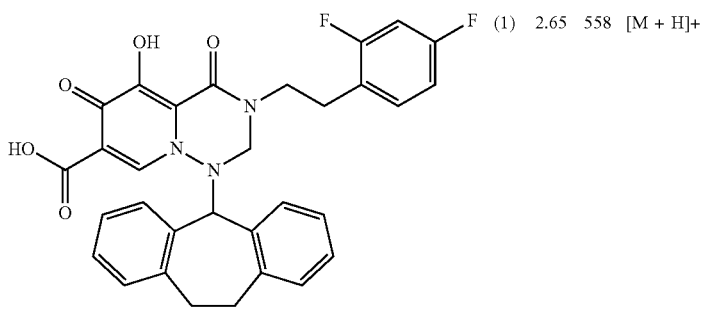 (1) 2.65 558 [M + H]+
III-012 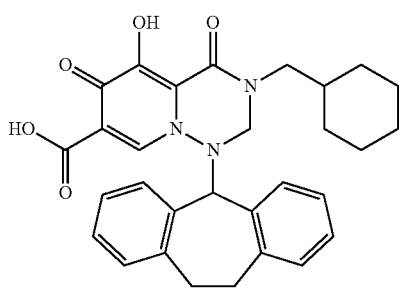 [SMILES: O=C(O)c1cn2c(c(O)c1=O)C(=O)N(CC1CCCCC1)CN2C1c2ccccc2CCc2ccccc21] (1) 2.85 514 [M + H]+
TABLE 17
III-013 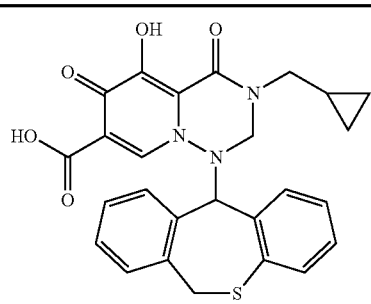 (1) 2.25 490 [M + H]+

TABLE 17-continued
| | | | | | |
|---|---|---|---|---|---|
| III-014 | 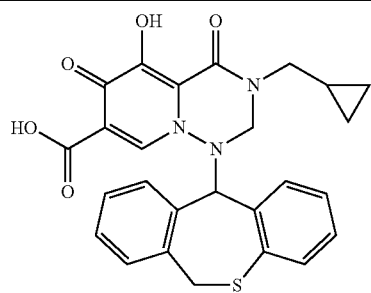 | (1) | 2.25 | 490 | [M + H]+ |
| III-015 | 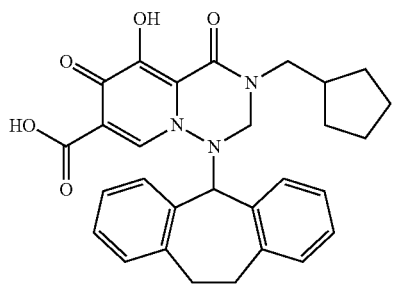 [SMILES: O=C(O)c1cn2c(c(O)c1=O)C(=O)N(CC1CCCC1)CN2C1c2ccccc2CCc2ccccc21] | (1) | 2.66 | 500 | [M + H]+ |
| III-016 | 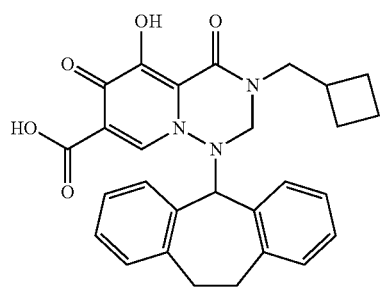 [SMILES: O=C(O)c1cn2c(c(O)c1=O)C(=O)N(CC1CCC1)CN2C1c2ccccc2CCc2ccccc21] | (1) | 2.44 | 486 | [M + H]+ |
TABLE 18
| | | | | | |
|---|---|---|---|---|---|
| III-017 | 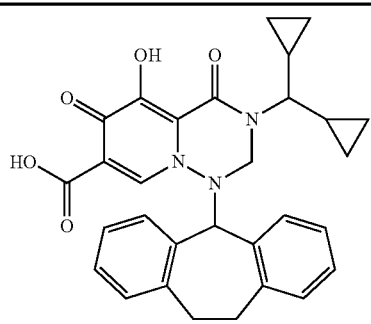 | (1) | 2.61 | 512 | [M + H]+ |
| III-018 | 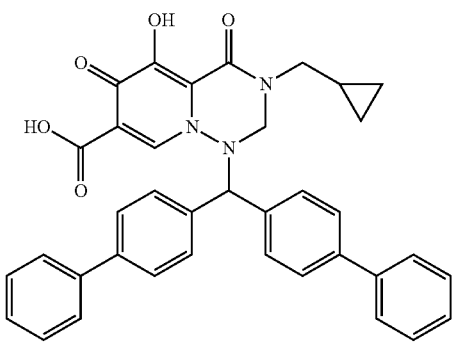 [SMILES: O=C(O)c1cn2c(c(O)c1=O)C(=O)N(CC1CC1)CN2C(c1ccc(-c2ccccc2)cc1)c1ccc(-c2ccccc2)cc1] | (1) | 2.96 | 598 | [M + H]+ |

TABLE 19
| Comp. No. | Structure |
|---|---|
| III-019 | 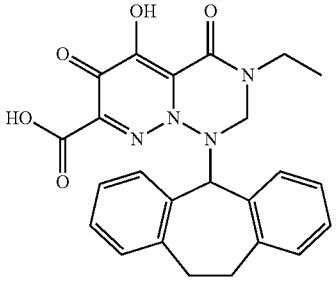 [SMILES: CCN1CN(C2c3ccccc3CCc3ccccc32)n2nc(C(=O)O)c(=O)c(O)c2C1=O] |
TABLE 20
| Comp. No. | Structure | Ms cond. | RT (min) | MS |
|---|---|---|---|---|
| III-020 | 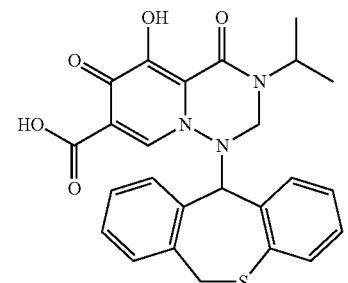 | (1) | 2.2 | 478 [M + H]+ |
| III-021 | 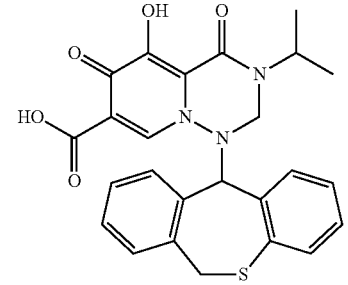 [SMILES: CC(C)N1CN(C2c3ccccc3CSc3ccccc32)n2cc(C(=O)O)c(=O)c(O)c2C1=O] | (1) | 2.2 | 478 [M + H]+ |
| III-022 | 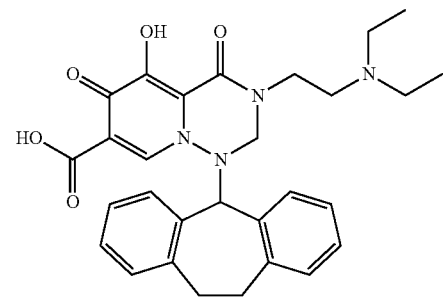 [SMILES: CCN(CC)CCN1CN(C2c3ccccc3CCc3ccccc32)n2cc(C(=O)O)c(=O)c(O)c2C1=O] | (1) | 1.66 | 517 [M + H]+ |
| III-023 | 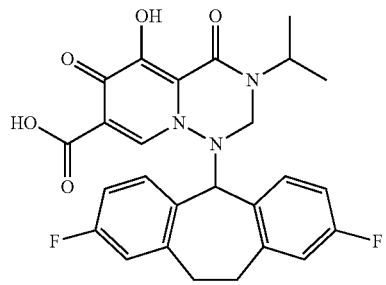 [SMILES: CC(C)N1CN(C2c3ccc(F)cc3CCc3cc(F)ccc32)n2cc(C(=O)O)c(=O)c(O)c2C1=O] | (1) | 2.37 | 496 [M + H]+ |

TABLE 20-continued

| Comp. No. | Structure | Ms cond. | RT (min) | MS |
|---|---|---|---|---|
| III-024 | 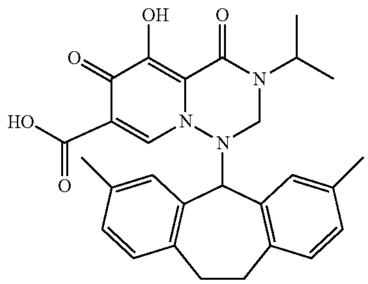 [SMILES: Cc1ccc2c(c1)C(N1CN(C(C)C)C(=O)c3c(O)c(=O)c(C(=O)O)cn31)c1cc(C)ccc1CC2] | (1) | 2.61 | 488 [M + H]+ |

TABLE 21

| | | | | |
|---|---|---|---|---|
| III-025 | | (1) | 2.68 | 528 [M + H]+ |
| III-026 | | (1) | 1.79 | 358 [M + H]+ |

TABLE 22

| | | | | |
|---|---|---|---|---|
| III-027 | | (1) | 2.21 | 446 [M + H]+ |

TABLE 22-continued
III-028 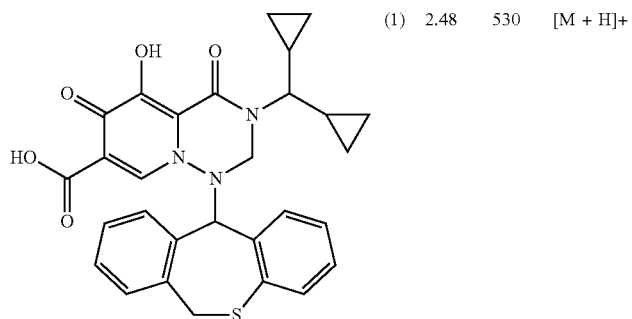 (1) 2.48 530 [M + H]+
III-029 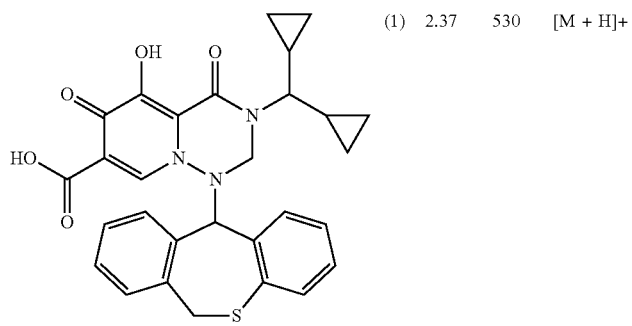 (1) 2.37 530 [M + H]+
III-030 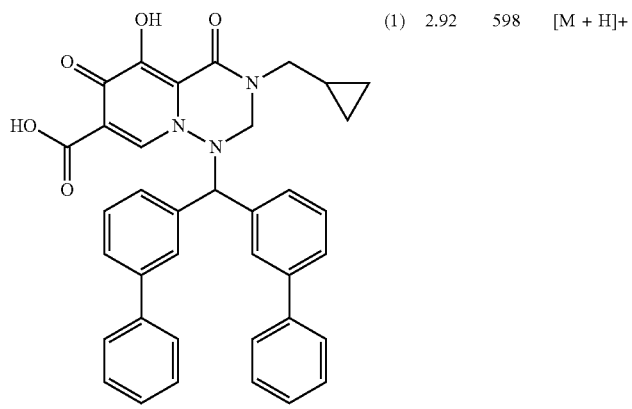 (1) 2.92 598 [M + H]+
III-031 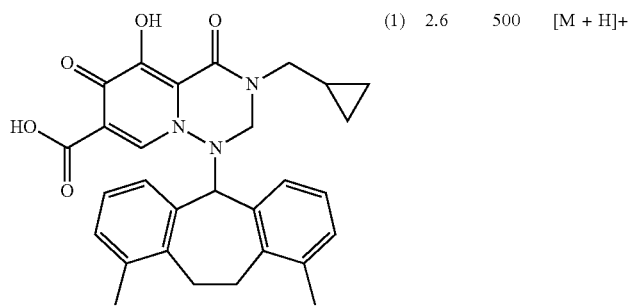 (1) 2.6 500 [M + H]+

TABLE 23
| | | | | | |
|---|---|---|---|---|---|
| III-032 | 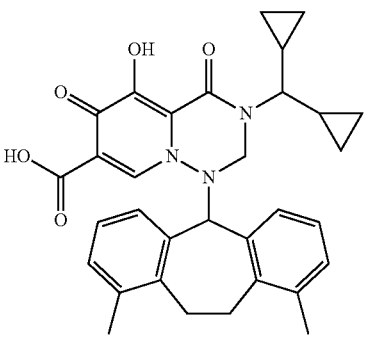 [SMILES: Cc1cccc2c1CCc1c(C)cccc1C2N1CN(C(C2CC2)C2CC2)C(=O)c2c(O)c(=O)c(C(=O)O)cn21] | (1) | 2.84 | 540 | [M + H]+ |
| III-033 | 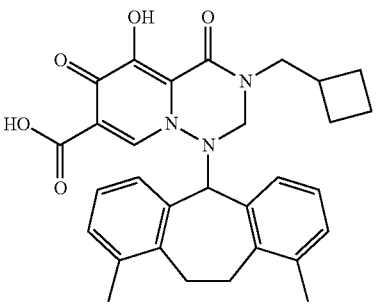 [SMILES: Cc1cccc2c1CCc1c(C)cccc1C2N1CN(CC2CCC2)C(=O)c2c(O)c(=O)c(C(=O)O)cn21] | (1) | 2.76 | 514 | [M + H]+ |
| III-034 | 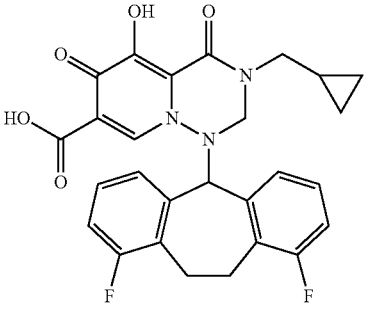 [SMILES: O=C(O)c1cn2c(c(O)c1=O)C(=O)N(CC1CC1)CN2C1c2cccc(F)c2CCc2c(F)cccc21] | (1) | 2.43 | 508 | [M + H]+ |
| III-035 | 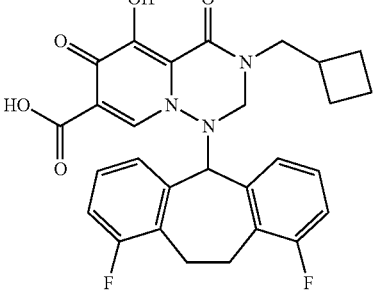 | (1) | 2.59 | 522 | [M + H]+ |
| III-036 | 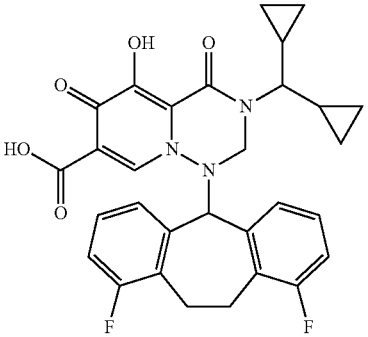 [SMILES: O=C(O)c1cn2c(c(O)c1=O)C(=O)N(C(C1CC1)C1CC1)CN2C1c2cccc(F)c2CCc2c(F)cccc21] | (1) | 2.56 | 548 | [M + H]+ |

The compounds according to the present invention are useful for symptoms and/or diseases which are induced by arenaviruses. Symptoms include fever, headache, fatigue, joint pain, pharyngeal pain, vomiting, diarrhea, hematemesis, blood in stool, mucosal bleeding, and other influenza-like symptoms, as well as encephalitis symptoms. In addition, bleeding (hematemesis, blood in stool) often leads to death when it becomes severe. After recovery, sensory neuropathy, gait ataxia, and hearing impairment as a sequelae may also be seen. In these viruses, infections are transmitted from humans to humans by blood, body fluids, and excrement of infected persons and patients. Thus, there is a possibility that hospital infection and family infection, and a major event leading to a global epidemic occur. Early treatment reduces the amount of virus in the body and prevents transmission, which makes it possible to prevent the global epidemics. The compounds according to the present invention are effective for treating and/or preventing and ameliorating symptoms of these.

Examples of the diseases induced by arenaviruses include arenavirus infections such as Lassa fever, Argentine hemorrhagic fever, Bolivia hemorrhagic fever, Brazil hemorrhagic fever, and Venezuela hemorrhagic fever. For example, the diseases include Lassa fever and Argentine hemorrhagic fever, particularly Lassa fever.

The compounds according to the present invention have a high proliferation inhibitory effect against arenaviruses (such as Junin Virus, LCMV virus, and Lassa virus), and can be useful medicaments. Furthermore, since the compounds according to the present invention also have advantages such as high metabolic stability, high solubility, good bioavailability, good clearance, high tissue migration, long half-life, high non-protein binding rate, low side effects, low hERG channel inhibition, low CYP inhibition, recognized Cytopathic Effect (CPE) inhibitory effect, and/or negative in phototoxicity, Ames, and genotoxicity tests, they can be excellent medicaments.

The compounds according to the present invention can be administered orally or parenterally. In the case of oral administration, the present compounds can also be used in a usual formulation, for example, as any form of solid agents such as tablets, powders, granules, and capsules: aqueous agents; oily suspensions; or liquids such as syrups or elixirs. In the case of parenteral administration, the compound according to the present invention can be used as aqueous or oily injectables or nose drops. Upon preparation of them, conventional excipients, binders, lubricants, aqueous solvents, oily solvents, emulsifiers, suspending agents, preservatives, stabilizers, or the like can be used as desired. The pharmaceutical composition of the present invention can be produced by combining (for example, mixing) a therapeutically effective amount of the present compound with a pharmaceutically acceptable carrier or diluent.

A dose of the compound according to the present invention is different depending on an administration method, an age, a weight and the state of a patient, and a kind of a disease, and, usually, in the case of oral administration, about 0.05 mg to 3000 mg, preferably about 0.1 mg to 1000 mg for adult per day may be administered, if necessary, by division. In addition, in the case of parenteral administration, about 0.01 mg to 1000 mg, preferably about 0.05 mg to 500 mg for adult per day is administered.

Test Example 1: CPE Inhibitory Effect Confirmation Test (Junin Virus)

<Material>
5% FBS E-MEM (adjusted by adding kanamycin, streptomycin, penicillin and FBS to Minimum Essential Medium (MEM) (Nissui))
293T cells 293T cells were adjusted to appropriate cell count ($2 \times 10^6$/mL) with 2% FBS E-MEM.
Absorbance meter (Biorad)
MTT liquid
3-(4,5-Dimethyl-2-thiazol)-2,5-diphenyl-2H-tetrazolium bromide (Merck) was dissolved in PBS to 5 µg/mL, and then filtered with a 0.45 µm filter.
Cell lysate liquid (virus inactivation liquid)
A cell lysate liquid was adjusted by adding 50 mL Triton X and 4 mL hydrochloric acid (12 N) to 500 mL isopropanol.
<Operation Procedure>
Dilution and Dispensation of Test Sample
As the culture medium, 2% FBS E-MEM was used to dilute the test sample, and 5% FBS E-MEM was used to dilute the virus and the cells.
A test sample was diluted with the culture medium to an appropriate concentration in advance, and then 2-fold serial dilution was prepared in 96-well plates (50 µL/well).
Dilution and Dispensation of Cells
Each 100 µL/well of cells which had been adjusted to the appropriate cell number was dispensed in the 96-well plate containing the test sample.
Dilution and Dispensation of Junin Virus
Junin virus was diluted with the culture medium to an appropriate concentration in advance, and each 50 µL/well was dispensed in the 96-well plate containing the test sample.
Those were mixed with a plate mixer, and incubated in a COs incubator for 4 days. Dispensation of MTT liquid and Cell lysate liquid
The cells in the 96-well plate which had been incubated for 4 days were observed visually and under a microscope, and the appearance of the cells and the presence or absence of crystals were checked. The MTT liquid was dispensed by 30 µL into each well, and the plates were incubated in a $CO_2$ incubator for 1 to 2 hours. The supernatant was removed by 150 µL from the plate so that the cells were not absorbed. The cell lysate liquid (virus inactivation liquid) was dispensed by 150 µL into each well. The plate was wrapped in a wrap to avoid drying and left overnight at room temperature. Those were mixed with a plate mixer.
Measurement of Absorbance
In the mixed 96-well plate, absorbance (OD) was measured with an absorbance meter at two wavelengths of 570 nm/630 nm.
<Calculation of Each Measurement Item Value>
The values were calculated using Microsoft Excel or a program having the equivalent calculation and processing ability, based on the following calculation equations.
Calculation of effective inhibition concentration to achieve 50% Junin virus infected cell death (EC50)
$EC50 = 10^Z$ $Z = (50\% \ OD - Low \ OD)/(High \ OD - Low \ OD) \times \{\log(High \ conc.) - \log(Low \ conc.)\} + \log(Low \ conc.)$ OD; absorbance, conc.; drug concentration $50\% \ OD = (OD(cell \ control) - OD(virus \ control)) \times 0.5 + OD(virus \ control)$ OD (cell control): the average of ODs of cell control wells
OD (virus control): the average of ODs of virus control wells
The EC50 was calculated from two points A-High (High OD, High conc.) and B-Low (Low OD, Low conc.) between the absorbance (OD) and the 50%6 OD value on the drug concentration (conc.) curve.

The EC50 values for the test substance against Junin virus are shown below.

TABLE 24

| Comp. No. | EC50 (nM) |
|---|---|
| I-001 | 111 |
| I-002 | 1501 |
| I-004 | 15 |
| I-005 | 28 |
| I-006 | 36 |
| I-007 | 138 |
| I-008 | 239 |
| I-009 | 405 |
| I-010 | 579 |
| I-011 | 1670 |
| I-012 | 3003 |
| I-019 | 6.9 |
| I-020 | 7.1 |
| I-021 | 8.2 |
| I-022 | 10 |
| I-023 | 11 |
| I-024 | 12 |
| I-025 | 13 |
| I-026 | 17 |
| I-027 | 19 |
| I-028 | 40 |
| I-029 | 42 |
| I-030 | 44 |
| I-031 | 45 |
| I-032 | 64 |
| I-033 | 68 |
| I-034 | 68 |
| I-035 | 71 |
| I-036 | 74 |
| I-037 | 82 |
| I-038 | 148 |
| I-039 | 240 |
| I-040 | 173 |
| I-041 | 180 |
| I-042 | 255 |
| I-043 | 281 |
| I-044 | 354 |
| I-045 | 374 |
| I-046 | 382 |
| I-047 | 414 |
| I-048 | 518 |
| I-049 | 620 |
| I-050 | 640 |
| I-051 | 739 |
| I-052 | 751 |
| I-053 | 987 |
| I-054 | 1624 |
| I-055 | 1873 |
| I-056 | 2028 |
| I-057 | 2185 |
| I-072 | 14 |
| I-073 | 65 |
| I-074 | 50 |
| I-075 | 1.7 |
| I-076 | 34 |
| I-077 | 1.8 |
| I-078 | 3.3 |
| I-079 | 5.0 |

TABLE 25

| Comp. No. | EC50 (nM) |
|---|---|
| I-080 | 437 |
| I-081 | 6.1 |
| II-001 | 4.5 |
| II-002 | 12 |
| II-003 | 6.7 |
| II-004 | 9.2 |
| III-001 | 110 |
| III-002 | 4.4 |
| III-003 | 302 |
| III-004 | 21 |
| III-005 | 243 |
| III-006 | 9.4 |
| III-007 | 16 |
| III-008 | 14 |
| III-009 | 19 |
| III-010 | 10 |
| III-011 | 97 |
| III-012 | 21 |
| III-013 | 3.7 |
| III-014 | 276 |
| III-015 | 25 |
| III-016 | 12 |
| III-017 | 4.9 |
| III-018 | 173 |
| III-019 | 72 |
| III-020 | >200 |
| III-021 | 6.2 |
| III-022 | ND |
| III-023 | 17 |
| III-024 | >200 |
| III-025 | 31 |
| III-026 | ND |
| III-027 | 13 |
| III-028 | 2.4 |
| III-029 | 182 |
| III-030 | 18 |
| III-031 | 4.5 |
| III-032 | 17 |
| III-033 | 6.4 |
| III-034 | 4.5 |
| III-035 | 9.6 |
| III-036 | 5.1 |

ND; Not Done

As described above, the compounds according to the present invention have good proliferation inhibitory activity against Junin virus.

Test Example 2: CPE Inhibitory Effect Confirmation Test (Lymphocytic Choriomeningitis Virus (LCMV))

<Material>
2% FBS E-MEM (adjusted by adding kanamycin, streptomycin, penicillin and FBS to Minimum Essential Medium (MEM) (Nissui))
KB Cells
KB Cells were adjusted to appropriate cell count ($2 \times 10^6$/mL) with 2% FBS E-MEM.
Absorbance meter (Biorad)
MTT liquid
3-(4,5-Dimethyl-2-thiazol)-2,5-diphenyl-2H-tetrazolium bromide (Merck) was dissolved in PBS to 5 μg/mL, and then filtered with a 0.45 μm filter.
Cell lysate liquid (virus inactivation liquid)
A cell lysate liquid was adjusted by adding 50 mL Triton X and 4 mL hydrochloric acid (12 N) to 500 mL isopropanol.
<Operation Procedure>
Dilution and Dispensation of Test Sample
As the culture medium, 2% FBS E-MEM was used to dilute the test sample, and to dilute the virus and the cells.
A test sample was diluted with a culture medium to an appropriate concentration in advance, and then 2-fold serial dilution was prepared in 96-well plates (50 μL/well).

Dilusion and Dispensation of Cells
Each 100 μL/well of cells which had been adjusted to the appropriate cell number was dispensed in the 96 well plate containing the test sample.
Dilution and Dispensation of LCMV
LCMV was diluted with a culture medium to an appropriate concentration in advance, and each 50 μL/well was dispensed in the 96-well plate containing the test sample.
Those were mixed with a plate mixer, and incubated in a $CO_2$ incubator for 4 days. Dispensation of MTT liquid and Cell lysate liquid
The cells in the 96-well plate which had been incubated for 4 days was observed visually and under a microscope, and the appearance of the cells and the presence or absence of crystals were checked. The MTT liquid was dispensed by 30 μL into each well, and the plates were incubated in a $CO_2$ incubator for 1 to 2 hours. The supernatant was removed by 150 μL from the plate so that the cells were not absorbed. The cell lysate liquid (virus inactivation liquid) was dispensed by 150 μL into each well. The plate was wrapped in a wrap to avoid drying and left overnight at room temperature. Those were mixed with a plate mixer.
Measurement of Absorbance
In the mixed 96-well plate, absorbance was measured with an absorbance meter at two wavelengths of 570 nm/630 nm.
<Calculation of Each Measurement Item Value>
The value was calculated using Microsoft Excel or a program having the equivalent calculation and processing ability, based on the following calculation equations.
Calculation of effective inhibition concentration to achieve 50% LCMV infected cell death (EC50)
$EC50 = 10^Z$ $Z = (50\% \text{ OD} - \text{Low OD})/(\text{High OD} - \text{Low OD}) \times \{\log(\text{High conc.}) - \log(\text{Low conc.})\} + \log(\text{Low conc.})$ OD; absorbance, conc.; drug concentration $50\% \text{ OD} = \{\text{OD(cell control)} - \text{OD(virus control)}\} \times 0.5 + \text{OD(virus control)}$ OD (cell control): the average of ODs of cell control wells
OD (virus control): the average of ODs of virus control wells
The EC50 was calculated from two points A-High (High OD, High conc.) and B-Low (Low OD, Low conc.) between the absorbance and the 50% OD value on the drug concentration curve.
The EC50 values for the test substance against LCMV are shown below.

TABLE 26

| Comp. No. | EC50 (nM) |
|---|---|
| I-001 | 115 |
| I-002 | 926 |
| I-005 | 53 |
| I-006 | 136 |
| I-007 | 65 |
| I-008 | 205 |
| I-009 | 143 |
| I-010 | 328 |
| I-011 | 1932 |
| I-019 | 2.2 |
| I-020 | 5.9 |
| I-021 | 2.0 |
| I-022 | 1.6 |
| I-023 | 2.2 |
| I-024 | 14 |
| I-025 | 5.0 |
| I-026 | 6.9 |
| I-027 | 9.4 |
| I-028 | 13 |

TABLE 26-continued

| Comp. No. | EC50 (nM) |
|---|---|
| I-029 | <31 |
| I-030 | 31 |
| I-031 | 20 |
| I-032 | 18 |
| I-033 | 15 |
| I-034 | 32 |
| I-035 | <6 |
| I-036 | 69 |
| I-037 | 24 |
| I-038 | 28 |
| I-039 | 17 |
| I-040 | 44 |
| I-041 | 6.2 |
| I-042 | 58 |
| I-043 | 119 |
| I-044 | 40 |
| I-045 | 24 |
| I-046 | 69 |
| I-047 | 372 |
| I-048 | 56 |
| I-049 | 160 |
| I-051 | 722 |
| I 053 | 275 |
| I-054 | 1956 |
| I-057 | 225 |
| I-059 | 772 |
| I-062 | 2414 |
| I-063 | 280 |
| I-066 | 250 |
| I-074 | 48 |
| I-075 | 3.1 |
| I-076 | 13 |
| I-077 | 3.3 |
| I-078 | 6.2 |
| I-079 | 5.3 |
| I-004 | 12 |

TABLE 27

| Comp. No. | EC50 (nM) |
|---|---|
| I-080 | 499 |
| I-081 | 24 |
| II-001 | 8.1 |
| II-002 | 7.1 |
| II-003 | 8 |
| II-004 | 24 |
| III-001 | 19 |
| III-002 | 11 |
| III-003 | 676 |
| III-004 | 27 |
| III-005 | 90 |
| III-006 | 25 |
| III-007 | 14 |
| III-008 | 19 |
| III-009 | 37 |
| III-010 | 9.9 |
| III-011 | 55 |
| III-012 | 38 |
| III-013 | 3.3 |
| III-014 | 130 |
| III-015 | 17 |
| III-016 | 7.3 |
| III-017 | 4.4 |
| III-018 | 399 |
| III-019 | 39 |
| III-020 | 121 |
| III-021 | 4.9 |
| III-022 | >1000 |
| III-023 | 14 |
| III-024 | 83 |
| III-025 | 17 |
| III-026 | >1000 |
| III-027 | 19 |
| III-028 | 2.1 |

TABLE 27-continued

| Comp. No. | EC50 (nM) |
|---|---|
| III-029 | 63 |
| III-030 | 78 |
| III-031 | 4.1 |
| III-032 | 28 |
| III-033 | 8.8 |
| III-034 | 3.5 |
| III-035 | 7.2 |
| III-036 | 6.3 |

As described above, the compounds according to the present invention have good proliferation inhibitory activity against lymphocytic choriomeningitis virus (LCMV). That is, the present invention exhibits strong drug efficacy against the New World arenaviruses to which Junin virus belongs and the Old World arenaviruses to which LCMV belongs. This indicates that the present invention has a broad antiviral activity against arenaviruses in general. In addition, it is expected that the present invention is effective against the South American hemorrhagic fever virus group which includes Junin virus. Also, as described in Non-patent Documents 2 to 4, LCMV has also been used in animal models as an alternative virus for Lassa virus, suggesting that the present invention also exhibits a drug efficacy similar to that against LCMV against Lassa virus.

Test Example 3: Lassa Virus Proliferation Inhibitory Effect Confirmation Test (Test Method) Vero E6 cells were dispersed in 10% FBS DMEM medium, dispensed in a 12-well plate (10/well), and cultured in a COs incubator (37° C.) for 24 hours. Lassa virus (Josiah strain, $10^4$ PFU/ml) was added at 100 μl (MOI=0.001) and allowed to react at 37° C. for 1 hour. After reaction, the mixture was washed 3 times with 2% FBS DMEM medium. The compounds of the present invention or control compounds diluted with 2% FBS DMEM medium were added to be a final concentration of 0.1 μM to 100 μM. (The compound of the present invention was used at 0.1 μM and 1 μM, and the control compound Ribavirin was used at 1 μM, 10 μM and 100 μM.)
They were cultured in a COs incubator (37° C.) and the culture supernatant in each well was collected at 24 hours after infection (24 h.p.i.) and 48 hours after infection (48 h.p.i.), and the virus infectivity titer was measured by a plaque method using Vero E6 cells. The drug efficacy (virus infectivity titer of the culture supernatant) of the compound of the present invention was compared with those of compound-free and control compound (Ribavirin)-added wells.
(Plaque Method)
VeroE6 cells were dispersed in 10% FBS DMEM medium, dispensed in a 12-well plate ($10^6$/well) and cultured in a $CO_2$ incubator (37° C.) for 24 hours. Measurement samples (culture supernatants) were serially diluted to $10$-$10^6$, and infected with each well. After 1 hour reaction, the wells were washed once with 2% FBS DMEM medium, and then 1 ml of 0.6% Tragacanth 2% FBS MEM medium was added thereto. After 7 days, the medium was removed, and the residue was fixed with 10% Formalin, then stained with crystal violet. The number of plaques (where cells not dyed due to death by virus form a focus) was measured, and the final virus infectivity titer was calculated.
(Result)
The results are shown below. In the Table, "24 h.p.i." means 24 hours after infection, and "48 h.p.i." means 48 hours after infection. The unit of virus infectivity titer is PFU/ml. PFU means plaque forming unit.

TABLE 28

| Compound | Compound concentration (μM) | Virus infectivity titer (24 h p.i., PFU/mD | Virus infectivity titer (48 h p.i., PFU/mD |
|---|---|---|---|
| I-021 | 0.1 | $5 \times 10^4$ | $5 \times 10^6$ |
|  | 1 | <10 | $5 \times 10^3$ |
| Ribavirin | 1 | $6 \times 10^4$ | $6 \times 10^6$ |
|  | 10 | $5 \times 10^4$ | $5 \times 10^6$ |
|  | 100 | $1.1 \times 10^2$ | $9 \times 10^4$ |
| Compound Free |  | $1.3 \times 10^5$ | $6 \times 10^6$ |

Compound I-021 of the present invention exhibited a significantly stronger Lassa virus proliferation inhibitory effect than the control compound Ribavirin.

Test Example 3-2: Lassa Virus Proliferation Inhibitory Effect Confirmation Test (Test Method) Vero cells were dispersed in 10% FBS DMEM medium, dispensed in a 12-well plate ($10^3$/well) and cultured in a COs incubator (37° ° C.) for 24 hours. Lassa virus (LF2384 strain) was added at 100 μl (MOI=0.01), and allowed to react at 37° C. for 1 hour. After reaction, the mixture was washed 3 times with 2% FBS DMEM medium. The compound of the present invention or the control compound diluted with 2% FBS DMEM medium were added to be a final concentration of 2 μM to 62.5 nM. They were cultured in a $CO_2$ incubator (37° C.) and the culture supernatant in each well was collected at 72 hours after infection (72 h.p.i.), and the virus infectivity titer was measured by a plaque method using Vero cells. The drug efficacy (virus infectivity titer of the culture supernatant) of the compound of the invention was compared with those of compound-free and control compound-added wells.
(Plaque Method)
Vero cells were dispersed in 10% FBS DMEM medium, dispensed in a 12-well plate ($10^3$/well) and cultured in a $CO_2$ incubator (37° C.) for 24 hours. Measurement samples (culture supernatants) were serially diluted to $10^6$, and infected with each well. After 1 hour reaction, the well was washed once with 2% FBS DMEM medium, and then 1 ml of 0.6% Tragacanth 2% FBS MEM medium was added thereto. After 7 days, the medium was removed, and the residue was fixed with 10% Formalin, then stained with crystal violet. The number of plaques was measured, and the final virus infectivity titer was calculated.
90% Virus proliferation inhibition concentration (IC90) was calculated as follows: Based on virus infectivity titers under each condition, the required drug concentration was calculated to reduce virus proliferation to one-tenth (90% inhibition of virus infectivity titer, IC90) compared to the condition in which the virus was most increased.
(Result)
The results are shown below and in FIG. 1.

TABLE 29

|  | $Log_{10}$ of IC90 (nM) |
|---|---|
| I-021 | 3.10 |
| II-003 | 2.53 |
| I-078 | 3.14 |

Biological test examples for the compounds of the present invention are described below.

Test Example 4: CYP Inhibition Test

CYP inhibition test using commercially available pooled human liver microsome, and employing, as markers, 7-ethoxyresorufin O-deethylation (CYP1A2), tolbutamide methyl-hydroxylation (CYP2C9), mephenytoin 4'-hydroxylation (CYP2C19), dextromethorphan O-demethylation (CYP2D6), and terfenadine hydroxylation (CYP3A4) as typical substrate metabolism reactions of human main five CYP enzyme forms (CYP1A2, 2C9, 2C19, 2D6, 3A4), an inhibitory degree of each metabolite production amount by the compound of the present invention was assessed.

The reaction conditions are as follows: substrate, 0.5 μmol/L ethoxyresorufin (CYP1A2), 100 μmol/L tolbutamide (CYP2C9), 50 μmol/L S-mephenitoin (CYP2C19), 5 μmol/L dextromethorphan (CYP2D6), 1 μmol/L terfenadine (CYP3A4); reaction time, 15 minutes; reaction temperature, 37° C.: enzyme, pooled human liver microsomes 0.2 mg protein/mL; concentration of the compound of the present invention, 1, 5, 10, 20 μmol/L (four points).

Each five kinds of substrates, human liver microsome, or the compound of the present invention in 50 mmol/L Hepes buffer as a reaction solution was added to 96-well plates at the composition described above, and NADPH, as a cofactor, was added thereto to initiate metabolism reactions as indexes. After reaction at 37° C. for 15 minutes, a methanollacetonitrile=1/1 (V/V) solution is added to stop the reaction. After the centrifugation at 3000 rpm for 15 minutes, resorufin (CYP1A2 metabolite) in the supernatant was quantified by a fluorescent multilabel counter or LC/MS/MS and hydroxytolbutamide (CYP2C9 metabolite), 4'hydroxymephenytoin (CYP2C19 metabolite), dextrorphan (CYP2D6 metabolite), and terfenadine alcohol metabolite (CYP3A4 metabolite) were quantified by LC/MS/MS.

The sample adding only DMSO which is a solvent of the compound of the present invention to a reaction system was adopted as a control (100%). Remaining activity (%) was calculated at each concentration of the compound of the present invention added to the solvent, and $IC_{50}$ was calculated by reverse presumption by a logistic model using a concentration and an inhibition rate.

Test Example 5-1: BA Test

Materials and Methods for experiments to evaluate oral absorption
(1) Animals used: mice or SD rats were used.
(2) Rearing condition: mice or SD rats were allowed to freely take solid feed and sterilized tap water.
(3) Setting of dosage and grouping: Oral administration and intravenous administration were performed with the predetermined dosage. Grouping was set as below. (Dosage was changed depending on the compound)
  Oral administration 1 to 30 mg/kg (n=2 to 3)
  Intravenous administration 0.5 to 10 mg/kg (n=2 to 3)
(4) Preparation of administration solutions: Oral administration was performed as solution or suspension. Intravenous administration was performed after solubilization.
(5) Routes of administration: Oral administration was performed mandatory into the stomach by oral sonde. Intravenous administration was performed into the tail vein with a needle-equipped syringe.
(6) Evaluation Items: Blood was collected over time, and concentration of the compound of the present invention in plasma was measured by LC/MS/MS.
(7) Statistical analysis: About transition of concentration of the compound of the present invention in plasma, an area under the plasma concentration-time curve (AUC) was calculated by non-linear least-squares method program, WinNonlin (R), and bioavailability (BA) of the compound of the present invention was calculated from AUCs of the oral administration group and the intravenous administration group.

Test Example 5-2: BA Test

Materials and Methods for experiments to evaluate oral absorption
(1) Animals used: SD rats were used.
(2) Rearing conditions: The SD rats were allowed to freely take solid feed and sterilized tap water.
(3) Setting of dosage and grouping: Oral administration and intravenous administration were performed with the predetermined dosage. Grouping was set as below.
  Oral administration: 2 μmol/kg (n=2)
  Intravenous administration: 1 μmol/kg (n=2)
(4) Preparation of administration solutions: Oral administration was performed as solution or suspension. Intravenous administration was performed after solubilization.
(5) Routes of administration: Oral administration was performed mandatory into the stomach by oral sonde. Intravenous administration was performed into the jugular vein with a needle-equipped syringe.
(6) Evaluation Items: Blood was collected over time, and concentration of the compound of the present invention in plasma was measured by LC/MS/MS.
(7) Statistical analysis: About transition of concentration of the compound of the present invention in plasma, an area under the plasma concentration-time curve (AUC) was calculated by the moment analysis method, and the bioavailability (BA) of the compound of the present invention was calculated from AUCs of the oral administration group and the intravenous administration group.

Test Example 6: Metabolic Stability Test

Using pooled human liver microsomes and pooled rat liver microsomes, the compound of the present invention was reacted for a certain time, and a remaining rate was calculated by comparing a reacted sample and an unreacted sample, thereby, a degree of metabolism in liver was assessed.

A reaction was performed (oxidative reaction) at 37° C. for 0 or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human or rat liver microsomes. After the reaction, 50 μL of the reaction solution is added to 100 μL of a methanollacetonitrile=1/1 (v/v) solution, mixed and centrifuged at 3000 rpm for 15 minutes. The compound of the present invention in the centrifugation supernatant was quantified by LC/MS/MS or solid-phase extraction (SPE)/MS. The amount of the compound of the present invention remaining after the reaction was calculated with the amount of the compound at 0 minutes of the reaction defined as 100%. Hydrolysis reaction is performed in the absence of NADPH, and glucuronidation reaction is performed in the presence of 5 mmol/L LDP-glucuronic acid in place of NADPH, followed by similar procedures. Dilution concentrations and dilution solvents were changed if necessary.

Test Example 7-1: CYP3A4 Fluorescent MBI Test

The CYP3A4 fluorescent MBI test is a test of investigating enhancement of CYP3A4 inhibition of the compound of the present invention by a metabolism reaction. 7-Benzyloxytrifluoromethylcoumarin (7-BFC) is debenzylated by CYP3A4 enzyme (*E. coli* expressing enzyme) to produce a fluorescent metabolite 7-hydroxytrifluoromethylcoumarin (7-HFC). CYP3A4 inhibition is evaluated using the 7-HFC generation reaction as an index.

The reaction conditions are as follows: substrate, 5.6 μmol/L 7-BFC; pre-reaction time, 0 or 30 minutes; reaction time, 15 minutes; reaction temperature, 25° C. (room temperature); CYP3A4 content (*Escherichia coli* expressing enzyme), at pre-reaction 62.5 μmol/mL, at reaction 6.25 μmol/mL (at 10-fold dilution); concentration of the compound of the present invention, 0.625, 1.25, 2.5, 5, 10, 20 μmol/L (six points).

An enzyme in a K-Pi buffer (pH 7.4) and a solution of the compound of the present invention as a pre-reaction solution are added to a 96-well plate at the composition of the pre-reaction described above, a part of it is transferred to another 96-well plate so that it is 1/10 diluted with a substrate and a K-Pi buffer, NADPH as a co-factor is added to initiate a reaction as an index (without pre-reaction) and, after a predetermined time of a reaction, acetonitrile/0.5 mol/L trishydroxyaminomethane (Tris)=4/1 (V/V) are added to stop a reaction. In addition, NADPH is added to a remaining pre-reaction solution to initiate a pre-reaction (with pre-reaction). After a predetermined time of a pre-reaction, a part is transferred to another plate so that it is 1/10 diluted with a substrate and a K-Pi buffer to initiate a reaction as an index.

After a predetermined time of a reaction, acetonitrile/0.5 mol/L trishydroxyaminomethane (Tris)=4/1 (V/V) is added to stop the reaction. For the plate on which each index reaction has been performed, a fluorescent value of 7-HFC which is a metabolite is measured with a fluorescent plate reader. (Ex=420 nm, Em=535 nm).

The sample in which only DMSO that is a solvent of the compound of the present invention is added to a reaction system is adopted as a control (100%). Remaining activity (%) is calculated at each concentration of the compound of the present invention compared to the control, and $IC_{50}$ is calculated by reverse presumption by a logistic model using a concentration and an inhibition rate. When a difference between $IC_{50}$ values is 5 μmol/L or more, this is defined as (+) and, when the difference is 3 μmol/L or less, this is defined as (−).

Test Example 7-2: CYP3A4 (MDZ) MBI Test

CYP3A4 (MDZ) MBI test is a test of investigating Mechanism based inhibition (MBI) potential on CYP3A4 by the enhancement of inhibitory degree of a metabolic reaction caused by the compound of the present invention. CYP3A4 inhibition was evaluated using pooled human liver microsomes by 1-hydroxylation reaction of midazolam (MDZ) as an index.

The reaction conditions are as follows: substrate, 10 μmol/L MDZ; pre-reaction time, 0 or 30 minutes; reaction time, 2 minutes; reaction temperature, 37° C.: pooled human liver microsomes, at pre-reaction time 0.5 mg/mL, at reaction time 0.05 mg/mL (at 10-fold dilution); concentration of the compound of the present invention at pre-reaction, 1, 5, 10, 20 μmol/L or 0.83, 5, 10, 20 μmol/L (four points).

Pooled human liver microsomes and a solution of the compound of the present invention in a K-Pi buffer (pH 7.4) as a pre-reaction solution were added to a 96-well plate at the composition of the pre-reaction. A part of pre-reaction solution was transferred to another 96-well plate, and 1/10 diluted with a substrate and a K-Pi buffer. NADPH as a co-factor was added to initiate a reaction as an index (without pre-reaction). After a predetermined time of a reaction, methanol/acetonitrile=1/1 (V/V) solution was added to stop the reaction. NADPH was also added to a remaining pre-reaction solution to initiate a pre-reaction (with pre-reaction) and, after a predetermined time of a pre-reaction, a part was transferred to another plate so that it was 1/10 diluted with a substrate and a K-Pi buffer to initiate a reaction as an index. After a predetermined time of a reaction, a solution of methanol/acetonitrile=1/1 (V/V) was added to stop the reaction. After the plate on which each index reaction has been performed was centrifuged at 3000 rpm for 15 minutes, 1-hydroxymidazolam in the supernatant was quantified by LC/MS/MS.

The sample adding only DMSO which is a solvent of the compound of the present invention to a reaction system is adopted as a control (100%). Remaining activity (%) is calculated at each concentration of the compound of the present invention compared to the control, and IC value is calculated by reverse-presumption by a logistic model using a concentration and an inhibition rate. Shifted IC value was calculated as "IC of preincubataion at 0 min/IC of preincubataion at 30 min". When a shifted IC was 1.5 or more, this was defined as positive, and when a shifted IC was 1.0 or less, this was defined as negative.

Test Example 8: Fluctuation Ames Test

Mutagenicity of the compounds of the present invention was evaluated.

A 20 μL of freezing-stored *Salmonella typhimurium* (TA98 strain, TA100 strain) is inoculated on 10 mL of a liquid nutrient medium (2.5% Oxoid nutrient broth No. 2), and this is incubated at 37° C. for 10 hours under shaking. The 7.70 to 8.0 mL of the bacterial solution of TA98 strain was centrifuged (2000×g, 10 minutes) to remove the culture solution. The bacteria was suspended in 7.7 to 8.0 mL of a Micro F buffer ($K_2HPO_4$: 3.5 g/L. $KH_2PO_4$: 1 g/L, $(NH_4)SO_4$: 1 g/L, trisodium citrate dihydrate: 0.25 g/L, $MgSO_4 \cdot 7H_2O$: 0.1 g/L), the suspension was added to 120 mL of an Exposure medium (Micro F buffer containing Biotin: 8 μg/mL, histidine: 0.2 μg/mL, glucose: 8 mg/mL). The TA100 strain was added to 120 to 130 mL of the Exposure medium relative to 3.10 to 3.42 mL of the bacterial solution to prepare a test bacterial solution. Each 12 μL of DMSO solution of a compound of the present invention (several stage dilution from maximum dose 50 mg/mL at 2 to 3 fold ratio), DMSO as a negative control, and 50 μg/mL of 4-nitroquinoline-1-oxide DMSO solution for the TA98 strain, 0.25 μg/mL of 2-(2-furyl)-3-(5-nitro-2-furyl)acrylamide DMSO solution for the TA100 strain under the non-metabolism activating condition, 20 μg/mL of 2-aminoanthracene DMSO solution for the TA98 strain, 40 μg/mL of 2-aminoanthracene DMSO solution for the TA100 strain under the metabolism activating condition as a positive control, and 588 μL of the test bacterial solution (a mixed solution of 498 μL of the test bacterial solution and 90 μL of 89 mix under the metabolism activating condition) are mixed, and this is shaking-cultured at 37° C. for 90 minutes. 460 μL of the bacterial solution exposed to the compound of the present invention was mixed with 2300 μL of an Indicator medium (Micro F buffer containing biotin: 8 μg/mL, histidine: 0.2 μg/mL, glucose: 8 mg/mL, Bromo Cresol Purple: 37.5 μg/mL), each 50 μL was dispensed into microplate 48 wells/dose, and this was subjected to stationary culture at 37° C. for 3 days. Since a well containing a bacterium which has obtained a proliferation ability by mutation of an amino acid (histidine) synthesizing enzyme gene turns from purple to yellow due to a pH change, the bacterium proliferation well which has turned to yellow in 48 wells per dose was counted, and was assessed by comparing with a negative control group. (−) means that mutagenicity is negative and (+) means that mutagenicity is positive.

Test Example 9: hERG Test

For the purpose of assessing risk of an electrocardiogram QT interval prolongation of the compound of the present invention, effects of the compound of the present invention on delayed rectifier K$^+$ current ($I_{Kr}$), which plays an important role in the ventricular repolarization process, is studied using HEK293 cells expressing human ether-a-go-go related gene (hERG) channel.

After a cell is retained at a membrane potential of −80 mV by whole cell patch clamp method using an automated patch clamp system (PatchXpress 7000A, Axon Instruments Inc.), $I_{Kr}$ induced by depolarization pulse stimulation at +40 mV for 2 seconds and, further, repolarization pulse stimulation at −50 mV for 2 seconds, is recorded. After the generated current is stabilized, extracellular solution (NaCl: 135 mmol/L, KCl: 5.4 mmol/L, NaH$_2$PO$_4$: 0.3 mmol/L, CaCl$_2$).2H$_2$O: 1.8 mmol/L. MgCl$_2$. 6H$_2$O: 1 mmol/L, glucose: 10 mmol/L, HEPES (4-(2-hydroxyethyl)-1-piperazine ethanesulfonic acid): 10 mmol/L, pH=7.4), in which the compound of the present invention has been dissolved at an objective concentration, is applied to the cell at room temperature for 10 minutes. From the recorded $I_{Kr}$, an absolute value of the tail peak current is measured based on the current value at the resting membrane potential using analysis software (DataXpress ver.1, Molecular Devices Corporation). Further, the % inhibition relative to the tail peak current before application of the compound of the present invention is calculated, and compared with the vehicle-applied group (0.1% dimethyl sulfoxide solution) to assess influence of the compound of the present invention on $I_{Kr}$.

Test Example 9-2: hERG Test

For the purpose of assessing risk of an electrocardiogram QT interval prolongation of the compound of the present invention, effects of the compound of the present invention on delayed rectifier K$^+$ current ($I_{Kr}$), which plays an important role in the ventricular repolarization process, was studied using CHO cells expressing human ether-a-go-go related gene (hERG) channel.

After a cell was retained at a membrane potential of −80 mV by whole cell patch clamp method using an automated patch clamp system (QPatch; Sophion Bioscience A/S) and gave a leak potential of −50 mV, $I_{Kr}$ induced by depolarization pulse stimulation at +20 mV for 2 seconds and, further, repolarization pulse stimulation at −50 mV for 2 seconds, was recorded. Extracellular solution (NaCl: 145 mmol/L, KCl: 4 mmol/L, CaCl$_2$): 2 mmol/L, MgCl$_2$: 1 mmol/L, glucose: 10 mmol/L, HEPES (4-(2-hydroxyethyl)-1-piperazine ethanesulfonic acid): 10 mmol/L. pH=7.4) adjusted to contain 0.1% dimethylsulfoxide was used as a vehicle. The extracellular solution in which the vehicle and the compound of the present invention had been dissolved at each objective concentration was applied to the cell for 7 minutes or more at room temperature. From the recorded $I_{Kr}$, an absolute value of the tail peak current was measured based on the current value at the resting membrane potential using analysis software (QPatch Assay software; Sophion Bioscience A/S). Further, the tail peak current after application of the compound of the present invention relative to the tail peak current after application of the vehicle was calculated as % inhibition to assess the influence of the compound of the present invention on Ir.

Test Example 10: Solubility Test

The solubility of the compound of the present invention was determined under conditions of 1% DMSO addition. 10 mmol/L solution of the compound is prepared with DMSO. 2 μL of the solution of the compound of the present invention is respectively added to 198 μL of JP-1 fluid (water is added to 2.0 g of sodium chloride and 7.0 mL of hydrochloric acid to reach 1000 mL) or JP-2 fluid (1 volume of water is added to 1 volume of the solution in which 3.40 g of potassium dihydrogen phosphate and 3.55 g of anhydrous disodium hydrogen phosphate are dissolved in water to reach 1000 mL). The mixture was shaked for 1 hour or more at a room temperature, and the mixture was filtered. The filtrate was 100-fold diluted with methanol/water=1/1 (V/V), and the compound concentration in the filtrate was measured with LC/MS by the absolute calibration method.

Test Example 11: Powder Solubility Test

Appropriate amounts of the compound of the present invention was put into vials, and each 200 μL of JP-1 Fluid (water was added to 2.0 g of sodium chloride and 7.0 mL of hydrochloride acid to reach 1000 mL), JP-2 Fluid (500 mL of water was added to 500 mL of phosphate buffer solution at pH 6.8) and 20 mmol/L sodium taurocholate (TCA)/JP-2 Fluid (JP-2 Fluid was added to 1.08 g of TCA to reach 100 mL) were added to each vial. When the whole amount was dissolved after the test solution addition, the compound of the present invention was appropriately further added. After sealing and shaking at 37° C. for 1 hour, solution is filtered and 100 μL of methanol is added to 100 μL of each filtrate to dilute two-fold. Each filtrate volume and dilution magnification were changed if necessary. After it was confirmed whether there were no air bubbles and precipitates in the vials, the vials were sealed and shaken. The compound of the present invention was quantified by the absolute calibration curve method using HPLC.

Test Example 12: Ames Test

Ames test is performed by using Salmonellas (*Salmonella typhimurium*) TA 98, TA100. TA1535 and TA1537 and *Escherichia coli* WP2uvrA as test strains with or without metabolic activation conditions in the pre-incubation method to check the presence or absence of gene mutagenicity of the compound of the present invention. 0.1 mL of a DMSO solution of the compound of the present invention is mixed with 0.5 mL of S9 mix under metabolic activation conditions or 0.5 mL of a phosphate buffer solution and 0.1 mL of each test bacterial solution under non-metabolic activation conditions, and the mixture is overlaid on a minimum glucose agar plate together with 2 mL of soft agar for overlay containing histidine and biotin, or tryptophan. At the same time therewith, a similar test is also conducted as to a negative control substance (DMSO) and a positive control substance (2-(2-furyl)-3-(5-nitro-2-furyl)acrylamide, sodium azide, 9-aminoacridine, or 2-aminoanthracene). After culture at 37° C. for 48 hours, revertant colonies that have appeared are counted and evaluated by comparison with the negative control group. When the number of revertant colonies increases in a concentration-dependent manner and becomes twice or more the number of colonies of the negative control group, positivity is determined.

Test Example 13: Photohemolysis Test

The compound of the present invention is dissolved at a concentration of interest. The solution is mixed with 0.1 to 0.0008% concentrations of red blood cell suspensions (2.5 v/v %) prepared from sheep defibrinated blood, on a microplate. The mixtures are irradiated with light (10 J/cm$^2$, 290 to 400 nm) in UVA and UVB regions using an ultraviolet fluorescent lamp (GL20SE lamp from Sankyo Electronics and FL20S-BLB lamp from Panasonic). The mixed solutions after the completion of light irradiation are collected and centrifuged. The supernatants after the centrifugation are collected and transferred to a microplate. Then, the absorbance (540 or 630 nm) of the supernatants is measured, and assessment based on the absorbance is performed. The absorbance data at wavelength of 540 nm and 630 nm are used as indexes of biomembrane damage (photohemolysis %) and hyperoxidation of lipid membrane (methemoglobin formation), respectively. When the rate of photohemolysis is less than 10% and the amount of change in absorbance at 630 nm is less than 0.05, the test sample is graded as (−). When the rate of photohemolysis is 10% or more and the amount of change in absorbance at 630 nm is 0.05 or more, the test sample is graded as (+).

Test Example 14: Clearance Evaluation Test

Experimental Material and Method
(1) Animals used: Rats were used.
(2) Rearing conditions: The rats were allowed to freely take solid feed and sterilized tap water.
(3) Dose and grouping setting: Intravenous administration was performed with the predetermined dosage. Groups were set as follows:
Intravenous administration: 1 μmol/kg (n=2)
(4) Preparation of dosing solution: The test sample was solubilized using a solvent of dimethyl sulfoxide/propylene glycol=1/1, and administered.
(5) Routes of administration: Administration was performed into the tail vein with a needle-equipped syringe.
(6) Evaluation Items: Blood was collected over time, and concentration of the compound of the present invention in plasma was measured by LC/MS/MS.
(7) Statistical analysis: About transition of concentration of the compound of the present invention in plasma, total body clearance (CLtot) and elimination half-life (t1/2) were calculated by the moment analysis method.

The following formulation examples are only exemplified and not intended to limit the scope of the invention.

The compound of the present invention can be administered as a pharmaceutical composition through any conventional route, particularly, enterally, for example, orally, in the form of, for example, a tablet or a capsule, parenterally in the form of, for example, an injection or a suspension, locally in the form of, for example, a lotion, a gel, an ointment or a cream, or in a transnasal form or a suppository form. A pharmaceutical composition containing the compound of the present invention in a free form or in a pharmaceutically acceptable salt form together with at least one pharmaceutically acceptable carrier or diluent can be produced by a mixing, granulation or coating method according to conventional methods. For example, an oral composition can be prepared as a tablet, a granule, or a capsule containing an excipient, a disintegrant, a binder, a lubricant, or the like and the active ingredient, etc. Also, an injectable composition can be prepared as a solution or a suspension and may be sterilized. The injectable composition may contain a preservative, a stabilizer, a buffering agent, or the like.

INDUSTRIAL APPLICABILITY

The compounds according to the present invention have arenavirus proliferation inhibitory activity after absorption into the body. The compounds according to the present invention can be medicaments useful as an agent for treating and/or preventing symptoms and/or diseases induced by infection with arenaviruses, preferably, the Old World arenaviruses (e.g., Lassa virus, Lujo virus, Luna virus, and lymphocytic choriomeningitis virus) and/or the New World arenaviruses (e.g., Junin virus).

The invention claimed is:
1. A method for inhibiting arenavirus proliferation in a human or an animal, comprising administering an effective amount of a compound represented by Formula (I) or a prodrug thereof or a pharmaceutically acceptable salt thereof to the human or animal:

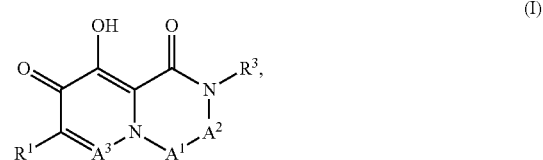

wherein:
R$^1$ is —Z$^X$—C(=O)—O—R$^{X15}$, —Z$^X$—C(=O)—N(R$^{X9}$)(R$^{X10}$), or —Z$^X$—N(R$^{X14}$)—C(=O)—O—R$^{X15}$,
wherein R$^{X9}$, R$^{X14}$, and R$^{X15}$ are each independently a hydrogen atom, alkyl optionally substituted with Substituent group E, alkenyl optionally substituted with Substituent group E, or alkynyl optionally substituted with Substituent group E;
R$^{X10}$ is a hydrogen atom, alkyl optionally substituted with Substituent group E, alkenyl optionally substituted with Substituent group E, alkynyl optionally substituted with Substituent group E, or alkyloxy optionally substituted with Substituent group E;
Z$^X$ is a single bond or a linear or branched alkylene;
R$^{X9}$ and R$^{X10}$ may be taken together with an adjacent atom to form a heterocycle;
A$^3$ is CR$^2$ or N;
R$^2$ is a hydrogen atom, halogen, hydroxy, carboxy, cyano, formyl, alkyl optionally substituted with Substituent group F, alkenyl optionally substituted with Substituent group F, alkynyl optionally substituted with Substituent group F, or alkyloxy optionally substituted with Substituent group F;
R$^3$ is a hydrogen atom, hydroxy, carboxy, cyano, formyl, alkyl optionally substituted with Substituent group F, alkenyl optionally substituted with Substituent group F, alkynyl optionally substituted with Substituent group F, alkyloxy optionally substituted with Substituent group F, alkenyloxy optionally substituted with Substituent group F, alkylcarbonyl optionally substituted with Substituent group F, alkyloxycarbonyl optionally substituted with Substituent group F, a carbocyclic group optionally substituted with Substituent group A, carbocyclealkyl optionally substituted with Substituent group A, carbocycleoxyalkyl optionally substituted with Substituent group A, carbocyclecarbonyl optionally substituted with Substituent group A, carbocycleoxy optionally substituted with Substituent group A, carbocycleoxycarbonyl optionally substituted with Substituent group A, a heterocyclic group optionally substituted with Substituent group A, heterocyclealkyl optionally substituted with Substituent group A, heterocycleoxyalkyl optionally substituted with Substituent group A, heterocyclecarbonyl optionally substituted with Substituent group A, heterocycleoxy optionally substituted with Substituent group A, heterocycleoxycarbonyl optionally substituted with Substituent group A, —$Z^Z$—N($R^{Z1}$)—$SO_2$—$R^{Z2}$,
—$Z^Z$—N($R^{Z3}$)—C(=O)—$R^{Z4}$,
—$Z^Z$—N($R^{Z5}$)—C(=O)—O—$R^{Z6}$,
—$Z^Z$—C(=O)—N($R^{Z7}$)($R^{Z8}$),
—$Z^Z$—N($R^{Z9}$)($R^{Z10}$),
—$Z^Z$—$SO_2$—$R^{Z11}$, or
—$Z^Z$—N($R^{Z12}$)—O—C(=O)—$R^{Z13}$, wherein $R^{Z1}$, $R^{Z3}$, $R^{Z4}$, $R^{Z5}$, $R^{Z6}$, $R^{Z7}$, $R^{Z8}$, $R^{Z9}$, $Z^{10}$, $Z^{12}$, and $Z^{13}$ are each independently selected from the group consisting of a hydrogen atom, alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;

$R^{Z2}$ and $R^{Z11}$ are each independently selected from the group consisting of alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;

$R^{Z7}$ and $R^{Z8}$ may be taken together with an adjacent atom to form a heterocycle;

$Z^Z$ is a single bond or a linear or branched alkylene;

a) either $A^1$ or $A^2$ is $CR^5R^6$, and the other is $NR^7$, or
b) $A^1$ is $CR^8R^9$, and $A^2$ is $CR^{10}R^{11}$;

$R^5$, $R^6$, $R^7$, $R^8$, $R^9$, $R^{10}$, and $R^{11}$ are each independently a hydrogen atom, carboxy, cyano, alkyl optionally substituted with Substituent group F, alkenyl optionally substituted with Substituent group F, alkynyl optionally substituted with Substituent group F, alkylcarbonyl optionally substituted with Substituent group F, alkyloxycarbonyl optionally substituted with Substituent group F, a carbocyclic group optionally substituted with Substituent group B, carbocyclealkyl optionally substituted with Substituent group B, carbocycleoxyalkyl optionally substituted with Substituent group B, carbocyclecarbonyl optionally substituted with Substituent group B, carbocycleoxycarbonyl optionally substituted with Substituent group B, a heterocyclic group optionally substituted with B, heterocyclealkyl optionally substituted with Substituent group B, heterocycleoxyalkyl optionally substituted with Substituent group B, heterocyclecarbonyl optionally substituted with Substituent group B, heterocycleoxycarbonyl optionally substituted with Substituent group B, —$Z^V$—S—$R^{V1}$,
—$Z^V$—S(=O)—$R^{V2}$,
—$Z^V$—$SO_2$—$R^{V3}$,
—C(=O)—C(=O)—$R^{V4}$,
—C(=O)—N($R^{V5}$)($R^{V6}$),
—$Z^V$—N($R^{V7}$)—C(=O)—O—$R^{V8}$, or
—$Z^V$—N($R^{V9}$)—C(=O)—$R^{V10}$, wherein $R^{V1}$, $R^{V4}$, $R^{V5}$, $R^{V6}$, $R^{V7}$, $R^{V8}$, $R^{V9}$, and $R^{V10}$ are each independently selected from the group consisting of a hydrogen atom, alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;

$R^{V2}$ and $R^{V3}$ are each independently selected from the group consisting of alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;

$R^{V5}$ and $R^{V6}$ may be taken together with an adjacent atom to form a heterocycle;

$Z^V$ is a single bond or a linear or branched alkylene;

$R^5$ and $R^6$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure;

$R^8$ and $R^9$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure;

$R^{10}$ and $R^{11}$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure;

1) When $A^1$ is $CR^5R^6$ and $A^2$ is $NR^7$, then $R^5$ and $R^7$ may be taken together to form a bond, or $R^5$ and $R^7$ may be taken together with an adjacent atom to form a heterocycle optionally substituted with Substituent group B, wherein the heterocycle may form a condensed ring and/or a spiro ring and/or a bridged structure, or $R^3$ and $R^7$ may be taken together with an adjacent atom to form a heterocycle optionally substituted with Substituent group B, wherein the heterocycle may form a condensed ring and/or a spiro ring and/or a bridged structure, 2) When $A^1$ is $NR^7$ and $A^2$ is $CR^5R^6$, then $R^7$ and $R^5$ may be taken together to form a bond, or $R^7$ and $R^5$ may be taken together with an adjacent atom to form a heterocycle optionally substituted with Substituent group B, wherein the heterocycle may form a condensed ring and/or a spiro ring and/or a bridged structure, or $R^3$ and $R^6$ may be taken together with an adjacent atom to form a heterocycle optionally substituted with Substituent group B, wherein the heterocycle may form a condensed ring and/or a spiro ring and/or a bridged structure, 3) when $A^1$ is $CR^8R^9$, and $A^2$ is $CR^{10}R^{11}$, then $R^8$ and $R^{10}$ may be taken together to form a bond, or $R^8$ and $R^{10}$ may be taken together with an adjacent atom to form a carbocycle optionally substituted with Substituent group B or a heterocycle optionally substituted with Substituent group B, wherein the carbocycle or the heterocycle may form a condensed ring and/or a spiro ring and/or a bridged structure, or $R^3$ and $R^{11}$ may be taken together with an adjacent atom to form a heterocycle optionally substituted with Substituent group B, wherein the heterocycle may form a condensed ring and/or a spiro ring and/or a bridged structure, with a proviso that following compounds of c) and d) are excluded:

c) $R^5$, $R^6$, and $R^7$ are all a hydrogen atom, d) $R^8$, $R^9$, $R^{10}$, and $R^{11}$ are all a hydrogen atom; and wherein Substituent group A is selected from the group consisting of halogen, cyano, hydroxy, carboxy, formyl, amino, oxo, nitro, alkyl, halogenoalkyl, alkyloxy, alkylthio, alkylamino, hydroxyalkyl, carboxyalkyl, aminoalkyl, a carbocyclic group, a heterocyclic group, an oxo-substituted heterocyclic group, carbocyclealkyloxy, carbocycleoxyalkyl, carbocyclealkyloxyalkyl, carbocyclealkylthio, heterocyclealkyloxy, heterocycleoxyalkyl, heterocyclealkyloxyalkyl, halogenoalkyloxy, alkyloxyalkyl, alkyloxyalkyloxy, alkylcarbonyl, alkylcarbonyloxy, alkyloxycarbonyl, alkyloxycarbonyloxy, alkylamino, alkylcarbonylamino, halogenoalkylcarbonylamino, alkylaminocarbonyl, alkyl sulfonyl, alkylsulfinyl, and alkylsulfonylamino;

wherein Substituent group B is selected from the group consisting of halogen, cyano, hydroxy, carboxy, formyl, amino, oxo, nitro, alkyl, halogenoalkyl, alkyloxy, alkylthio, alkylamino, hydroxyalkyl, carboxyalkyl, alkylamino, carbocyclealkyloxy, heterocyclealkyloxy, halogenoalkyloxy, alkyloxyalkyl, alkyloxyalkyloxy, alkylcarbonyl, alkyloxycarbonyl, alkyloxycarbonyloxy, alkylamino, alkylcarbonylamino, alkylaminocarbonyl, alkyl sulfonyl, alkylsulfonylamino, a carbocyclic group optionally substituted with Substituent group A, a heterocyclic group optionally substituted with Substituent group A, carbocyclealkyl optionally substituted with Substituent group A, heterocyclealkyl optionally substituted with Substituent group A, carbocyclealkyloxy optionally substituted with Substituent group A, heterocyclealkyloxy optionally substituted with Substituent group A, carbocyclealkylthio optionally substituted with Substituent group A, heterocyclealkylthio optionally substituted with Substituent group A, carbocycleoxyalkyl optionally substituted with Substituent group A, heterocycleoxyalkyl optionally substituted with Substituent group A, carbocyclealkyloxyalkyl optionally substituted with Substituent group A, and heterocyclealkyloxyalkyl optionally substituted with Substituent group A;

wherein Substituent group E is selected from the group consisting of halogen, hydroxy, carboxy, alkyloxy, alkylcarbonyl, alkyloxycarbonyl, alkylcarbonyloxy, alkylaminocarbonyl, and alkyl sulfonyl; and wherein Substituent group F is selected from the group consisting of halogen, cyano, hydroxy, carboxy, formyl, amino, oxo, nitro, alkyloxy, alkylthio, a carbocyclic group, a heterocyclic group, an oxo-substituted heterocyclic group, carbocyclealkyloxy, carbocyclealkylthio, heterocyclealkyloxy, halogenoalkyloxy, alkyloxyalkyloxy, alkylcarbonyl, alkylcarbonyloxy, alkyloxycarbonyl, alkyloxycarbonyloxy, alkylamino, alkylcarbonylamino, halogenoalkylcarbonylamino, alkylaminocarbonyl, alkyl sulfonyl, alkylsulfinyl, and alkylsulfonylamino.

2. The method according to claim 1, wherein a) either $A^1$ or $A^2$ is $CR^5R^6$, and the other is $NR^7$, or b) $A^1$ is $CR^8R^9$, and $A^2$ is $CR^{10}R^{11}$, $R^5$, $R^6$, $R^7$, $R^8$, $R^9$, $R^{10}$, and $R^{11}$ are each independently a hydrogen atom, carboxy, cyano, alkyl optionally substituted with Substituent group F, alkenyl optionally substituted with Substituent group F, alkynyl optionally substituted with Substituent group F, alkylcarbonyl optionally substituted with Substituent group F, alkyloxycarbonyl optionally substituted with Substituent group F, a carbocyclic group optionally substituted with Substituent group B, carbocyclealkyl optionally substituted with Substituent group B, carbocycleoxyalkyl optionally substituted with Substituent group B, carbocyclecarbonyl optionally substituted with Substituent group B, carbocycleoxycarbonyl optionally substituted with Substituent group B, a heterocyclic group optionally substituted with Substituent group B, heterocyclealkyl optionally substituted with Substituent group B, heterocycleoxyalkyl optionally substituted with Substituent group B, heterocyclecarbonyl optionally substituted with Substituent group B, heterocycleoxycarbonyl optionally substituted with Substituent group B,

—$Z^V$—S—$R^{V1}$,

—$Z^V$—S(=O)—$R^{V2}$,

—$Z^V$—$SO_2$—$R^{V3}$,

—C(=O)—C(=O)—$R^{V4}$,

—C(=O)—N($R^{V5}$)($R^{V6}$),

—$Z^V$—N($R^{V7}$)—C(=O)—O—$R^{V8}$, or

—$Z^V$—N($R^{V9}$)—C(=O)—$R^{V10}$, wherein $R^{V1}$, $R^{V4}$, $R^{V5}$, $R^{V6}$, $R^{V7}$, $R^{V8}$, $R^{V9}$, and $R^{V10}$ are each independently selected from the group consisting of a hydrogen atom, alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;

$R^{V2}$ and $R^{V3}$ are each independently selected from the group consisting of alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;

R$^{V5}$ and R$^{V6}$ may be taken together with an adjacent atom to form a heterocycle;

Z$^V$ is a single bond or a linear or branched alkylene;

R$^5$ and R$^6$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure;

R$^8$ and R$^9$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure; and R$^{10}$ and R$^{11}$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure;

with a proviso that when A$^1$ is CR$^5$R$^6$ and A$^2$ is NR$^7$, then the 1) defined in claim 1 is not applied; when A$^1$ is NR$^7$ and A$^2$ is CR$^5$R$^6$, then the 2) defined in claim 1 is not applied; and when A$^1$ is CR$^8$R$^9$ and A$^2$ is CR$^{10}$R$^{11}$, then the 3) defined in claim 1 is not applied.

3. The method according to claim 1, wherein A$^1$ is NR$^7$, and A$^2$ is CR$^5$R$^6$.

4. The method according to claim 1, wherein
R$^7$ is a carbocyclic group optionally substituted with Substituent group B, carbocyclealkyl optionally substituted with Substituent group B, a heterocyclic group optionally substituted with Substituent group B, or heterocyclealkyl optionally substituted with Substituent group B;
R$^5$ is a hydrogen atom; and
R$^6$ is a hydrogen atom or alkyl optionally substituted with Substituent group F.

5. The method according to claim 1, wherein R$^1$ is carboxy.

6. The method according to claim 1, wherein
R$^2$ is a hydrogen atom or alkyl; and
R$^3$ is alkyl optionally substituted with Substituent group F, alkenyl optionally substituted with Substituent group F, alkynyl optionally substituted with Substituent group F, carbocyclealkyl optionally substituted with Substituent group A, a carbocyclic group optionally substituted with Substituent group A, heterocyclealkyl optionally substituted with Substituent group A, or carbocycleoxyalkyl optionally substituted with Substituent group A.

7. The method according to claim 1, wherein A$^3$ is CR$^2$.

8. The method according to claim 1, wherein when either A$^1$ or A$^2$ is CR$^5$R$^6$ and the other is NR$^7$, then either R$^5$ or R$^7$ is a group shown below; and when A$^1$ is CR$^8$R$^9$ and A$^2$ is CR$^{10}$R$^{11}$, then either R$^8$ or R$^{10}$ is a group shown below:

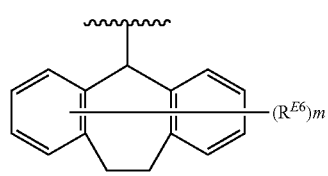

-continued

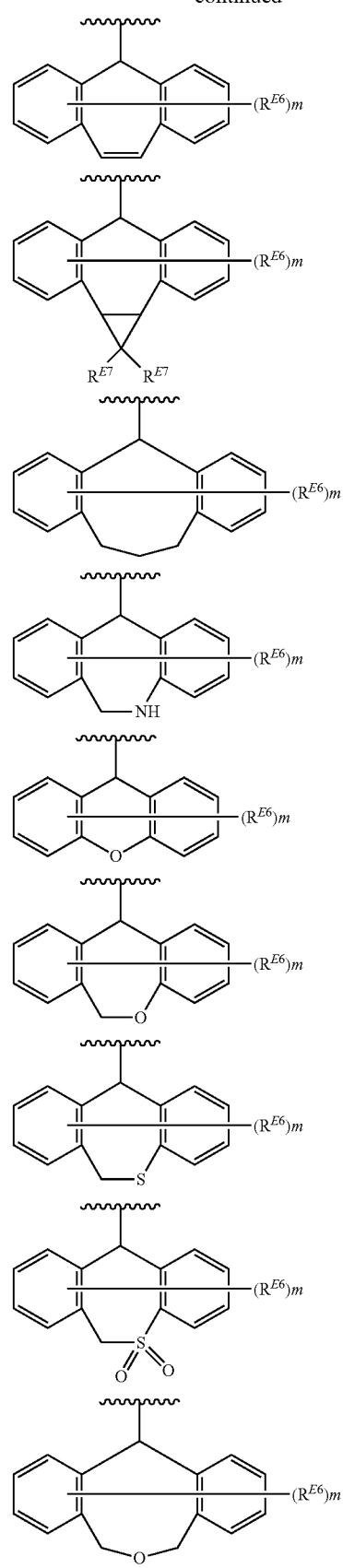

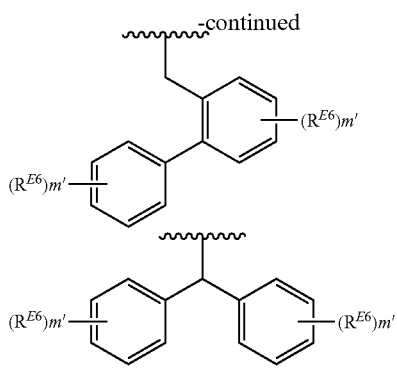

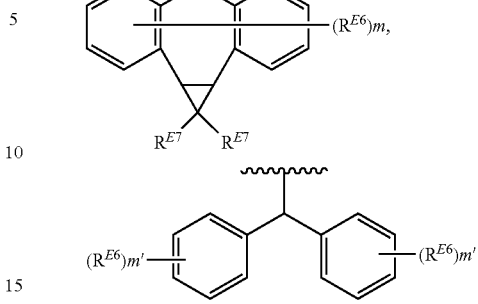

wherein $R^{E6}$ are each independently a group selected from Substituent group A; and $R^{E7}$ are each independently a hydrogen atom, halogen, or alkyl;

m are each independently an integer of 0 to 7;

m' are each independently an integer of 0 to 4; and

Substituent group A is as defined in claim 1.

9. The method according to claim 1, wherein $A^3$ is $CR^2$;

$R^1$ is carboxy;

$R^2$ is a hydrogen atom;

$R^3$ is alkyl optionally substituted with Substituent group F, alkenyl optionally substituted with Substituent group F, a carbocycle optionally substituted with Substituent group A, carbocyclealkyl optionally substituted with Substituent group A, or heterocyclealkyl optionally substituted with Substituent group A;

a) $A^1$ is $NR^7$, $A^2$ is $CR^5R^6$, or b) $A^1$ is $CR^8R^9$, $A^2$ is $CR^{10}R^{11}$;

$R^5$ and $R^6$ are each independently a hydrogen atom or alkyl optionally substituted with alkyloxy or alkylthio;

$R^9$, $R^{10}$, and $R^{11}$ are each a hydrogen atom; and $R^7$ or $R^8$ is a group shown below:

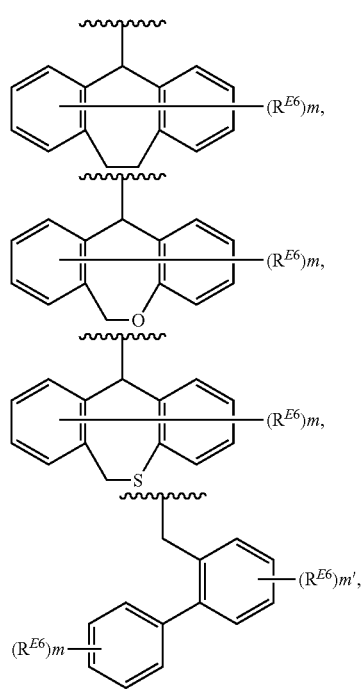

or wherein $R^{E6}$ are each independently a group selected from Substituent group A;

$R^{E7}$ are each independently a hydrogen atom, halogen, or alkyl;

m are each independently an integer of 0 to 7;

m' are each independently an integer of 0 to 4; and

Substituent group A is as defined in claim 1.

10. The method according to claim 1, wherein the compound is selected from the group consisting of

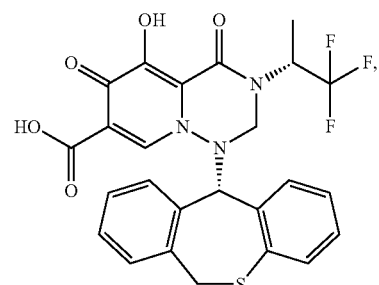

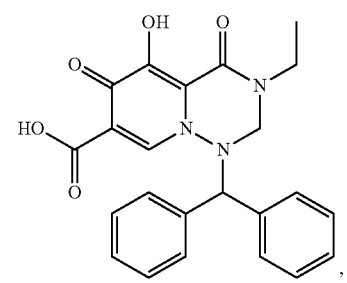

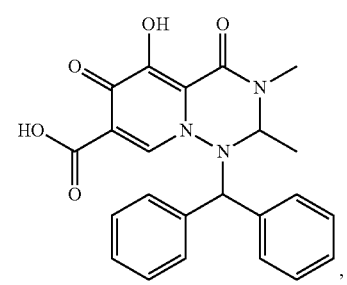

175
-continued
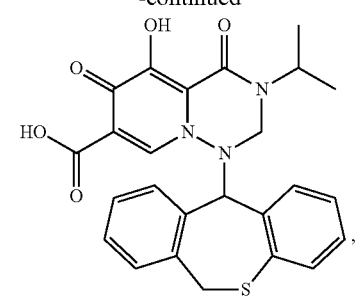
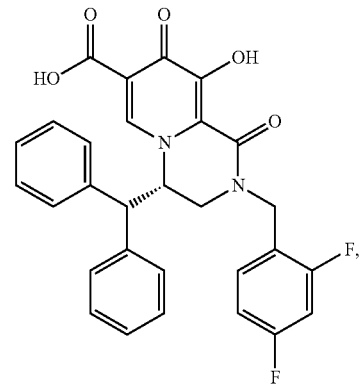
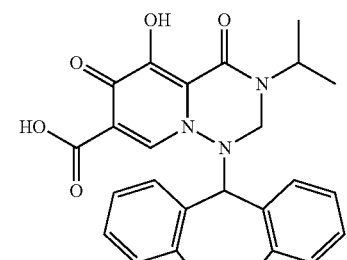
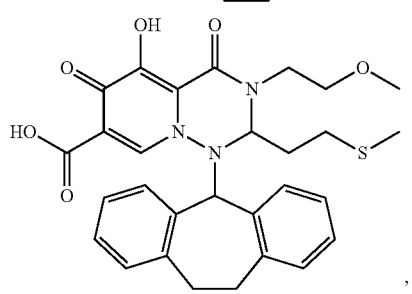
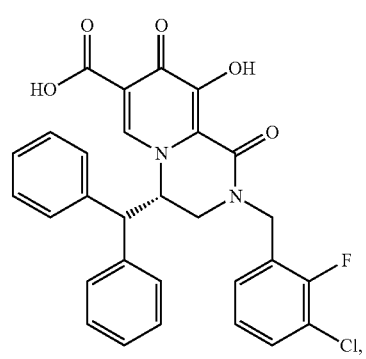
176
-continued
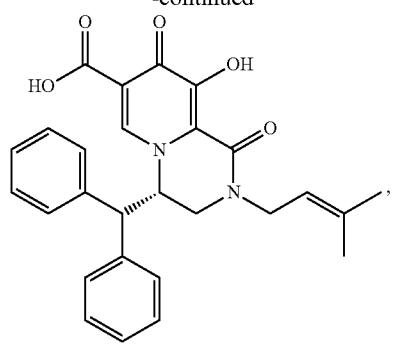
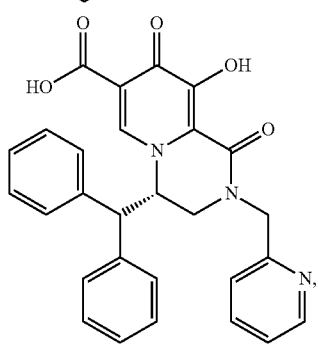
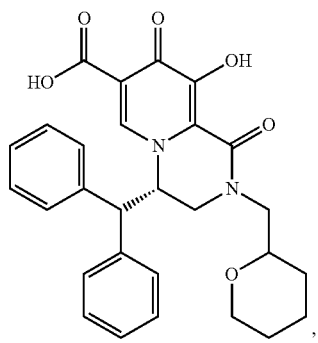
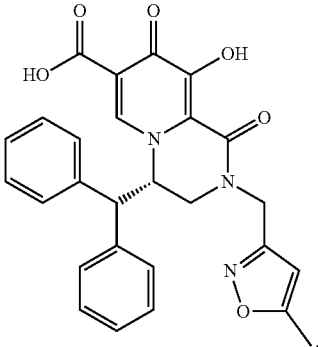
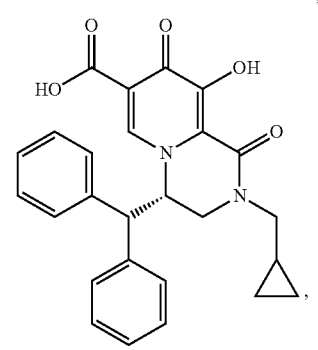

177
-continued
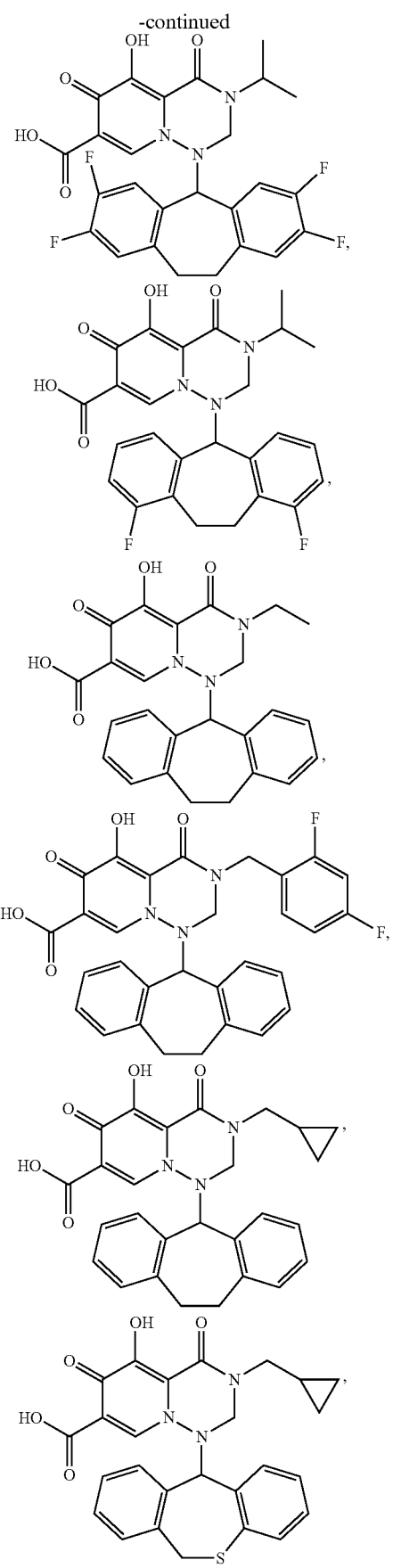
178
-continued
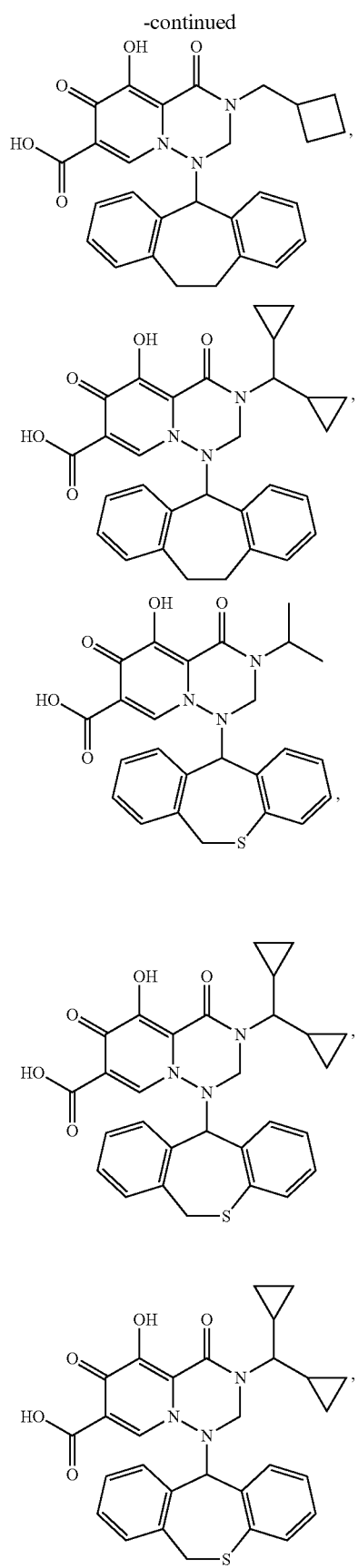

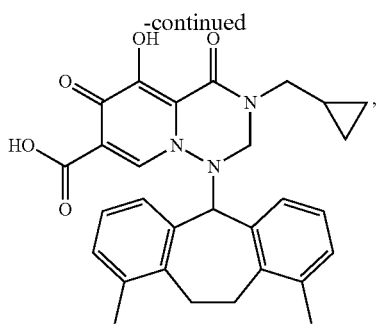,

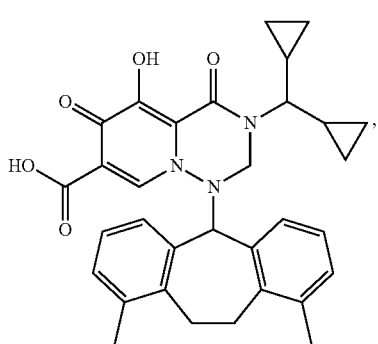,

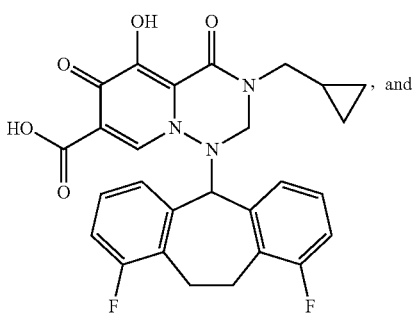, and

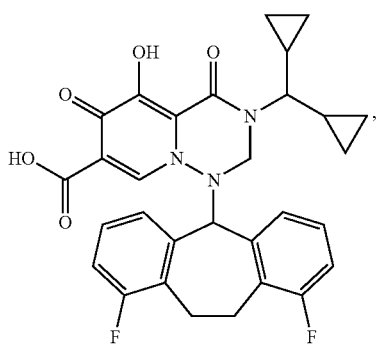, or a prodrug thereof or a pharmaceutically acceptable salt thereof.

11. A method for preventing and/or treating an arenavirus infection in a human or an animal, comprising administering an effective amount of a compound represented by Formula (I) or a prodrug thereof or a pharmaceutically acceptable salt thereof to the human or animal:

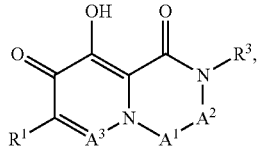

wherein:
$R^1$ is $-Z^X-C(=O)-O-R^{X15}$, $-Z^X-C(=O)-N(R^{X9})(R^{X10})$, or $-Z^X-N(R^{X14})-C(=O)-O-R^{X15}$, wherein $R^{X9}$, $R^{X14}$, and $R^{X15}$ are each independently a hydrogen atom, alkyl optionally substituted with Substituent group E, alkenyl optionally substituted with Substituent group E, or alkynyl optionally substituted with Substituent group E;

$R^{X10}$ is a hydrogen atom, alkyl optionally substituted with Substituent group E, alkenyl optionally substituted with Substituent group E, alkynyl optionally substituted with Substituent group E, or alkyloxy optionally substituted with Substituent group E;

$Z^X$ is a single bond or a linear or branched alkylene;

$R^{X9}$ and $R^{X10}$ may be taken together with an adjacent atom to form a heterocycle) a heterocycle;

$A^3$ is $CR^2$ or N;

$R^2$ is a hydrogen atom, halogen, hydroxy, carboxy, cyano, formyl, alkyl optionally substituted with Substituent group F, alkenyl optionally substituted with Substituent group F, alkynyl optionally substituted with Substituent group F, or alkyloxy optionally substituted with Substituent group F;

$R^3$ is a hydrogen atom, hydroxy, carboxy, cyano, formyl, alkyl optionally substituted with Substituent group F, alkenyl optionally substituted with Substituent group F, alkynyl optionally substituted with Substituent group F, alkyloxy optionally substituted with Substituent group F, alkenyloxy optionally substituted with Substituent group F, alkylcarbonyl optionally substituted with Substituent group F, alkyloxycarbonyl optionally substituted with Substituent group F, a carbocyclic group optionally substituted with Substituent group A, carbocyclealkyl optionally substituted with Substituent group A, carbocycleoxyalkyl optionally substituted with Substituent group A, carbocyclecarbonyl optionally substituted with Substituent group A, carbocycleoxy optionally substituted with Substituent group A, carbocycleoxycarbonyl optionally substituted with Substituent group A, a heterocyclic group optionally substituted with Substituent group A, heterocyclealkyl optionally substituted with Substituent group A, heterocycleoxyalkyl optionally substituted with Substituent group A, heterocyclecarbonyl optionally substituted with Substituent group A, heterocycleoxy optionally substituted with Substituent group A, heterocycleoxycarbonyl optionally substituted with Substituent group A, $-Z^Z-N(R^{Z1})-SO_2-R^{Z2}$,
$-Z^Z-N(R^{Z3})-C(=O)-R^{Z4}$,
$-Z^Z-N(R^{Z5})-C(=O)-O-R^{Z6}$,
$-Z^Z-C(=O)-N(R^{Z7})(R^{Z8})$,
$-Z^Z-N(R^{Z9})(R^{Z10})$,
$-Z^Z-SO_2-R^{Z11}$, or
$-Z^Z-N(R^{Z12})-O-C(=O)-R^{Z13}$, wherein $R^{Z1}$, $R^{Z3}$, $R^{Z4}$, $R^{Z5}$, $R^{Z6}$, $R^{Z7}$, $R^{Z8}$, $R^{Z9}$, $R^{Z10}$, $R^{Z12}$, and $R^{Z13}$ are each independently selected from the group consisting of a hydrogen atom, alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;

$R^{Z2}$ and $R^{Z11}$ are each independently selected from the group consisting of alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;

$R^{Z7}$ and $R^{Z8}$ may be taken together with an adjacent atom to form a heterocycle;

$Z^Z$ is a single bond or a linear or branched alkylene;

a) either $A^1$ or $A^2$ is $CR^5R^6$, and the other is $NR^7$, or b) $A^1$ is $CR^8R^9$, and $A^2$ is $CR^{10}R^{11}$;

$R^5$, $R^6$, $R^7$, $R^8$, $R^9$, $R^{10}$, and $R^{11}$ are each independently a hydrogen atom, carboxy, cyano, alkyl optionally substituted with Substituent group F, alkenyl optionally substituted with Substituent group F, alkynyl optionally substituted with Substituent group F, alkylcarbonyl optionally substituted with Substituent group F, alkyloxycarbonyl optionally substituted with Substituent group F, a carbocyclic group optionally substituted with Substituent group B, carbocyclealkyl optionally substituted with Substituent group B, carbocycleoxyalkyl optionally substituted with Substituent group B, carbocyclecarbonyl optionally substituted with Substituent group B, carbocycleoxycarbonyl optionally substituted with Substituent group B, a heterocyclic group optionally substituted with B, heterocyclealkyl optionally substituted with Substituent group B, heterocycleoxyalkyl optionally substituted with Substituent group B, heterocyclecarbonyl optionally substituted with Substituent group B, heterocycleoxycarbonyl optionally substituted with Substituent group B, —$Z^V$—S—$R^{V1}$,
—$Z^V$—S(=O)—$R^{V2}$,
—$Z^V$—SO$_2$—$R^{V3}$,
—C(=O)—C(=O)—$R^{V4}$,
—C(=O)—N($R^{V5}$)($R^{V6}$),
—$Z^V$—N($R^{V7}$)—C(=O)—O—$R^{V8}$, or
—$Z^V$—N($R^{V9}$)—C(=O)—$R^{V10}$, wherein $R^{V1}$, $R^{V4}$, $R^{V5}$, $R^{V6}$, $R^{V7}$, $R^{V8}$, $R^{V9}$, and $R^{V10}$ are each independently selected from the group consisting of a hydrogen atom, alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;

$R^{V2}$ and $R^{V3}$ are each independently selected from the group consisting of alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;

$R^{V5}$ and $R^{V6}$ may be taken together with an adjacent atom to form a heterocycle;

$Z^V$ is a single bond or a linear or branched alkylene;

$R^5$ and $R^6$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure;

$R^8$ and $R^9$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure;

$R^{10}$ and $R^{11}$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure;

1) When $A^1$ is $CR^5R^6$ and $A^2$ is $NR^7$, then $R^5$ and $R^7$ may be taken together to form a bond, or $R^5$ and $R^7$ may be taken together with an adjacent atom to form a heterocycle optionally substituted with Substituent group B, wherein the heterocycle may form a condensed ring and/or a spiro ring and/or a bridged structure, or $R^3$ and $R^7$ may be taken together with an adjacent atom to form a heterocycle optionally substituted with Substituent group B, wherein the heterocycle may form a condensed ring and/or a spiro ring and/or a bridged structure, 2) When $A^1$ is $NR^7$ and $A^2$ is $CR^5R^6$, then $R^7$ and $R^5$ may be taken together to form a bond, or $R^7$ and $R^5$ may be taken together with an adjacent atom to form a heterocycle optionally substituted with Substituent group B, wherein the heterocycle may form a condensed ring and/or a spiro ring and/or a bridged structure, or $R^3$ and $R^6$ may be taken together with an adjacent atom to form a heterocycle optionally substituted with Substituent group B, wherein the heterocycle may form a condensed ring and/or a spiro ring and/or a bridged structure, 3) when $A^1$ is $CR^8R^9$, and $A^2$ is $CR^{10}R^{11}$, then $R^8$ and $R^{10}$ may be taken together to form a bond, or $R^8$ and $R^{10}$ may be taken together with an adjacent atom to form a carbocycle optionally substituted with Substituent group B or a heterocycle optionally substituted with Substituent group B, wherein the carbocycle or the heterocycle may form a condensed ring and/or a spiro ring and/or a bridged structure, or $R^3$ and $R^{11}$ may be taken together with an adjacent atom to form a heterocycle optionally substituted with Substituent group B, wherein the heterocycle may form a condensed ring and/or a spiro ring and/or a bridged structure, with a proviso that following compounds of c) and d) are excluded:

c) $R^5$, $R^6$, and $R^7$ are all a hydrogen atom, d) $R^8$, $R^9$, $R^{10}$, and $R^{11}$ are all a hydrogen atom; and wherein Substituent group A is selected from the group consisting of halogen, cyano, hydroxy, carboxy, formyl, amino, oxo, nitro, alkyl, halogenoalkyl, alkyloxy, alkylthio, alkylamino, hydroxyalkyl, carboxyalkyl, aminoalkyl, a carbocyclic group, a heterocyclic group, an oxo-substituted heterocyclic group, carbocyclealkyloxy, carbocycleoxyalkyl, carbocyclealkyloxyalkyl, carbocyclealkylthio, heterocyclealkyloxy, heterocycleoxyalkyl, heterocyclealkyloxyalkyl, halogenoalkyloxy, alkyloxyalkyl, alkyloxyalkyloxy, alkylcarbonyl, alkylcarbonyloxy, alkyloxycarbonyl, alkyloxycarbonyloxy, alkylamino, alkylcarbonylamino, halogenoalkylcarbonylamino, alkylaminocarbonyl, alkyl sulfonyl, alkylsulfinyl, and alkylsulfonylamino;

wherein Substituent group B is selected from the group consisting of halogen, cyano, hydroxy, carboxy, formyl, amino, oxo, nitro, alkyl, halogenoalkyl, alkyloxy, alkylthio, alkylamino, hydroxyalkyl, carboxyalkyl, alkylamino, carbocyclealkyloxy, heterocyclealkyloxy, halogenoalkyloxy, alkyloxyalkyl, alkyloxyalkyloxy, alkylcarbonyl, alkyloxycarbonyl, alkyloxycarbonyloxy, alkylamino, alkylcarbonylamino, alkylaminocarbonyl, alkyl sulfonyl, alkylsulfonylamino, a carbocyclic group optionally substituted with Substituent group A, a heterocyclic group optionally substituted with Substituent group A, carbocyclealkyl optionally substituted with Substituent group A, heterocyclealkyl optionally substituted with Substituent group A, carbocyclealkyloxy optionally substituted with Substituent group A, heterocyclealkyloxy optionally substituted with Substituent group A, carbocyclealkylthio optionally substituted with Substituent group A, heterocyclealkylthio optionally substituted with Substituent group A, carbocycleoxyalkyl optionally substituted with Substituent group A, heterocycleoxyalkyl optionally substituted with Substituent group A, carbocyclealkyloxyalkyl optionally substituted with Substituent group A, and heterocyclealkyloxyalkyl optionally substituted with Substituent group A;

wherein Substituent group E is selected from the group consisting of halogen, hydroxy, carboxy, alkyloxy, alkylcarbonyl, alkyloxycarbonyl, alkylcarbonyloxy, alkylaminocarbonyl, and alkylsulfonyl; and wherein Substituent group F is selected from the group consisting of halogen, cyano, hydroxy, carboxy, formyl, amino, oxo, nitro, alkyloxy, alkylthio, a carbocyclic group, a heterocyclic group, an oxo-substituted heterocyclic group, carbocyclealkyloxy, carbocyclealkylthio, heterocyclealkyloxy, halogenoalkyloxy, alkyloxyalkyloxy, alkylcarbonyl, alkylcarbonyloxy, alkyloxycarbonyl, alkyloxycarbonyloxy, alkylamino, alkylcarbonylamino, halogenoalkylcarbonylamino, alkylaminocarbonyl, alkyl sulfonyl, alkylsulfinyl, and alkylsulfonylamino.

12. The method according to claim 11, wherein the arenavirus infection is Lassa fever, Argentine hemorrhagic fever, Bolivia hemorrhagic fever, Brazil hemorrhagic fever, or Venezuela hemorrhagic fever.

13. A method for inhibiting Lassa virus proliferation in a human or an animal, comprising administering an effective amount of a compound represented by Formula (I) or a prodrug thereof or a pharmaceutically acceptable salt thereof to the human or animal:

wherein:
$R^1$ is $-Z^X-C(=O)-O-R^{X15}$, $-Z^X-C(=O)-N(R^{X9})(R^{X10})$, or $-Z^X-N(R^{X14})-C(=O)-O-R^{X15}$,
wherein $R^{X9}$, $R^{X14}$, and $R^{X15}$ are each independently a hydrogen atom, alkyl optionally substituted with Substituent group E, alkenyl optionally substituted with Substituent group E, or alkynyl optionally substituted with Substituent group E;
$R^{X10}$ is a hydrogen atom, alkyl optionally substituted with Substituent group E, alkenyl optionally substituted with Substituent group E, alkynyl optionally substituted with Substituent group E, or alkyloxy optionally substituted with Substituent group E;
$Z^X$ is a single bond or a linear or branched alkylene;
$R^{X9}$ and $R^{X10}$ may be taken together with an adjacent atom to form a heterocycle;
$A^3$ is $CR^2$ or N;
$R^2$ is a hydrogen atom, halogen, hydroxy, carboxy, cyano, formyl, alkyl optionally substituted with Substituent group F, alkenyl optionally substituted with Substituent group F, alkynyl optionally substituted with Substituent group F, or alkyloxy optionally substituted with Substituent group F;
$R^3$ is a hydrogen atom, hydroxy, carboxy, cyano, formyl, alkyl optionally substituted with Substituent group F, alkenyl optionally substituted with Substituent group F, alkynyl optionally substituted with Substituent group F, alkyloxy optionally substituted with Substituent group F, alkenyloxy optionally substituted with Substituent group F, alkylcarbonyl optionally substituted with Substituent group F, alkyloxycarbonyl optionally substituted with Substituent group F, a carbocyclic group optionally substituted with Substituent group A, carbocyclealkyl optionally substituted with Substituent group A, carbocycleoxyalkyl optionally substituted with Substituent group A, carbocyclecarbonyl optionally substituted with Substituent group A, carbocycleoxy optionally substituted with Substituent group A, carbocycleoxycarbonyl optionally substituted with Substituent group A, a heterocyclic group optionally substituted with Substituent group A, heterocyclealkyl optionally substituted with Substituent group A, heterocycleoxyalkyl optionally substituted with Substituent group A, heterocyclecarbonyl optionally substituted with Substituent group A, heterocycleoxy optionally substituted with Substituent group A, heterocycleoxycarbonyl optionally substituted with Substituent group A,
$-Z^Z-N(R^{Z1})-SO_2-R^{Z2}$,
$-Z^Z-N(R^{Z3})-C(=O)-R^{Z4}$,
$-Z^Z-N(R^{Z5})-C(=O)-O-R^{Z6}$,
$-Z^Z-C(=O)-N(R^{Z7})(R^{Z8})$,
$-Z^Z-N(R^{Z9})(R^{Z10})$,
$-Z^Z-SO_2-R^{Z11}$, or
$-Z^Z-N(R^{Z12})-O-C(=O)-R^{Z13}$,
wherein $R^{Z1}$, $R^{Z3}$, $R^{Z4}$, $R^{Z5}$, $R^{Z6}$, $R^{Z7}$, $R^{Z8}$, $R^{Z9}$, $R^{Z10}$, $R^{Z12}$, and $R^{Z13}$ are each independently selected from the group consisting of a hydrogen atom, alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;

$R^{Z2}$ and $R^{Z11}$ are each independently selected from the group consisting of alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;

$R^{Z7}$ and $R^{Z8}$ may be taken together with an adjacent atom to form a heterocycle;

$Z^Z$ is a single bond or a linear or branched alkylene;

a) either $A^1$ or $A^2$ is $CR^5R^6$, and the other is $NR^7$, or
b) $A^1$ is $CR^8R^9$, and $A^2$ is $CR^{10}R^{11}$;

$R^5$, $R^6$, $R^7$, $R^8$, $R^9$, $R^{10}$, and $R^{11}$ are each independently a hydrogen atom, carboxy, cyano, alkyl optionally substituted with Substituent group F, alkenyl optionally substituted with Substituent group F, alkynyl optionally substituted with Substituent group F, alkylcarbonyl optionally substituted with Substituent group F, alkyloxycarbonyl optionally substituted with Substituent group F, a carbocyclic group optionally substituted with Substituent group B, carbocyclealkyl optionally substituted with Substituent group B, carbocycleoxyalkyl optionally substituted with Substituent group B, carbocyclecarbonyl optionally substituted with Substituent group B, carbocycleoxycarbonyl optionally substituted with Substituent group B, a heterocyclic group optionally substituted with B, heterocyclealkyl optionally substituted with Substituent group B, heterocycleoxyalkyl optionally substituted with Substituent group B, heterocyclecarbonyl optionally substituted with Substituent group B, heterocycleoxycarbonyl optionally substituted with Substituent group B,
—$Z^V$—S—$R^{V1}$,
—$Z^V$—S(=O)—$R^{V2}$,
—$Z^V$—SO$_2$—$R^{V3}$,
—C(=O)—C(=O)—$R^{V4}$,
—C(=O)—N($R^{V5}$)($R^{V6}$),
—$Z^V$—N($R^{V7}$)—C(=O)—O—$R^{V8}$, or
—$Z^V$—N($R^{V9}$)—C(=O)—$R^{V10}$, wherein $R^{V1}$, $R^{V4}$, $R^{V5}$, $R^{V6}$, $R^{V7}$, $R^{V8}$, $R^{V9}$, and $R^{V10}$ are each independently selected from the group consisting of a hydrogen atom, alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;

$R^{V2}$ and $R^{V3}$ are each independently selected from the group consisting of alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;

$R^{V5}$ and $R^{V6}$ may be taken together with an adjacent atom to form a heterocycle;

$Z^V$ is a single bond or a linear or branched alkylene;

$R^5$ and $R^6$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure;

$R^8$ and $R^9$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure;

$R^{10}$ and $R^{11}$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure;

1) When $A^1$ is $CR^5R^6$ and $A^2$ is $NR^7$,
then $R^5$ and $R^7$ may be taken together to form a bond, or $R^5$ and $R^7$ may be taken together with an adjacent atom to form a heterocycle optionally substituted with Substituent group B, wherein the heterocycle may form a condensed ring and/or a spiro ring and/or a bridged structure, or $R^3$ and $R^7$ may be taken together with an adjacent atom to form a heterocycle optionally substituted with Substituent group B, wherein the heterocycle may form a condensed ring and/or a spiro ring and/or a bridged structure, 2) When $A^1$ is $NR^7$ and $A^2$ is $CR^5R^6$,
then $R^7$ and $R^5$ may be taken together to form a bond, or $R^7$ and $R^5$ may be taken together with an adjacent atom to form a heterocycle optionally substituted with Substituent group B, wherein the heterocycle may form a condensed ring and/or a spiro ring and/or a bridged structure, or $R^3$ and $R^6$ may be taken together with an adjacent atom to form a heterocycle optionally substituted with Substituent group B, wherein the heterocycle may form a condensed ring and/or a spiro ring and/or a bridged structure, 3) when $A^1$ is $CR^8R^9$, and $A^2$ is $CR^{10}R^{11}$,
then $R^8$ and $R^{10}$ may be taken together to form a bond, or $R^8$ and $R^{10}$ may be taken together with an adjacent atom to form a carbocycle optionally substituted with Substituent group B or a heterocycle optionally substituted with Substituent group B, wherein the carbocycle or the heterocycle may form a condensed ring and/or a spiro ring and/or a bridged structure, or $R^3$ and $R^{11}$ may be taken together with an adjacent atom to form a heterocycle optionally substituted with Substituent group B, wherein the heterocycle may form a condensed ring and/or a spiro ring and/or a bridged structure, with a proviso that following compounds of c) and d) are excluded:
c) $R^5$, $R^6$, and $R^7$ are all a hydrogen atom,
d) $R^8$, $R^9$, $R^{10}$, and $R^{11}$ are all a hydrogen atom; and
wherein Substituent group A is selected from the group consisting of halogen, cyano, hydroxy, carboxy, formyl, amino, oxo, nitro, alkyl, halogenoalkyl, alkyloxy, alkylthio, alkylamino, hydroxyalkyl, carboxyalkyl, aminoalkyl, a carbocyclic group, a heterocyclic group, an oxo-substituted heterocyclic group, carbocyclealkyloxy, carbocycleoxyalkyl, carbocyclealkyloxyalkyl, carbocyclealkylthio, heterocyclealkyloxy, heterocycleoxyalkyl, heterocyclealkyloxyalkyl, halogenoalkyloxy, alkyloxyalkyl, alkyloxyalkyloxy, alkylcarbonyl, alkylcarbonyloxy, alkyloxycarbonyl, alkyloxycarbonyloxy, alkylamino, alkylcarbonylamino, halogenoalkylcarbonylamino, alkylaminocarbonyl, alkyl sulfonyl, alkylsulfinyl, and alkylsulfonylamino;

wherein Substituent group B is selected from the group consisting of halogen, cyano, hydroxy, carboxy, formyl, amino, oxo, nitro, alkyl, halogenoalkyl, alkyloxy, alkylthio, alkylamino, hydroxyalkyl, carboxyalkyl, alkylamino, carbocyclealkyloxy, heterocyclealkyloxy, halogenoalkyloxy, alkyloxyalkyl, alkyloxyalkyloxy, alkylcarbonyl, alkyloxycarbonyl, alkyloxycarbonyloxy, alkylamino, alkylcarbonylamino, alkylaminocarbonyl, alkyl sulfonyl, alkylsulfonylamino, a carbocyclic group optionally substituted with Substituent group A, a heterocyclic group optionally substituted with Substituent group A, carbocyclealkyl optionally substituted with Substituent group A, heterocyclealkyl optionally substituted with Substituent group A, carbocyclealkyloxy optionally substituted with Substituent group A, heterocyclealkyloxy optionally substituted with Substituent group A, carbocyclealkylthio optionally substituted with Substituent group A, heterocyclealkylthio optionally substituted with Substituent group A, carbocycleoxyalkyl optionally substituted with Substituent group A, heterocycleoxyalkyl optionally substituted with Substituent group A, carbocyclealkyloxyalkyl optionally substituted with Substituent group A, and heterocyclealkyloxyalkyl optionally substituted with Substituent group A;

wherein Substituent group E is selected from the group consisting of halogen, hydroxy, carboxy, alkyloxy, alkylcarbonyl, alkyloxycarbonyl, alkylcarbonyloxy, alkylaminocarbonyl, and alkylsulfonyl; and wherein Substituent group F is selected from the group consisting of halogen, cyano, hydroxy, carboxy, formyl, amino, oxo, nitro, alkyloxy, alkylthio, a carbocyclic group, a heterocyclic group, an oxo-substituted heterocyclic group, carbocyclealkyloxy, carbocyclealkylthio, heterocyclealkyloxy, halogenoalkyloxy, alkyloxyalkyloxy, alkylcarbonyl, alkylcarbonyloxy, alkyloxycarbonyl, alkyloxycarbonyloxy, alkylamino, alkylcarbonylamino, halogenoalkylcarbonylamino, alkylaminocarbonyl, alkyl sulfonyl, alkylsulfinyl, and alkylsulfonylamino.

14. A method for inhibiting arenavirus proliferation in vitro, comprising contacting an arenavirus with an effective amount of a compound represented by Formula (I) or a prodrug thereof or a pharmaceutically acceptable salt thereof in vitro:

(I)

wherein:
$R^1$ is $-Z^X-C(=O)-O-R^{X15}$, $-Z^X-C(=O)-N(R^{X9})(R^{X10})$, or $-Z^X-N(R^{X14})-C(=O)-O-R^{X15}$, wherein $R^{X9}$, $R^{X14}$, and $R^{X15}$ are each independently a hydrogen atom, alkyl optionally substituted with Substituent group E, alkenyl optionally substituted with Substituent group E, or alkynyl optionally substituted with Substituent group E;

$R^{X10}$ is a hydrogen atom, alkyl optionally substituted with Substituent group E, alkenyl optionally substituted with Substituent group E, alkynyl optionally substituted with Substituent group E, or alkyloxy optionally substituted with Substituent group E;

$Z^X$ is a single bond or a linear or branched alkylene;

$R^{X9}$ and $R^{X10}$ may be taken together with an adjacent atom to form a heterocycle;

$A^3$ is $CR^2$ or N;

$R^2$ is a hydrogen atom, halogen, hydroxy, carboxy, cyano, formyl, alkyl optionally substituted with Substituent group F, alkenyl optionally substituted with Substituent group F, alkynyl optionally substituted with Substituent group F, or alkyloxy optionally substituted with Substituent group F;

$R^3$ is a hydrogen atom, hydroxy, carboxy, cyano, formyl, alkyl optionally substituted with Substituent group F, alkenyl optionally substituted with Substituent group F, alkynyl optionally substituted with Substituent group F, alkyloxy optionally substituted with Substituent group F, alkenyloxy optionally substituted with Substituent group F, alkylcarbonyl optionally substituted with Substituent group F, alkyloxycarbonyl optionally substituted with Substituent group F, a carbocyclic group optionally substituted with Substituent group A, carbocyclealkyl optionally substituted with Substituent group A, carbocycleoxyalkyl optionally substituted with Substituent group A, carbocyclecarbonyl optionally substituted with Substituent group A, carbocycleoxy optionally substituted with Substituent group A, carbocycleoxycarbonyl optionally substituted with Substituent group A, a heterocyclic group optionally substituted with Substituent group A, heterocyclealkyl optionally substituted with Substituent group A, heterocycleoxyalkyl optionally substituted with Substituent group A, heterocyclecarbonyl optionally substituted with Substituent group A, heterocycleoxy optionally substituted with Substituent group A, heterocycleoxycarbonyl optionally substituted with Substituent group A, $-Z^Z-N(R^{Z1})-SO_2-R^{Z2}$,
$-Z^Z-N(R^{Z3})-C(=O)-R^{Z4}$,
$-Z^Z-N(R^{Z5})-C(=O)-O-R^{Z6}$,
$-Z^Z-C(=O)-N(R^{Z7})(R^{Z8})$,
$-Z^Z-N(R^{Z9})(R^{Z10})$,
$-Z^Z-SO_2-R^{Z11}$, or
$-Z^Z-N(R^{Z12})-O-C(=O)-R^{Z13}$, wherein $R^{Z1}$, $R^{Z3}$, $R^{Z4}$, $R^{Z5}$, $R^{Z6}$, $R^{Z7}$, $R^{Z8}$, $R^{Z9}$, $R^{Z10}$, $R^{Z12}$, and $R^{Z13}$ are each independently selected from the group consisting of a hydrogen atom, alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;

$R^{Z2}$ and $R^{Z11}$ are each independently selected from the group consisting of alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;

$R^{Z7}$ and $R^{Z8}$ may be taken together with an adjacent atom to form a heterocycle;

$Z^Z$ is a single bond or a linear or branched alkylene;

a) either $A^1$ or $A^2$ is $CR^5R^6$, and the other is $NR^7$, or b) $A^1$ is $CR^8R^9$, and $A^2$ is $CR^{10}R^{11}$;

$R^5$, $R^6$, $R^7$, $R^8$, $R^9$, $R^{10}$, and $R^{11}$ are each independently a hydrogen atom, carboxy, cyano, alkyl optionally substituted with Substituent group F, alkenyl optionally substituted with Substituent group F, alkynyl optionally substituted with Substituent group F, alkylcarbonyl optionally substituted with Substituent group F, alkyloxycarbonyl optionally substituted with Substituent group F, a carbocyclic group optionally substituted with Substituent group B, carbocyclealkyl optionally substituted with Substituent group B, carbocycleoxyalkyl optionally substituted with Substituent group B, carbocyclecarbonyl optionally substituted with Substituent group B, carbocycleoxycarbonyl optionally substituted with Substituent group B, a heterocyclic group optionally substituted with B, heterocyclealkyl optionally substituted with Substituent group B, heterocycleoxyalkyl optionally substituted with Substituent group B, heterocyclecarbonyl optionally substituted with Substituent group B, heterocycleoxycarbonyl optionally substituted with Substituent group B, —$Z^V$—S—$R^{V1}$,
—$Z^V$—S(=O)—$R^{V2}$,
—$Z^V$—SO$_2$—$R^{V3}$,
—C(=O)—C(=O)—$R^{V4}$,
—C(=O)—N($R^{V5}$)($R^{V6}$),
—$Z^V$—N($R^{V7}$)—C(=O)—O—$R^{V8}$, or
—$Z^V$—N($R^{V9}$)—C(=O)—$R^{V10}$;

wherein $R^{V1}$, $R^{V4}$, $R^{V5}$, $R^{V6}$, $R^{V7}$, $R^{V8}$, $R^{V9}$, and $R^{V10}$ are each independently selected from the group consisting of a hydrogen atom, alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;

$R^{V2}$ and $R^{V3}$ are each independently selected from the group consisting of alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;

$R^{V5}$ and $R^{V6}$ may be taken together with an adjacent atom to form a heterocycle;

$Z^V$ is a single bond or a linear or branched alkylene;

$R^5$ and $R^6$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure;

$R^8$ and $R^9$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure;

$R^{10}$ and $R^{11}$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure;

1) When $A^1$ is $CR^5R^6$ and $A^2$ is $NR^7$, then $R^5$ and $R^7$ may be taken together to form a bond, or $R^5$ and $R^7$ may be taken together with an adjacent atom to form a heterocycle optionally substituted with Substituent group B, wherein the heterocycle may form a condensed ring and/or a spiro ring and/or a bridged structure, or $R^3$ and $R^7$ may be taken together with an adjacent atom to form a heterocycle optionally substituted with Substituent group B, wherein the heterocycle may form a condensed ring and/or a spiro ring and/or a bridged structure, 2) When $A^1$ is $NR^7$ and $A^2$ is $CR^5R^6$, then $R^7$ and $R^5$ may be taken together to form a bond, or $R^7$ and $R^5$ may be taken together with an adjacent atom to form a heterocycle optionally substituted with Substituent group B, wherein the heterocycle may form a condensed ring and/or a spiro ring and/or a bridged structure, or $R^3$ and $R^6$ may be taken together with an adjacent atom to form a heterocycle optionally substituted with Substituent group B, wherein the heterocycle may form a condensed ring and/or a spiro ring and/or a bridged structure, 3) when $A^1$ is $CR^8R^9$, and $A^2$ is $CR^{10}R^{11}$, then $R^8$ and $R^{10}$ may be taken together to form a bond, or $R^8$ and $R^{10}$ may be taken together with an adjacent atom to form a carbocycle optionally substituted with Substituent group B or a heterocycle optionally substituted with Substituent group B, wherein the carbocycle or the heterocycle may form a condensed ring and/or a spiro ring and/or a bridged structure, or $R^3$ and $R^{11}$ may be taken together with an adjacent atom to form a heterocycle optionally substituted with Substituent group B, wherein the heterocycle may form a condensed ring and/or a spiro ring and/or a bridged structure, with a proviso that following compounds of c) and d) are excluded:

c) $R^5$, $R^6$, and $R^7$ are all a hydrogen atom, d) $R^8$, $R^9$, $R^{10}$, and $R^{11}$ are all a hydrogen atom; and wherein Substituent group A is selected from the group consisting of halogen, cyano, hydroxy, carboxy, formyl, amino, oxo, nitro, alkyl, halogenoalkyl, alkyloxy, alkylthio, alkylamino, hydroxyalkyl, carboxyalkyl, aminoalkyl, a carbocyclic group, a heterocyclic group, an oxo-substituted heterocyclic group, carbocyclealkyloxy, carbocycleoxyalkyl, carbocyclealkyloxyalkyl, carbocyclealkylthio, heterocyclealkyloxy, heterocycleoxyalkyl, heterocyclealkyloxyalkyl, halogenoalkyloxy, alkyloxyalkyl, alkyloxyalkyloxy, alkylcarbonyl, alkylcarbonyloxy, alkyloxycarbonyl, alkyloxycarbonyloxy, alkylamino, alkylcarbonylamino, halogenoalkylcarbonylamino, alkylaminocarbonyl, alkyl sulfonyl, alkylsulfinyl, and alkylsulfonylamino;

wherein Substituent group B is selected from the group consisting of halogen, cyano, hydroxy, carboxy, formyl, amino, oxo, nitro, alkyl, halogenoalkyl, alkyloxy, alkylthio, alkylamino, hydroxyalkyl, carboxyalkyl, alkylamino, carbocyclealkyloxy, heterocyclealkyloxy, halogenoalkyloxy, alkyloxyalkyl, alkyloxyalkyloxy, alkylcarbonyl, alkyloxycarbonyl, alkyloxycarbonyloxy, alkylamino, alkylcarbonylamino, alkylaminocarbonyl, alkyl sulfonyl, alkylsulfonylamino, a carbocyclic group optionally substituted with Substituent group A, a heterocyclic group optionally substituted with Substituent group A, carbocyclealkyl optionally substituted with Substituent group A, heterocyclealkyl optionally substituted with Substituent group A, carbocyclealkyloxy optionally substituted with Substituent group A, heterocyclealkyloxy optionally substituted with Substituent group A, carbocyclealkylthio optionally substituted with Substituent group A, heterocyclealkylthio optionally substituted with Substituent group A, carbocycleoxyalkyl optionally substituted with Substituent group A, heterocycleoxyalkyl optionally substituted with Substituent group A, carbocyclealkyloxyalkyl optionally substituted with Substituent group A, and heterocyclealkyloxyalkyl optionally substituted with Substituent group A;

wherein Substituent group E is selected from the group consisting of halogen, hydroxy, carboxy, alkyloxy, alkylcarbonyl, alkyloxycarbonyl, alkylcarbonyloxy, alkylaminocarbonyl, and alkylsulfonyl; and wherein Substituent group F is selected from the group consisting of halogen, cyano, hydroxy, carboxy, formyl, amino, oxo, nitro, alkyloxy, alkylthio, a carbocyclic group, a heterocyclic group, an oxo-substituted heterocyclic group, carbocyclealkyloxy, carbocyclealkylthio, heterocyclealkyloxy, halogenoalkyloxy, alkyloxyalkyloxy, alkylcarbonyl, alkylcarbonyloxy, alkyloxycarbonyl, alkyloxycarbonyloxy, alkylamino, alkylcarbonylamino, halogenoalkylcarbonylamino, alkylaminocarbonyl, alkyl sulfonyl, alkyl sulfinyl, and alkylsulfonylamino.

15. The method according to claim 14, wherein
a) either $A^1$ or $A^2$ is $CR^5R^6$, and the other is $NR^7$, or
b) $A^1$ is $CR^8R^9$, and $A^2$ is $CR^{10}R^{11}$,
$R^5$, $R^6$, $R^7$, $R^8$, $R^9$, $R^{10}$, and $R^{11}$ are each independently a hydrogen atom, carboxy, cyano, alkyl optionally substituted with Substituent group F, alkenyl optionally substituted with Substituent group F, alkynyl optionally substituted with Substituent group F, alkylcarbonyl optionally substituted with Substituent group F, alkyloxycarbonyl optionally substituted with Substituent group F, a carbocyclic group optionally substituted with Substituent group B, carbocyclealkyl optionally substituted with Substituent group B, carbocycleoxyalkyl optionally substituted with Substituent group B, carbocyclecarbonyl optionally substituted with Substituent group B, carbocycleoxycarbonyl optionally substituted with Substituent group B, a heterocyclic group optionally substituted with Substituent group B, heterocyclealkyl optionally substituted with Substituent group B, heterocycleoxyalkyl optionally substituted with Substituent group B, heterocyclecarbonyl optionally substituted with Substituent group B, heterocycleoxycarbonyl optionally substituted with Substituent group B, —$Z^V$—S—$R^{V1}$,
—$Z^V$—S(=O)—$R^{V2}$,
—$Z^V$—SO$_2$—$R^{V3}$,
—C(=O)—C(=O)—$R^{V4}$,
—C(=O)—N($R^{V5}$)($R^{V6}$),
—$Z^V$—N($R^{V7}$)—C(=O)—O—$R^{V8}$, or
—$Z^V$—N($R^{V9}$)—C(=O)—$R^{V10}$, wherein $R^{V1}$, $R^{V4}$, $R^{V5}$, $R^{V6}$, $R^{V7}$, $R^{V8}$, $R^{V9}$, and $R^{V10}$ are each independently selected from the group consisting of a hydrogen atom, alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;

$R^{V2}$ and $R^{V3}$ are each independently selected from the group consisting of alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;

$R^{V5}$ and $R^{V6}$ may be taken together with an adjacent atom to form a heterocycle;

$Z^V$ is a single bond or a linear or branched alkylene;

$R^5$ and $R^6$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure;

$R^8$ and $R^9$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure; and $R^{10}$ and $R^{11}$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure;

with a proviso that when $A^1$ is $CR^5R^6$ and $A^2$ is $NR^7$, then the 1) defined in claim 14 is not applied; when $A^1$ is $NR^7$ and $A^2$ is $CR^5R^6$, then the 2) defined in claim 14 is not applied; and when $A^1$ is $CR^8R^9$ and $A^2$ is $CR^{10}R^{11}$, then the 3) defined in claim 14 is not applied.

16. The method according to claim 14, wherein $A^1$ is $NR^7$, and $A^2$ is $CR^5R^6$.

17. The method according to claim 14, wherein
$R^7$ is a carbocyclic group optionally substituted with Substituent group B, carbocyclealkyl optionally substituted with Substituent group B, a heterocyclic group optionally substituted with Substituent group B, or heterocyclealkyl optionally substituted with Substituent group B;

$R^5$ is a hydrogen atom; and $R^6$ is a hydrogen atom or alkyl optionally substituted with Substituent group F.

18. The method according to claim 14, wherein $R^1$ is carboxy.

19. The method according to claim 14, wherein $R^2$ is a hydrogen atom or alkyl; and $R^3$ is alkyl optionally substituted with Substituent group F, alkenyl optionally substituted with Substituent group F, alkynyl optionally substituted with Substituent group F, carbocyclealkyl optionally substituted with Substituent group A, a carbocyclic group optionally substituted with Substituent group A, heterocyclealkyl optionally substituted with Substituent group A, or carbocycleoxyalkyl optionally substituted with Substituent group A.

20. The method according to claim 14, wherein $A^3$ is $CR^2$.

21. The method according to claim 14, wherein when either $A^1$ or $A^2$ is $CR^5R^6$ and the other is $NR^7$, then either $R^5$ or $R^7$ is a group shown below; and when $A^1$ is $CR^8R^9$ and $A^2$ is $CR^{10}R^{11}$, then either $R^8$ or $R^{10}$ is a group shown below:

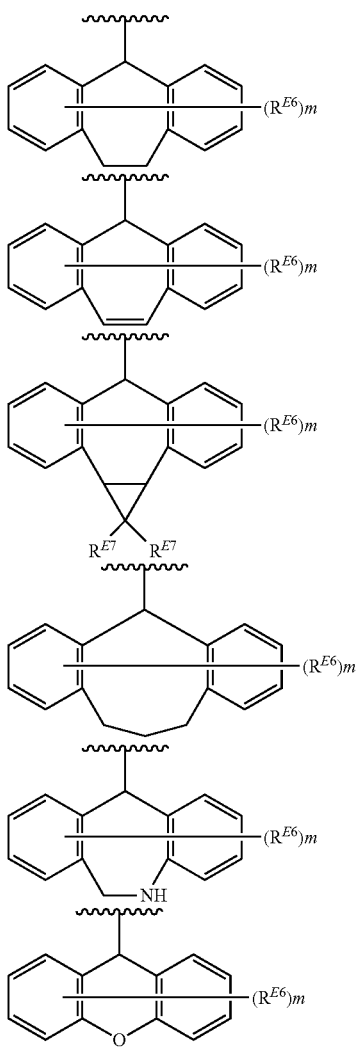

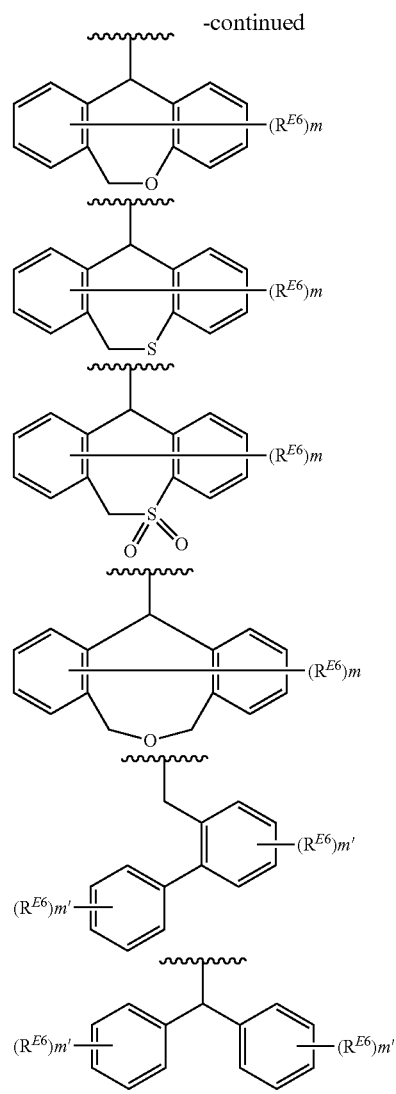

wherein $R^{E6}$ are each independently a group selected from Substituent group A;

$R^{E7}$ are each independently a hydrogen atom, halogen, or alkyl;

m are each independently an integer of 0 to 7;

m' are each independently an integer of 0 to 4; and

Substituent group A is as defined in claim 14.

22. The method according to claim 14, wherein $A^3$ is $CR^2$;

$R^1$ is carboxy;

$R^2$ is a hydrogen atom;

$R^3$ is alkyl optionally substituted with Substituent group F, alkenyl optionally substituted with Substituent group F, a carbocycle optionally substituted with Substituent group A, carbocyclealkyl optionally substituted with Substituent group A, or heterocyclealkyl optionally substituted with Substituent group A;

a) $A^1$ is $NR^7$, $A^2$ is $CR^5R^6$, or b) $A^1$ is $CR^8R^9$, $A^2$ is $CR^{10}R^{11}$;

$R^5$ and $R^6$ are each independently a hydrogen atom or alkyl optionally substituted with alkyloxy or alkylthio;

$R^9$, $R^{10}$, and $R^{11}$ are each a hydrogen atom; and $R^7$ or $R^8$ is a group shown below:

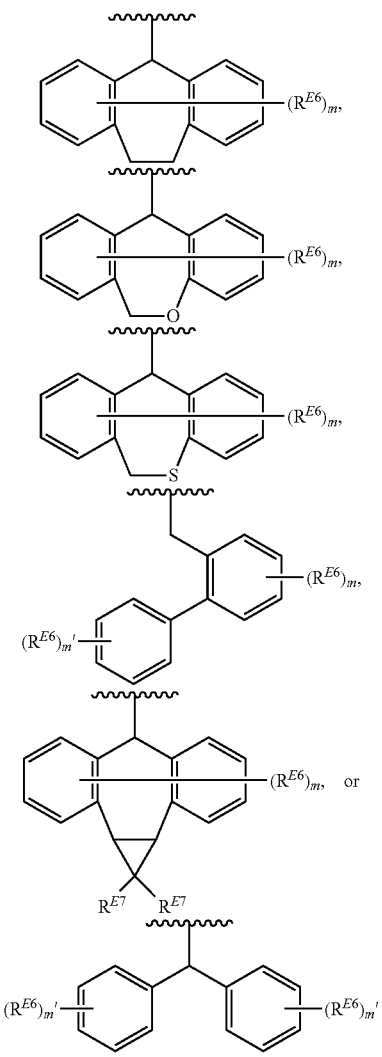

wherein $R^{E6}$ are each independently a group selected from Substituent group A;
$R^{E7}$ are each independently a hydrogen atom, halogen, or alkyl;
m are each independently an integer of 0 to 7;
m' are each independently an integer of 0 to 4; and
Substituent group A is as defined in claim 14.

23. The method according to claim 14, wherein the compound is selected from the group consisting of

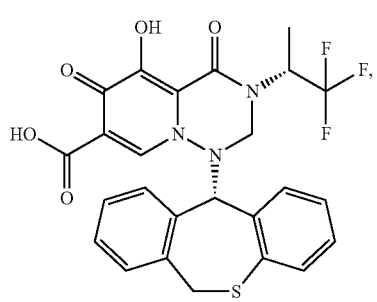

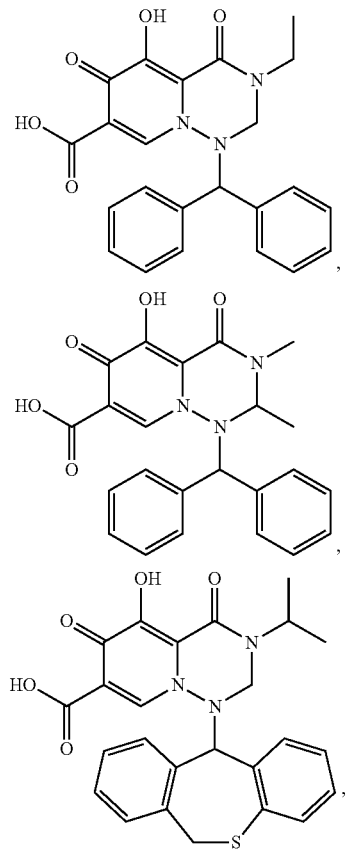

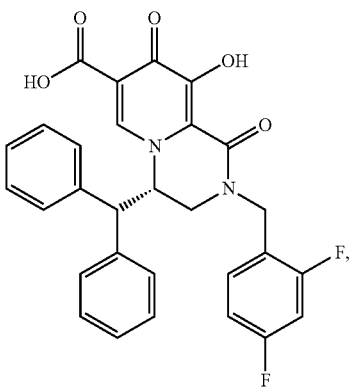

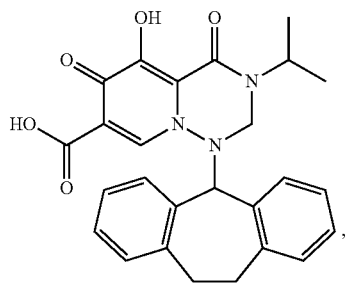

197
-continued
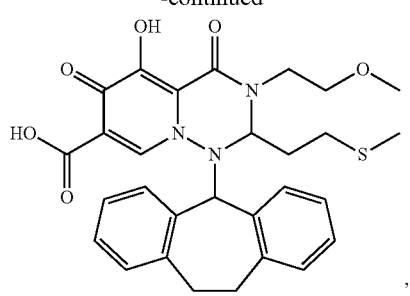,
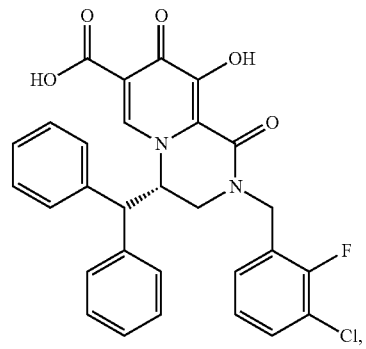,
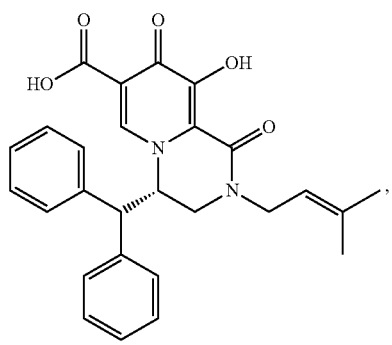,
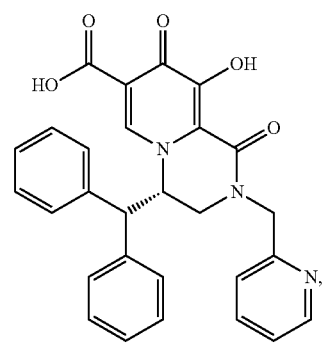,
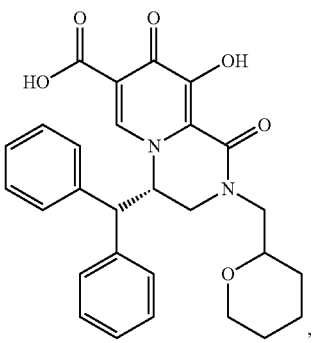,
198
-continued
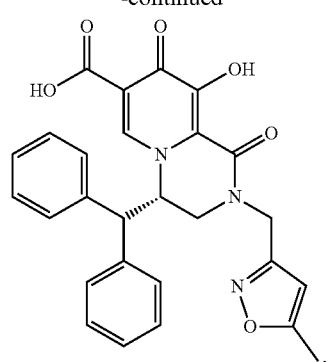,
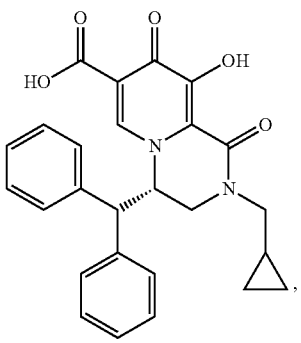,
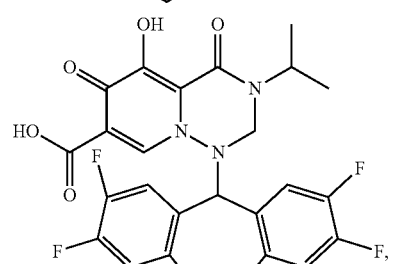,
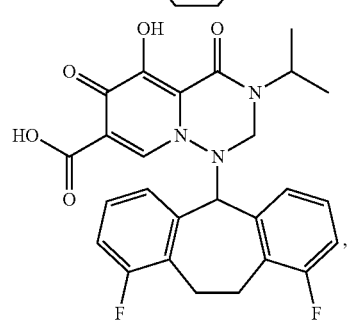,
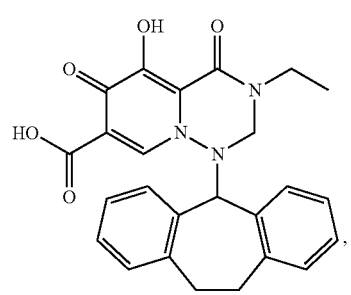, 199
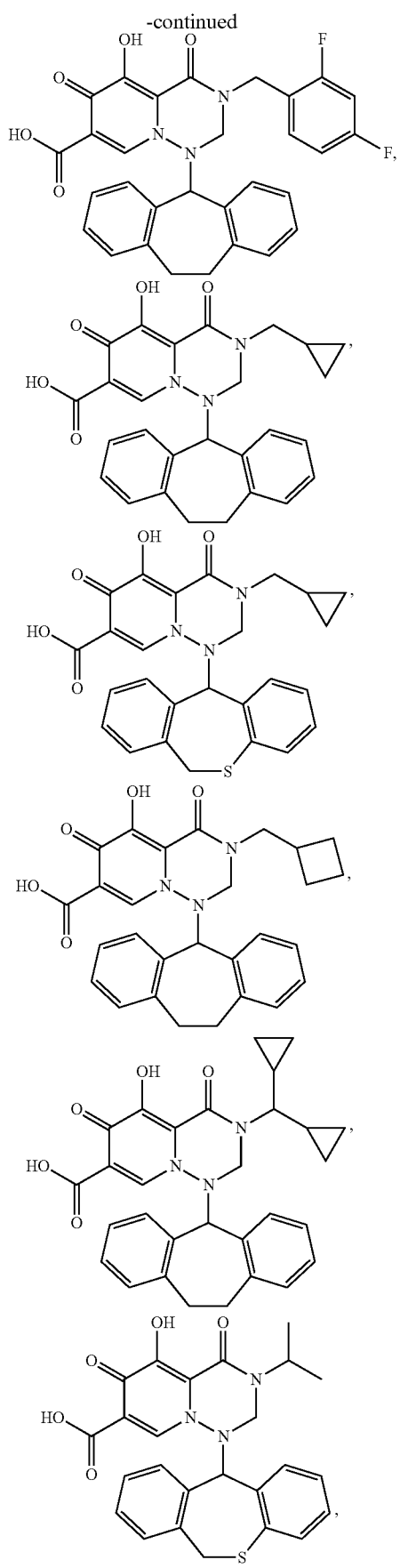
200
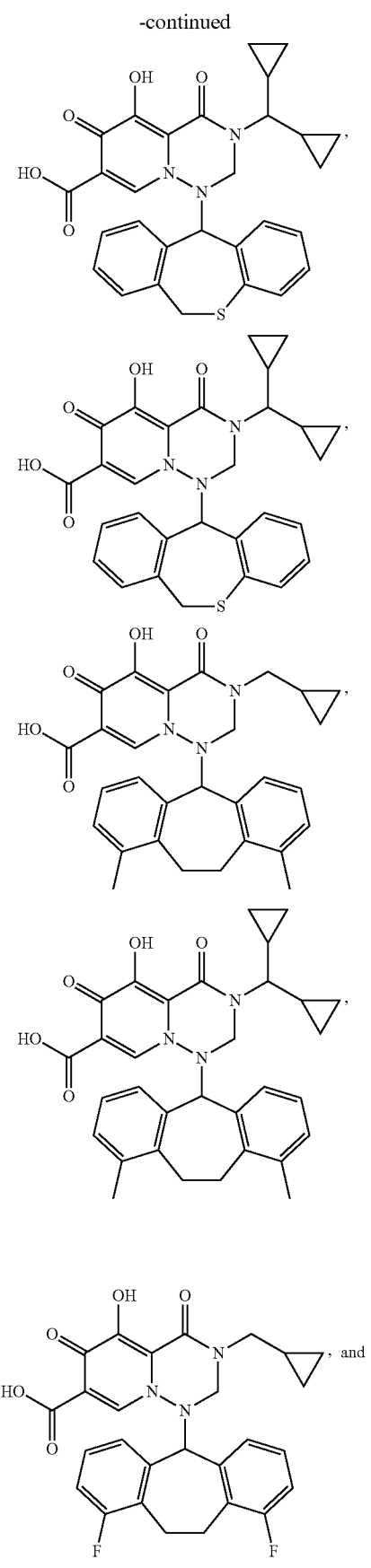

-continued

[Chemical structure shown]

or a prodrug thereof or a pharmaceutically acceptable salt thereof.

24. A method for inhibiting Lassa virus proliferation in vitro, comprising contacting a Lassa virus with an effective amount of a compound represented by Formula (I) or a prodrug thereof or a pharmaceutically acceptable salt thereof in vitro:

$$(I)$$

[Chemical structure of Formula (I) showing OH, O, $R^3$, $A^2$, $A^1$, $A^3$, N, $R^1$]

wherein:
$R^1$ is —$Z^X$—C(=O)—O—$R^{X15}$, —$Z^X$—C(=O)—N($R^{X9}$)($R^{X10}$), or —$Z^X$—N($R^{X14}$)—C(=O)—O—$R^{X15}$, wherein $R^{X9}$, $R^{X14}$, and $R^{X15}$ are each independently a hydrogen atom, alkyl optionally substituted with Substituent group E, alkenyl optionally substituted with Substituent group E, or alkynyl optionally substituted with Substituent group E;

$R^{X10}$ is a hydrogen atom, alkyl optionally substituted with Substituent group E, alkenyl optionally substituted with Substituent group E, alkynyl optionally substituted with Substituent group E, or alkyloxy optionally substituted with Substituent group E;

$Z^X$ is a single bond or a linear or branched alkylene;
$R^{X9}$ and $R^{X10}$ may be taken together with an adjacent atom to form a heterocycle;

$A^3$ is $CR^2$ or N;

$R^2$ is a hydrogen atom, halogen, hydroxy, carboxy, cyano, formyl, alkyl optionally substituted with Substituent group F, alkenyl optionally substituted with Substituent group F, alkynyl optionally substituted with Substituent group F, or alkyloxy optionally substituted with Substituent group F;

$R^3$ is a hydrogen atom, hydroxy, carboxy, cyano, formyl, alkyl optionally substituted with Substituent group F, alkenyl optionally substituted with Substituent group F, alkynyl optionally substituted with Substituent group F, alkyloxy optionally substituted with Substituent group F, alkenyloxy optionally substituted with Substituent group F, alkylcarbonyl optionally substituted with Substituent group F, alkyloxycarbonyl optionally substituted with Substituent group F, a carbocyclic group optionally substituted with Substituent group A, carbocyclealkyl optionally substituted with Substituent group A, carbocycleoxyalkyl optionally substituted with Substituent group A, carbocyclecarbonyl optionally substituted with Substituent group A, carbocycleoxy optionally substituted with Substituent group A, carbocycleoxycarbonyl optionally substituted with Substituent group A, a heterocyclic group optionally substituted with Substituent group A, heterocyclealkyl optionally substituted with Substituent group A, heterocycleoxyalkyl optionally substituted with Substituent group A, heterocyclecarbonyl optionally substituted with Substituent group A, heterocycleoxy optionally substituted with Substituent group A, heterocycleoxycarbonyl optionally substituted with Substituent group A, —$Z^Z$—N($R^{Z1}$)—$SO_2$—$R^{Z2}$,
—$Z^Z$—N($R^{Z3}$)—C(=O)—$R^{Z4}$,
—$Z^Z$—N($R^{Z5}$)—C(=O)—O—$R^{Z6}$,
—$Z^Z$—C(=O)—N($R^{Z7}$)($R^{Z8}$),
—$Z^Z$—N($R^{Z9}$)($R^{Z10}$),
—$Z^Z$—$SO_2$—$R^{Z11}$, or
—$Z^Z$—N($R^{Z12}$)—O—C(=O)—$R^{Z13}$, wherein $R^{Z1}$, $R^{Z3}$, $R^{Z4}$, $R^{Z5}$, $R^{Z6}$, $R^{Z7}$, $R^{Z8}$, $R^{Z9}$, $R^{Z10}$, $R^{Z12}$, and $R^{Z13}$ are each independently selected from the group consisting of a hydrogen atom, alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;

$R^{Z2}$ and $R^{Z11}$ are each independently selected from the group consisting of alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;

$R^{Z7}$ and $R^{Z8}$ may be taken together with an adjacent atom to form a heterocycle;

$Z^Z$ is a single bond or a linear or branched alkylene;

a) either $A^1$ or $A^2$ is $CR^5R^6$, and the other is $NR^7$, or b) $A^1$ is $CR^8R^9$, and $A^2$ is $CR^{10}R^{11}$;

$R^5$, $R^6$, $R^7$, $R^8$, $R^9$, $R^{10}$, and $R^{11}$ are each independently a hydrogen atom, carboxy, cyano, alkyl optionally substituted with Substituent group F, alkenyl optionally substituted with Substituent group F, alkynyl optionally substituted with Substituent group F, alkylcarbonyl optionally substituted with Substituent group F, alkyloxycarbonyl optionally substituted with Substituent group F, a carbocyclic group optionally substituted with Substituent group B, carbocyclealkyl optionally substituted with Substituent group B, carbocycleoxyalkyl optionally substituted with Substituent group B, carbocyclecarbonyl optionally substituted with Substituent group B, carbocycleoxycarbonyl optionally substituted with Substituent group B, a heterocyclic group optionally substituted with B, heterocyclealkyl optionally substituted with Substituent group B, heterocycleoxyalkyl optionally substituted with Substituent group B, heterocyclecarbonyl optionally substituted with Substituent group B, heterocycleoxycarbonyl optionally substituted with Substituent group B, —$Z^V$—S—$R^{V1}$,
—$Z^V$—S(=O)—$R^{V2}$,
—$Z^V$—$SO_2$—$R^{V3}$,
—C(=O)—C(=O)—$R^{V4}$,
—C(=O)—N($R^{V5}$)($R^{V6}$),
—$Z^V$—N($R^{V7}$)—C(=O)—O—$R^{V8}$, or
—$Z^V$—N($R^{V9}$)—C(=O)—$R^{V10}$,
wherein $R^{V1}$, $R^{V4}$, $R^{V5}$, $R^{V6}$, $R^{V7}$, $R^{V8}$, $R^{V9}$, and $R^{V10}$ are each independently selected from the group consisting of a hydrogen atom, alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;

$R^{V2}$ and $R^{V3}$ are each independently selected from the group consisting of alkyl optionally substituted with Substituent group F, alkenyl optionally substituted with Substituent group F, alkynyl optionally substituted with Substituent group F, a carbocyclic group optionally substituted with Substituent group A, a heterocyclic group optionally substituted with Substituent group A, carbocyclealkyl optionally substituted with Substituent group A, and heterocyclealkyl optionally substituted with Substituent group A;

$R^{V5}$ and $R^{V6}$ may be taken together with an adjacent atom to form a heterocycle;

$Z^V$ is a single bond or a linear or branched alkylene;

$R^5$ and $R^6$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure;

$R^8$ and $R^9$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure;

$R^{10}$ and $R^{11}$ may be taken together with an adjacent atom to form a carbocycle optionally substituted with Substituent group B or a heterocycle optionally substituted with Substituent group B, wherein the carbocycle or the heterocycle may form a condensed ring and/or a bridged structure;

1) When $A^1$ is $CR^5R^6$ and $A^2$ is $NR^7$,
then $R^5$ and $R^7$ may be taken together to form a bond, or $R^5$ and $R^7$ may be taken together with an adjacent atom to form a heterocycle optionally substituted with Substituent group B, wherein the heterocycle may form a condensed ring and/or a spiro ring and/or a bridged structure, or $R^3$ and $R^7$ may be taken together with an adjacent atom to form a heterocycle optionally substituted with Substituent group B, wherein the heterocycle may form a condensed ring and/or a spiro ring and/or a bridged structure, 2) When $A^1$ is $NR^7$ and $A^2$ is $CR^5R^6$,
then $R^7$ and $R^5$ may be taken together to form a bond, or $R^7$ and $R^5$ may be taken together with an adjacent atom to form a heterocycle optionally substituted with Substituent group B, wherein the heterocycle may form a condensed ring and/or a spiro ring and/or a bridged structure, or $R^3$ and $R^6$ may be taken together with an adjacent atom to form a heterocycle optionally substituted with Substituent group B, wherein the heterocycle may form a condensed ring and/or a spiro ring and/or a bridged structure, 3) when $A^1$ is $CR^8R^9$, and $A^2$ is $CR^{10}R^{11}$,
then $R^8$ and $R^{10}$ may be taken together to form a bond, or $R^8$ and $R^{10}$ may be taken together with an adjacent atom to form a carbocycle optionally substituted with Substituent group B or a heterocycle optionally substituted with Substituent group B, wherein the carbocycle or the heterocycle may form a condensed ring and/or a spiro ring and/or a bridged structure, or $R^3$ and $R^{11}$ may be taken together with an adjacent atom to form a heterocycle optionally substituted with Substituent group B, wherein the heterocycle may form a condensed ring and/or a spiro ring and/or a bridged structure, with a proviso that following compounds of c) and d) are excluded:
c) $R^5$, $R^6$, and $R^7$ are all a hydrogen atom,
d) $R^8$, $R^9$, $R^{10}$, and $R^{11}$ are all a hydrogen atom; and wherein Substituent group A is selected from the group consisting of halogen, cyano, hydroxy, carboxy, formyl, amino, oxo, nitro, alkyl, halogenoalkyl, alkyloxy, alkylthio, alkylamino, hydroxyalkyl, carboxyalkyl, aminoalkyl, a carbocyclic group, a heterocyclic group, an oxo-substituted heterocyclic group, carbocyclealkyloxy, carbocycleoxyalkyl, carbocyclealkyloxyalkyl, carbocyclealkylthio, heterocyclealkyloxy, heterocycleoxyalkyl, heterocyclealkyloxyalkyl, halogenoalkyloxy, alkyloxyalkyl, alkyloxyalkyloxy, alkylcarbonyl, alkylcarbonyloxy, alkyloxycarbonyl, alkyloxycarbonyloxy, alkylamino, alkylcarbonylamino, halogenoalkylcarbonylamino, alkylaminocarbonyl, alkyl sulfonyl, alkylsulfinyl, and alkylsulfonylamino;

wherein Substituent group B is selected from the group consisting of halogen, cyano, hydroxy, carboxy, formyl, amino, oxo, nitro, alkyl, halogenoalkyl, alkyloxy, alkylthio, alkylamino, hydroxyalkyl, carboxyalkyl, alkylamino, carbocyclealkyloxy, heterocyclealkyloxy, halogenoalkyloxy, alkyloxyalkyl, alkyloxyalkyloxy, alkylcarbonyl, alkyloxycarbonyl, alkyloxycarbonyloxy, alkylamino, alkylcarbonylamino, alkylaminocarbonyl, alkyl sulfonyl, alkylsulfonylamino, a carbocyclic group optionally substituted with Substituent group A, a heterocyclic group optionally substituted with Substituent group A, carbocyclealkyl optionally substituted with Substituent group A, heterocyclealkyl optionally substituted with Substituent group A, carbocyclealkyloxy optionally substituted with Substituent group A, heterocyclealkyloxy optionally substituted with Substituent group A, carbocyclealkylthio optionally substituted with Substituent group A, heterocyclealkylthio optionally substituted with Substituent group A, carbocycleoxyalkyl optionally substituted with Substituent group A, heterocycleoxyalkyl optionally substituted with Substituent group A, carbocyclealkyloxyalkyl optionally substituted with Substituent group A, and heterocyclealkyloxyalkyl optionally substituted with Substituent group A;

wherein Substituent group E is selected from the group consisting of halogen, hydroxy, carboxy, alkyloxy, alkylcarbonyl, alkyloxycarbonyl, alkylcarbonyloxy, alkylaminocarbonyl, and alkylsulfonyl; and wherein Substituent group F is selected from the group consisting of halogen, cyano, hydroxy, carboxy, formyl, amino, oxo, nitro, alkyloxy, alkylthio, a carbocyclic group, a heterocyclic group, an oxo-substituted heterocyclic group, carbocyclealkyloxy, carbocyclealkylthio, heterocyclealkyloxy, halogenoalkyloxy, alkyloxyalkyloxy, alkylcarbonyl, alkylcarbonyloxy, alkyloxycarbonyl, alkyloxycarbonyloxy, alkylamino, alkylcarbonylamino, halogenoalkylcarbonylamino, alkylaminocarbonyl, alkyl sulfonyl, alkylsulfinyl, and alkyl sulfonylamino.

* * * * *